United States Patent [19]

Reitz

[11] Patent Number: 5,155,117
[45] Date of Patent: Oct. 13, 1992

[54] 1-ARYLHETEROARYLALKYL SUBSTITUTED-1H-1,2,4-TRIAZOLE COMPOUNDS FOR TREATMENT OF CIRCULATORY DISORDERS

[75] Inventor: David B. Reitz, Chesterfield, Mo.

[73] Assignee: G. D. Searle & Co., Chicago, Ill.

[21] Appl. No.: 686,324

[22] Filed: Apr. 12, 1991

[51] Int. Cl.$^5$ .......................................... A01N 43/40
[52] U.S. Cl. ................................. 514/340; 546/276
[58] Field of Search .................... 546/276; 514/340

[56] References Cited

U.S. PATENT DOCUMENTS

| | | | |
|---|---|---|---|
| 4,118,487 | 10/1978 | Regel et al. | 424/232 |
| 4,381,306 | 4/1983 | Regel et al. | 424/269 |
| 4,480,114 | 10/1984 | Regel et al. | 549/563 |
| 4,575,555 | 3/1986 | Temple, Jr. et al. | 546/276 |
| 4,742,068 | 5/1988 | Kykla | 546/276 |
| 4,845,231 | 7/1989 | Kees | 546/276 |
| 4,880,804 | 11/1989 | Carini et al. | 514/234.5 |
| 5,075,324 | 12/1991 | Feigerio et al. | 514/340 |

FOREIGN PATENT DOCUMENTS

| | | | |
|---|---|---|---|
| 253310 | 1/1988 | European Pat. Off. | 233/68 |
| 323841 | 7/1989 | European Pat. Off. | 249/02 |

OTHER PUBLICATIONS

P. C. Wong et al., *J. Pharmacol, Exp. ther.*, 247(1), 1-7 (1988).
A. T. Chiu et al., *European J. Pharmacol.*, 157, 13-21 (1988).
A. T. Chiu et al., *J. Pharmacol. Exp. Ther.*, 250(3), 867-874 (1989).

*Primary Examiner*—C. Warren Ivy
*Assistant Examiner*—Raymond Covington
*Attorney, Agent, or Firm*—J. Timothy Keane; Paul D. Matukaitis

[57] ABSTRACT

A class of 1-arylheteroarylalkyl substituted-1H-1,2,4-triazole compounds is described for use in treatment of circulatory disorders such as hypertension. Compounds of particular interest are angiotensin II antagonists of the formula wherein A is selected from wherein m is one; wherein $R^1$ is selected from ethyl, n-propyl, isopropyl, n-butyl, sec-butyl, isobutyl, tert-butyl, 4-methylbutyl, n-pentyl, neopentyl, benzyl, cyclohexyl, cyclohexylmethyl, 2-butenyl, 3-butenyl, 2-butynyl, 3-butynyl and 2-hydroxybutyl; wherein $R^2$ is selected from ethyl, n-propyl, isopropyl, n-butyl, sec-butyl, isobutyl, 4-methylbutyl, tert-butyl, n-pentyl, neopentyl, 1-oxoethyl, 1-oxopropyl, 1-oxobutyl, 1-oxopentyl, 1,1-dimethoxypropyl, 1,1-dimethoxypentyl, halo, difluoromethyl, 1-oxo-2-phenylethyl, 1-oxo-2-cyclohexylethyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, 1-

(Abstract continued on next page.)

ABSTRACT butenyl, 2-butenyl, 3-butenyl, 1-butynyl, 2-butynyl, 3-butynyl, propylthio and butylthio; wherein each of $R^3$, $R^4$, $R^6$ through $R^{11}$ is hydrido and $R^5$ is selected from COOH, SH, $PO_3H_2$, $SO_3H$, $CONHNH_2$, $CONHNHSO_2CF_3$, OH,

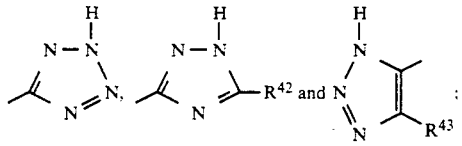

wherein each of $R^{42}$ and $R^{43}$ is independently selected from chloro, cyano, nitro, trifluoromethyl, methoxycarbonyl and trifluoromethylsulfonyl.

32 Claims, No Drawings

1-ARYLHETEROARYLALKYL SUBSTITUTED-1H-1,2,4-TRIAZOLE COMPOUNDS FOR TREATMENT OF CIRCULATORY DISORDERS

FIELD OF THE INVENTION

Non-peptidic 1-arylheteroarylalkyl substituted-1H-1,2,4-triazole compounds are described for use in treatment of circulatory disorders such as hypertension and congestive heart failure. Of particular interest are angiotensin II antagonist compounds provided by 1H-1,2,4-triazoles having a arylheteroarylmethyl moiety attached to the nitrogen atom at the one-position of the 1H-1,2,4-triazole.

BACKGROUND OF THE INVENTION

The renin-angiotensin system is one of the hormonal mechanisms involved in regulation of pressure/volume homeostasis and in expression of hypertension. Activation of the renin-angiotensin cascade begins with renin secretion from the juxtaglomerular apparatus of the kidney and culminates in the formation of angiotensin II, the primary active species of this system. This octapeptide, angiotensin II, is a potent vasoconstrictor agent and also produces other physiological effects such as promoting aldosterone secretion, promoting sodium and fluid retention, inhibiting renin secretion, increasing sympathetic nervous system activity, increasing vasopressin secretion, causing positive cardiac inotropic effect and modulating other hormonal systems.

Previous studies have shown that antagonizing angiotensin II at its receptors is a viable approach to inhibit the renin-angiotensin system, given the pivotal role of this octapeptide which mediates the actions of the renin-angiotensin system through interaction with various tissue receptors. There are several known angiotensin II antagonists, most of which are peptidic in nature. Such peptidic compounds are of limited use due to their lack of oral bioavailability or their short duration of action. Also, commercially-available peptidic angiotensin II antagonists (e.g., Saralasin) have a significant residual agonist activity which further limit their therapeutic application.

Non-peptidic compounds with angiotensin II antagonist properties are known. For example, the sodium salt of 2-n-butyl-4-chloro-1-(2-chlorobenzyl)imidazole-5-acetic acid has specific competitive angiotensin II antagonist activity as shown in a series of binding experiments, functional assays and in vivo tests [P. C. Wong et al, *J. Pharmacol. Exp. Ther.*, 247 (1), 1–7 (1988)]. Also, the sodium salt of 2-butyl-4-chloro-1-(2-nitrobenzyl)imidazole-5-acetic acid has specific competitive angiotensin II antagonist activity as shown in a series of binding experiments, functional assays and in vivo tests [A. T. Chiu et al, *European J. Pharmacol.*, 157, 13–21 (1988)]. A family of 1-benzylimidazole-5-acetate derivatives has been shown to have competitive angiotensin II antagonist properties [A. T. Chiu et al, *J. Pharmacol. Exp. Ther.*, 250 (3), 867–874 (1989)]. U.S. Pat. No. 4,816,463 to Blankey et al describes a family of 4,5,6,7-tetrahydro-1H-imidazo(4,5-c)-tetrahydro-pyridine derivatives useful as antihypertensives, some of which are reported to antagonize the binding of labelled angiotensin II to rat adrenal receptor preparation and thus cause a significant decrease in mean arterial blood pressure in conscious hypertensive rats. EP No. 253,310, published Jan. 20, 1988, describes a series of aralkyl imidazole compounds, including in particular a family of biphenylmethyl substituted imidazoles, as antagonists to the angiotensin II receptor. EP No. 323,841 published Jul. 12, 1989 describes four classes of angiotensin II antagonists, namely, biphenylmethylpyrroles, biphenylmethylpyrazoles, biphenylmethyl-1,2,3-triazoles and biphenylmethyl 4-substituted-4H-1,2,4-triazoles, including the compound 3,5-dibutyl-4-[(2'-carboxybiphenyl-4-yl)methyl]-4H-1,2,4-triazole. U.S. Pat. No. 4,880,804 to Carini et al describes a family of biphenylmethylbenzimidazole compounds as angiotensin II receptor blockers for use in treatment of hypertension and congestive heart failure.

There are several families of 1,2,4-triazole compounds having substituents attached to the nitrogen atom at the one-position of the 1H-triazole. For example, U.S. Pat. No. 4,118,487 to Regel et al describes a family azol-1-ylmethane compounds for use as antimycotic and antibacterial agents including, specifically, the compound (1-biphenyl-4-yl-1-phenyl)methyl-1H-1,2,4-triazole. U.S. Pat. No. 4,381,306 to Regel et al describes a family of hydroxypropyl-triazole compounds for use as antimycotic agents including, specifically, the compound (1,2,4-triazol-1-yl)methyl-4-chlorobenzyl-biphenyl-4-ylcarbinol. U.S. Pat. No. 4,480,114 to Regel describes a family of 2-(4-biphenyl)-2-(halophenyl)-oxirane compounds having antimycotic activity including, specifically, the compound (1,2,4-triazol-1-yl)methyl-4-chlorophenyl-4-chlorobiphenyl-4-ylcarbinol.

DESCRIPTION OF THE INVENTION

A class of 1-arylheteroarylalkyl substituted-1H-1,2,4-triazole compounds useful in treating circulatory disorders, particularly cardiovascular disorders, is defined by Formula I:

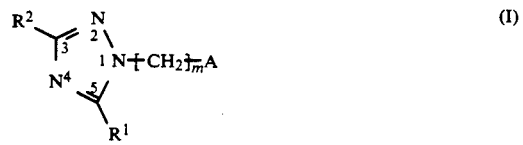

wherein A is selected from

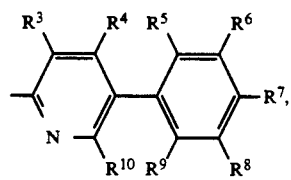

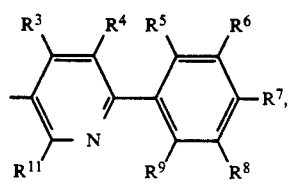

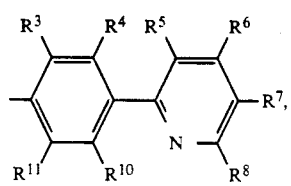

-continued

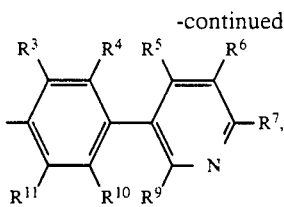

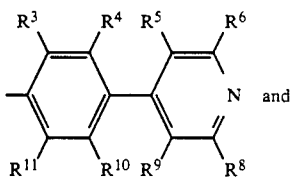

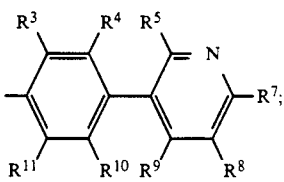

wherein m is a number selected from one to four, inclusive;
wherein $R^1$ is selected from hydrido, alkyl, hydroxyalkyl, haloalkyl, cycloalkyl, cycloalkylalkyl, formyl, aralkyl, aryl, aroyl, alkoxyalkyl, alkylcarbonyl, alkylcarbonylalkyl, alkoxycarbonyl, alkenyl, cycloalkenyl, aralkoxycarbonyl, alkynyl, alkylthiocarbonyl, alkylthiothiocarbonyl, arylthiocarbonyl, arylthiothiocarbonyl, aralkylthiocarbonyl, alkylthiocarbonyl, alkylsulfinyl, alkylsulfonyl, aralkylsulfinyl, aralkylsulfonyl, arylsulfinyl, arylsulfonyl, heteroaryl having one or more ring atoms selected from oxygen, sulfur and nitrogen atoms, and amido radicals of the formula

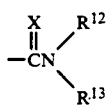

wherein X is oxygen atom or sulfur atom;
wherein each of $R^{12}$ and $R^{13}$ is independently selected from hydrido, alkyl, cycloalkyl, cyano, amino, monoalkylamino, dialkylamino, hydroxyalkyl, cycloalkylalkyl, alkoxyalkyl, aralkyl and aryl, and wherein $R^{12}$ and $R^{13}$ taken together may form a heterocyclic group having five to seven ring members including the nitrogen atom of said amido radical and which heterocyclic group may further contain one or more hetero atoms as ring members selected from oxygen, nitrogen and sulfur atoms and which heterocyclic group may be saturated or partially unsaturated; wherein each of $R^{12}$ and $R^{13}$ taken together may form an aromatic heterocyclic group having five ring members including the nitrogen atom of said amido radical and which aromatic heterocyclic group may further contain one or more additional nitrogen atoms;
wherein each of $R^2$ through $R^{11}$ is independently selected from hydrido, alkyl, hydroxyalkyl, halo, haloalkyl, cycloalkyl, cycloalkylalkyl, cycloalkylhaloalkyl, cycloalkylcarbonyl, formyl, alkoxy, aralkyl, aralkylhaloalkyl, aryl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptothiocarbonyl, mercaptoalkyl, alkoxycarbonyloxy, alkylthio, cycloalkylthio, cycloalkylalkylthio, alkylthiocarbonyl, alkylcarbonylthio, alkylthiocarbonyloxy, alkylthiocarbonylthio, alkylthiothiocarbonyl, alkylthiothiocarbonylthio, arylthio, arylthiocarbonyl, arylcarbonylthio, arylthiocarbonyloxy, arylthiocarbonylthio, arylthiothiocarbonyl, arylthiothiocarbonylthio, aralkylthio, aralkylthiocarbonyl, aralkylcarbonylthio, aralkylthiocarbonyloxy, aralkylthiocarbonylthio, alkylthiocarbonyl, aralkylthiocarbonylthio, mercapto, alkylsulfinyl, alkylsulfonyl, aralkylsulfinyl, aralkylsulfonyl, arylsulfinyl, arylsulfonyl, phthalimido, phthalimidoalkyl, heteroaryl, heteroarylalkyl, cycloheteroalkyl, cycloheteroalkylalkyl and cycloheteroalkylcarbonylalkyl wherein each of said heteroaryl- and cyclohetero-containing groups has one or more ring atoms selected from oxygen, sulfur and nitrogen atoms, and wherein each of $R^2$ through $R^{11}$ may be further independently selected from amino and amido radicals of the formula

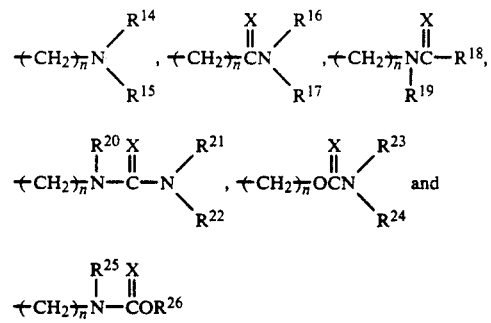

wherein X is oxygen atom or sulfur atom;
wherein each n is a number independently selected from zero to six, inclusive;
wherein each of $R^{14}$ through $R^{26}$ is independently selected from hydrido, alkyl, cycloalkyl, cyano, amino, monoalkylamino, dialkylamino, hydroxyalkyl, cycloalkylalkyl, alkoxyalkyl, aralkyl and aryl, and wherein $R^{14}$ and $R^{15}$ taken together, $R^{16}$ and $R^{17}$ taken together, $R^{18}$ and $R^{19}$ taken together, $R^{21}$ and $R^{22}$ taken together and $R^{23}$ and $R^{24}$ taken together may each form a heterocyclic group having five to seven ring members including the nitrogen atom of said amino or amido radical and which heterocyclic group may further contain one or more hetero atoms as ring members selected from oxygen, nitrogen and sulfur atoms and which heterocyclic group may be saturated or partially unsaturated; wherein $R^{14}$ and $R^{15}$ taken together, $R^{16}$ and $R^{17}$ taken together, $R^{21}$ and $R^{22}$ taken together and $R^{23}$ and $R^{24}$ taken together may each form an aromatic heterocyclic group having five ring members including the nitrogen atom of said amino or amido radical and which aromatic heterocyclic group may further contain one or more hetero atoms as ring atoms selected from oxygen, nitrogen and sulfur atoms;
and wherein each of $R^3$ through $R^{11}$ may be further independently selected from hydroxy and acidic moieties of the formula $$-Y_n A$$

wherein n is a number selected from zero through three, inclusive, and wherein A is an acidic group selected to contain at least one acidic hydrogen atom, and the amide, ester and salt derivatives of said acidic moieties; wherein Y is a spacer group independently selected from one or more of alkyl, cycloalkyl, cycloalkylalkyl, alkenyl, alkynyl, aryl, aralkyl and heteroaryl having one or more ring atoms selected from oxygen, sulfur and nitrogen atoms;

and wherein any of the foregoing $R^1$ through $R^{26}$, Y and A groups having a substitutable position may be substituted by one or more groups independently selected from hydroxy, alkyl, alkenyl, alkynyl, aralkyl, hydroxyalkyl, haloalkyl, halo, oxo, alkoxy, aryloxy, aralkoxy, aralkylthio, alkoxyalkyl, cycloalkyl, cycloalkylalkyl, aryl, aroyl, cycloalkenyl, cyano, cyanoamino, nitro, alkylcarbonyloxy, alkoxycarbonyloxy, alkylcarbonyl, alkoxycarbonyl, aralkoxycarbonyl, carboxyl, mercapto, mercaptocarbonyl, alkylthio, arylthio, alkylthiocarbonyl, alkylsulfinyl, alkylsulfonyl, haloalkylsulfonyl, aralkylsulfinyl, aralkylsulfonyl, arylsulfinyl, arylsulfonyl, heteroaryl having one or more ring atoms selected from oxygen, sulfur and nitrogen atoms, and amino and amido radicals of the formula

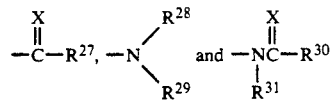

wherein X is oxygen atom or sulfur atom; wherein each of $R^{27}$ through $R^{31}$ is independently selected from hydrido, alkyl, cycloalkyl, cycloalkylalkyl, aralkyl, aryl, $DR^{32}$ and

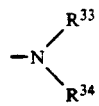

wherein D is selected from oxygen atom and sulfur atom and $R^{32}$ is selected from hydrido, alkyl, cycloalkyl, cycloalkylalkyl, aralkyl and aryl; wherein each of $R^{27}$, $R^{28}$, $R^{29}$, $R^{30}$, $R^{31}$, $R^{33}$ and $R^{34}$ is independently selected from hydrido, alkyl, cycloalkyl, cyano, hydroxyalkyl, haloalkyl, cycloalkylalkyl, alkoxyalkyl, alkylcarbonyl, alkoxycarbonyl, carboxyl, alkylsulfinyl, alkylsulfonyl, arylsulfinyl, arylsulfonyl, haloalkylsulfinyl, haloalkylsulfonyl, aralkyl and aryl, and wherein each of $R^{27}$, $R^{28}$, $R^{29}$, $R^{30}$, $R^{31}$, $R^{33}$ and $R^{34}$ is further independently selected from amino and amido radicals of the formula

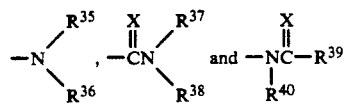

wherein X is oxygen atom or sulfur atom; wherein each of $R^{35}$, $R^{36}$, $R^{37}$, $R^{38}$, $R^{39}$ and $R^{40}$ is independently selected from hydrido, alkyl, cycloalkyl, cyano, hydroxyalkyl, cycloalkylalkyl, alkoxyalkyl, haloalkylsulfinyl, haloalkylsulfonyl, aralkyl and aryl, and wherein each of $R^{28}$ and $R^{29}$ taken together and each of $R^{30}$ and $R^{31}$ taken together may form a heterocyclic group having five to seven ring members including the nitrogen atom of said amino or amido radical, which heterocyclic group may further contain one or more hetero atoms as ring members selected from oxygen, nitrogen and sulfur atoms and which heterocyclic group may be saturated or partially unsaturated; wherein each of $R^{28}$ and $R^{29}$ taken together and each of $R^{33}$ and $R^{34}$ taken together may form an aromatic heterocyclic group having five ring members including the nitrogen atom of said amino or amido radical and which aromatic heterocyclic group may further contain one or more hetero atoms as ring atoms selected from oxygen, nitrogen and sulfur atoms; or a tautomer thereof or a pharmaceutically-acceptable salt thereof.

Compounds of Formula I would be useful in treating a variety of circulatory disorders, including cardiovascular disorders, such as hypertension, congestive heart failure and arteriosclerosis, and to treat other disorders such as glaucoma. These compounds would also be useful as adjunctive therapies. For example, compounds of Formula I may be used in combination with other drugs, such as a diuretic, to treat hypertension. Also, compounds of Formula I could be used in conjunction with certain surgical procedures. For example, these compounds could be used to prevent post-angioplasty re-stenosis. Compounds of Formula I are therapeutically effective in treatment of cardiovascular disorders by acting as antagonists to, or blockers of, the angiotensin II (AII) receptor. Compounds of Formula I would be therapeutically effective in treatment of the above-mentioned circulatory and cardiovascular disorders or would be precursors to, or prodrugs of, therapeutically-effective compounds.

The phrase "acidic group selected to contain at least one acidic hydrogen atom", as used to define the $-Y_nA$ moiety, is intended to embrace chemical groups which, when attached to any of the $R^3$ through $R^{11}$ positions of Formula I, confers acidic character to the compound of Formula I. "Acidic character" means proton-donor capability, that is, the capacity of the compound of Formula I to be a proton donor in the presence of a proton-receiving substance such as water. Typically, the acidic group should be selected to have proton-donor capability such that the product compound of Formula I has a $pK_a$ in a range from about one to about twelve. More typically, the Formula I compound would have a $pK_a$ in a range from about two to about seven. An example of an acidic group containing at least one acidic hydrogen atom is carboxyl group (—COOH). Where n is zero and A is —COOH, in the $-Y_nA$ moiety, such carboxyl group would be attached directly to one of the $R^3$ through $R^{11}$ positions. The Formula I compound may have one $-Y_nA$ moiety attached at one of the $R^3$ through $R^{11}$ positions, or may have a plurality of such $-Y_nA$ moieties attached at more than one of the $R^3$ through $R^{11}$ positions, up to a maximum of nine such $-Y_nA$ moieties. There are many examples of acidic groups other than carboxyl group, selectable to contain at least one acidic hydrogen atom. Such other acidic groups may be collectively referred to as "bioisosteres of carboxylic acid" or referred to as "acidic bioisosteres". Specific examples of such acidic bioisosteres are described hereinafter. Compounds of Formula I having the $-Y_nA$ moiety attached at one of positions $R^5$, $R^6$, $R^8$ and $R^9$ would be expected to have preferred properties, while attachment at $R^5$ or $R^9$ would be more preferred. Compounds of Formula I may have one or more acidic protons and, therefore, may have one or more $pK_a$ values. It is preferred, however, that at least one of these $pK_a$ values of the Formula I compound as conferred by the $-Y_nA$ moiety be in a range from about two to about seven. The $-Y_nA$ moiety may be attached to one of the $R^3$ through $R^{11}$ positions through any portion of the $-Y_nA$ moiety which results in a Formula I compound being relatively stable and also having a labile or acidic proton to meet the foregoing $pK_a$ criteria. For example, where the $-Y_nA$ acid moiety is tetrazole, the tetrazole is attached at the ring carbon atom.

A preferred class of compounds consists of those compounds of Formula I wherein m is one; wherein $R^1$ is selected from hydrido, alkyl, hydroxyalkyl, haloalkyl, cycloalkyl, cycloalkylalkyl, aralkyl, aryl, aroyl, alkoxyalkyl, alkylcarbonyl, alkoxycarbonyl, alkenyl, cycloalkenyl, alkynyl, cycloalkynyl, carboxyl, alkylthiocarbonyl, arylthiocarbonyl, arylthiothiocarbonyl, aralkylthiocarbonyl, alkylsulfonyl, aralkylsulfonyl, arylsulfonyl, heteroaryl having one or more ring atoms selected from oxygen, sulfur and nitrogen atoms, and amido radicals of the formula

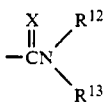

wherein X is oxygen atom or sulfur atom; wherein each of $R^{12}$ and $R^{13}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;

wherein $R^2$ is selected from hydrido, alkyl, hydroxyalkyl, halo, haloalkyl, cycloalkyl, cycloalkylalkyl, cycloalkylhaloalkyl, cycloalkylcarbonyl, alkoxy, aralkyl, aralkylhaloalkyl, aryl, aroyl, aryloxy, aryloxyalkyl, aralkoxy, alkoxyalkyl, alkylcarbonyl, alkoxycarbonyl, alkenyl, cycloalkenyl, alkynyl, cycloalkynyl, cyano, nitro, carboxyl, carboxalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptothiocarbonyl, mercaptoalkyl, alkoxycarbonyloxy, alkylthio, cycloalkylthio, cycloalkylalkylthio, alkylthiocarbonyl, alkylcarbonylthio, alkylthiocarbonyloxy, alkylthiocarbonylthio, alkylthiothiocarbonyl, alkylthiothiocarbonylthio, arylthio, arylthiocarbonyl, arylcarbonylthio, arylthiocarbonyloxy, arylthiocarbonylthio, arylthiothiocarbonyl, arylthiothiocarbonylthio, aralkylthio, aralkylthiocarbonyl, aralkylcarbonylthio, aralkylthiocarbonyloxy, aralkylthiocarbonylthio, aralkylthiothiocarbonyl, aralkylthiothiocarbonylthio, mercapto, alkylsulfinyl, alkylsulfonyl, aralkylsulfinyl, aralkylsulfonyl, arylsulfinyl, arylsulfonyl, phthalimido, phthalimidoalkyl, heteroaryl, heteroarylalkyl, cycloheteroalkyl, cycloheteroalkylalkyl and cycloheteroalkylcarbonylalkyl wherein each of said heteroaryl- and cycloheteroalkyl-containing groups has one or more hetero ring atoms selected from oxygen, sulfur and nitrogen atoms, and wherein each of $R^2$ through $R^{11}$ may be further independently selected from amino and amido radicals of the formula

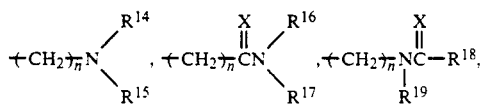

-continued

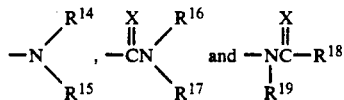

wherein X is selected from oxygen atom or sulfur atom; wherein each n is a number independently selected from zero to six, inclusive;

wherein each of $R^{14}$ through $R^{26}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;

wherein each of $R^3$ through $R^{11}$ is independently selected from hydrido, hydroxy, alkyl, hydroxyalkyl, halo, haloalkyl, cycloalkyl, cycloalkylalkyl, alkoxy, aralkyl, aryl, aroyl, aryloxy, aralkoxy, alkoxyalkyl, alkylcarbonyl, alkoxycarbonyl, alkenyl, cycloalkenyl, alkynyl, cycloalkynyl, cyano, nitro, carboxyl, alkylcarbonyloxy, mercaptocarbonyl, mercaptothiocarbonyl, alkoxycarbonyloxy, alkylthio, alkylthiocarbonyl, alkylcarbonylthio, alkylthiocarbonyloxy, alkylthiocarbonylthio, alkylthiothiocarbonyl, arylthio, arylthiocarbonyl, arylcarbonylthio, arylthiocarbonyloxy, arylthiothiocarbonyl, aralkylthio, aralkylthiocarbonyl, aralkylcarbonylthio, aralkylthiocarbonyloxy, aralkylthiocarbonylthio, aralkylthiothiocarbonyl, aralkylthiocarbonylthio, mercapto, alkylsulfonyl, aralkylsulfonyl and arylsulfonyl, and amino and amido radicals of the formula $$-N\begin{matrix}R^{14}\\ \\R^{15}\end{matrix}, -C\begin{matrix}X\\ \|\\N\end{matrix}\begin{matrix}R^{16}\\ \\R^{17}\end{matrix} \text{ and } -N\begin{matrix}X\\ \|\\C-R^{18}\\ |\\R^{19}\end{matrix}$$

wherein X is oxygen atom or sulfur atom; wherein each of $R^{14}$, $R^{15}$, $R^{16}$, $R^{17}$, $R^{18}$ and $R^{19}$ is independently selected from hydrido, alkyl, cycloalkyl, cyano, hydroxyalkyl, cycloalkylalkyl, alkoxyalkyl, aralkyl and aryl;

and wherein each of $R^3$ through $R^{11}$ may be further independently selected from acidic moieties of the formula $$-Y_nA$$

wherein n is a number selected from zero through three, inclusive; wherein A is an acidic group selected from acids containing one or more atoms selected from oxygen, sulfur, phosphorus and nitrogen atoms, and wherein said acidic group is selected to contain at least one acidic hydrogen atom, and the amide, ester and salt derivatives of said acidic moieties; wherein Y is a spacer group independently selected from one or more of alkyl, cycloalkyl, cycloalkylalkyl, alkenyl, alkynyl, aryl, aralkyl and heteroaryl having one or more ring atoms selected from oxygen, sulfur and nitrogen atoms;

and wherein any of the foregoing $R^1$ through $R^{26}$, Y and A groups having a substitutable position may be substituted by one or more groups independently selected from hydroxy, alkyl, alkenyl, aralkyl, hydroxyalkyl, halo, haloalkyl, oxo, alkoxy, aryloxy, aralkoxy, alkoxyalkyl, alkylcarbonyl, alkoxycarbonyl, carboxyl, cyano, nitro, alkylsulfonyl, haloalkylsulfonyl, aryl, aralkyl, mercaptocarbonyl, alkylthio and alkylthiocarbonyl, and amino and amido radicals of the formula

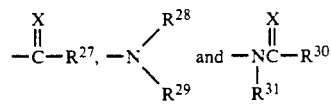

wherein X is oxygen atom or sulfur atom; wherein each of $R^{27}$ through $R^{31}$ is independently selected from hydrido, alkyl, cycloalkyl, cycloalkylalkyl, aralkyl, aryl, and $DR^{32}$ and

wherein D is selected from oxygen atom and sulfur atom, and $R^{32}$ is selected from hydrido, alkyl, cycloalkyl, cycloalkylalkyl, aralkyl and aryl; wherein each of $R^{27}$, $R^{28}$, $R^{29}$, $R^{30}$, $R^{31}$, $R^{33}$ and $R^{34}$ is independently selected from hydrido, alkyl, cycloalkyl, cyano, hydroxyalkyl, haloalkyl, cycloalkylalkyl, alkoxyalkyl, alkanoyl, alkoxycarbonyl, carboxyl, haloalkylsulfinyl, haloalkylsulfonyl, aralkyl and aryl; or a tautomer thereof or a pharmaceutically-acceptable salt thereof.

A more preferred class of compounds consists of those compounds of Formula I wherein m is one; wherein $R^1$ is selected from alkyl, hydroxyalkyl, haloalkyl, cycloalkyl, cycloalkylalkyl, aralkyl, aryl, aroyl, alkoxyalkyl, alkylcarbonyl, alkoxycarbonyl, alkenyl, cycloalkenyl, alkynyl, cycloalkynyl, carboxyl, alkylsulfonyl, aralkylsulfonyl and arylsulfonyl, and amido radicals of the formula

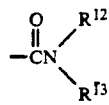

wherein each of $R^{12}$ and $R^{13}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;
wherein $R^2$ is selected from hydrido, alkyl, hydroxyalkyl, halo, haloalkyl, cycloalkyl, cycloalkylalkyl, cycloalkylhaloalkyl, cycloalkylcarbonyl, alkoxy, aralkyl, aralkylhaloalkyl, aryl, aroyl, aryloxy, aryloxyalkyl, aralkoxy, alkoxyalkyl, alkylcarbonyl, alkoxycarbonyl, alkenyl, cycloalkenyl, alkynyl, cycloalkynyl, cyano, nitro, carboxyl, carboxyalkyl, alkylcarbonyloxy, mercaptocarbonyl, alkoxycarbonyloxy, alkylcarbonyloxyalkyl, alkoxycarbonylalkyl, aralkoxycarbonylalkyl, aralkylcarbonyloxyalkyl, alkylthio, cycloalkylthio, cycloalkylalkylthio, arylthio, aralkylthio, aralkylthiocarbonylthio, mercapto, alkylsulfinyl, alkylsulfonyl, aralkylsulfinyl, aralkylsulfonyl, arylsulfinyl, arylsulfonyl, phthalimido, phthalimidoalkyl, heteroaryl, heteroarylalkyl, cycloheteroalkyl, cycloheteroalkylalkyl and cycloheteroalkylcarbonylalkyl wherein each of said heteroaryl- and cycloheteroalkyl-containing groups has one or more hetero ring atoms selected from oxygen, sulfur and nitrogen atoms, and wherein $R^2$ may be further selected from amino and amido radicals of the formula

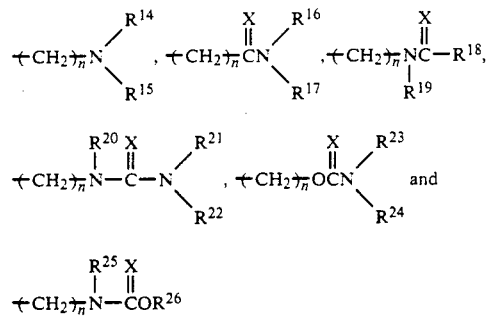

wherein X is selected from oxygen atom or sulfur atom; wherein each n is a number independently selected from zero to six, inclusive;
wherein each of $R^{14}$ through $R^{26}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;
wherein each of $R^3$ through $R^{11}$ is independently selected from hydrido, hydroxy, alkyl, hydroxyalkyl, halo, haloalkyl, cycloalkyl, alkoxy, aralkyl, aryl, aroyl, aryloxy, aralkoxy, alkoxyalkyl, alkylcarbonyl, alkoxycarbonyl, alkenyl, cycloalkenyl, alkynyl, cyano, nitro, carboxyl, alkylcarbonyloxy, mercaptocarbonyl, alkoxycarbonyloxy, alkylthio, arylthio, aralkylthio, mercapto, alkylsulfonyl, aralkylsulfonyl and arylsulfonyl, and amino and amido radicals of the formula

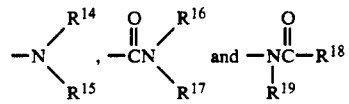

wherein each of $R^{14}$, $R^{15}$, $R^{16}$, $R^{17}$, $R^{18}$ and $R^{19}$ is independently selected from hydrido, alkyl, cycloalkyl, cyano, amino, monoalkylamino, dialkylamino, hydroxyalkyl, cycloalkylalkyl, alkoxyalkyl, aralkyl and aryl; and wherein each of $R^3$ through $R^{11}$ may be further independently selected from acidic moieties of the formula —$Y_n A$ wherein n is a number selected from zero through three, inclusive;
wherein the A group is selected to have an acidic proton, such that when the —$Y_n A$ moiety is incorporated within a compound of Formula I, there is provided a compound of Formula I having a $pK_a$ in a range from about two to about seven, said A group selected from carboxylic acid and bioisosteres of carboxylic acid selected from

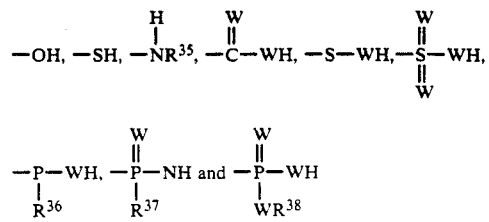

wherein each W is independently selected from oxygen atom, sulfur atom and $NR^{39}$; wherein each of $R^{35}$, $R^{36}$, $R^{37}$, $R^{38}$ and $R^{39}$ is independently selected from hydrido, alkyl, haloalkyl, haloalkylsulfonyl, haloalkylcarbonyl, cycloalkyl, cycloalkylalkyl, aryl and aralkyl; wherein each of $R^{35}$, $R^{36}$, $R^{37}$ and $R^{39}$ may be further independently selected from amino radical of the formula

wherein each of $R^{40}$ and $R^{41}$ is independently selected from hydrido, alkyl, cycloalkyl, hydroxyalkyl, haloalkyl, cycloalkylalkyl, alkoxyalkyl, aralkyl and aryl, and wherein $R^{40}$ and $R^{41}$ taken together may form a heterocyclic group having five to seven ring members including the nitrogen atom of said amino radical, which heterocyclic group may further contain one or more hetero atoms as ring members selected from oxygen, nitrogen and sulfur atoms and which heterocyclic group may be saturated or partially unsaturated; wherein $R^{40}$ and $R^{41}$ taken together may form an aromatic heterocyclic group having five ring members including the nitrogen atom of said amino radical and which aromatic heterocyclic group may further contain one or more hetero atoms as ring atoms selected from oxygen, nitrogen and sulfur atoms; wherein each of $R^{36}$ and $R^{37}$ may be further independently selected from hydroxy, alkoxy, alkylthio, aryloxy, arylthio, aralkylthio and aralkoxy; and the amide, ester and salt derivatives of said acidic groups;

wherein said bioisostere of carboxylic acid may be further selected from heterocyclic acidic groups consisting of heterocyclic rings of four to about nine ring members, which heterocyclic ring contains at least one hetero atom selected from oxygen, sulfur and nitrogen atoms, which heterocyclic ring may be saturated, fully unsaturated or partially unsaturated, and which heterocyclic ring may be attached at a single position selected from $R^3$ through $R^{11}$ or may be attached at any two adjacent positions selected from $R^3$ through $R^{11}$ so as to form a fused-ring system with one of the phenyl rings of Formula I; and the amide, ester and salt derivatives of said heterocyclic acidic groups; wherein Y is a spacer group independently selected from one or more of alkyl, cycloalkyl, cycloalkylalkyl, alkenyl, aryl and aralkyl;

and wherein any of the foregoing $R^1$ through $R^{26}$ and $R^{35}$ through $R^{41}$, Y and A groups having a substitutable position may be substituted by one or more groups independently selected from hydroxy, alkyl, alkenyl, aralkyl, hydroxyalkyl, halo, oxo, haloalkyl, alkoxy, aryloxy, aralkoxy, alkoxyalkyl, alkylcarbonyl, alkoxycarbonyl, carboxyl, cyano, nitro, alkylsulfonyl, haloalkylsulfonyl, aryl, aralkyl, mercaptocarbonyl, alkylthio and alkylthiocarbonyl, and amino and amido radicals of the formula

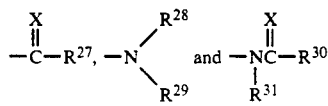

wherein X is selected from oxygen atom and sulfur atom; wherein $R^{27}$ is selected from hydrido, alkyl, cycloalkyl, cycloalkylalkyl, aralkyl, aryl and $DR^{32}$ and

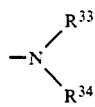

wherein D is selected from oxygen atom and sulfur atom; wherein $R^{32}$ is selected from hydrido, alkyl, cycloalkyl, cycloalkylalkyl, aralkyl and aryl;

wherein each of $R^{27}$, $R^{28}$, $R^{29}$, $R^{30}$, $R^{31}$, $R^{33}$ and $R^{34}$ is independently selected from hydrido, alkyl, cycloalkyl, cyano, hydroxyalkyl, haloalkyl, cycloalkylalkyl, alkoxyalkyl, alkanoyl, alkoxycarbonyl, carboxyl, haloalkylsulfinyl, haloalkylsulfonyl, aralkyl and aryl; or a tautomer thereof or a pharmaceutically-acceptable salt thereof.

An even more preferred class of compounds consists of those compounds of Formula I wherein m is one; wherein $R^1$ is selected from hydrido, alkyl, hydroxyalkyl, haloalkyl, cycloalkyl, cycloalkylalkyl, aralkyl, aryl, aroyl, alkoxyalkyl, alkylcarbonyl, alkenyl, cycloalkenyl, alkynyl, mercaptocarbonyl, alkylsulfonyl, aralkylsulfonyl, arylsulfonyl and amido radicals of the formula

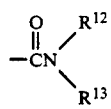

wherein each of $R^{12}$ and $R^{13}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;

wherein $R^2$ is selected from hydrido, alkyl, hydroxyalkyl, halo, haloalkyl, cycloalkyl, cycloalkylalkyl, cycloalkylhaloalkyl, cycloalkylcarbonyl, alkoxy, aralkyl, aralkylhaloalkyl, aryl, aroyl, aryloxy, aryloxyalkyl, aralkoxy, alkoxyalkyl, alkylcarbonyl, alkoxycarbonyl, alkenyl, cycloalkenyl, alkynyl, cycloalkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptoalkyl, alkoxycarbonyloxy, alkylthio, cycloalkylthio, cycloalkylalkylthio, arylthio, aralkylthio, mercapto, alkylsulfinyl, alkylsulfonyl, aralkylsulfinyl, aralkylsulfonyl, arylsulfinyl, arylsulfonyl, phthalimido, phthalimidoalkyl, heteroaryl, heteroarylalkyl, cycloheteroalkyl, cycloheteroalkylalkyl and cycloheteroalkylcarbonylalkyl wherein each of said heteroaryl- and cycloheteroalkyl-containing groups has one or more hetero ring atoms selected from oxygen, sulfur and nitrogen atoms, and wherein each of $R^2$ through $R^{11}$ may be further independently selected from amino and amido radicals of the formula

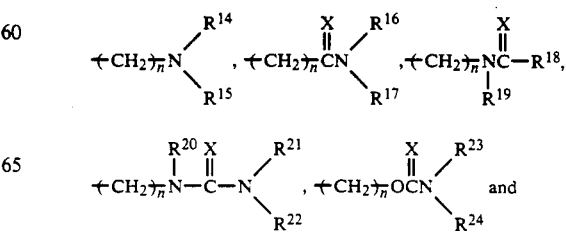

-continued

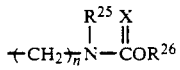

wherein X is selected from oxygen atom and sulfur atom;

wherein each n is a number independently selected from zero to six, inclusive;

wherein each of $R^{14}$ through $R^{26}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;

wherein each of $R^3$ through $R^{11}$ is independently selected from hydrido, hydroxy, alkyl, hydroxyalkyl, halo, haloalkyl, cycloalkyl, alkoxy, aralkyl, aryl, aroyl, aryloxy, aralkoxy, alkoxyalkyl, alkylcarbonyl, alkoxycarbonyl, alkenyl, cycloalkenyl, alkynyl, cyano, nitro, carboxyl, alkylthio, aralkylthio and mercapto;

and wherein each of $R^3$ and $R^{11}$ may be further independently selected from acidic moieties of the formula

wherein n is a number selected from zero through three, inclusive; wherein A is selected from carboxylic acid and bioisosteres of carboxylic acid selected from

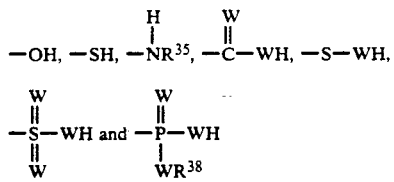

wherein each W is independently selected from oxygen atom, sulfur atom and $NR^{39}$; wherein each of $R^{35}$, $R^{38}$ and $R^{39}$ is independently selected from hydrido, alkyl, haloalkyl, haloalkylsulfonyl, haloalkylcarbonyl, cycloalkyl, cycloalkylalkyl, aryl and aralkyl; wherein each of $R^{35}$ and $R^{39}$ may be further independently selected from amino radical of the formula

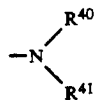

wherein each of $R^{40}$ and $R^{41}$ is independently selected from hydrido, alkyl, cycloalkyl, hydroxyalkyl, haloalkyl, cycloalkylalkyl, alkoxyalkyl, aralkyl and aryl, and wherein $R^{40}$ and $R^{41}$ taken together may form a heterocyclic group having five to seven ring members including the nitrogen atom of said amino radical, which heterocyclic group may further contain one or more hetero atoms as ring members selected from oxygen, nitrogen and sulfur atoms, and which heterocyclic group may be saturated or partially unsaturated; wherein $R^{40}$ and $R^{41}$ taken together may form an aromatic heterocyclic group having five ring members including the nitrogen atom of said amino radical and which aromatic heterocyclic group may further contain one or more hetero atoms as ring atoms selected from oxygen, nitrogen and sulfur atoms; and the amide, ester and salt derivatives of said acidic groups; wherein said bioisostere of carboxylic acid may be further selected from heterocyclic acidic groups consisting of heterocyclic rings of four to about nine ring members, which ring contains at least one hetero atom, selected from oxygen, sulfur and nitrogen atoms, which heterocyclic ring may be saturated, fully unsaturated or partially unsaturated, and which heterocyclic ring may be attached at a single position selected from $R^3$ through $R^{11}$ or may be attached at any two adjacent positions selected from $R^3$ through $R^{11}$ so as to form a fused-ring system with one of the phenyl rings of Formula I; and the amide, ester and salt derivatives of said heterocyclic acidic groups;

wherein Y is a spacer group independently selected from one or more of alkyl, cycloalkyl, cycloalkylalkyl, alkenyl, aryl and aralkyl;

wherein each of $R^1$ through $R^{26}$, $R^{35}$ and $R^{38}$ through $R^{41}$, Y and A independently may be substituted at any substitutable position with one or more groups selected from alkyl, hydroxy, halo, oxo, haloalkyl, alkoxycarbonyl, cyano, nitro, alkylsulfonyl, haloalkylsulfonyl, aryl, aralkyl, alkoxy, aryloxy and aralkoxy;

or a tautomer thereof or a pharmaceutically-acceptable salt thereof.

A highly preferred class of compounds within Formula I consists of those compounds wherein m is one; wherein $R^1$ is selected from hydrido, alkyl, hydroxyalkyl, haloalkyl, cycloalkyl, cycloalkylalkyl, aralkyl, aryl, aroyl, alkoxyalkyl, alkylcarbonyl, alkenyl, alkynyl alkylsulfonyl, aralkylsulfonyl, arylsulfonyl and amido radicals of the formula

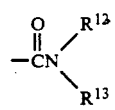

wherein each of $R^{12}$ and $R^{13}$ is independently selected from hydrido, alkyl, cycloalkyl, cyano, amino, hydroxyalkyl, alkoxyalkyl, phenalkyl and phenyl; wherein $R^2$ is selected from hydrido, alkyl, hydroxyalkyl, halo, haloalkyl, cycloalkyl, cycloalkylalkyl, cycloalkylhaloalkyl, cycloalkylcarbonyl, alkoxy, aralkyl, aralkylhaloalkyl, aryl, benzoyl, phenoxy, phenoxyalkyl, phenalkyloxy, phenylthio, phenalkylthio, aralkoxy, alkoxyalkyl, alkylcarbonyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptoalkyl, alkoxycarbonyloxy, alkylthio, cycloalkylthio, cycloalkylalkylthio, phthalimido, phthalimidoalkyl, heteroaryl, heteroarylalkyl, cycloheteroalkyl, cycloheteroalkylalkyl and cycloheteroalkylcarbonylalkyl wherein each of said heteroaryl- and cycloheteroalkyl-containing groups has one or more hetero ring atoms selected from oxygen, sulfur and nitrogen atoms, and wherein each of $R^2$ through $R^{11}$ may be further independently selected from amino and amido radicals of the formula

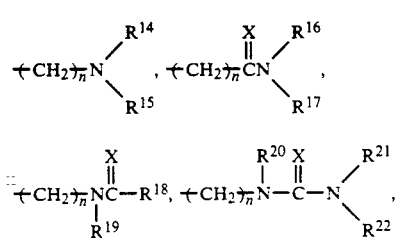

-continued

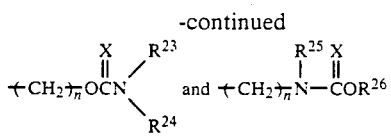

wherein X is selected from oxygen atom and sulfur atom;
wherein each n is a number independently selected from zero to six, inclusive;
wherein each of $R^{14}$ through $R^{26}$ is independently selected from hydrido, alkyl, cycloalkyl, cyano, amino, hydroxyalkyl, alkoxyalkyl, phenalkyl and phenyl;
wherein each of $R^3$ through $R^{11}$ is independently selected from hydrido, hydroxy, alkyl, hydroxyalkyl, halo, haloalkyl, cycloalkyl, alkoxy, phenalkyl, phenyl, benzoyl, phenoxy, phenalkyloxy, alkoxyalkyl, alkylcarbonyl, alkoxycarbonyl, alkenyl, cyano, nitro, carboxyl, alkylthio and mercapto;
and wherein each of $R^3$ through $R^{11}$ may be further independently selected from acidic moieties of the formula

 $-Y_nA$ wherein n is a number selected from zero through two, inclusive; wherein A is selected from carboxylic acid and bioisosteres of carboxylic acid selected from

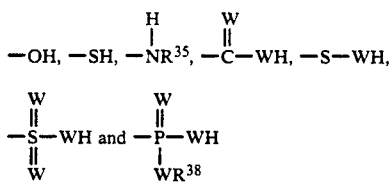

wherein each W is independently selected from oxygen atom, sulfur atom and $NR^{39}$; wherein each of $R^{35}$, $R^{38}$ and $R^{39}$ is independently selected from hydrido, alkyl, haloalkyl, haloalkylsulfonyl, haloalkylcarbonyl, cycloalkyl, phenyl and benzyl; wherein each of $R^{35}$ and $R^{39}$ may be further independently selected from amino radical of the formula

wherein each of $R^{40}$ and $R^{41}$ is independently selected from hydrido, alkyl, cycloalkyl, hydroxyalkyl, haloalkyl, alkoxyalkyl, benzyl and phenyl; and the amide, ester and salt derivatives of said acidic groups;
wherein said bioisostere of carboxylic acid may be further selected from heterocyclic acidic groups consisting of heterocyclic rings of four to about nine ring members, which ring contains at least one hetero atom, selected from oxygen, sulfur and nitrogen atoms, which heterocyclic ring may be saturated, fully unsaturated or partially unsaturated, and which heterocyclic ring may be attached at a single position selected from $R^3$ through $R^{11}$ or may be attached at any two adjacent positions selected from $R^3$ through $R^{11}$ so as to form a fused-ring system with one of the phenyl rings of Formula I; and the amide, ester and salt derivatives of said heterocyclic acidic groups;

wherein Y is a spacer group independently selected from one or more of alkyl, cycloalkyl, cycloalkylalkyl, alkenyl, phenyl, phenalkyl and aralkyl;
wherein each of $R^1$ through $R^{26}$, $R^{35}$ and $R^{38}$ through $R^{41}$, Y and A and independently may be substituted at any substitutable position with one or more groups selected from alkyl, cycloalkyl, cycloalkylalkyl, hydroxy, halo, oxo, haloalkyl, alkoxycarbonyl, cyano, nitro, alkylsulfonyl, haloalkylsulfonyl, aryl, aralkyl, alkoxy, aryloxy and aralkoxy;
or a tautomer thereof or a pharmaceutically-acceptable salt thereof.

An even more highly preferred class of compounds consists of those compounds of Formula I wherein m is one; wherein $R^1$ is selected from hydrido, alkyl, hydroxyalkyl, haloalkyl, cycloalkyl, cycloalkylalkyl, aralkyl, aryl, benzoyl, alkoxyalkyl, alkylcarbonyl, alkoxycarbonyl, alkenyl and alkynyl;
wherein $R^2$ is selected from alkyl, aminoalkyl, hydroxyalkyl, halo, haloalkyl, cycloalkyl, cycloalkylalkyl, alkylcarbonyl, cycloalkylhaloalkyl, cycloalkylcarbonyl, alkoxy, aralkyl, aralkylhaloalkyl, aryl, benzoyl, phenoxy, phenoxyalkyl, phenalkyloxy, phenylthio, phenalkylthio, aralkoxy, alkoxyalkyl, acetyl, alkoxycarbonyl, alkenyl, cycloalkenyl, alkynyl, cyano, nitro, carboxyl, carboxalkyl, alkylcarbonyloxy, mercaptoalkyl, mercaptocarbonyl, alkoxycarbonyloxy, alkylcarbonyloxyalkyl, alkoxycarbonylalkyl, aralkoxycarbonylalkyl, aralkylcarbonyloxyalkyl, phthalimido, phthalimidoalkyl, imidazoalkyl, tetrazole, tetrazolealkyl, alkylthio, cycloalkylthio, cycloalkylalkylthio, and amino and amido radicals of the formula

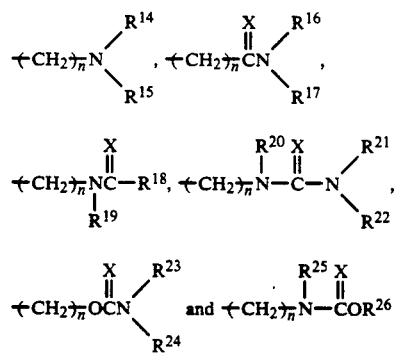

wherein X is selected from oxygen atom and sulfur atom;
wherein each n is a number independently selected from zero to six, inclusive;
wherein each of $R^{14}$ through $R^{26}$ is independently selected from hydrido, alkyl, cycloalkyl, cyano, amino, hydroxyalkyl, alkoxyalkyl, phenalkyl and phenyl;
wherein each of $R^3$ through $R^{11}$ is independently selected from hydrido, hydroxy, alkyl, hydroxyalkyl, halo, haloalkyl, alkoxy, phenyl, benzoyl, phenoxy, alkoxyalkyl, acetyl, alkoxycarbonyl, alkenyl, cyano, nitro, carboxyl, alkylthio and mercapto;
and wherein each of $R^3$ through $R^{11}$ may be further independently selected from acidic moieties consisting of $CO_2H$, $CO_2CH_3$, SH, $CH_2SH$, $C_2H_4SH$, $PO_3H_2$, $NHSO_2CF_3$, $NHSO_2C_6F_5$, $SO_3H$, $CONHNH_2$, $CONHNHSO_2CF_3$, $CONHOCH_3$, $CONHOC_2H_5$, $CONHCF_3$, OH, $CH_2OH$, $C_2H_4OH$, $OPO_3H_2$, $OSO_3H$,

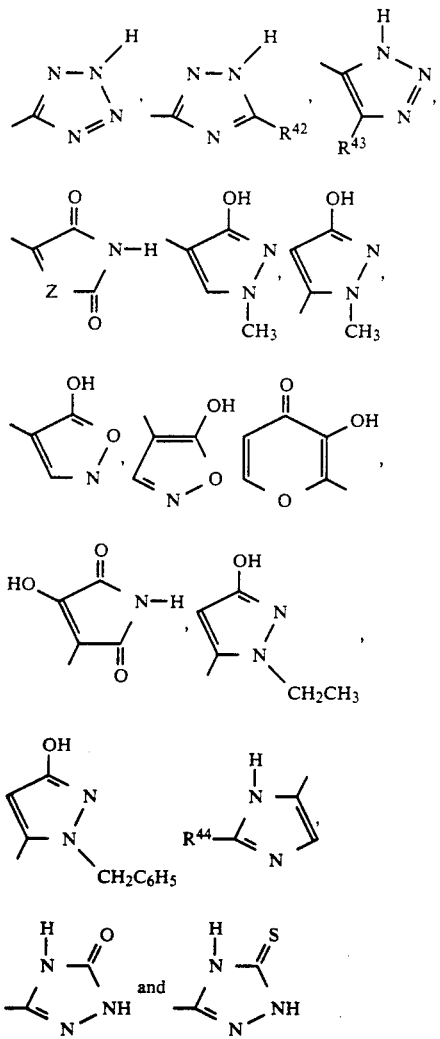

wherein each of $R^{42}$, $R^{43}$ and $R^{44}$ is independently selected from H, Cl, CN, $NO_2$, $CF_3$, $C_2F_5$, $C_3F_7$, $CHF_2$, $CH_2F$, $CO_2CH_3$, $CO_2C_2H_5$, $SO_2CH_3$, $SO_2CF_3$ and $SO_2C_6F_5$; wherein Z is selected from O, S, $NR^{45}$ and $CH_2$; wherein $R^{45}$ is selected from hydrido, $CH_3$ and $CH_2C_6H_5$; and wherein said acidic moiety may be a heterocyclic acidic group attached at any two adjacent positions of $R^3$ through $R^{11}$ so as to form a fused ring system with one of the phenyl rings of the biphenyl moiety of Formula I, said biphenyl fused ring system selected from

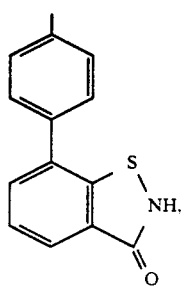

and the esters, amides and salts of said acidic moieties; or a tautomer thereof or a pharmaceutically-acceptable salt thereof.

A class of compounds of particular interest consists of those compounds of Formula I wherein m is one; wherein $R^1$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, 2-butenyl, 3-butenyl, 2-butynyl, 3-butynyl and 2-hydroxybutyl; wherein $R^2$ is selected from $C_4H_9(n)$, $CH_3CH_2CH=CH$, $C_3H_7(n)$, $SC_3H_7$,

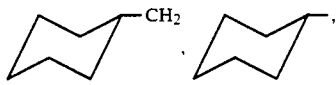

$C_2H_5$, $C_5H_{11}(n)$, $C_6H_{13}(n)$, $SC_4H_9$,

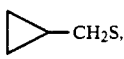

$CH_3CH=CH$, $CH_3CH_2CH_2CH=CH-$, amino, aminomethyl, aminoethyl, aminopropyl, acetyl, $CH_2OH$, $CH_2OCOCH_3$, $CH_2Cl$, $Cl$, $CH_2OCH_3$, $CH_2OCH(CH_3)_2$, I, CHO, $CH_2CO_2H$, $CH(CH_3)CO_2H$, $NO_2$, Cl,

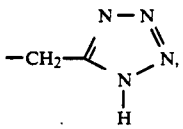

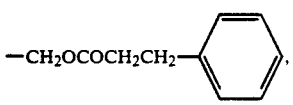

$-CO_2CH_3$, $-CONH_2$, $-CONHCH_3$, $CON(CH_3)_2$, $-CH_2-NHCO_2C_2H_5$,

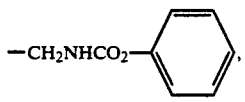

$-CH_2NHCO_2CH_3$, $-CH_2NHCO_2C_3H_7$, $-CH_2NHCO_2CH_2(CH_3)_2$, $-CH_2NHCO_2C_4H_9$, $CH_2NHCO_2$-adamantyl, $-CH_2NHCO_2$-(1-napthyl), $-CH_2NHCONHC_2H_5$, $-CH_2NHCONHC_3H_7$, $-CH_2NHCONHC_4H_9$, $-CH_2NHCONHCH(CH_3)_2$, $-CH_2NHCONH(1$-napthyl$)$, $-CH_2NHCONH(1$-adamantyl$)$, $CO_2H$,

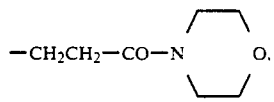

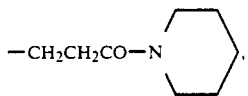

$-CH_2CH_2CH_2CO_2H$, $-CH_2CH_2F$, $-CH_2OCONHCH_3$, $-CH_2OCSNHCH_3$, $-CH_2NHCSOC_3H_7$, $-CH_2CH_2CH_2F$, $-CH_2ONO_2$,

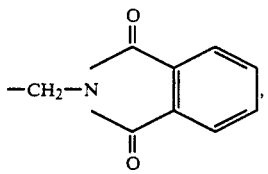

$-CH_2SH$,

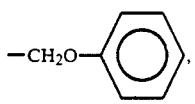

H, Cl, $NO_2$, $CF_3$, $CH_2OH$, Br, F, I, methyl, ethyl, n-propyl, isopropyl, n-butyl, sec-butyl, isobutyl, tert-butyl, n-pentyl, isopentyl, neopentyl, phenyl, cyclohexyl, cyclohexylmethyl, 1-oxoethyl, 1-oxopropyl, 1-oxobutyl, 1-oxopentyl, 1,1-dimethoxypropyl, 1,1-dimethoxypentyl, hydroxyalkyl, halo, 1-oxo-2-phenylethyl, 1-oxo-2-cyclohexylethyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, 1-butenyl, 2-butenyl, 3-butenyl, 1-butynyl, 2-butynyl, 3-butynyl and difluoromethyl; wherein each of $R^3$ through $R^{11}$ is hydrido with the proviso that at least one of $R^5$, $R^6$, $R^8$ and $R^9$ is an acidic group selected from $CO_2H$, SH, $PO_3H_2$, $SO_3H$, $CONHNH_2$, $CONHNHSO_2CF_3$, OH,

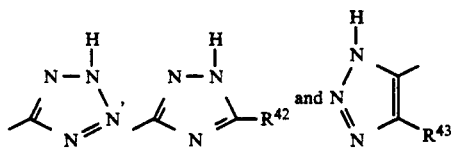

wherein each of $R^{42}$ and $R^{43}$ is independently selected from chloro, cyano, nitro, trifluoromethyl, methoxycarbonyl and trifluoromethylsulfonyl; or a tautomer thereof or a pharmaceutically-acceptable salt thereof.

A class of compounds of more particular interest consists of those compounds of Formula I wherein m is one; wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, 2-butenyl, 3-butenyl, 2-butynyl, 3-butynyl and 2-hydroxybutyl; wherein $R^2$ is selected from ethyl, n-propyl, isopropyl, n-butyl, sec-butyl, isobutyl, 4-methylbutyl, tert-butyl, n-pentyl, neopentyl, 1-oxoethyl, 1-oxopropyl, 1-oxobutyl, 1-oxopentyl 1-oxo-2-phenylethyl, 1-oxo-2- cyclohexylethyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, acetyl, 1-butenyl, 2-butenyl, 3-butenyl, 1-butynyl, 2-butynyl, 3-butynyl, propylthio and butylthio; wherein each of $R^3$ through $R^{11}$ is hydrido with the proviso that at least one of $R^5$, $R^6$, $R^8$ and $R^9$ is an acidic group selected from $CO_2H$, $SH$, $PO_3H_2$, $SO_3H$, $CONHNH_2$, $CONHNHSO_2CF_3$, $OH$,

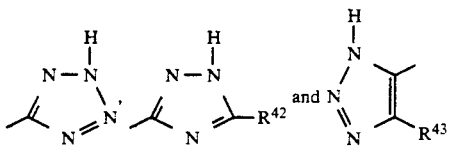

wherein each of $R^{42}$ and $R^{43}$ is independently selected from chloro, cyano, nitro, trifluoromethyl, methoxycarbonyl and trifluoromethylsulfonyl;
or a tautomer thereof or a pharmaceutically-acceptable salt thereof.

A subclass of compounds of Formula I which is of even more particular interest consists of those compounds of Formula II

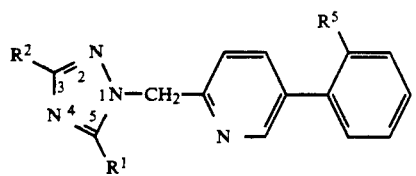

wherein m is one; wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, 2-butenyl, 3-butenyl, 2-butynyl, 3-butynyl and 2-hydroxybutyl; wherein $R^2$ is selected from ethyl, n-propyl, isopropyl, n-butyl, sec-butyl, isobutyl, 4-methylbutyl, n-pentyl, 1-oxo-2-phenylethyl, 1-oxo-2-cyclohexylethyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, 1-butenyl, 2-butenyl, 3-butenyl, 1-butynyl, 2-butynyl, 3-butynyl, propylthio and butylthio; wherein $R^5$ is an acidic group selected from $CO_2H$ and

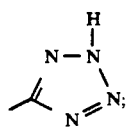

or a tautomer thereof or a pharmaceutically-acceptable salt thereof.

A family of specific compounds of particular interest within Formula II consists of compounds and pharmaceutically-acceptable salts thereof as follows:
2-[6-[(3-methyl-5-propyl-1H-1,2,4-triazol-1-yl)methyl]-3-pyridinyl]benzoic acid;
2-[6-[(3-ethyl-5-propyl-1H-1,2,4-triazol-1-yl)methyl]-3-pyridinyl]benzoic acid;
2-[6-[(3,5-dipropyl-1H-1,2,4-triazol-1-yl)methyl]-3-pyridinyl]benzoic acid;
2-[6-[(3-isopropyl-5-propyl-1H-1,2,4-triazol-1-yl)methyl]-3-pyridinyl]benzoic acid;
2-[6-[(3-butyl-5-propyl-1H-1,2,4-triazol-1-yl)methyl]-3-pyridinyl]benzoic acid;
2-[6-[(3-secbutyl-5-propyl-1H-1,2,4-triazol-1-yl)methyl]-3-pyridinyl]benzoic acid;
2-[6-[(3-isobutyl-5-propyl-1H-1,2,4-triazol-1-yl)methyl]-3-pyridinyl]benzoic acid;
2-[6-[(3-tertbutyl-5-propyl-1H-1,2,4-triazol-1-yl)methyl]-3-pyridinyl]benzoic acid;
2-[6-[(3-pentyl-5-propyl-1H-1,2,4-triazol-1-yl)methyl]-3-pyridinyl]benzoic acid;
2-[6-[(3-isopentyl-5-propyl-1H-1,2,4-triazol-1-yl)methyl]-3-pyridinyl]benzoic acid;
2-[6-[(3-cyclohexyl-5-propyl-1H-1,2,4-triazol-1-yl)methyl]-3-pyridinyl]benzoic acid;
2-[6-[(3-cyclohexylmethyl-5-propyl-1H-1,2,4-triazol-1-yl)methyl]-3-pyridinyl]benzoic acid;
2-[6-[(3-benzoyl-5-propyl-1H-1,2,4-triazol-1-yl)methyl]-3-pyridinyl]benzoic acid;
2-[6-[(3-phenyl-5-propyl-1H-1,2,4-triazol-1-yl)methyl]-3-pyridinyl]benzoic acid;
2-[6-[(3-phenylmethyl-5-propyl-1H-1,2,4-triazol-1-yl)methyl]-3-pyridinyl]benzoic acid;
2-[6-[(3-cyclohenanoyl-5-propyl-1H-1,2,4-triazol-1-yl)methyl]-3-pyridinyl]benzoic acid;
2-[6-[[3-(2-phenylethyl)-5-propyl-1H-1,2,4-triazol-1-yl]methyl]-3-pyridinyl]benzoic acid;
2-[6-[[3-(1-oxo-2-cyclohexylethyl)-5-propyl-1H-1,2,4-triazol-1-yl]methyl]-3-pyridinyl]benzoic acid;
2-[6-[[3-(2-cyclohexylethyl)-5-propyl-1H-1,2,4-triazol-1-yl]methyl]-3-pyridinyl]benzoic acid;
2-[6-[[3-(1-oxo-2-phenylethyl)-5-propyl-1H-1,2,4-triazol-1-yl]methyl]-3-pyridinyl]benzoic acid;
2-[6-[[3-(1,1-dimethoxypropyl)-5-propyl-1H-1,2,4-triazol-1-yl]methyl]-3-pyridinyl]benzoic acid;
2-[6-[[3-(1,1-dimethoxybutyl)-5-propyl-1H-1,2,4-triazol-1-yl]methyl]-3-pyridinyl]benzoic acid;
2-[6-[[3-(1,1-dimethoxypentyl)-5-propyl-1H-1,2,4-triazol-1-yl]methyl]-3-pyridinyl]benzoic acid;
2-[6-[[3-(1-oxopropyl)-5-propyl-1H-1,2,4-triazol-1-yl]methyl]-3-pyridinyl]benzoic acid;
2-[6-[[3-(1-oxobutyl)-5-propyl-1H-1,2,4-triazol-1-yl]methyl]-3-pyridinyl]benzoic acid;
2-[6-[[3-(1-oxopentyl)-5-propyl-1H-1,2,4-triazol-1-yl]methyl]-3-pyridinyl]benzoic acid;
2-[6-[[3-(1,1-difluorobutyl)-5-propyl-1H-1,2,4-triazol-1-yl]methyl]-3-pyridinyl]benzoic acid;
2-[6-[(3-methyl-5-butyl-1H-1,2,4-triazol-1-yl)methyl]-3-pyridinyl]benzoic acid;
2-[6-[(3-ethyl-5-butyl-1H-1,2,4-triazol-1-yl)methyl]-3-pyridinyl]benzoic acid;
2-[6-[(3-propyl-5-butyl-1H-1,2,4-triazol-1-yl)methyl]-3-pyridinyl]benzoic acid;
2-[6-[(3-isopropyl-5-butyl-1H-1,2,4-triazol-1-yl)methyl]-3-pyridinyl]benzoic acid;
2-[6-[(3,5-dibutyl-1H-1,2,4-triazol-1-yl)methyl]-3-pyridinyl]benzoic acid;
2-[6-[(3-secbutyl-5-butyl-1H-1,2,4-triazol-1-yl)methyl]-3-pyridinyl]benzoic acid;
2-[6-[(3-isobutyl-5-butyl-1H-1,2,4-triazol-1-yl)methyl]-3-pyridinyl]benzoic acid;
2-[6-[(3-tertbutyl-5-butyl-1H-1,2,4-triazol-1-yl)methyl]-3-pyridinyl]benzoic acid;

2-[6-[(3-pentyl-5-butyl-1H-1,2,4-triazol-1-yl)methyl]-3-pyridinyl]benzoic acid;

2-[6-[(3-isopentyl-5-butyl-1H-1,2,4-triazol-1-yl)methyl]-3-pyridinyl]benzoic acid;

2-[6-[(3-cyclohexyl-5-butyl-1H-1,2,4-triazol-1-yl)methyl]-3-pyridinyl]benzoic acid;

2-[6-[(3-cyclohexylmethyl-5-butyl-1H-1,2,4-triazol-1-yl)methyl]-3-pyridinyl]benzoic acid;

2-[6-[(3-benzoyl-5-butyl-1H-1,2,4-triazol-1-yl)methyl]-3-pyridinyl]benzoic acid;

2-[6-[(3-phenyl-5-butyl-1H-1,2,4-triazol-1-yl)methyl]-3-pyridinyl]benzoic acid;

2-[6-[(3-phenylmethyl-5-butyl-1H-1,2,4-triazol-1-yl)methyl]-3-pyridinyl]benzoic acid;

2-[6-[(3-cyclohenanoyl-5-butyl-1H-1,2,4-triazol-1-yl)methyl]-3-pyridinyl]benzoic acid;

2-[6-[[3-(2-phenylethyl)-5-butyl-1H-1,2,4-triazol-1-yl]methyl]-3-pyridinyl]benzoic acid;

2-[6-[[3-(1-oxo-2-cyclohexylethyl)-5-butyl-1H-1,2,4-triazol-1-yl]methyl]-3-pyridinyl]benzoic acid;

2-[6-[[3-(2-cyclohexylethyl)-5-butyl-1H-1,2,4-triazol-1-yl]methyl]-3-pyridinyl]benzoic acid;

2-[6-[[3-(1-oxo-2-phenylethyl)-5-butyl-1H-1,2,4-triazol-1-yl]methyl]-3-pyridinyl]benzoic acid;

2-[6-[[3-(1,1-dimethoxypropyl)-5-butyl-1H-1,2,4-triazol-1-yl]methyl]-3-pyridinyl]benzoic acid;

2-[6-[[3-(1,1-dimethoxybutyl)-5-butyl-1H-1,2,4-triazol-1-yl]methyl]-3-pyridinyl]benzoic acid;

2-[6-[[3-(1,1-dimethoxypentyl)-5-butyl-1H-1,2,4-triazol-1-yl]methyl]-3-pyridinyl]benzoic acid;

2-[6-[[3-(1-oxopropyl)-5-butyl-1H-1,2,4-triazol-1-yl]methyl]-3-pyridinyl]benzoic acid;

2-[6-[[3-(1-oxobutyl)-5-butyl-1H-1,2,4-triazol-1-yl]methyl]-3-pyridinyl]benzoic acid;

2-[6-[[3-(1-oxopentyl)-5-butyl-1H-1,2,4-triazol-1-yl]methyl]-3-pyridinyl]benzoic acid;

2-[6-[[3-(1,1-difluorobutyl)-5-butyl-1H-1,2,4-triazol-1-yl]methyl]-3-pyridinyl]benzoic acid;

2-[6-[(3-methyl-5-pentyl-1H-1,2,4-triazol-1-yl)methyl]-3-pyridinyl]benzoic acid;

2-[6-[(3-ethyl-5-pentyl-1H-1,2,4-triazol-1-yl)methyl]-3-pyridinyl]benzoic acid;

2-[6-[(3-propyl-5-pentyl-1H-1,2,4-triazol-1-yl)methyl]-3-pyridinyl]benzoic acid;

2-[6-[(3-isopropyl-5-pentyl-1H-1,2,4-triazol-1-yl)methyl]-3-pyridinyl]benzoic acid;

2-[6-[(3-butyl-5-pentyl-1H-1,2,4-triazol-1-yl)methyl]-3-pyridinyl]benzoic acid;

2-[6-[(3-secbutyl-5-pentyl-1H-1,2,4-triazol-1-yl)methyl]-3-pyridinyl]benzoic acid;

2-[6-[(3-isobutyl-5-pentyl-1H-1,2,4-triazol-1-yl)methyl]-3-pyridinyl]benzoic acid;

2-[6-[(3-tertbutyl-5-pentyl-1H-1,2,4-triazol-1-yl)methyl]-3-pyridinyl]benzoic acid;

2-[6-[(3,5-dipentyl-1H-1,2,4-triazol-1-yl)methyl]-3-pyridinyl]benzoic acid;

2-[6-[(3-isopentyl-5-pentyl-1H-1,2,4-triazol-1-yl)methyl]-3-pyridinyl]benzoic acid;

2-[6-[(3-cyclohexyl-5-pentyl-1H-1,2,4-triazol-1-yl)methyl]-3-pyridinyl]benzoic acid;

2-[6-[(3-cyclohexylmethyl-5-pentyl-1H-1,2,4-triazol-1-yl)methyl]-3-pyridinyl]benzoic acid;

2-[6-[(3-benzoyl-5-pentyl-1H-1,2,4-triazol-1-yl)methyl]-3-pyridinyl]benzoic acid;

2-[6-[(3-phenyl-5-pentyl-1H-1,2,4-triazol-1-yl)methyl]-3-pyridinyl]benzoic acid;

2-[6-[(3-phenylmethyl-5-pentyl-1H-1,2,4-triazol-1-yl)methyl]-3-pyridinyl]benzoic acid;

2-[6-[(3-cyclohenanoyl-5-pentyl-1H-1,2,4-triazol-1-yl)methyl]-3-pyridinyl]benzoic acid;

2-[6-[[3-(2-phenylethyl)-5-pentyl-1H-1,2,4-triazol-1-yl]methyl]-3-pyridinyl]benzoic acid;

2-[6-[[3-(1-oxo-2-cyclohexylethyl)-5-pentyl-1H-1,2,4-triazol-1-yl]methyl]-3-pyridinyl]benzoic acid;

2-[6-[[3-(2-cyclohexylethyl)-5-pentyl-1H-1,2,4-triazol-1-yl]methyl]-3-pyridinyl]benzoic acid;

2-[6-[[3-(1-oxo-2-phenylethyl)-5-pentyl-1H-1,2,4-triazol-1-yl]methyl]-3-pyridinyl]benzoic acid;

2-[6-[[3-(1,1-dimethoxypropyl)-5-pentyl-1H-1,2,4-triazol-1-yl]methyl]-3-pyridinyl]benzoic acid;

2-[6-[[3-(1,1-dimethoxybutyl)-5-pentyl-1H-1,2,4-triazol-1-yl]methyl]-3-pyridinyl]benzoic acid;

2-[6-[[3-(1,1-dimethoxypentyl)-5-pentyl-1H-1,2,4-triazol-1-yl]methyl]-3-pyridinyl]benzoic acid;

2-[6-[[3-(1-oxopropyl)-5-pentyl-1H-1,2,4-triazol-1-yl]methyl]-3-pyridinyl]benzoic acid;

2-[6-[[3-(1-oxobutyl)-5-pentyl-1H-1,2,4-triazol-1-yl]methyl]-3-pyridinyl]benzoic acid;

2-[6-[[3-(1-oxopentyl)-5-pentyl-1H-1,2,4-triazol-1-yl]methyl]-3-pyridinyl]benzoic acid;

2-[6-[[3-(1,1-difluorobutyl)-5-pentyl-1H-1,2,4-triazol-1-yl]methyl]-3-pyridinyl]benzoic acid;

5-[2-[6-[(3-methyl-5-propyl-1H-1,2,4-triazol-1-yl)methyl]-3-pyridinyl]phenyl]-1H-tetrazole;

5-[2-[6-[(3-ethyl-5-propyl-1H-1,2,4-triazol-1-yl)methyl]-3-pyridinyl]phenyl]-1H-tetrazole;

5-[2-[6-[(3,5-dipropyl-1H-1,2,4-triazol-1-yl)methyl]-3-pyridinyl]phenyl]-1H-tetrazole;

5-[2-[6-[(3-isopropyl-5-propyl-1H-1,2,4-triazol-1-yl)methyl]-3-pyridinyl]phenyl]-1H-tetrazole;

5-[2-[6-[(3-butyl-5-propyl-1H-1,2,4-triazol-1-yl)methyl]-3-pyridinyl]phenyl]-1H-tetrazole;

5-[2-[6-[(3-secbutyl-5-propyl-1H-1,2,4-triazol-1-yl)methyl]-3-pyridinyl]phenyl]-1H-tetrazole;

5-[2-[6-[(3-isobutyl-5-propyl-1H-1,2,4-triazol-1-yl)methyl]-3-pyridinyl]phenyl]-1H-tetrazole;

5-[2-[6-[(3-tertbutyl-5-propyl-1H-1,2,4-triazol-1-yl)methyl]-3-pyridinyl]phenyl]-1H-tetrazole;

5-[2-[6-[(3-pentyl-5-propyl-1H-1,2,4-triazol-1-yl)methyl]-3-pyridinyl]phenyl]-1H-tetrazole;

5-[2-[6-[(3-isopentyl-5-propyl-1H-1,2,4-triazol-1-yl)methyl]-3-pyridinyl]phenyl]-1H-tetrazole;

5-[2-[6-[(3-cyclohexyl-5-propyl-1H-1,2,4-triazol-1-yl)methyl]-3-pyridinyl]phenyl]-1H-tetrazole;

5-[2-[6-[(3-cyclohexylmethyl-5-propyl-1H-1,2,4-triazol-1-yl)methyl]-3-pyridinyl]phenyl]-1H-tetrazole;

5-[2-[6-[(3-benzoyl-5-propyl-1H-1,2,4-triazol-1-yl)methyl]-3-pyridinyl]phenyl]-1H-tetrazole;

5-[2-[6-[(3-phenyl-5-propyl-1H-1,2,4-triazol-1-yl)methyl]-3-pyridinyl]phenyl]-1H-tetrazole;

5-[2-[6-[(3-phenylmethyl-5-propyl-1H-1,2,4-triazol-1-yl)methyl]-3-pyridinyl]phenyl]-1H-tetrazole;

5-[2-[6-[(3-cyclohenanoyl-5-propyl-1H-1,2,4-triazol-1-yl)methyl]-3-pyridinyl]phenyl]-1H-tetrazole;

5-[2-[6-[[3-(2-phenylethyl)-5-propyl-1H-1,2,4-triazol-1-yl]methyl]-3-pyridinyl]phenyl]-1H-tetrazole;

5-[2-[6-[[3-(1-oxo-2-cyclohexylethyl)-5-propyl-1H-1,2,4-triazol-1-yl]methyl]-3-pyridinyl]phenyl]-1H-tetrazole;

5-[2-[6-[[3-(2-cyclohexylethyl)-5-propyl-1H-1,2,4-triazol-1-yl]methyl]-3-pyridinyl]phenyl]-1H-tetrazole;

5-[2-[6-[[3-(1-oxo-2-phenylethyl)-5-propyl-1H-1,2,4-triazol-1-yl]methyl]-3-pyridinyl]phenyl]-1H-tetrazole;

5-[2-[6-[[3-(1,1-dimethoxypropyl)-5-propyl-1H-1,2,4-triazol-1-yl]methyl]-3-pyridinyl]phenyl]-1H-tetrazole;
5-[2-[6-[[3-(1,1-dimethoxybutyl)-5-propyl-1H-1,2,4-triazol-1-yl]methyl]-3-pyridinyl]phenyl]-1H-tetrazole;
5-[2-[6-[[3-(1,1-dimethoxypentyl)-5-propyl-1H-1,2,4-triazol-1-yl]methyl]-3-pyridinyl]phenyl]-1H-tetrazole;
5-[2-[6-[[3-(1-oxopropyl)-5-propyl-1H-1,2,4-triazol-1-yl]methyl]-3-pyridinyl]phenyl]-1H-tetrazole;
5-[2-[6-[[3-(1-oxobutyl)-5-propyl-1H-1,2,4-triazol-1-yl]methyl]-3-pyridinyl]phenyl]-1H-tetrazole;
5-[2-[6-[[3-(1-oxopentyl)-5-propyl-1H-1,2,4-triazol-1-yl]methyl]-3-pyridinyl]phenyl]-1H-tetrazole;
5-[2-[6-[[3-(1,1-difluorobutyl)-5-propyl-1H-1,2,4-triazol-1-yl]methyl]-3-pyridinyl]phenyl]-1H-tetrazole;
5-[2-[6-[(3-methyl-5-butyl-1H-1,2,4-triazol-1-yl)methyl]-3-pyridinyl]phenyl]-1H-tetrazole;
5-[2-[6-[(3-ethyl-5-butyl-1H-1,2,4-triazol-1-yl)methyl]-3-pyridinyl]phenyl]-1H-tetrazole;
5-[2-[6-[(3-propyl-5-butyl-1H-1,2,4-triazol-1-yl)methyl]-3-pyridinyl]phenyl]-1H-tetrazole;
5-[2-[6-[(3-isopropyl-5-butyl-1H-1,2,4-triazol-1-yl)methyl]-3-pyridinyl]phenyl]-1H-tetrazole;
5-[2-[6-[(3,5-dibutyl-1H-1,2,4-triazol-1-yl)methyl]-3-pyridinyl]phenyl]-1H-tetrazole;
5-[2-[6-[(3-secbutyl-5-butyl-1H-1,2,4-triazol-1-yl)methyl]-3-pyridinyl]phenyl]-1H-tetrazole;
5-[2-[6-[(3-isobutyl-5-butyl-1H-1,2,4-triazol-1-yl)methyl]-3-pyridinyl]phenyl]-1H-tetrazole;
5-[2-[6-[(3-tertbutyl-5-butyl-1H-1,2,4-triazol-1-yl)methyl]-3-pyridinyl]phenyl]-1H-tetrazole;
5-[2-[6-[(3-pentyl-5-butyl-1H-1,2,4-triazol-1-yl)methyl]-3-pyridinyl]phenyl]-1H-tetrazole;
5-[2-[6-[(3-isopentyl-5-butyl-1H-1,2,4-triazol-1-yl)methyl]-3-pyridinyl]phenyl]-1H-tetrazole;
5-[2-[6-[(3-cyclohexyl-5-butyl-1H-1,2,4-triazol-1-yl)methyl]-3-pyridinyl]phenyl]-1H-tetrazole;
5-[2-[6-[(3-cyclohexylmethyl-5-butyl-1H-1,2,4-triazol-1-yl)methyl]-3-pyridinyl]phenyl]-1H-tetrazole;
5-[2-[6-[(3-benzoyl-5-butyl-1H-1,2,4-triazol-1-yl)methyl]-3-pyridinyl]phenyl]-1H-tetrazole;
5-[2-[6-[(3-phenyl-5-butyl-1H-1,2,4-triazol-1-yl)methyl]-3-pyridinyl]phenyl]-1H-tetrazole;
5-[2-[6-[(3-phenylmethyl-5-butyl-1H-1,2,4-triazol-1-yl)methyl]-3-pyridinyl]phenyl]-1H-tetrazole;
5-[2-[6-[(3-cyclohenanoyl-5-butyl-1H-1,2,4-triazol-1-yl)methyl]-3-pyridinyl]phenyl]-1H-tetrazole;
5-[2-[6-[[3-(2-phenylethyl)-5-butyl-1H-1,2,4-triazol-1-yl]methyl]-3-pyridinyl]phenyl]-1H-tetrazole;
5-[2-[6-[[3-(1-oxo-2-cyclohexylethyl)-5-butyl-1H-1,2,4-triazol-1-yl]methyl]-3-pyridinyl]phenyl]-1H-tetrazole;
5-[2-[6-[[3-(2-cyclohexylethyl)-5-butyl-1H-1,2,4-triazol-1-yl]methyl]-3-pyridinyl]phenyl]-1H-tetrazole;
5-[2-[6-[[3-(1-oxo-2-phenylethyl)-5-butyl-1H-1,2,4-triazol-1-yl]methyl]-3-pyridinyl]phenyl]-1H-tetrazole;
5-[2-[6-[[3-(1,1-dimethoxypropyl)-5-butyl-1H-1,2,4-triazol-1-yl]methyl]-3-pyridinyl]phenyl]-1H-tetrazole;
5-[2-[6-[[3-(1,1-dimethoxybutyl)-5-butyl-1H-1,2,4-triazol-1-yl]methyl]-3-pyridinyl]phenyl]-1H-tetrazole;
5-[2-[6-[[3-(1,1-dimethoxypentyl)-5-butyl-1H-1,2,4-triazol-1-yl]methyl]-3-pyridinyl]phenyl]-1H-tetrazole;
5-[2-[6-[[3-(1-oxopropyl)-5-butyl-1H-1,2,4-triazol-1-yl]methyl]-3-pyridinyl]phenyl]-1H-tetrazole;
5-[2-[6-[[3-(1-oxobutyl)-5-butyl-1H-1,2,4-triazol-1-yl]methyl]-3-pyridinyl]phenyl]-1H-tetrazole;
5-[2-[6-[[3-(1-oxopentyl)-5-butyl-1H-1,2,4-triazol-1-yl]methyl]-3-pyridinyl]phenyl]-1H-tetrazole;
5-[2-[6-[[3-(1,1-difluorobutyl)-5-butyl-1H-1,2,4-triazol-1-yl]methyl]-3-pyridinyl]phenyl]-1H-tetrazole;
5-[2-[6-[(3-methyl-5-pentyl-1H-1,2,4-triazol-1-yl)methyl]-3-pyridinyl]phenyl]-1H-tetrazole;
5-[2-[6-[(3-ethyl-5-pentyl-1H-1,2,4-triazol-1-yl)methyl]-3-pyridinyl]phenyl]-1H-tetrazole;
5-[2-[6-[(3-propyl-5-pentyl-1H-1,2,4-triazol-1-yl)methyl]-3-pyridinyl]phenyl]-1H-tetrazole;
5-[2-[6-[(3-isopropyl-5-pentyl-1H-1,2,4-triazol-1-yl)methyl]-3-pyridinyl]phenyl]-1H-tetrazole;
5-[2-[6-[(3-butyl-5-pentyl-1H-1,2,4-triazol-1-yl)methyl]-3-pyridinyl]phenyl]-1H-tetrazole;
5-[2-[6-[(3-secbutyl-5-pentyl-1H-1,2,4-triazol-1-yl)methyl]-3-pyridinyl]phenyl]-1H-tetrazole;
5-[2-[6-[(3-isobutyl-5-pentyl-1H-1,2,4-triazol-1-yl)methyl]-3-pyridinyl]phenyl]-1H-tetrazole;
5-[2-[6-[(3-tertbutyl-5-pentyl-1H-1,2,4-triazol-1-yl)methyl]-3-pyridinyl]phenyl]-1H-tetrazole;
5-[2-[6-[(3,5-dipentyl-1H-1,2,4-triazol-1-yl)methyl]-3-pyridinyl]phenyl]-1H-tetrazole;
5-[2-[6-[(3-isopentyl-5-pentyl-1H-1,2,4-triazol-1-yl)methyl]-3-pyridinyl]phenyl]-1H-tetrazole;
5-[2-[6-[(3-cyclohexyl-5-pentyl-1H-1,2,4-triazol-1-yl)methyl]-3-pyridinyl]phenyl]-1H-tetrazole;
5-[2-[6-[(3-cyclohexylmethyl-5-pentyl-1H-1,2,4-triazol-1-yl)methyl]-3-pyridinyl]phenyl]-1H-tetrazole;
5-[2-[6-[(3-benzoyl-5-pentyl-1H-1,2,4-triazol-1-yl)methyl]-3-pyridinyl]phenyl]-1H-tetrazole;
5-[2-[6-[(3-phenyl-5-pentyl-1H-1,2,4-triazol-1-yl)methyl]-3-pyridinyl]phenyl]-1H-tetrazole;
5-[2-[6-[(3-phenylmethyl-5-pentyl-1H-1,2,4-triazol-1-yl)methyl]-3-pyridinyl]phenyl]-1H-tetrazole;
5-[2-[6-[(3-cyclohenanoyl-5-pentyl-1H-1,2,4-triazol-1-yl)methyl]-3-pyridinyl]phenyl]-1H-tetrazole;
5-[2-[6-[[3-(2-phenylethyl)-5-pentyl-1H-1,2,4-triazol-1-yl]methyl]-3-pyridinyl]phenyl]-1H-tetrazole;
5-[2-[6-[[3-(1-oxo-2-cyclohexylethyl)-5-pentyl-1H-1,2,4-triazol-1-yl]methyl]-3-pyridinyl]phenyl]-1H-tetrazole;
5-[2-[6-[[3-(2-cyclohexylethyl)-5-pentyl-1H-1,2,4-triazol-1-yl]methyl]-3-pyridinyl]phenyl]-1H-tetrazole;
5-[2-[6-[[3-(1-oxo-2-phenylethyl)-5-pentyl-1H-1,2,4-triazol-1-yl]methyl]-3-pyridinyl]phenyl]-1H-tetrazole;
5-[2-[6-[[3-(1,1-dimethoxypropyl)-5-pentyl-1H-1,2,4-triazol-1-yl]methyl]-3-pyridinyl]phenyl]-1H-tetrazole;
5-[2-[6-[[3-(1,1-dimethoxybutyl)-5-pentyl-1H-1,2,4-triazol-1-yl]methyl]-3-pyridinyl]phenyl]-1H-tetrazole;
5-[2-[6-[[3-(1,1-dimethoxypentyl)-5-pentyl-1H-1,2,4-triazol-1-yl]methyl]-3-pyridinyl]phenyl]-1H-tetrazole;
5-[2-[6-[[3-(1-oxopropyl)-5-pentyl-1H-1,2,4-triazol-1-yl]methyl]-3-pyridinyl]phenyl]-1H-tetrazole;
5-[2-[6-[[3-(1-oxobutyl)-5-pentyl-1H-1,2,4-triazol-1-yl]methyl]-3-pyridinyl]phenyl]-1H-tetrazole;
5-[2-[6-[[3-(1-oxopentyl)-5-pentyl-1H-1,2,4-triazol-1-yl]methyl]-3-pyridinyl]phenyl]-1H-tetrazole; and
5-[2-[6-[[3-(1,1-difluorobutyl)-5-pentyl-1H-1,2,4-triazol-1-yl]methyl]-3-pyridinyl]phenyl]-1H-tetrazole.

A family of specific compounds of more particular interest within Formula II consists of compounds and pharmaceutically-acceptable salts thereof as follows:

2-[6-[(3-methyl-5-butyl-1H-1,2,4-triazol-1-yl)methyl]-3-pyridinyl]benzoic acid;
2-[6-[(3-ethyl-5-butyl-1H-1,2,4-triazol-1-yl)methyl]-3-pyridinyl]benzoic acid;
2-[6-[(3-propyl-5-butyl-1H-1,2,4-triazol-1-yl)methyl]-3-pyridinyl]benzoic acid;
2-[6-[(3-isopropyl-5-butyl-1H-1,2,4-triazol-1-yl)methyl]-3-pyridinyl]benzoic acid;
2-[6-[(3,5-dibutyl-1H-1,2,4-triazol-1-yl)methyl]-3-pyridinyl]benzoic acid;
2-[6-[(3-secbutyl-5-butyl-1H-1,2,4-triazol-1-yl)methyl]-3-pyridinyl]benzoic acid;
2-[6-[(3-isobutyl-5-butyl-1H-1,2,4-triazol-1-yl)methyl]-3-pyridinyl]benzoic acid;
2-[6-[(3-tertbutyl-5-butyl-1H-1,2,4-triazol-1-yl)methyl]-3-pyridinyl]benzoic acid;
2-[6-[(3-pentyl-5-butyl-1H-1,2,4-triazol-1-yl)methyl]-3-pyridinyl]benzoic acid;
2-[6-[(3-isopentyl-5-butyl-1H-1,2,4-triazol-1-yl)methyl]-3-pyridinyl]benzoic acid;
2-[6-[(3-cyclohexyl-5-butyl-1H-1,2,4-triazol-1-yl)methyl]-3-pyridinyl]benzoic acid;
2-[6-[(3-cyclohexylmethyl-5-butyl-1H-1,2,4-triazol-1-yl)methyl]-3-pyridinyl]benzoic acid;
2-[6-[(3-phenyl-5-butyl-1H-1,2,4-triazol-1-yl)methyl]-3-pyridinyl]benzoic acid;
2-[6-[(3-phenylmethyl-5-butyl-1H-1,2,4-triazol-1-yl)methyl]-3-pyridinyl]benzoic acid;
2-[6-[[3-(2-cyclohexylethyl)-5-butyl-1H-1,2,4-triazol-1-yl]methyl]-3-pyridinyl]benzoic acid;
2-[6-[[3-(2-phenylethyl)-5-butyl-1H-1,2,4-triazol-1-yl]methyl]-3-pyridinyl]benzoic acid;
2-[6-[[3-(1-oxo-2-phenylethyl)-5-butyl-1H-1,2,4-triazol-1-yl]methyl]-3-pyridinyl]benzoic acid;
2-[6-[[3-(1-oxobutyl)-5-butyl-1H-1,2,4-triazol-1-yl]methyl]-3-pyridinyl]benzoic acid;
2-[6-[[3-(1,1-difluorobutyl)-5-butyl-1H-1,2,4-triazol-1-yl]methyl]-3-pyridinyl]benzoic acid;
2-[6-[[3-(1,1-dimethoxybutyl)-5-butyl-1H-1,2,4-triazol-1-yl]methyl]-3-pyridinyl]benzoic acid;
5-[2-[6-[(3-methyl-5-butyl-1H-1,2,4-triazol-1-yl)methyl]-3-pyridinyl]phenyl]-1H-tetrazole;
5-[2-[6-[(3-ethyl-5-butyl-1H-1,2,4-triazol-1-yl)methyl]-3-pyridinyl]phenyl]-1H-tetrazole;
5-[2-[6-[(3-propyl-5-butyl-1H-1,2,4-triazol-1-yl)methyl]-3-pyridinyl]phenyl]-1H-tetrazole;
5-[2-[6-[(3-isopropyl-5-butyl-1H-1,2,4-triazol-1-yl)methyl]-3-pyridinyl]phenyl]-1H-tetrazole;
5-[2-[6-[(3,5-dibutyl-1H-1,2,4-triazol-1-yl)methyl]-3-pyridinyl]phenyl]-1H-tetrazole;
5-[2-[6-[(3-secbutyl-5-butyl-1H-1,2,4-triazol-1-yl)methyl]-3-pyridinyl]phenyl]-1H-tetrazole;
5-[2-[6-[(3-isobutyl-5-butyl-1H-1,2,4-triazol-1-yl)methyl]-3-pyridinyl]phenyl]-1H-tetrazole;
5-[2-[6-[(3-tertbutyl-5-butyl-1H-1,2,4-triazol-1-yl)methyl]-3-pyridinyl]phenyl]-1H-tetrazole;
5-[2-[6-[(3-pentyl-5-butyl-1H-1,2,4-triazol-1-yl)methyl]-3-pyridinyl]phenyl]-1H-tetrazole;
5-[2-[6-[(3-isopentyl-5-butyl-1H-1,2,4-triazol-1-yl)methyl]-3-pyridinyl]phenyl]-1H-tetrazole;
5-[2-[6-[(3-cyclohexyl-5-butyl-1H-1,2,4-triazol-1-yl)methyl]-3-pyridinyl]phenyl]-1H-tetrazole;
5-[2-[6-[(3-cyclohexylmethyl-5-butyl-1H-1,2,4-triazol-1-yl)methyl]-3-pyridinyl]phenyl]-1H-tetrazole;
5-[2-[6-[(3-phenyl-5-butyl-1H-1,2,4-triazol-1-yl)methyl]-3-pyridinyl]phenyl]-1H-tetrazole;
5-[2-[6-[(3-phenylmethyl-5-butyl-1H-1,2,4-triazol-1-yl)methyl]-3-pyridinyl]phenyl]-1H-tetrazole;
5-[2-[6-[[3-(2-cyclohexylethyl)-5-butyl-1H-1,2,4-triazol-1-yl]methyl]-3-pyridinyl]phenyl]-1H-tetrazole;
5-[2-[6-[[3-(2-phenylethyl)-5-butyl-1H-1,2,4-triazol-1-yl]methyl]-3-pyridinyl]phenyl]-1H-tetrazole;
5-[2-[6-[[3-(1-oxo-2-phenylethyl)-5-butyl-1H-1,2,4-triazol-1-yl]methyl]-3-pyridinyl]phenyl]-1H-tetrazole;
5-[2-[6-[[3-(1-oxobutyl)-5-butyl-1H-1,2,4-triazol-1-yl]methyl]-3-pyridinyl]phenyl]-1H-tetrazole;
5-[2-[6-[[3-(1,1-difluorobutyl)-5-butyl-1H-1,2,4-triazol-1-yl]methyl]-3-pyridinyl]phenyl]-1H-tetrazole; and
5-[2-[6-[[3-(1,1-dimethoxybutyl)-5-butyl-1H-1,2,4-triazol-1-yl]methyl]-3-pyridinyl]phenyl]-1H-tetrazole.

A second subclass of compounds of Formula I which is of even more particular interest consists of those compounds of Formula III

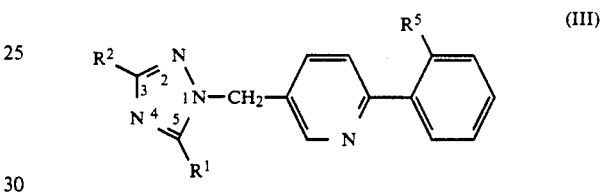

(III)

wherein m is one; wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, 2-butenyl, 3-butenyl, 2-butynyl, 3-butynyl and 2-hydroxybutyl; wherein $R^2$ is selected from ethyl, n-propyl, isopropyl, n-butyl, sec-butyl, isobutyl, 4-methylbutyl, n-pentyl, 1-oxo-2-phenylethyl, 1-oxo-2-cyclohexylethyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, 1-butenyl, 2-butenyl, 3-butenyl, 1-butynyl, 2-butynyl, 3-butynyl, propylthio and butylthio; wherein $R^5$ is an acidic group selected from $CO_2H$ and

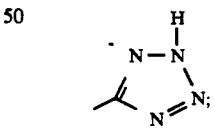

or a tautomer thereof or a pharmaceutically-acceptable salt thereof.

A family of specific compounds of particular interest within Formula III consists of compounds and pharmaceutically-acceptable salts thereof as follows:

2-[5-[(3-methyl-5-propyl-1H-1,2,4-triazol-1-yl)methyl]-2-pyridinyl]benzoic acid;
2-[5-[(3-ethyl-5-propyl-1H-1,2,4-triazol-1-yl)methyl]-2-pyridinyl]benzoic acid;
2-[5-[(3,5-dipropyl-1H-1,2,4-triazol-1-yl)methyl]-2-pyridinyl]benzoic acid;
2-[5-[(3-isopropyl-5-propyl-1H-1,2,4-triazol-1-yl)methyl]-2-pyridinyl]benzoic acid;

2-[5-[(3-butyl-5-propyl-1H-1,2,4-triazol-1-yl)methyl]-2-pyridinyl]benzoic acid;
2-[5-[(3-secbutyl-5-propyl-1H-1,2,4-triazol-1-yl)methyl]-2-pyridinyl]benzoic acid;
2-[5-[(3-isobutyl-5-propyl-1H-1,2,4-triazol-1-yl)methyl]-2-pyridinyl]benzoic acid;
2-[5-[(3-tertbutyl-5-propyl-1H-1,2,4-triazol-1-yl)methyl]-2-pyridinyl]benzoic acid;
2-[5-[(3-pentyl-5-propyl-1H-1,2,4-triazol-1-yl)methyl]-2-pyridinyl]benzoic acid;
2-[5-[(3-isopentyl-5-propyl-1H-1,2,4-triazol-1-yl)methyl]-2-pyridinyl]benzoic acid;
2-[5-[(3-cyclohexyl-5-propyl-1H-1,2,4-triazol-1-yl)methyl]-2-pyridinyl]benzoic acid;
2-[5-[(3-cyclohexylmethyl-5-propyl-1H-1,2,4-triazol-1-yl)methyl]-2-pyridinyl]benzoic acid;
2-[5-[(3-benzoyl-5-propyl-1H-1,2,4-triazol-1-yl)methyl]-2-pyridinyl]benzoic acid;
2-[5-[(3-phenyl-5-propyl-1H-1,2,4-triazol-1-yl)methyl]-2-pyridinyl]benzoic acid;
2-[5-[(3-phenylmethyl-5-propyl-1H-1,2,4-triazol-1-yl)methyl]-2-pyridinyl]benzoic acid;
2-[5-[(3-cyclohenanoyl-5-propyl-1H-1,2,4-triazol-1-yl)methyl]-2-pyridinyl]benzoic acid;
2-[5-[[3-(2-phenylethyl)-5-propyl-1H-1,2,4-triazol-1-yl]methyl]-2-pyridinyl]benzoic acid;
2-[5-[[3-(1-oxo-2-cyclohexylethyl)-5-propyl-1H-1,2,4-triazol-1-yl]methyl]-2-pyridinyl]benzoic acid;
2-[5-[[3-(2-cyclohexylethyl)-5-propyl-1H-1,2,4-triazol-1-yl]methyl]-2-pyridinyl]benzoic acid;
2-[5-[[3-(1-oxo-2-phenylethyl)-5-propyl-1H-1,2,4-triazol-1-yl]methyl]-2-pyridinyl]benzoic acid;
2-[5-[[3-(1,1-dimethoxypropyl)-5-propyl-1H-1,2,4-triazol-1-yl]methyl]-2-pyridinyl]benzoic acid;
2-[5-[[3-(1,1-dimethoxybutyl)-5-propyl-1H-1,2,4-triazol-1-yl]methyl]-2-pyridinyl]benzoic acid;
2-[5-[[3-(1,1-dimethoxypentyl)-5-propyl-1H-1,2,4-triazol-1-yl]methyl]-2-pyridinyl]benzoic acid;
2-[5-[[3-(1-oxopropyl)-5-propyl-1H-1,2,4-triazol-1-yl]methyl]-2-pyridinyl]benzoic acid;
2-[5-[[3-(1-oxobutyl)-5-propyl-1H-1,2,4-triazol-1-yl]methyl]-2-pyridinyl]benzoic acid;
2-[5-[[3-(1-oxopentyl)-5-propyl-1H-1,2,4-triazol-1-yl]methyl]-2-pyridinyl]benzoic acid;
2-[5-[[3-(1,1-difluorobutyl)-5-propyl-1H-1,2,4-triazol-1-yl]methyl]-2-pyridinyl]benzoic acid;
2-[5-[(3-methyl-5-butyl-1H-1,2,4-triazol-1-yl)methyl]-2-pyridinyl]benzoic acid;
2-[5-[(3-ethyl-5-butyl-1H-1,2,4-triazol-1-yl)methyl]-2-pyridinyl]benzoic acid;
2-[5-[(3-propyl-5-butyl-1H-1,2,4-triazol-1-yl)methyl]-2-pyridinyl]benzoic acid;
2-[5-[(3-isopropyl-5-butyl-1H-1,2,4-triazol-1-yl)methyl]-2-pyridinyl]benzoic acid;
2-[5-[(3,5-dibutyl-1H-1,2,4-triazol-1-yl)methyl]-2-pyridinyl]benzoic acid;
2-[5-[(3-secbutyl-5-butyl-1H-1,2,4-triazol-1-yl)methyl]-2-pyridinyl]benzoic acid;
2-[5-[(3-isobutyl-5-butyl-1H-1,2,4-triazol-1-yl)methyl]-2-pyridinyl]benzoic acid;
2-[5-[(3-tertbutyl-5-butyl-1H-1,2,4-triazol-1-yl)methyl]-2-pyridinyl]benzoic acid;
2-[5-[(3-pentyl-5-butyl-1H-1,2,4-triazol-1-yl)methyl]-2-pyridinyl]benzoic acid;
2-[5-[(3-isopentyl-5-butyl-1H-1,2,4-triazol-1-yl)methyl]-2-pyridinyl]benzoic acid;
2-[5-[(3-cyclohexyl-5-butyl-1H-1,2,4-triazol-1-yl)methyl]-2-pyridinyl]benzoic acid;
2-[5-[(3-cyclohexylmethyl-5-butyl-1H-1,2,4-triazol-1-yl)methyl]-2-pyridinyl]benzoic acid;
2-[5-[(3-benzoyl-5-butyl-1H-1,2,4-triazol-1-yl)methyl]-2-pyridinyl]benzoic acid;
2-[5-[(3-phenyl-5-butyl-1H-1,2,4-triazol-1-yl)methyl]-2-pyridinyl]benzoic acid;
2-[5-[(3-phenylmethyl-5-butyl-1H-1,2,4-triazol-1-yl)methyl]-2-pyridinyl]benzoic acid;
2-[5-[(3-cyclohenanoyl-5-butyl-1H-1,2,4-triazol-1-yl)methyl]-2-pyridinyl]benzoic acid;
2-[5-[[3-(2-phenylethyl)-5-butyl-1H-1,2,4-triazol-1-yl]methyl]-2-pyridinyl]benzoic acid;
2-[5-[[3-(1-oxo-2-cyclohexylethyl)-5-butyl-1H-1,2,4-triazol-1-yl]methyl]-2-pyridinyl]benzoic acid;
2-[5-[[3-(2-cyclohexylethyl)-5-butyl-1H-1,2,4-triazol-1-yl]methyl]-2-pyridinyl]benzoic acid;
2-[5-[[3-(1-oxo-2-phenylethyl)-5-butyl-1H-1,2,4-triazol-1-yl]methyl]-2-pyridinyl]benzoic acid;
2-[5-[[3-(1,1-dimethoxypropyl)-5-butyl-1H-1,2,4-triazol-1-yl]methyl]-2-pyridinyl]benzoic acid;
2-[5-[[3-(1,1-dimethoxybutyl)-5-butyl-1H-1,2,4-triazol-1-yl]methyl]-2-pyridinyl]benzoic acid;
2-[5-[[3-(1,1-dimethoxypentyl)-5-butyl-1H-1,2,4-triazol-1-yl]methyl]-2-pyridinyl]benzoic acid;
2-[5-[[3-(1-oxopropyl)-5-butyl-1H-1,2,4-triazol-1-yl]methyl]-2-pyridinyl]benzoic acid;
2-[5-[[3-(1-oxobutyl)-5-butyl-1H-1,2,4-triazol-1-yl]methyl]-2-pyridinyl]benzoic acid;
2-[5-[[3-(1-oxopentyl)-5-butyl-1H-1,2,4-triazol-1-yl]methyl]-2-pyridinyl]benzoic acid;
2-[5-[[3-(1,1-difluorobutyl)-5-butyl-1H-1,2,4-triazol-1-yl]methyl]-2-pyridinyl]benzoic acid;
2-[5-[(3-methyl-5-pentyl-1H-1,2,4-triazol-1-yl)methyl]-2-pyridinyl]benzoic acid;
2-[5-[(3-ethyl-5-pentyl-1H-1,2,4-triazol-1-yl)methyl]-2-pyridinyl]benzoic acid;
2-[5-[(3-propyl-5-pentyl-1H-1,2,4-triazol-1-yl)methyl]-2-pyridinyl]benzoic acid;
2-[5-[(3-isopropyl-5-pentyl-1H-1,2,4-triazol-1-yl)methyl]-2-pyridinyl]benzoic acid;
2-[5-[(3-butyl-5-pentyl-1H-1,2,4-triazol-1-yl)methyl]-2-pyridinyl]benzoic acid;
2-[5-[(3-secbutyl-5-pentyl-1H-1,2,4-triazol-1-yl)methyl]-2-pyridinyl]benzoic acid;
2-[5-[(3-isobutyl-5-pentyl-1H-1,2,4-triazol-1-yl)methyl]-2-pyridinyl]benzoic acid;
2-[5-[(3-tertbutyl-5-pentyl-1H-1,2,4-triazol-1-yl)methyl]-2-pyridinyl]benzoic acid;
2-[5-[(3,5-dipentyl-1H-1,2,4-triazol-1-yl)methyl]-2-pyridinyl]benzoic acid;
2-[5-[(3-isopentyl-5-pentyl-1H-1,2,4-triazol-1-yl)methyl]-2-pyridinyl]benzoic acid;
2-[5-[(3-cyclohexyl-5-pentyl-1H-1,2,4-triazol-1-yl)methyl]-2-pyridinyl]benzoic acid;
2-[5-[(3-cyclohexylmethyl-5-pentyl-1H-1,2,4-triazol-1-yl)methyl]-2-pyridinyl]benzoic acid;
2-[5-[(3-benzoyl-5-pentyl-1H-1,2,4-triazol-1-yl)methyl]-2-pyridinyl]benzoic acid;
2-[5-[(3-phenyl-5-pentyl-1H-1,2,4-triazol-1-yl)methyl]-2-pyridinyl]benzoic acid;
2-[5-[(3-phenylmethyl-5-pentyl-1H-1,2,4-triazol-1-yl)methyl]-2-pyridinyl]benzoic acid;
2-[5-[(3-cyclohenanoyl-5-pentyl-1H-1,2,4-triazol-1-yl)methyl]-2-pyridinyl]benzoic acid;
2-[5-[[3-(2-phenylethyl)-5-pentyl-1H-1,2,4-triazol-1-yl]methyl]-2-pyridinyl]benzoic acid;
2-[5-[[3-(1-oxo-2-cyclohexylethyl)-5-pentyl-1H-1,2,4-triazol-1-yl]methyl]-2-pyridinyl]benzoic acid;

2-[5-[[3-(2-cyclohexylethyl)-5-pentyl-1H-1,2,4-triazol-1-yl]methyl]-2-pyridinyl]benzoic acid;
2-[5-[[3-(1-oxo-2-phenylethyl)-5-pentyl-1H-1,2,4-triazol-1-yl]methyl]-2-pyridinyl]benzoic acid;
2-[5-[[3-(1,1-dimethoxypropyl)-5-pentyl-1H-1,2,4-triazol-1-yl]methyl]-2-pyridinyl]benzoic acid;
2-[5-[[3-(1,1-dimethoxybutyl)-5-pentyl-1H-1,2,4-triazol-1-yl]methyl]-2-pyridinyl]benzoic acid;
2-[5-[[3-(1,1-dimethoxypentyl)-5-pentyl-1H-1,2,4-triazol-1-yl]methyl]-2-pyridinyl]benzoic acid;
2-[5-[[3-(1-oxopropyl)-5-pentyl-1H-1,2,4-triazol-1-yl]methyl]-2-pyridinyl]benzoic acid;
2-[5-[[3-(1-oxobutyl)-5-pentyl-1H-1,2,4-triazol-1-yl]methyl]-2-pyridinyl]benzoic acid;
2-[5-[[3-(1-oxopentyl)-5-pentyl-1H-1,2,4-triazol-1-yl]methyl]-2-pyridinyl]benzoic acid;
2-[5-[[3-(1,1-difluorobutyl)-5-pentyl-1H-1,2,4-triazol-1-yl]methyl]-2-pyridinyl]benzoic acid;
5-[2-[5-[(3-methyl-5-propyl-1H-1,2,4-triazol-1-yl)methyl]-2-pyridinyl]phenyl]-1H-tetrazole;
5-[2-[5-[(3-ethyl-5-propyl-1H-1,2,4-triazol-1-yl)methyl]-2-pyridinyl]phenyl]-1H-tetrazole;
5-[2-[5-[(3,5-dipropyl-1H-1,2,4-triazol-1-yl)methyl]-2-pyridinyl]phenyl]-1H-tetrazole;
5-[2-[5-[(3-isopropyl-5-propyl-1H-1,2,4-triazol-1-yl)methyl]-2-pyridinyl]phenyl]-1H-tetrazole;
5-[2-[5-[(3-butyl-5-propyl-1H-1,2,4-triazol-1-yl)methyl]-2-pyridinyl]phenyl]-1H-tetrazole;
5-[2-[5-[(3-secbutyl-5-propyl-1H-1,2,4-triazol-1-yl)methyl]-2-pyridinyl]phenyl]-1H-tetrazole;
5-[2-[5-[(3-isobutyl-5-propyl-1H-1,2,4-triazol-1-yl)methyl]-2-pyridinyl]phenyl]-1H-tetrazole;
5-[2-[5-[(3-tertbutyl-5-propyl-1H-1,2,4-triazol-1-yl)methyl]-2-pyridinyl]phenyl]-1H-tetrazole;
5-[2-[5-[(3-pentyl-5-propyl-1H-1,2,4-triazol-1-yl)methyl]-2-pyridinyl]phenyl]-1H-tetrazole;
5-[2-[5-[(3-isopentyl-5-propyl-1H-1,2,4-triazol-1-yl)methyl]-2-pyridinyl]phenyl]-1H-tetrazole;
5-[2-[5-[(3-cyclohexyl-5-propyl-1H-1,2,4-triazol-1-yl)methyl]-2-pyridinyl]phenyl]-1H-tetrazole;
5-[2-[5-[(3-cyclohexylmethyl-5-propyl-1H-1,2,4-triazol-1-yl)methyl]-2-pyridinyl]phenyl]-1H-tetrazole;
5-[2-[5-[(3-benzoyl-5-propyl-1H-1,2,4-triazol-1-yl)methyl]-2-pyridinyl]phenyl]-1H-tetrazole;
5-[2-[5-[(3-phenyl-5-propyl-1H-1,2,4-triazol-1-yl)methyl]-2-pyridinyl]phenyl]-1H-tetrazole;
5-[2-[5-[(3-phenylmethyl-5-propyl-1H-1,2,4-triazol-1-yl)methyl]-2-pyridinyl]phenyl]-1H-tetrazole;
5-[2-[5-[(3-cyclohenanoyl-5-propyl-1H-1,2,4-triazol-1-yl)methyl]-2-pyridinyl]phenyl]-1H-tetrazole;
5-[2-[5-[[3-(2-phenylethyl)-5-propyl-1H-1,2,4-triazol-1-yl]methyl]-2-pyridinyl]phenyl]-1H-tetrazole;
5-[2-[5-[[3-(1-oxo-2-cyclohexylethyl)-5-propyl-1H-1,2,4-triazol-1-yl]methyl]-2-pyridinyl]phenyl]-1H-tetrazole;
5-[2-[5-[[3-(2-cyclohexylethyl)-5-propyl-1H-1,2,4-triazol-1-yl]methyl]-2-pyridinyl]phenyl]-1H-tetrazole;
5-[2-[5-[[3-(1-oxo-2-phenylethyl)-5-propyl-1H-1,2,4-triazol-1-yl]methyl]-2-pyridinyl]phenyl]-1H-tetrazole;
5-[2-[5-[[3-(1,1-dimethoxypropyl)-5-propyl-1H-1,2,4-triazol-1-yl]methyl]-2-pyridinyl]phenyl]-1H-tetrazole;
5-[2-[5-[[3-(1,1-dimethoxybutyl)-5-propyl-1H-1,2,4-triazol-1-yl]methyl]-2-pyridinyl]phenyl]-1H-tetrazole;
5-[2-[5-[[3-(1,1-dimethoxypentyl)-5-propyl-1H-1,2,4-triazol-1-yl]methyl]-2-pyridinyl]phenyl]-1H-tetrazole;
5-[2-[5-[[3-(1-oxopropyl)-5-propyl-1H-1,2,4-triazol-1-yl]methyl]-2-pyridinyl]phenyl]-1H-tetrazole;
5-[2-[5-[[3-(1-oxobutyl)-5-propyl-1H-1,2,4-triazol-1-yl]methyl]-2-pyridinyl]phenyl]-1H-tetrazole;
5-[2-[5-[[3-(1-oxopentyl)-5-propyl-1H-1,2,4-triazol-1-yl]methyl]-2-pyridinyl]phenyl]-1H-tetrazole;
5-[2-[5-[[3-(1,1-difluorobutyl)-5-propyl-1H-1,2,4-triazol-1-yl]methyl]-2-pyridinyl]phenyl]-1H-tetrazole;
5-[2-[5-[(3-methyl-5-butyl-1H-1,2,4-triazol-1-yl)methyl]-2-pyridinyl]phenyl]-1H-tetrazole;
5-[2-[5-[(3-ethyl-5-butyl-1H-1,2,4-triazol-1-yl)methyl]-2-pyridinyl]phenyl]-1H-tetrazole;
5-[2-[5-[(3-propyl-5-butyl-1H-1,2,4-triazol-1-yl)methyl]-2-pyridinyl]phenyl]-1H-tetrazole;
5-[2-[5-[(3-isopropyl-5-butyl-1H-1,2,4-triazol-1-yl)methyl]-2-pyridinyl]phenyl]-1H-tetrazole;
5-[2-[5-[(3,5-dibutyl-1H-1,2,4-triazol-1-yl)methyl]-2-pyridinyl]phenyl]-1H-tetrazole;
5-[2-[5-[(3-secbutyl-5-butyl-1H-1,2,4-triazol-1-yl)methyl]-2-pyridinyl]phenyl]-1H-tetrazole;
5-[2-[5-[(3-isobutyl-5-butyl-1H-1,2,4-triazol-1-yl)methyl]-2-pyridinyl]phenyl]-1H-tetrazole;
5-[2-[5-[(3-tertbutyl-5-butyl-1H-1,2,4-triazol-1-yl)methyl]-2-pyridinyl]phenyl]-1H-tetrazole;
5-[2-[5-[(3-pentyl-5-butyl-1H-1,2,4-triazol-1-yl)methyl]-2-pyridinyl]phenyl]-1H-tetrazole;
5-[2-[5-[(3-isopentyl-5-butyl-1H-1,2,4-triazol-1-yl)methyl]-2-pyridinyl]phenyl]-1H-tetrazole;
5-[2-[5-[(3-cyclohexyl-5-butyl-1H-1,2,4-triazol-1-yl)methyl]-2-pyridinyl]phenyl]-1H-tetrazole;
5-[2-[5-[(3-cyclohexylmethyl-5-butyl-1H-1,2,4-triazol-1-yl)methyl]-2-pyridinyl]phenyl]-1H-tetrazole;
5-[2-[5-[(3-benzoyl-5-butyl-1H-1,2,4-triazol-1-yl)methyl]-2-pyridinyl]phenyl]-1H-tetrazole;
5-[2-[5-[(3-phenyl-5-butyl-1H-1,2,4-triazol-1-yl)methyl]-2-pyridinyl]phenyl]-1H-tetrazole;
5-[2-[5-[(3-phenylmethyl-5-butyl-1H-1,2,4-triazol-1-yl)methyl]-2-pyridinyl]phenyl]-1H-tetrazole;
5-[2-[5-[(3-cyclohenanoyl-5-butyl-1H-1,2,4-triazol-1-yl)methyl]-2-pyridinyl]phenyl]-1H-tetrazole;
5-[2-[5-[[3-(2-phenylethyl)-5-butyl-1H-1,2,4-triazol-1-yl]methyl]-2-pyridinyl]phenyl]-1H-tetrazole;
5-[2-[5-[[3-(1-oxo-2-cyclohexylethyl)-5-butyl-1,2,4-triazol-1-yl]methyl]-2-pyridinyl]phenyl]-1H-tetrazole;
5-[2-[5-[[3-(2-cyclohexylethyl)-5-butyl-1H-1,2,4-triazol-1-yl]methyl]-2-pyridinyl]phenyl]-1H-tetrazole;
5-[2-[5-[[3-(1-oxo-2-phenylethyl)-5-butyl-1H-1,2,4-triazol-1-yl]methyl]-2-pyridinyl]phenyl]-1H-tetrazole;
5-[2-[5-[[3-(1,1-dimethoxypropyl)-5-butyl-1H-1,2,4-triazol-1-yl]methyl]-2-pyridinyl]phenyl]-1H-tetrazole;
5-[2-[5-[[3-(1,1-dimethoxybutyl)-5-butyl-1H-1,2,4-triazol-1-yl]methyl]-2-pyridinyl]phenyl]-1H-tetrazole;
5-[2-[5-[[3-(1,1-dimethoxypentyl)-5-butyl-1H-1,2,4-triazol-1-yl]methyl]-2-pyridinyl]phenyl]-1H-tetrazole;
5-[2-[5-[[3-(1-oxopropyl)-5-butyl-1H-1,2,4-triazol-1-yl]methyl]-2-pyridinyl]phenyl]-1H-tetrazole;
5-[2-[5-[[3-(1-oxobutyl)-5-butyl-1H-1,2,4-triazol-1-yl]methyl]-2-pyridinyl]phenyl]-1H-tetrazole;
5-[2-[5-[[3-(1-oxopentyl)-5-butyl-1H-1,2,4-triazol-1-yl]methyl]-2-pyridinyl]phenyl]-1H-tetrazole;

5-[2-[5-[[3-(1,1-difluorobutyl)-5-butyl-1H-1,2,4-triazol-1-yl]methyl]-2-pyridinyl]phenyl]-1H-tetrazole;
5-[2-[5-[(3-methyl-5-pentyl-1H-1,2,4-triazol-1-yl)methyl]-2-pyridinyl]phenyl]-1H-tetrazole;
5-[2-[5-[(3-ethyl-5-pentyl-1H-1,2,4-triazol-1-yl)methyl]-2-pyridinyl]phenyl]-1H-tetrazole;
5-[2-[5-[(3-propyl-5-pentyl-1H-1,2,4-triazol-1-yl)methyl]-2-pyridinyl]phenyl]-1H-tetrazole;
5-[2-[5-[(3-isopropyl-5-pentyl-1H-1,2,4-triazol-1-yl)methyl]-2-pyridinyl]phenyl]-1H-tetrazole;
5-[2-[5-[(3-butyl-5-pentyl-1H-1,2,4-triazol-1-yl)methyl]-2-pyridinyl]phenyl]-1H-tetrazole;
5-[2-[5-[(3-secbutyl-5-pentyl-1H-1,2,4-triazol-1-yl)methyl]-2-pyridinyl]phenyl]-1H-tetrazole;
5-[2-[5-[(3-isobutyl-5-pentyl-1H-1,2,4-triazol-1-yl)methyl]-2-pyridinyl]phenyl]-1H-tetrazole;
5-[2-[5-[(3-tertbutyl-5-pentyl-1H-1,2,4-triazol-1-yl)methyl]-2-pyridinyl]phenyl]-1H-tetrazole;
5-[2-[5-[(3,5-dipentyl-1H-1,2,4-triazol-1-yl)methyl]-2-pyridinyl]phenyl]-1H-tetrazole;
5-[2-[5-[(3-isopentyl-5-pentyl-1H-1,2,4-triazol-1-yl)methyl]-2-pyridinyl]phenyl]-1H-tetrazole;
5-[2-[5-[(3-cyclohexyl-5-pentyl-1H-1,2,4-triazol-1-yl)methyl]-2-pyridinyl]phenyl]-1H-tetrazole;
5-[2-[5-[(3-cyclohexylmethyl-5-pentyl-1H-1,2,4-triazol-1-yl)methyl]-2-pyridinyl]phenyl]-1H-tetrazole;
5-[2-[5-[(3-benzoyl-5-pentyl-1H-1,2,4-triazol-1-yl)methyl]-2-pyridinyl]phenyl]-1H-tetrazole;
5-[2-[5-[(3-phenyl-5-pentyl-1H-1,2,4-triazol-1-yl)methyl]-2-pyridinyl]phenyl]-1H-tetrazole;
5-[2-[5-[(3-phenylmethyl-5-pentyl-1H-1,2,4-triazol-1-yl)methyl]-2-pyridinyl]phenyl]-1H-tetrazole;
5-[2-[5-[(3-cyclohenanoyl-5-pentyl-1H-1,2,4-triazol-1-yl)methyl]-2-pyridinyl]phenyl]-1H-tetrazole;
5-[2-[5-[[3-(2-phenylethyl)-5-pentyl-1H-1,2,4-triazol-1-yl]methyl]-2-pyridinyl]phenyl]-1H-tetrazole;
5-[2-[5-[[3-(1-oxo-2-cyclohexylethyl)-5-pentyl-1H-1,2,4-triazol-1-yl]methyl]-2-pyridinyl]phenyl]-1H-tetrazole;
5-[2-[5-[[3-(2-cyclohexylethyl)-5-pentyl-1H-1,2,4-triazol-1-yl]methyl]-2-pyridinyl]phenyl]-1H-tetrazole;
5-[2-[5-[[3-(1-oxo-2-phenylethyl)-5-pentyl-1H-1,2,4-triazol-1-yl]methyl]-2-pyridinyl]phenyl]-1H-tetrazole;
5-[2-[5-[[3-(1,1-dimethoxypropyl)-5-pentyl-1H-1,2,4-triazol-1-yl]methyl]-2-pyridinyl]phenyl]-1H-tetrazole;
5-[2-[5-[[3-(1,1-dimethoxybutyl)-5-pentyl-1H-1,2,4-triazol-1-yl]methyl]-2-pyridinyl]phenyl]-1H-tetrazole;
5-[2-[5-[[3-(1,1-dimethoxypentyl)-5-pentyl-1H-1,2,4-triazol-1-yl]methyl]-2-pyridinyl]phenyl]-1H-tetrazole;
5-[2-[5-[[3-(1-oxopropyl)-5-pentyl-1H-1,2,4-triazol-1-yl]methyl]-2-pyridinyl]phenyl]-1H-tetrazole;
5-[2-[5-[[3-(1-oxobutyl)-5-pentyl-1H-1,2,4-triazol-1-yl]methyl]-2-pyridinyl]phenyl]-1H-tetrazole;
5-[2-[5-[[3-(1-oxopentyl)-5-pentyl-1H-1,2,4-triazol-1-yl]methyl]-2-pyridinyl]phenyl]-1H-tetrazole; and
5-[2-[5-[[3-(1,1-difluorobutyl)-5-pentyl-1H-1,2,4-triazol-1-yl]methyl]-2-pyridinyl]phenyl]-1H-tetrazole.

A family of specific compounds of more particular interest within Formula III consists of compounds and pharmaceutically-acceptable salts thereof as follows:
2-[5-[(3-methyl-5-butyl-1H-1,2,4-triazol-1-yl)methyl]-2-pyridinyl]benzoic acid;
2-[5-[(3-ethyl-5-butyl-1H-1,2,4-triazol-1-yl)methyl]-2-pyridinyl]benzoic acid;
2-[5-[(3-propyl-5-butyl-1H-1,2,4-triazol-1-yl)methyl]-2-pyridinyl]benzoic acid;
2-[5-[(3-isopropyl-5-butyl-1H-1,2,4-triazol-1-yl)methyl]-2-pyridinyl]benzoic acid;
2-[5-[(3,5-dibutyl-1H-1,2,4-triazol-1-yl)methyl]-2-pyridinyl]benzoic acid;
2-[5-[(3-secbutyl-5-butyl-1H-1,2,4-triazol-1-yl)methyl]-2-pyridinyl]benzoic acid;
2-[5-[(3-isobutyl-5-butyl-1H-1,2,4-triazol-1-yl)methyl]-2-pyridinyl]benzoic acid;
2-[5-[(3-tertbutyl-5-butyl-1H-1,2,4-triazol-1-yl)methyl]-2-pyridinyl]benzoic acid;
2-[5-[(3-pentyl-5-butyl-1H-1,2,4-triazol-1-yl)methyl]-2-pyridinyl]benzoic acid;
2-[5-[(3-isopentyl-5-butyl-1H-1,2,4-triazol-1-yl)methyl]-2-pyridinyl]benzoic acid;
2-[5-[(3-cyclohexyl-5-butyl-1H-1,2,4-triazol-1-yl)methyl]-2-pyridinyl]benzoic acid;
2-[5-[(3-cyclohexylmethyl-5-butyl-1H-1,2,4-triazol-1-yl)methyl]-2-pyridinyl]benzoic acid;
2-[5-[(3-phenyl-5-butyl-1H-1,2,4-triazol-1-yl)methyl]-2-pyridinyl]benzoic acid;
2-[5-[(3-phenylmethyl-5-butyl-1H-1,2,4-triazol-1-yl)methyl]-2-pyridinyl]benzoic acid;
2-[5-[[3-(2-cyclohexylethyl)-5-butyl-1H-1,2,4-triazol-1-yl]methyl]-2-pyridinyl]benzoic acid;
2-[5-[[3-(2-phenylethyl)-5-butyl-1H-1,2,4-triazol-1-yl]methyl]-2-pyridinyl]benzoic acid;
2-[5-[[3-(1-oxo-2-phenylethyl)-5-butyl-1H-1,2,4-triazol-1-yl]methyl]-2-pyridinyl]benzoic acid;
2-[5-[[3-(1-oxobutyl)-5-butyl-1H-1,2,4-triazol-1-yl]methyl]-2-pyridinyl]benzoic acid;
2-[5-[[3-(1,1-difluorobutyl)-5-butyl-1H-1,2,4-triazol-1-yl]methyl]-2-pyridinyl]benzoic acid;
2-[5-[[3-(1,1-dimethoxybutyl)-5-butyl-1H-1,2,4-triazol-1-yl]methyl]-2-pyridinyl]benzoic acid;
5-[2-[5-[(3-methyl-5-butyl-1H-1,2,4-triazol-1-yl)methyl]-2-pyridinyl]phenyl]-1H-tetrazole;
5-[2-[5-[(3-ethyl-5-butyl-1H-1,2,4-triazol-1-yl)methyl]-2-pyridinyl]phenyl]-1H-tetrazole;
5-[2-[5-[(3-propyl-5-butyl-1H-1,2,4-triazol-1-yl)methyl]-2-pyridinyl]phenyl]-1H-tetrazole;
5-[2-[5-[(3-isopropyl-5-butyl-1H-1,2,4-triazol-1-yl)methyl]-2-pyridinyl]phenyl]-1H-tetrazole;
5-[2-[5-[(3,5-dibutyl-1H-1,2,4-triazol-1-yl)methyl]-2-pyridinyl]phenyl]-1H-tetrazole;
5-[2-[5-[(3-secbutyl-5-butyl-1H-1,2,4-triazol-1-yl)methyl]-2-pyridinyl]phenyl]-1H-tetrazole;
5-[2-[5-[(3-isobutyl-5-butyl-1H-1,2,4-triazol-1-yl)methyl]-2-pyridinyl]phenyl]-1H-tetrazole;
5-[2-[5-[(3-tertbutyl-5-butyl-1H-1,2,4-triazol-1-yl)methyl]-2-pyridinyl]phenyl]-1H-tetrazole;
5-[2-[5-[(3-pentyl-5-butyl-1H-1,2,4-triazol-1-yl)methyl]-2-pyridinyl]phenyl]-1H-tetrazole;
5-[2-[5-[(3-isopentyl-5-butyl-1H-1,2,4-triazol-1-yl)methyl]-2-pyridinyl]phenyl]-1H-tetrazole;
5-[2-[5-[(3-cyclohexyl-5-butyl-1H-1,2,4-triazol-1-yl)methyl]-2-pyridinyl]phenyl]-1H-tetrazole;
5-[2-[5-[(3-cyclohexylmethyl-5-butyl-1H-1,2,4-triazol-1-yl)methyl]-2-pyridinyl]phenyl]-1H-tetrazole;
5-[2-[5-[(3-phenyl-5-butyl-1H-1,2,4-triazol-1-yl)methyl]-2-pyridinyl]phenyl]-1H-tetrazole;
5-[2-[5-[(3-phenylmethyl-5-butyl-1H-1,2,4-triazol-1-yl)methyl]-2-pyridinyl]phenyl]-1H-tetrazole;
5-[2-[5-[[3-(2-cyclohexylethyl)-5-butyl-1H-1,2,4-triazol-1-yl]methyl]-2-pyridinyl]phenyl]-1H-tetrazole;

5-[2-[5-[[3-(2-phenylethyl)-5-butyl-1H-1,2,4-triazol-1-yl]methyl]-2-pyridinyl]phenyl]-1H-tetrazole;

5-[2-[5-[[3-(1-oxo-2-phenylethyl)-5-butyl-1H-1,2,4-triazol-1-yl]methyl]-2-pyridinyl]phenyl]-1H-tetrazole;

5-[2-[5-[[3-(1-oxobutyl)-5-butyl-1H-1,2,4-triazol-1-yl]methyl]-2-pyridinyl]phenyl]-1H-tetrazole;

5-[2-[5-[[3-(1,1-difluorobutyl)-5-butyl-1H-1,2,4-triazol-1-yl]methyl]-2-pyridinyl]phenyl]-1H-tetrazole; and 5-[2-[5-[[3-(1,1-dimethoxybutyl)-5-butyl-1H-1,2,4-triazol-1-yl]methyl]-2-pyridinyl]phenyl]-1H-tetrazole.

A third subclass of compounds of Formula I which is of even more particular interest consists of those compounds of Formula IV

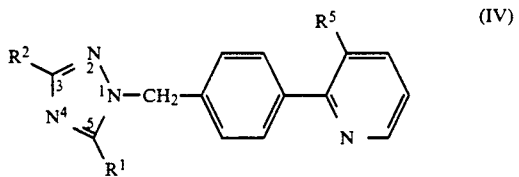

wherein m is one; wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, 2-butenyl, 3-butenyl, 2-butynyl, 3-butynyl and 2-hydroxybutyl; wherein $R^2$ is selected from ethyl, n-propyl, isopropyl, n-butyl, sec-butyl, isobutyl, 4-methylbutyl, n-pentyl, 1-oxo-2-phenylethyl, 1-oxo-2-cyclohexylethyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, 1-butenyl, 2-butenyl, 3-butenyl, 1-butynyl, 2-butynyl, 3-butynyl, propylthio and butylthio; wherein $R^5$ is an acidic group selected from $CO_2H$ and

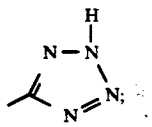

or a tautomer thereof or a pharmaceutically-acceptable salt thereof.

A family of specific compounds of particular interest within Formula IV consists of compounds and pharmaceutically-acceptable salts thereof as follows:

2-[4-[(3-methyl-5-propyl-1H-1,2,4-triazol-1-yl)methyl]phenyl]-3-pyridininecarboxylic acid;
2-[4-[(3-ethyl-5-propyl-1H-1,2,4-triazol-1-yl)methyl]phenyl]-3-pyridininecarboxylic acid;
2-[4-[(3,5-dipropyl-1H-1,2,4-triazol-1-yl)methyl]phenyl]-3-pyridininecarboxylic acid;
2-[4-[(3-isopropyl-5-propyl-1H-1,2,4-triazol-1-yl)methyl]phenyl]-3-pyridininecarboxylic acid;
2-[4-[(3-butyl-5-propyl-1H-1,2,4-triazol-1-yl)methyl]phenyl]-3-pyridininecarboxylic acid;
2-[4-[(3-secbutyl-5-propyl-1H-1,2,4-triazol-1-yl)methyl]phenyl]-3-pyridininecarboxylic acid;
2-[4-[(3-isobutyl-5-propyl-1H-1,2,4-triazol-1-yl)methyl]phenyl]-3-pyridininecarboxylic acid;
2-[4-[(3-tertbutyl-5-propyl-1H-1,2,4-triazol-1-yl)methyl]phenyl]-3-pyridininecarboxylic acid;
2-[4-[(3-pentyl-5-propyl-1H-1,2,4-triazol-1-yl)methyl]phenyl]-3-pyridininecarboxylic acid;
2-[4-[(3-isopentyl-5-propyl-1H-1,2,4-triazol-1-yl)methyl]phenyl]-3-pyridininecarboxylic acid;
2-[4-[(3-cyclohexyl-5-propyl-1H-1,2,4-triazol-1-yl)methyl]phenyl]-3-pyridininecarboxylic acid;
2-[4-[(3-cyclohexylmethyl-5-propyl-1H-1,2,4-triazol-1-yl)methyl]phenyl]-3-pyridininecarboxylic acid;
2-[4-[(3-benzoyl-5-propyl-1H-1,2,4-triazol-1-yl)methyl]phenyl]-3-pyridininecarboxylic acid;
2-[4-[(3-phenyl-5-propyl-1H-1,2,4-triazol-1-yl)methyl]phenyl]-3-pyridininecarboxylic acid;
2-[4-[(3-phenylmethyl-5-propyl-1H-1,2,4-triazol-1-yl)methyl]phenyl]-3-pyridininecarboxylic acid;
2-[4-[(3-cyclohenanoyl-5-propyl-1H-1,2,4-triazol-1-yl)methyl]phenyl]-3-pyridininecarboxylic acid;
2-[4-[[3-(2-phenylethyl)-5-propyl-1H-1,2,4-triazol-1-yl]methyl]phenyl]-3-pyridininecarboxylic acid;
2-[4-[[3-(1-oxo-2-cyclohexylethyl)-5-propyl-1H-1,2,4-triazol-1-yl]methyl]phenyl]-3-pyridininecarboxylic acid;
2-[4-[[3-(2-cyclohexylethyl)-5-propyl-1H-1,2,4-triazol-1-yl]methyl]phenyl]-3-pyridininecarboxylic acid;
2-[4-[[3-(1-oxo-2-phenylethyl)-5-propyl-1H-1,2,4-triazol-1-yl]methyl]phenyl]-3-pyridininecarboxylic acid;
2-[4-[[3-(1,1-dimethoxypropyl)-5-propyl-1H-1,2,4-triazol-1-yl]methyl]phenyl]-3-pyridininecarboxylic acid;
2-[4-[[3-(1,1-dimethoxybutyl)-5-propyl-1H-1,2,4-triazol-1-yl]methyl]phenyl]-3-pyridininecarboxylic acid;
2-[4-[[3-(1,1-dimethoxypentyl)-5-propyl-1H-1,2,4-triazol-1-yl]methyl]phenyl]-3-pyridininecarboxylic acid;
2-[4-[[3-(1-oxopropyl-5-propyl-1H-1,2,4-triazol-1-yl]methyl]phenyl]-3-pyridininecarboxylic acid;
2-[4-[[3-(1-oxobutyl)-5-propyl-1H-1,2,4-triazol-1-yl]methyl]phenyl]-3-pyridininecarboxylic acid;
2-[4-[[3-(1-oxopentyl)-5-propyl-1H-1,2,4-triazol-1-yl]methyl]phenyl]-3-pyridininecarboxylic acid;
2-[4-[[3-(1,1-difluorobutyl)-5-propyl-1H-1,2,4-triazol-1-yl]methyl]phenyl]-3-pyridininecarboxylic acid;
2-[4-[(3-methyl-5-butyl-1H-1,2,4-triazol-1-yl)methyl]phenyl]-3-pyridininecarboxylic acid;
2-[4-[(3-ethyl-5-butyl-1H-1,2,4-triazol-1-yl)methyl]phenyl]-3-pyridininecarboxylic acid;
2-[4-[(3-propyl-5-butyl-1H-1,2,4-triazol-1-yl)methyl]phenyl]-3-pyridininecarboxylic acid;
2-[4-[(3-isopropyl-5-butyl-1H-1,2,4-triazol-1-yl)methyl]phenyl]-3-pyridininecarboxylic acid;
2-[4-[(3,5-dibutyl-1H-1,2,4-triazol-1-yl)methyl]phenyl]-3-pyridininecarboxylic acid;
2-[4-[(3-secbutyl-5-butyl-1H-1,2,4-triazol-1-yl)methyl]phenyl]-3-pyridininecarboxylic acid;
2-[4-[(3-isobutyl-5-butyl-1H-1,2,4-triazol-1-yl)methyl]phenyl]-3-pyridininecarboxylic acid;
2-[4-[(3-tertbutyl-5-butyl-1H-1,2,4-triazol-1-yl)methyl]phenyl]-3-pyridininecarboxylic acid;
2-[4-[(3-pentyl-5-butyl-1H-1,2,4-triazol-1-yl)methyl]phenyl]-3-pyridininecarboxylic acid;
2-[4-[(3-isopentyl-5-butyl-1H-1,2,4-triazol-1-yl)methyl]phenyl]-3-pyridininecarboxylic acid;
2-[4-[(3-cyclohexyl-5-butyl-1H-1,2,4-triazol-1-yl)methyl]phenyl]-3-pyridininecarboxylic acid;
2-[4-[(3-cyclohexylmethyl-5-butyl-1H-1,2,4-triazol-1-yl)methyl]phenyl]-3-pyridininecarboxylic acid;

2-[4-[(3-benzoyl-5-butyl-1H-1,2,4-triazol-1-yl)methyl]-
phenyl]-3-pyridininecarboxylic acid;
2-[4-[(3-phenyl-5-butyl-1H-1,2,4-triazol-1-yl)methyl]-
phenyl]-3-pyridininecarboxylic acid;
2-[4-[(3-phenylmethyl-5-butyl-1H-1,2,4-triazol-1-yl)me-
thyl]phenyl]-3-pyridininecarboxylic acid;
2-[4-[(3-cyclohenanoyl-5-butyl-1H-1,2,4-triazol-1-
yl)methyl]phenyl]-3-pyridininecarboxylic acid;
2-[4-[[3-(2-phenylethyl)-5-butyl-1H-1,2,4-triazol-1-
yl]methyl]phenyl]-3-pyridininecarboxylic acid;
2-[4-[[3-(1-oxo-2-cyclohexylethyl)-5-butyl-1H-1,2,4-
triazol-1-yl]methyl]phenyl]-3-pyridininecarboxylic
acid;
2-[4-[[3-(2-cyclohexylethyl)-5-butyl-1H-1,2,4-triazol-1-
yl]methyl]phenyl]-3-pyridininecarboxylic acid;
2-[4-[[3-(1-oxo-2-phenylethyl)-5-butyl-1H-1,2,4-triazol-
1-yl]methyl]phenyl]-3-pyridininecarboxylic acid;
2-[4-[[3-(1,1-dimethoxypropyl)-5-butyl-1H-1,2,4-triazol-
1-yl]methyl]phenyl]-3-pyridininecarboxylic acid;
2-[4-[[3-(1,1-dimethoxybutyl)-5-butyl-1H-1,2,4-triazol-
1-yl]methyl]phenyl]-3-pyridininecarboxylic acid;
2-[4-[[3-(1,1-dimethoxypentyl)-5-butyl-1H-1,2,4-triazol-
1-yl]methyl]phenyl]-3-pyridininecarboxylic acid;
2-[4-[[3-(1-oxopropyl)-5-butyl-1H-1,2,4-triazol-1-yl]me-
thyl]phenyl]-3-pyridininecarboxylic acid;
2-[4-[[3-(1-oxobutyl)-5-butyl-1H-1,2,4-triazol-1-yl]me-
thyl]phenyl]-3-pyridininecarboxylic acid;
2-[4-[[3-(1-oxopentyl)-5-butyl-1H-1,2,4-triazol-1-yl]me-
thyl]phenyl]-3-pyridininecarboxylic acid;
2-[4-[[3-(1,1-difluorobutyl)-5-butyl-1H-1,2,4-triazol-1-
yl]methyl]phenyl]-3-pyridininecarboxylic acid;
2-[4-[(3-methyl-5-pentyl-1H-1,2,4-triazol-1-yl)methyl]-
phenyl]-3-pyridininecarboxylic acid;
2-[4-[(3-ethyl-5-pentyl-1H-1,2,4-triazol-1-yl)methyl]-
phenyl]-3-pyridininecarboxylic acid;
2-[4-[(3-propyl-5-pentyl-1H-1,2,4-triazol-1-yl)methyl]-
phenyl]-3-pyridininecarboxylic acid;
2-[4-[(3-isopropyl-5-pentyl-1H-1,2,4-triazol-1-yl)me-
thyl]phenyl]-3-pyridininecarboxylic acid;
2-[4-[(3-butyl-5-pentyl-1H-1,2,4-triazol-1-yl)methyl]-
phenyl]-3-pyridininecarboxylic acid;
2-[4-[(3-secbutyl-5-pentyl-1H-1,2,4-triazol-1-yl)methyl]-
phenyl]-3-pyridininecarboxylic acid;
2-[4-[(3-isobutyl-5-pentyl-1H-1,2,4-triazol-1-yl)methyl]-
phenyl]-3-pyridininecarboxylic acid;
2-[4-[(3-tertbutyl-5-pentyl-1H-1,2,4-triazol-1-yl)me-
thyl]phenyl]-3-pyridininecarboxylic acid;
2-[4-[(3,5-dipentyl-1H-1,2,4-triazol-1-yl)methyl]-
phenyl]-3-pyridininecarboxylic acid;
2-[4-[(3-isopentyl-5-pentyl-1H-1,2,4-triazol-1-yl)me-
thyl]phenyl]-3-pyridininecarboxylic acid;
2-[4-[(3-cyclohexyl-5-pentyl-1H-1,2,4-triazol-1-yl)me-
thyl]phenyl]-3-pyridininecarboxylic acid;
2-[4-[(3-cyclohexylmethyl-5-pentyl-1H-1,2,4-triazol-1-
yl)methyl]phenyl]-3-pyridininecarboxylic acid;
2-[4-[(3-benzoyl-5-pentyl-1H-1,2,4-triazol-1-yl)methyl]-
phenyl]-3-pyridininecarboxylic acid;
2-[4-[(3-phenyl-5-pentyl-1H-1,2,4-triazol-1-yl)methyl]-
phenyl]-3-pyridininecarboxylic acid;
2-[4-[(3-phenylmethyl-5-pentyl-1H-1,2,4-triazol-1-
yl)methyl]phenyl]-3-pyridininecarboxylic acid;
2-[4-[(3-cyclohenanoyl-5-pentyl-1H-1,2,4-triazol-1-
yl)methyl]phenyl]-3-pyridininecarboxylic acid;
2-[4-[[3-(2-phenylethyl)-5-pentyl-1H-1,2,4-triazol-1-
yl]methyl]phenyl]-3-pyridininecarboxylic acid;
2-[4-[[3-(1-oxo-2-cyclohexylethyl)-5-pentyl-1H-1,2,4-
triazol-1-yl]methyl]phenyl]-3-pyridininecarboxylic
acid;
2-[4-[[3-(2-cyclohexylethyl)-5-pentyl-1H-1,2,4-triazol-1-
yl]methyl]phenyl]-3-pyridininecarboxylic acid;
2-[4-[[3-(1-oxo-2-phenylethyl)-5-pentyl-1H-1,2,4-
triazol-1-yl]methyl]phenyl]-3-pyridininecarboxylic
acid;
2-[4-[[3-(1,1-dimethoxypropyl)-5-pentyl-1H-1,2,4-
triazol-1-yl]methyl]phenyl]-3-pyridininecarboxylic
acid;
2-[4-[[3-(1,1-dimethoxybutyl)-5-pentyl-1H-1,2,4-triazol-
1-yl]methyl]phenyl]-3-pyridininecarboxylic acid;
2-[4-[[3-(1,1-dimethoxypentyl)-5-pentyl-1H-1,2,4-
triazol-1-yl]methyl]phenyl]-3-pyridininecarboxylic
acid;
2-[4-[[3-(1-oxopropyl)-5-pentyl-1H-1,2,4-triazol-1-
yl]methyl]phenyl]-3-pyridininecarboxylic acid;
2-[4-[[3-(1-oxobutyl)-5-pentyl-1H-1,2,4-triazol-1-yl]me-
thyl]phenyl]-3-pyridininecarboxylic acid;
2-[4-[[3-(1-oxopentyl)-5-pentyl-1H-1,2,4-triazol-1-
yl]methyl]phenyl]-3-pyridininecarboxylic acid;
2-[4-[[3-(1,1-difluorobutyl)-5-pentyl-1H-1,2,4-triazol-1-
yl]methyl]phenyl]-3-pyridininecarboxylic acid;
5-[2-[4-[(3-methyl-5-propyl-1H-1,2,4-triazol-1-yl)me-
thyl]phenyl]-3-pyridinyl]-1H-tetrazole;
5-[2-[4-[(3-ethyl-5-propyl-1H-1,2,4-triazol-1-yl)methyl]-
phenyl]-3-pyridinyl]-1H-tetrazole;
5-[2-[4-[(3,5-dipropyl-1H-1,2,4-triazol-1-yl)methyl]-
phenyl]-3-pyridinyl]-1H-tetrazole;
5-[2-[4-[(3-isopropyl-5-propyl-1H-1,2,4-triazol-1-yl)me-
thyl]phenyl]-3-pyridinyl]-1H-tetrazole;
5-[2-[4-[(3-butyl-5-propyl-1H-1,2,4-triazol-1-yl)methyl]-
phenyl]-3-pyridinyl]-1H-tetrazole;
5-[2-[4-[(3-secbutyl-5-propyl-1H-1,2,4-triazol-1-yl)me-
thyl]phenyl]-3-pyridinyl]-1H-tetrazole;
5-[2-[4-[(3-isobutyl-5-propyl-1H-1,2,4-triazol-1-yl)me-
thyl]phenyl]-3-pyridinyl]-1H-tetrazole;
5-[2-[4-[(3-tertbutyl-5-propyl-1H-1,2,4-triazol-1-yl)me-
thyl]phenyl]-3-pyridinyl]-1H-tetrazole;
5-[2-[4-[(3-pentyl-5-propyl-1H-1,2,4-triazol-1-yl)me-
thyl]phenyl]-3-pyridinyl]-1H-tetrazole;
5-[2-[4-[(3-isopentyl-5-propyl-1H-1,2,4-triazol-1-yl)me-
thyl]phenyl]-3-pyridinyl]-1H-tetrazole;
5-[2-[4-[(3-cyclohexyl-5-propyl-1H-1,2,4-triazol-1-
yl)methyl]phenyl]-3-pyridinyl]-1H-tetrazole;
5-[2-[4-[(3-cyclohexylmethyl-5-propyl-1H-1,2,4-triazol-
1-yl)methyl]phenyl]-3-pyridinyl]-1H-tetrazole;
5-[2-[4-[(3-benzoyl-5-propyl-1H-1,2,4-triazol-1-yl)me-
thyl]phenyl]-3-pyridinyl]-1H-tetrazole;
5-[2-[4-[(3-phenyl-5-propyl-1H-1,2,4-triazol-1-yl)me-
thyl]phenyl]-3-pyridinyl]-1H-tetrazole;
5-[2-[4-[(3-phenylmethyl-5-propyl-1H-1,2,4-triazol-1-
yl)methyl]phenyl]-3-pyridinyl]-1H-tetrazole;
5-[2-[4-[(3-cyclohenanoyl-5-propyl-1H-1,2,4-triazol-1-
yl)methyl]phenyl]-3-pyridinyl]-1H-tetrazole;
5-[2-[4-[[3-(2-phenylethyl)-5-propyl-1H-1,2,4-triazol-1-
yl]methyl]phenyl]-3-pyridinyl]-1H-tetrazole;
5-[2-[4-[[3-(1-oxo-2-cyclohexylethyl)-5-propyl-1H-
1,2,4-triazol-1-yl]methyl]phenyl]-3-pyridinyl]-1H-tet-
razole;
5-[2-[4-[[3-(2-cyclohexylethyl)-5-propyl-1H-1,2,4-
triazol-1-yl]methyl]phenyl]-3-pyridinyl]-1H-tet-
razole;
5-[2-[4-[[3-(1-oxo-2-phenylethyl)-5-propyl-1H-1,2,4-
triazol-1-yl]methyl]phenyl]-3-pyridinyl]-1H-tet-
razole;
5-[2-[4-[[3-(1,1-dimethoxypropyl)-5-propyl-1H-1,2,4-
triazol-1-yl]methyl]phenyl]-3-pyridinyl]-1H-tet-
razole;

5-[2-[4-[[3-(1,1-dimethoxybutyl)-5-propyl-1H-1,2,4-triazol-1-yl]methyl]phenyl]-3-pyridinyl]-1H-tetrazole;
5-[2-[4-[[3-(1,1-dimethoxypentyl)-5-propyl-1H-1,2,4-triazol-1-yl]methyl]phenyl]-3-pyridinyl]-1H-tetrazole;
5-[2-[4-[[3-(1-oxopropyl)-5-propyl-1H-1,2,4-triazol-1-yl]methyl]phenyl]-3-pyridinyl]-1H-tetrazole;
5-[2-[4-[[3-(1-oxobutyl)-5-propyl-1H-1,2,4-triazol-1-yl]methyl]phenyl]-3-pyridinyl]-1H-tetrazole;
5-[2-[4-[[3-(1-oxopentyl)-5-propyl-1H-1,2,4-triazol-1-yl]methyl]phenyl]-3-pyridinyl]-1H-tetrazole;
5-[2-[4-[[3-(1,1-difluorobutyl)-5-propyl-1H-1,2,4-triazol-1-yl]methyl]phenyl]-3-pyridinyl]-1H-tetrazole;
5-[2-[4-[(3-methyl-5-butyl-1H-1,2,4-triazol-1-yl)methyl]phenyl]-3-pyridinyl]-1H-tetrazole;
5-[2-[4-[(3-ethyl-5-butyl-1H-1,2,4-triazol-1-yl)methyl]phenyl]-3-pyridinyl]-1H-tetrazole;
5-[2-[4-[(3-propyl-5-butyl-1H-1,2,4-triazol-1-yl)methyl]phenyl]-3-pyridinyl]-1H-tetrazole;
5-[2-[4-[(3-isopropyl-5-butyl-1H-1,2,4-triazol-1-yl)methyl]phenyl]-3-pyridinyl]-1H-tetrazole;
5-[2-[4-[(3,5-dibutyl-1H-1,2,4-triazol-1-yl)methyl]phenyl]-3-pyridinyl]-1H-tetrazole;
5-[2-[4-[(3-secbutyl-5-butyl-1H-1,2,4-triazol-1-yl)methyl]phenyl]-3-pyridinyl]-1H-tetrazole;
5-[2-[4-[(3-isobutyl-5-butyl-1H-1,2,4-triazol-1-yl)methyl]phenyl]-3-pyridinyl]-1H-tetrazole;
5-[2-[4-[(3-tertbutyl-5-butyl-1H-1,2,4-triazol-1-yl)methyl]phenyl]-3-pyridinyl]-1H-tetrazole;
5-[2-[4-[(3-pentyl-5-butyl-1H-1,2,4-triazol-1-yl)methyl]phenyl]-3-pyridinyl]-1H-tetrazole;
5-[2-[4-[(3-isopentyl-5-butyl-1H-1,2,4-triazol-1-yl)methyl]phenyl]-3-pyridinyl]-1H-tetrazole;
5-[2-[4-[(3-cyclohexyl-5-butyl-1H-1,2,4-triazol-1-yl)methyl]phenyl]-3-pyridinyl]-1H-tetrazole;
5-[2-[4-[(3-cyclohexylmethyl-5-butyl-1H-1,2,4-triazol-1-yl)methyl]phenyl]-3-pyridinyl]-1H-tetrazole;
5-[2-[4-[(3-benzoyl-5-butyl-1H-1,2,4-triazol-1-yl)methyl]phenyl]-3-pyridinyl]-1H-tetrazole;
5-[2-[4-[(3-phenyl-5-butyl-1H-1,2,4-triazol-1-yl)methyl]phenyl]-3-pyridinyl]-1H-tetrazole;
5-[2-[4-[(3-phenylmethyl-5-butyl-1H-1,2,4-triazol-1-yl)methyl]phenyl]-3-pyridinyl]-1H-tetrazole;
5-[2-[4-[(3-cyclohenanoyl-5-butyl-1H-1,2,4-triazol-1-yl)methyl]phenyl]-3-pyridinyl]-1H-tetrazole;
5-[2-[4-[[3-(2-phenylethyl)-5-butyl-1H-1,2,4-triazol-1-yl]methyl]phenyl]-3-pyridinyl]-1H-tetrazole;
5-[2-[4-[[3-(1-oxo-2-cyclohexylethyl)-5-butyl-1H-1,2,4-triazol-1-yl]methyl]phenyl]-3-pyridinyl]-1H-tetrazole;
5-[2-[4-[[3-(2-cyclohexylethyl)-5-butyl-1H-1,2,4-triazol-1-yl]methyl]phenyl]-3-pyridinyl]-1H-tetrazole;
5-[2-[4-[[3-(1-oxo-2-phenylethyl)-5-butyl-1H-1,2,4-triazol-1-yl]methyl]phenyl]-3-pyridinyl]-1H-tetrazole;
5-[2-[4-[[3-(1,1-dimethoxypropyl)-5-butyl-1H-1,2,4-triazol-1-yl]methyl]phenyl]-3-pyridinyl]-1H-tetrazole;
5-[2-[4-[[3-(1,1-dimethoxybutyl)-5-butyl-1H-1,2,4-triazol-1-yl]methyl]phenyl]-3-pyridinyl]-1H-tetrazole;
5-[2-[4-[[3-(1,1-dimethoxypentyl)-5-butyl-1H-1,2,4-triazol-1-yl]methyl]phenyl]-3-pyridinyl]-1H-tetrazole;
5-[2-[4-[[3-(1-oxopropyl)-5-butyl-1H-1,2,4-triazol-1-yl]methyl]phenyl]-3-pyridinyl]-1H-tetrazole;
5-[2-[4-[[3-(1-oxobutyl)-5-butyl-1H-1,2,4-triazol-1-yl]methyl]phenyl]-3-pyridinyl]-1H-tetrazole;
5-[2-[4-[[3-(1-oxopentyl)-5-butyl-1H-1,2,4-triazol-1-yl]methyl]phenyl]-3-pyridinyl]-1H-tetrazole;
5-[2-[4-[[3-(1,1-difluorobutyl)-5-butyl-1H-1,2,4-triazol-1-yl]methyl]phenyl]-3-pyridinyl]-1H-tetrazole;
5-[2-[4-[(3-methyl-5-pentyl-1H-1,2,4-triazol-1-yl)methyl]phenyl]-3-pyridinyl]-1H-tetrazole;
5-[2-[4-[(3-ethyl-5-pentyl-1H-1,2,4-triazol-1-yl)methyl]phenyl]-3-pyridinyl]-1H-tetrazole;
5-[2-[4-[(3-propyl-5-pentyl-1H-1,2,4-triazol-1-yl)methyl]phenyl]-3-pyridinyl]-1H-tetrazole;
5-[2-[4-[(3-isopropyl-5-pentyl-1H-1,2,4-triazol-1-yl)methyl]phenyl]-3-pyridinyl]-1H-tetrazole;
5-[2-[4-[(3-butyl-5-pentyl-1H-1,2,4-triazol-1-yl)methyl]phenyl]-3-pyridinyl]-1H-tetrazole;
5-[2-[4-[(3-secbutyl-5-pentyl-1H-1,2,4-triazol-1-yl)methyl]phenyl]-3-pyridinyl]-1H-tetrazole;
5-[2-[4-[(3-isobutyl-5-pentyl-1H-1,2,4-triazol-1-yl)methyl]phenyl]-3-pyridinyl]-1H-tetrazole;
5-[2-[4-[(3-tertbutyl-5-pentyl-1H-1,2,4-triazol-1-yl)methyl]phenyl]-3-pyridinyl]-1H-tetrazole;
5-[2-[4-[(3,5-dipentyl-1H-1,2,4-triazol-1-yl)methyl]phenyl]-3-pyridinyl]-1H-tetrazole;
5-[2-[4-[(3-isopentyl-5-pentyl-1H-1,2,4-triazol-1-yl)methyl]phenyl]-3-pyridinyl]-1H-tetrazole;
5-[2-[4-[(3-cyclohexyl-5-pentyl-1H-1,2,4-triazol-1-yl)methyl]phenyl]-3-pyridinyl]-1H-tetrazole;
5-[2-[4-[(3-cyclohexylmethyl-5-pentyl-1H-1,2,4-triazol-1-yl)methyl]phenyl]-3-pyridinyl]-1H-tetrazole;
5-[2-[4-[(3-benzoyl-5-pentyl-1H-1,2,4-triazol-1-yl)methyl]phenyl]-3-pyridinyl]-1H-tetrazole;
5-[2-[4-[(3-phenyl-5-pentyl-1H-1,2,4-triazol-1-yl)methyl]phenyl]-3-pyridinyl]-1H-tetrazole;
5-[2-[4-[(3-phenylmethyl-5-pentyl-1H-1,2,4-triazol-1-yl)methyl]phenyl]-3-pyridinyl]-1H-tetrazole;
5-[2-[4-[(3-cyclohenanoyl-5-pentyl-1H-1,2,4-triazol-1-yl)methyl]phenyl]-3-pyridinyl]-1H-tetrazole;
5-[2-[4-[[3-(2-phenylethyl)-5-pentyl-1H-1,2,4-triazol-1-yl]methyl]phenyl]-3-pyridinyl]-1H-tetrazole;
5-[2-[4-[[3-(1-oxo-2-cyclohexylethyl)-5-pentyl-1H-1,2,4-triazol-1-yl]methyl]phenyl]-3-pyridinyl]-1H-tetrazole;
5-[2-[4-[[3-(2-cyclohexylethyl)-5-pentyl-1H-1,2,4-triazol-1-yl]methyl]phenyl]-3-pyridinyl]-1H-tetrazole;
5-[2-[4-[[3-(1-oxo-2-phenylethyl)-5-pentyl-1H-1,2,4-triazol-1-yl]methyl]phenyl]-3-pyridinyl]-1H-tetrazole;
5-[2-[4-[[3-(1,1-dimethoxypropyl)-5-pentyl-1H-1,2,4-triazol-1-yl]methyl]phenyl]-3-pyridinyl]-1H-tetrazole;
5-[2-[4-[[3-(1,1-dimethoxybutyl)-5-pentyl-1H-1,2,4-triazol-1-yl]methyl]phenyl]-3-pyridinyl]-1H-tetrazole;
5-[2-[4-[[3-(1,1-dimethoxypentyl)-5-pentyl-1H-1,2,4-triazol-1-yl]methyl]phenyl]-3-pyridinyl]-1H-tetrazole;
5-[2-[4-[[3-(1-oxopropyl)-5-pentyl-1H-1,2,4-triazol-1-yl]methyl]phenyl]-3-pyridinyl]-1H-tetrazole;
5-[2-[4-[[3-(1-oxobutyl)-5-pentyl-1H-1,2,4-triazol-1-yl]methyl]phenyl]-3-pyridinyl]-1H-tetrazole;
5-[2-[4-[[3-(1-oxopentyl)-5-pentyl-1H-1,2,4-triazol-1-yl]methyl]phenyl]-3-pyridinyl]-1H-tetrazole;
5-[2-[4-[[3-(1,1-difluorobutyl)-5-pentyl-1H-1,2,4-triazol-1-yl]methyl]phenyl]-3-pyridinyl]-1H-tetrazole;

A family of specific compounds of more particular interest within Formula IV consists of and pharmaceutically-acceptable salts thereof as follows:

2-[4-[(3-methyl-5-butyl-1H-1,2,4-triazol-1-yl)methyl]-phenyl]-3-pyridinecarboxylic acid;
2-[4-[(3-ethyl-5-butyl-1H-1,2,4-triazol-1-yl)methyl]-phenyl]-3-pyridinecarboxylic acid;
2-[4-[(3-propyl-5-butyl-1H-1,2,4-triazol-1-yl)methyl]-phenyl]-3-pyridinecarboxylic acid;
2-[4-[(3-isopropyl-5-butyl-1H-1,2,4-triazol-1-yl)methyl]-phenyl]-3-pyridinecarboxylic acid;
2-[4-[(3,5-dibutyl-1H-1,2,4-triazol-1-yl)methyl]phenyl]-3-pyridinecarboxylic acid;
2-[4-[(3-secbutyl-5-butyl-1H-1,2,4-triazol-1-yl)methyl]-phenyl]-3-pyridinecarboxylic acid;
2-[4-[(3-isobutyl-5-butyl-1H-1,2,4-triazol-1-yl)methyl]-phenyl]-3-pyridinecarboxylic acid;
2-[4-[(3-tertbutyl-5-butyl-1H-1,2,4-triazol-1-yl)methyl]-phenyl]-3-pyridinecarboxylic acid;
2-[4-[(3-pentyl-5-butyl-1H-1,2,4-triazol-1-yl)methyl]-phenyl]-3-pyridinecarboxylic acid;
2-[4-[(3-isopentyl-5-butyl-1H-1,2,4-triazol-1-yl)methyl]-phenyl]-3-pyridinecarboxylic acid;
2-[4-[(3-cyclohexyl-5-butyl-1H-1,2,4-triazol-1-yl)methyl]phenyl]-3-pyridinecarboxylic acid;
2-[4-[(3-cyclohexylmethyl-5-butyl-1H-1,2,4-triazol-1-yl)methyl]phenyl]-3-pyridinecarboxylic acid;
2-[4-[(3-phenyl-5-butyl-1H-1,2,4-triazol-1-yl)methyl]-phenyl]-3-pyridinecarboxylic acid;
2-[4-[(3-phenylmethyl-5-butyl-1H-1,2,4-triazol-1-yl)methyl]phenyl]-3-pyridinecarboxylic acid;
2-[4-[[3-(2-cyclohexylethyl)-5-butyl-1H-1,2,4-triazol-1-yl]methyl]phenyl]-3-pyridinecarboxylic acid;
2-[4-[[3-(2-phenylethyl)-5-butyl-1H-1,2,4-triazol-1-yl]methyl]phenyl]-3-pyridinecarboxylic acid;
2-[4-[[3-(1-oxo-2-phenylethyl)-5-butyl-1H-1,2,4-triazol-1-yl]methyl]phenyl]-3-pyridinecarboxylic acid;
2-[4-[[3-(1-oxobutyl)-5-butyl-1H-1,2,4-triazol-1-yl]methyl]phenyl]-3-pyridinecarboxylic acid;
2-[4-[[3-(1,1-difluorobutyl)-5-butyl-1H-1,2,4-triazol-1-yl]methyl]phenyl]-3-pyridinecarboxylic acid;
2-[4-[[3-(1,1-dimethoxybutyl)-5-butyl-1H-1,2,4-triazol-1-yl]methyl]phenyl]-3-pyridinecarboxylic acid;
5-[2-[4-[(3-methyl-5-butyl-1H-1,2,4-triazol-1-yl)methyl]phenyl]-3-pyridinyl]-1H-tetrazole;
5-[2-[4-[(3-ethyl-5-butyl-1H-1,2,4-triazol-1-yl)methyl]-phenyl]-3-pyridinyl]-1H-tetrazole;
5-[2-[4-[(3-propyl-5-butyl-1H-1,2,4-triazol-1-yl)methyl]-phenyl]-3-pyridinyl]-1H-tetrazole;
5-[2-[4-[(3-isopropyl-5-butyl-1H-1,2,4-triazol-1-yl)methyl]phenyl]-3-pyridinyl]-1H-tetrazole;
5-[2-[4-[(3,5-dibutyl-1H-1,2,4-triazol-1-yl)methyl]-phenyl]-3-pyridinyl]-1H-tetrazole;
5-[2-[4-[(3-secbutyl-5-butyl-1H-1,2,4-triazol-1-yl)methyl]phenyl]-3-pyridinyl]-1H-tetrazole;
5-[2-[4-[(3-isobutyl-5-butyl-1H-1,2,4-triazol-1-yl)methyl]phenyl]-3-pyridinyl]-1H-tetrazole;
5-[2-[4-[(3-tertbutyl-5-butyl-1H-1,2,4-triazol-1-yl)methyl]phenyl]-3-pyridinyl]-1H-tetrazole;
5-[2-[4-[(3-pentyl-5-butyl-1H-1,2,4-triazol-1-yl)methyl]-phenyl]-3-pyridinyl]-1H-tetrazole;
5-[2-[4-[(3-isopentyl-5-butyl-1H-1,2,4-triazol-1-yl)methyl]phenyl]-3-pyridinyl]-1H-tetrazole;
5-[2-[4-[(3-cyclohexyl-5-butyl-1H-1,2,4-triazol-1-yl)methyl]phenyl]-3-pyridinyl]-1H-tetrazole;
5-[2-[4-[(3-cyclohexylmethyl-5-butyl-1H-1,2,4-triazol-1-yl)methyl]phenyl]-3-pyridinyl]-1H-tetrazole;
5-[2-[4-[(3-phenyl-5-butyl-1H-1,2,4-triazol-1-yl)methyl]-phenyl]-3-pyridinyl]-1H-tetrazole;
5-[2-[4-[(3-phenylmethyl-5-butyl-1H-1,2,4-triazol-1-yl)methyl]phenyl]-3-pyridinyl]-1H-tetrazole;
5-[2-[4-[[3-(2-cyclohexylethyl)-5-butyl-1H-1,2,4-triazol-1-yl]methyl]phenyl]-3-pyridinyl]-1H-tetrazole;
5-[2-[4-[[3-(2-phenylethyl)-5-butyl-1H-1,2,4-triazol-1-yl]methyl]phenyl]-3-pyridinyl]-1H-tetrazole;
5-[2-[4-[[3-(1-oxo-2-phenylethyl)-5-butyl-1H-1,2,4-triazol-1-yl]methyl]phenyl]-3-pyridinyl]-1H-tetrazole;
5-[2-[4-[[3-(1-oxobutyl)-5-butyl-1H-1,2,4-triazol-1-yl]methyl]phenyl]-3-pyridinyl]-1H-tetrazole;
5-[2-[4-[[3-(1,1-difluorobutyl)-5-butyl-1H-1,2,4-triazol-1-yl]methyl]phenyl]-3-pyridinyl]-1H-tetrazole; and
5-[2-[4-[[3-(1,1-dimethoxybutyl)-5-butyl-1H-1,2,4-triazol-1-yl]methyl]phenyl]-3-pyridinyl]-1H-tetrazole.

A fourth subclass of compounds of Formula I which is of even more particular interest consists of those compounds of Formula V

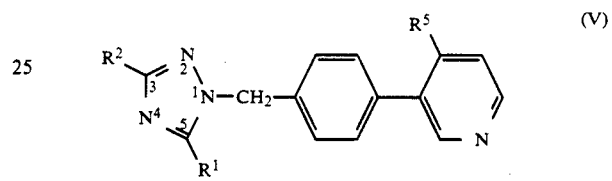

wherein m is one; wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, 2-butenyl, 3-butenyl, 2-butynyl, 3-butynyl and 2-hydroxybutyl; wherein $R^2$ is selected from ethyl, n-propyl, isopropyl, n-butyl, sec-butyl, isobutyl, 4-methylbutyl, n-pentyl, 1-oxo-2-phenylethyl, 1-oxo-2-cyclohexylethyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, 1-butenyl, 2-butenyl, 3-butenyl, 1-butynyl, 2-butynyl, 3-butynyl, propylthio and butylthio; wherein $R^5$ is an acidic group selected from $CO_2H$ and

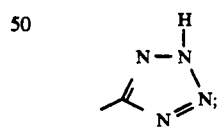

or a tautomer thereof or a pharmaceutically-acceptable salt thereof.

A family of specific compounds of particular interest within Formula V consists of compounds and pharmaceutically-acceptable salts thereof as follows:

3-[4-[(3-methyl-5-propyl-1H-1,2,4-triazol-1-yl)methyl]-phenyl]-4-pyridininecarboxylic acid;
3-[4-[(3-ethyl-5-propyl-1H-1,2,4-triazol-1-yl)methyl]-phenyl]-4-pyridininecarboxylic acid;
3-[4-[(3,5-dipropyl-1H-1,2,4-triazol-1-yl)methyl]-phenyl]-4-pyridininecarboxylic acid;
3-[4-[(3-isopropyl-5-propyl-1H-1,2,4-triazol-1-yl)methyl]phenyl]-4-pyridininecarboxylic acid;

3-[4-[(3-butyl-5-propyl-1H-1,2,4-triazol-1-yl)methyl]-phenyl]-4-pyridininecarboxylic acid;
3-[4-[(3-secbutyl-5-propyl-1H-1,2,4-triazol-1-yl)methyl]phenyl]-4-pyridininecarboxylic acid;
3-[4-[(3-isobutyl-5-propyl-1H-1,2,4-triazol-1-yl)methyl]-phenyl]-4-pyridininecarboxylic acid;
3-[4-[(3-tertbutyl-5-propyl-1H-1,2,4-triazol-1-yl)methyl]phenyl]-4-pyridininecarboxylic acid;
3-[4-[(3-pentyl-5-propyl-1H-1,2,4-triazol-1-yl)methyl]-phenyl]-4-pyridininecarboxylic acid;
3-[4-[(3-isopentyl-5-propyl-1H-1,2,4-triazol-1-yl)methyl]phenyl]-4-pyridininecarboxylic acid;
3-[4-[(3-cyclohexyl-5-propyl-1H-1,2,4-triazol-1-yl)methyl]phenyl]-4-pyridininecarboxylic acid;
3-[4-[(3-cyclohexylmethyl-5-propyl-1H-1,2,4-triazol-1-yl)methyl]phenyl]-4-pyridininecarboxylic acid;
3-[4-[(3-benzoyl-5-propyl-1H-1,2,4-triazol-1-yl)methyl]-phenyl]-4-pyridininecarboxylic acid;
3-[4-[(3-phenyl-5-propyl-1H-1,2,4-triazol-1-yl)methyl]-phenyl]-4-pyridininecarboxylic acid;
3-[4-[(3-phenylmethyl-5-propyl-1H-1,2,4-triazol-1-yl)methyl]phenyl]-4-pyridininecarboxylic acid;
3-[4-[(3-cyclohenanoyl-5-propyl-1H-1,2,4-triazol-1-yl)methyl]phenyl]-4-pyridininecarboxylic acid;
3-[4-[[3-(2-phenylethyl)-5-propyl-1H-1,2,4-triazol-1-yl]methyl]phenyl]-4-pyridininecarboxylic acid;
3-[4-[[3-(1-oxo-2-cyclohexylethyl)-5-propyl-1H-1,2,4-triazol-1-yl]methyl]phenyl]-4-pyridininecarboxylic acid;
3-[4-[[3-(2-cyclohexylethyl)-5-propyl-1H-1,2,4-triazol-1-yl]methyl]phenyl]-4-pyridininecarboxylic acid;
3-[4-[[3-(1-oxo-2-phenylethyl)-5-propyl-1H-1,2,4-triazol-1-yl]methyl]phenyl]-4-pyridininecarboxylic acid;
3-[4-[[3-(1,1-dimethoxypropyl)-5-propyl-1H-1,2,4-triazol-1-yl]methyl]phenyl]-4-pyridininecarboxylic acid;
3-[4-[[3-(1,1-dimethoxybutyl)-5-propyl-1H-1,2,4-triazol-1-yl]methyl]phenyl]-4-pyridininecarboxylic acid;
3-[4-[[3-(1,1-dimethoxypentyl)-5-propyl-1H-1,2,4-triazol-1-yl]methyl]phenyl]-4-pyridininecarboxylic acid;
3-[4-[[3-(1-oxopropyl)-5-propyl-1H-1,2,4-triazol-1-yl]methyl]phenyl]-4-pyridininecarboxylic acid;
3-[4-[[3-(1-oxobutyl)-5-propyl-1H-1,2,4-triazol-1-yl]methyl]phenyl]-4-pyridininecarboxylic acid;
3-[4-[[3-(1-oxopentyl)-5-propyl-1H-1,2,4-triazol-1-yl]methyl]phenyl]-4-pyridininecarboxylic acid;
3-[4-[[3-(1,1-difluorobutyl)-5-propyl-1H-1,2,4-triazol-1-yl]methyl]phenyl]-4-pyridininecarboxylic acid;
3-[4-[(3-methyl-5-butyl-1H-1,2,4-triazol-1-yl)methyl]phenyl]-4-pyridininecarboxylic acid;
3-[4-[(3-ethyl-5-butyl-1H-1,2,4-triazol-1-yl)methyl]phenyl]-4-pyridininecarboxylic acid;
3-[4-[(3-propyl-5-butyl-1H-1,2,4-triazol-1-yl)methyl]phenyl]-4-pyridininecarboxylic acid;
3-[4-[(3-isopropyl-5-butyl-1H-1,2,4-triazol-1-yl)methyl]phenyl]-4-pyridininecarboxylic acid;
3-[4-[(3,5-dibutyl-1H-1,2,4-triazol-1-yl)methyl]phenyl]-4-pyridininecarboxylic acid;
3-[4-[(3-secbutyl-5-butyl-1H-1,2,4-triazol-1-yl)methyl]phenyl]-4-pyridininecarboxylic acid;
3-[4-[(3-isobutyl-5-butyl-1H-1,2,4-triazol-1-yl)methyl]phenyl]-4-pyridininecarboxylic acid;
3-[4-[(3-tertbutyl-5-butyl-1H-1,2,4-triazol-1-yl)methyl]phenyl]-4-pyridininecarboxylic acid;
3-[4-[(3-pentyl-5-butyl-1H-1,2,4-triazol-1-yl)methyl]phenyl]-4-pyridininecarboxylic acid;
3-[4-[(3-isopentyl-5-butyl-1H-1,2,4-triazol-1-yl)methyl]phenyl]-4-pyridininecarboxylic acid;
3-[4-[(3-cyclohexyl-5-butyl-1H-1,2,4-triazol-1-yl)methyl]phenyl]-4-pyridininecarboxylic acid;
3-[4-[(3-cyclohexylmethyl-5-butyl-1H-1,2,4-triazol-1-yl)methyl]phenyl]-4-pyridininecarboxylic acid;
3-[4-[(3-benzoyl-5-butyl-1H-1,2,4-triazol-1-yl)methyl]phenyl]-4-pyridininecarboxylic acid;
3-[4-[(3-phenyl-5-butyl-1H-1,2,4-triazol-1-yl)methyl]phenyl]-4-pyridininecarboxylic acid;
3-[4-[(3-phenylmethyl-5-butyl-1H-1,2,4-triazol-1-yl)methyl]phenyl]-4-pyridininecarboxylic acid;
3-[4-[(3-cyclohenanoyl-5-butyl-1H-1,2,4-triazol-1-yl)methyl]phenyl]-4-pyridininecarboxylic acid;
3-[4-[[3-(2-phenylethyl)-5-butyl-1H-1,2,4-triazol-1-yl]methyl]phenyl]-4-pyridininecarboxylic acid;
3-[4-[[3-(1-oxo-2-cyclohexylethyl)-5-butyl-1H-1,2,4-triazol-1-yl]methyl]phenyl]-4-pyridininecarboxylic acid;
3-[4-[[3-(2-cyclohexylethyl)-5-butyl-1H-1,2,4-triazol-1-yl]methyl]phenyl]-4-pyridininecarboxylic acid;
3-[4-[[3-(1-oxo-2-phenylethyl)-5-butyl-1H-1,2,4-triazol-1-yl]methyl]phenyl]-4-pyridininecarboxylic acid;
3-[4-[[3-(1,1-dimethoxypropyl)-5-butyl-1H-1,2,4-triazol-1-yl]methyl]phenyl]-4-pyridininecarboxylic acid;
3-[4-[[3-(1,1-dimethoxybutyl)-5-butyl-1H-1,2,4-triazol-1-yl]methyl]phenyl]-4-pyridininecarboxylic acid;
3-[4-[[3-(1,1-dimethoxypentyl)-5-butyl-1H-1,2,4-triazol-1-yl]methyl]phenyl]-4-pyridininecarboxylic acid;
3-[4-[[3-(1-oxopropyl)-5-butyl-1H-1,2,4-triazol-1-yl]methyl]phenyl]-4-pyridininecarboxylic acid;
3-[4-[[3-(1-oxobutyl)-5-butyl-1H-1,2,4-triazol-1-yl]methyl]phenyl]-4-pyridininecarboxylic acid;
3-[4-[[3-(1-oxopentyl)-5-butyl-1H-1,2,4-triazol-1-yl]methyl]phenyl]-4-pyridininecarboxylic acid;
3-[4-[[3-(1,1-difluorobutyl)-5-butyl-1H-1,2,4-triazol-1-yl]methyl]phenyl]-4-pyridininecarboxylic acid;
3-[4-[(3-methyl-5-pentyl-1H-1,2,4-triazol-1-yl)methyl]-phenyl]-4-pyridininecarboxylic acid;
3-[4-[(3-ethyl-5-pentyl-1H-1,2,4-triazol-1-yl)methyl]-phenyl]-4-pyridininecarboxylic acid;
3-[4-[(3-propyl-5-pentyl-1H-1,2,4-triazol-1-yl)methyl]-phenyl]-4-pyridininecarboxylic acid;
3-[4-[(3-isopropyl-5-pentyl-1H-1,2,4-triazol-1-yl)methyl]phenyl]-4-pyridininecarboxylic acid;
3-[4-[(3-butyl-5-pentyl-1H-1,2,4-triazol-1-yl)methyl]-phenyl]-4-pyridininecarboxylic acid;
3-[4-[(3-secbutyl-5-pentyl-1H-1,2,4-triazol-1-yl)methyl]phenyl]-4-pyridininecarboxylic acid;
3-[4-[(3-isobutyl-5-pentyl-1H-1,2,4-triazol-1-yl)methyl]phenyl]-4-pyridininecarboxylic acid;
3-[4-[(3-tertbutyl-5-pentyl-1H-1,2,4-triazol-1-yl)methyl]phenyl]-4-pyridininecarboxylic acid;
3-[4-[(3,5-dipentyl-1H-1,2,4-triazol-1-yl)methyl]-phenyl]-4-pyridininecarboxylic acid;
3-[4-[(3-isopentyl-5-pentyl-1H-1,2,4-triazol-1-yl)methyl]phenyl]-4-pyridininecarboxylic acid;
3-[4-[(3-cyclohexyl-5-pentyl-1H-1,2,4-triazol-1-yl)methyl]phenyl]-4-pyridininecarboxylic acid;
3-[4-[(3-cyclohexylmethyl-5-pentyl-1H-1,2,4-triazol-1-yl)methyl]phenyl]-4-pyridininecarboxylic acid;
3-[4-[(3-benzoyl-5-pentyl-1H-1,2,4-triazol-1-yl)methyl]-phenyl]-4-pyridininecarboxylic acid;
3-[4-[(3-phenyl-5-pentyl-1H-1,2,4-triazol-1-yl)methyl]-phenyl]-4-pyridininecarboxylic acid;
3-[4-[(3-phenylmethyl-5-pentyl-1H-1,2,4-triazol-1-yl)methyl]phenyl]-4-pyridininecarboxylic acid;

3-[4-[(3-cyclohenanoyl-5-pentyl-1H-1,2,4-triazol-1-yl)methyl]phenyl]-4-pyridininecarboxylic acid;
3-[4-[[3-(2-phenylethyl)-5-pentyl-1H-1,2,4-triazol-1-yl]methyl]phenyl]-4-pyridininecarboxylic acid;
3-[4-[[3-(1-oxo-2-cyclohexylethyl)-5-pentyl-1H-1,2,4-triazol-1-yl]methyl]phenyl]-4-pyridininecarboxylic acid;
3-[4-[[3-(2-cyclohexylethyl)-5-pentyl-1H-1,2,4-triazol-1-yl]methyl]phenyl]-4-pyridininecarboxylic acid;
3-[4-[[3-(1-oxo-2-phenylethyl)-5-pentyl-1H-1,2,4-triazol-1-yl]methyl]phenyl]-4-pyridininecarboxylic acid;
3-[4-[[3-(1,1-dimethoxypropyl)-5-pentyl-1H-1,2,4-triazol-1-yl]methyl]phenyl]-4-pyridininecarboxylic acid;
3-[4-[[3-(1,1-dimethoxybutyl)-5-pentyl-1H-1,2,4-triazol-1-yl]methyl]phenyl]-4-pyridininecarboxylic acid;
3-[4-[[3-(1,1-dimethoxypentyl)-5-pentyl-1H-1,2,4-triazol-1-yl]methyl]phenyl]-4-pyridininecarboxylic acid;
3-[4-[[3-(1-oxopropyl)-5-pentyl-1H-1,2,4-triazol-1-yl]methyl]phenyl]-4-pyridininecarboxylic acid;
3-[4-[[3-(1-oxobutyl)-5-pentyl-1H-1,2,4-triazol-1-yl]methyl]phenyl]-4-pyridininecarboxylic acid;
3-[4-[[3-(1-oxopentyl)-5-pentyl-1H-1,2,4-triazol-1-yl]methyl]phenyl]-4-pyridininecarboxylic acid;
3-[4-[[3-(1,1-difluorobutyl)-5-pentyl-1H-1,2,4-triazol-1-yl]methyl]phenyl]-4-pyridininecarboxylic acid;
5-[3-[4-[(3-methyl-5-propyl-1H-1,2,4-triazol-1-yl)methyl]phenyl]-4-pyridinyl]-1H-tetrazole;
5-[3-[4-[(3-ethyl-5-propyl-1H-1,2,4-triazol-1-yl)methyl]phenyl]-4-pyridinyl]-1H-tetrazole;
5-[3-[4-[(3,5-dipropyl-1H-1,2,4-triazol-1-yl)methyl]phenyl]-4-pyridinyl]-1H-tetrazole;
5-[3-[4-[(3-isopropyl-5-propyl-1H-1,2,4-triazol-1-yl)methyl]phenyl]-4-pyridinyl]-1H-tetrazole;
5-[3-[4-[(3-butyl-5-propyl-1H-1,2,4-triazol-1-yl)methyl]phenyl]-4-pyridinyl]-1H-tetrazole;
5-[3-[4-[(3-secbutyl-5-propyl-1H-1,2,4-triazol-1-yl)methyl]phenyl]-4-pyridinyl]-1H-tetrazole;
5-[3-[4-[(3-isobutyl-5-propyl-1H-1,2,4-triazol-1-yl)methyl]phenyl]-4-pyridinyl]-1H-tetrazole;
5-[3-[4-[(3-tertbutyl-5-propyl-1H-1,2,4-triazol-1-yl)methyl]phenyl]-4-pyridinyl]-1H-tetrazole;
5-[3-[4-[(3-pentyl-5-propyl-1H-1,2,4-triazol-1-yl)methyl]phenyl]-4-pyridinyl]-1H-tetrazole;
5-[3-[4-[(3-isopentyl-5-propyl-1H-1,2,4-triazol-1-yl)methyl]phenyl]-4-pyridinyl]-1H-tetrazole;
5-[3-[4-[(3-cyclohexyl-5-propyl-1H-1,2,4-triazol-1-yl)methyl]phenyl]-4-pyridinyl]-1H-tetrazole;
5-[3-[4-[(3-cyclohexylmethyl-5-propyl-1H-1,2,4-triazol-1-yl)methyl]phenyl]-4-pyridinyl]-1H-tetrazole;
5-[3-[4-[(3-benzoyl-5-propyl-1H-1,2,4-triazol-1-yl)methyl]phenyl]-4-pyridinyl]-1H-tetrazole;
5-[3-[4-[(3-phenyl-5-propyl-1H-1,2,4-triazol-1-yl)methyl]phenyl]-4-pyridinyl]-1H-tetrazole;
5-[3-[4-[(3-phenylmethyl-5-propyl-1H-1,2,4-triazol-1-yl)methyl]phenyl]-4-pyridinyl]-1H-tetrazole;
5-[3-[4-[(3-cyclohenanoyl-5-propyl-1H-1,2,4-triazol-1-yl)methyl]phenyl]-4-pyridinyl]-1H-tetrazole;
5-[3-[4-[[3-(2-phenylethyl)-5-propyl-1H-1,2,4-triazol-1-yl]methyl]phenyl]-4-pyridinyl]-1H-tetrazole;
5-[3-[4-[[3-(1-oxo-2-cyclohexylethyl)-5-propyl-1H-1,2,4-triazol-1-yl]methyl]phenyl]-4-pyridinyl]-1H-tetrazole;
5-[3-[4-[[3-(2-cyclohexylethyl)-5-propyl-1H-1,2,4-triazol-1-yl]methyl]phenyl]-4-pyridinyl]-1H-tetrazole;
5-[3-[4-[[3-(1-oxo-2-phenylethyl)-5-propyl-1H-1,2,4-triazol-1-yl]methyl]phenyl]-4-pyridinyl]-1H-tetrazole;
5-[3-[4-[[3-(1,1-dimethoxypropyl)-5-propyl-1H-1,2,4-triazol-1-yl]methyl]phenyl]-4-pyridinyl]-1H-tetrazole;
5-[3-[4-[[3-(1,1-dimethoxybutyl)-5-propyl-1H-1,2,4-triazol-1-yl]methyl]phenyl]-4-pyridinyl]-1H-tetrazole;
5-[3-[4-[[3-(1,1-dimethoxypentyl)-5-propyl-1H-1,2,4-triazol-1-yl]methyl]phenyl]-4-pyridinyl]-1H-tetrazole;
5-[3-[4-[[3-(1-oxopropyl)-5-propyl-1H-1,2,4-triazol-1-yl]methyl]phenyl]-4-pyridinyl]-1H-tetrazole;
5-[3-[4-[[3-(1-oxobutyl)-5-propyl-1H-1,2,4-triazol-1-yl]methyl]phenyl]-4-pyridinyl]-1H-tetrazole;
5-[3-[4-[[3-(1-oxopentyl)-5-propyl-1H-1,2,4-triazol-1-yl]methyl]phenyl]-4-pyridinyl]-1H-tetrazole;
5-[3-[4-[[3-(1,1-difluorobutyl)-5-propyl-1H-1,2,4-triazol-1-yl]methyl]phenyl]-4-pyridinyl]-1H-tetrazole;
5-[3-[4-[(3-methyl-5-butyl-1H-1,2,4-triazol-1-yl)methyl]phenyl]-4-pyridinyl]-1H-tetrazole;
5-[3-[4-[(3-ethyl-5-butyl-1H-1,2,4-triazol-1-yl)methyl]phenyl]-4-pyridinyl]-1H-tetrazole;
5-[3-[4-[(3-propyl-5-butyl-1H-1,2,4-triazol-1-yl)methyl]phenyl]-4-pyridinyl]-1H-tetrazole;
5-[3-[4-[(3-isopropyl-5-butyl-1H-1,2,4-triazol-1-yl)methyl]phenyl]-4-pyridinyl]-1H-tetrazole;
5-[3-[4-[(3,5-dibutyl-1H-1,2,4-triazol-1-yl)methyl]phenyl]-4-pyridinyl]-1H-tetrazole;
5-[3-[4-[(3-secbutyl-5-butyl-1H-1,2,4-triazol-1-yl)methyl]phenyl]-4-pyridinyl]-1H-tetrazole;
5-[3-[4-[(3-isobutyl-5-butyl-1H-1,2,4-triazol-1-yl)methyl]phenyl]-4-pyridinyl]-1H-tetrazole;
5-[3-[4-[(3-tertbutyl-5-butyl-1H-1,2,4-triazol-1-yl)methyl]phenyl]-4-pyridinyl]-1H-tetrazole;
5-[3-[4-[(3-pentyl-5-butyl-1H-1,2,4-triazol-1-yl)methyl]phenyl]-4-pyridinyl]-1H-tetrazole;
5-[3-[4-[(3-isopentyl-5-butyl-1H-1,2,4-triazol-1-yl)methyl]phenyl]-4-pyridinyl]-1H-tetrazole;
5-[3-[4-[(3-cyclohexyl-5-butyl-1H-1,2,4-triazol-1-yl)methyl]phenyl]-4-pyridinyl]-1H-tetrazole;
5-[3-[4-[(3-cyclohexylmethyl-5-butyl-1H-1,2,4-triazol-1-yl)methyl]phenyl]-4-pyridinyl]-1H-tetrazole;
5-[3-[4-[(3-benzoyl-5-butyl-1H-1,2,4-triazol-1-yl)methyl]phenyl]-4-pyridinyl]-1H-tetrazole;
5-[3-[4-[(3-phenyl-5-butyl-1H-1,2,4-triazol-1-yl)methyl]phenyl]-4-pyridinyl]-1H-tetrazole;
5-[3-[4-[(3-phenylmethyl-5-butyl-1H-1,2,4-triazol-1-yl)methyl]phenyl]-4-pyridinyl]-1H-tetrazole;
5-[3-[4-[(3-cyclohenanoyl-5-butyl-1H-1,2,4-triazol-1-yl)methyl]phenyl]-4-pyridinyl]-1H-tetrazole;
5-[3-[4-[[3-(2-phenylethyl)-5-butyl-1H-1,2,4-triazol-1-yl]methyl]phenyl]-4-pyridinyl]-1H-tetrazole;
5-[3-[4-[[3-(1-oxo-2-cyclohexylethyl)-5-butyl-1H-1,2,4-triazol-1-yl]methyl]phenyl]-4-pyridinyl]-1H-tetrazole;
5-[3-[4-[[3-(2-cyclohexylethyl)-5-butyl-1H-1,2,4-triazol-1-yl]methyl]phenyl]-4-pyridinyl]-1H-tetrazole;
5-[3-[4-[[3-(1-oxo-2-phenylethyl)-5-butyl-1H-1,2,4-triazol-1-yl]methyl]phenyl]-4-pyridinyl]-1H-tetrazole;
5-[3-[4-[[3-(1,1-dimethoxypropyl)-5-butyl-1H-1,2,4-triazol-1-yl]methyl]phenyl]-4-pyridinyl]-1H-tetrazole;
5-[3-[4-[[3-(1,1-dimethoxybutyl)-5-butyl-1H-1,2,4-triazol-1-yl]methyl]phenyl]-4-pyridinyl]-1H-tetrazole;

5-[3-[4-[[3-(1,1-dimethoxypentyl)-5-butyl-1H-1,2,4-triazol-1-yl]methyl]phenyl]-4-pyridinyl]-1H-tetrazole;
5-[3-[4-[[3-(1-oxopropyl)-5-butyl-1H-1,2,4-triazol-1-yl]methyl]phenyl]-4-pyridinyl]-1H-tetrazole;
5-[3-[4-[[3-(1-oxobutyl)-5-butyl-1H-1,2,4-triazol-1-yl]methyl]phenyl]-4-pyridinyl]-1H-tetrazole;
5-[3-[4-[[3-(1-oxopentyl)-5-butyl-1H-1,2,4-triazol-1-yl]methyl]phenyl]-4-pyridinyl]-1H-tetrazole;
5-[3-[4-[[3-(1,1-difluorobutyl)-5-butyl-1H-1,2,4-triazol-1-yl]methyl]phenyl]-4-pyridinyl]-1H-tetrazole;
5-[3-[4-[(3-methyl-5-pentyl-1H-1,2,4-triazol-1-yl)methyl]phenyl]-4-pyridinyl]-1H-tetrazole;
5-[3-[4-[(3-ethyl-5-pentyl-1H-1,2,4-triazol-1-yl)methyl]phenyl]-4-pyridinyl]-1H-tetrazole;
5-[3-[4-[(3-propyl-5-pentyl-1H-1,2,4-triazol-1-yl)methyl]phenyl]-4-pyridinyl]-1H-tetrazole;
5-[3-[4-[(3-isopropyl-5-pentyl-1H-1,2,4-triazol-1-yl)methyl]phenyl]-4-pyridinyl]-1H-tetrazole;
5-[3-[4-[(3-butyl-5-pentyl-1H-1,2,4-triazol-1-yl)methyl]phenyl]-4-pyridinyl]-1H-tetrazole;
5-[3-[4-[(3-secbutyl-5-pentyl-1H-1,2,4-triazol-1-yl)methyl]phenyl]-4-pyridinyl]-1H-tetrazole;
5-[3-[4-[(3-isobutyl-5-pentyl-1H-1,2,4-triazol-1-yl)methyl]phenyl]-4-pyridinyl]-1H-tetrazole;
5-[3-[4-[(3-tertbutyl-5-pentyl-1H-1,2,4-triazol-1-yl)methyl]phenyl]-4-pyridinyl]-1H-tetrazole;
5-[3-[4-[(3,5-dipentyl-1H-1,2,4-triazol-1-yl)methyl]phenyl]-4-pyridinyl]-1H-tetrazole;
5-[3-[4-[(3-isopentyl-5-pentyl-1H-1,2,4-triazol-1-yl)methyl]phenyl]-4-pyridinyl]-1H-tetrazole;
5-[3-[4-[(3-cyclohexyl-5-pentyl-1H-1,2,4-triazol-1-yl)methyl]phenyl]-4-pyridinyl]-1H-tetrazole;
5-[3-[4-[(3-cyclohexylmethyl-5-pentyl-1H-1,2,4-triazol-1-yl)methyl]phenyl]-4-pyridinyl]-1H-tetrazole;
5-[3-[4-[(3-benzoyl-5-pentyl-1H-1,2,4-triazol-1-yl)methyl]phenyl]-4-pyridinyl]-1H-tetrazole;
5-[3-[4-[(3-phenyl-5-pentyl-1H-1,2,4-triazol-1-yl)methyl]phenyl]-4-pyridinyl]-1H-tetrazole;
5-[3-[4-[(3-phenylmethyl-5-pentyl-1H-1,2,4-triazol-1-yl)methyl]phenyl]-4-pyridinyl]-1H-tetrazole;
5-[3-[4-[(3-cyclohenanoyl-5-pentyl-1H-1,2,4-triazol-1-yl)methyl]phenyl]-4-pyridinyl]-1H-tetrazole;
5-[3-[4-[[3-(2-phenylethyl)-5-pentyl-1H-1,2,4-triazol-1-yl]methyl]phenyl]-4-pyridinyl]-1H-tetrazole;
5-[3-[4-[[3-(1-oxo-2-cyclohexylethyl)-5-pentyl-1H-1,2,4-triazol-1-yl]methyl]phenyl]-4-pyridinyl]-1H-tetrazole;
5-[3-[4-[[3-(2-cyclohexylethyl)-5-pentyl-1H-1,2,4-triazol-1-yl]methyl]phenyl]-4-pyridinyl]-1H-tetrazole;
5-[3-[4-[[3-(1-oxo-2-phenylethyl)-5-pentyl-1H-1,2,4-triazol-1-yl]methyl]phenyl]-4-pyridinyl]-1H-tetrazole;
5-[3-[4-[[3-(1,1-dimethoxypropyl)-5-pentyl-1H-1,2,4-triazol-1-yl]methyl]phenyl]-4-pyridinyl]-1H-tetrazole;
5-[3-[4-[[3-(1,1-dimethoxybutyl)-5-pentyl-1H-1,2,4-triazol-1-yl]methyl]phenyl]-4-pyridinyl]-1H-tetrazole;
5-[3-[4-[[3-(1,1-dimethoxypentyl)-5-pentyl-1H-1,2,4-triazol-1-yl]methyl]phenyl]-4-pyridinyl]-1H-tetrazole;
5-[3-[4-[[3-(1-oxopropyl)-5-pentyl-1H-1,2,4-triazol-1-yl]methyl]phenyl]-4-pyridinyl]-1H-tetrazole;
5-[3-[4-[[3-(1-oxobutyl)-5-pentyl-1H-1,2,4-triazol-1-yl]methyl]phenyl]-4-pyridinyl]-1H-tetrazole;
5-[3-[4-[[3-(1-oxopentyl)-5-pentyl-1H-1,2,4-triazol-1-yl]methyl]phenyl]-4-pyridinyl]-1H-tetrazole; and
5-[3-[4-[[3-(1,1-difluorobutyl)-5-pentyl-1H-1,2,4-triazol-1-yl]methyl]phenyl]-4-pyridinyl]-1H-tetrazole.

A family of specific compounds of more particular interest within Formula V consists of compounds and pharmaceutically-acceptable salts thereof as follows:
3-[4-[(3-methyl-5-butyl-1H-1,2,4-triazol-1-yl)methyl]phenyl]-4-pyridinecarboxylic acid;
3-[4-[(3-ethyl-5-butyl-1H-1,2,4-triazol-1-yl)methyl]phenyl]-4-pyridinecarboxylic acid;
3-[4-[(3-propyl-5-butyl-1H-1,2,4-triazol-1-yl)methyl]phenyl]-4-pyridinecarboxylic acid;
3-[4-[(3-isopropyl-5-butyl-1H-1,2,4-triazol-1-yl)methyl]phenyl]-4-pyridinecarboxylic acid;
3-[4-[(3,5-dibutyl-1H-1,2,4-triazol-1-yl)methyl]phenyl]-4-pyridinecarboxylic acid;
3-[4-[(3-secbutyl-5-butyl-1H-1,2,4-triazol-1-yl)methyl]phenyl]-4-pyridinecarboxylic acid;
3-[4-[(3-isobutyl-5-butyl-1H-1,2,4-triazol-1-yl)methyl]phenyl]-4-pyridinecarboxylic acid;
3-[4-[(3-tertbutyl-5-butyl-1H-1,2,4-triazol-1-yl)methyl]phenyl]-4-pyridinecarboxylic acid;
3-[4-[(3-pentyl-5-butyl-1H-1,2,4-triazol-1-yl)methyl]phenyl]-4-pyridinecarboxylic acid;
3-[4-[(3-isopentyl-5-butyl-1H-1,2,4-triazol-1-yl)methyl]phenyl]-4-pyridinecarboxylic acid;
3-[4-[(3-cyclohexyl-5-butyl-1H-1,2,4-triazol-1-yl)methyl]phenyl]-4-pyridinecarboxylic acid;
3-[4-[(3-cyclohexylmethyl-5-butyl-1H-1,2,4-triazol-1-yl)methyl]phenyl]-4-pyridinecarboxylic acid;
3-[4-[(3-phenyl-5-butyl-1H-1,2,4-triazol-1-yl)methyl]phenyl]-4-pyridinecarboxylic acid;
3-[4-[(3-phenylmethyl-5-butyl-1H-1,2,4-triazol-1-yl)methyl]phenyl]-4-pyridinecarboxylic acid;
3-[4-[[3-(2-cyclohexylethyl)-5-butyl-1H-1,2,4-triazol-1-yl]methyl]phenyl]-4-pyridinecarboxylic acid;
3-[4-[[3-(2-phenylethyl)-5-butyl-1H-1,2,4-triazol-1-yl]methyl]phenyl]-4-pyridinecarboxylic acid;
3-[4-[[3-(1-oxo-2-phenylethyl)-5-butyl-1H-1,2,4-triazol-1-yl]methyl]phenyl]-4-pyridinecarboxylic acid;
3-[4-[[3-(1-oxobutyl)-5-butyl-1H-1,2,4-triazol-1-yl]methyl]phenyl]-4-pyridinecarboxylic acid;
3-[4-[[3-(1,1-difluorobutyl)-5-butyl-1H-1,2,4-triazol-1-yl]methyl]phenyl]-4-pyridinecarboxylic acid;
3-[4-[[3-(1,1-dimethoxybutyl)-5-butyl-1H-1,2,4-triazol-1-yl]methyl]phenyl]-4-pyridinecarboxylic acid;
5-[3-[4-[(3-methyl-5-butyl-1H-1,2,4-triazol-1-yl)methyl]phenyl]-4-pyridinyl]-1H-tetrazole;
5-[3-[4-[(3-ethyl-5-butyl-1H-1,2,4-triazol-1-yl)methyl]phenyl]-4-pyridinyl]-1H-tetrazole;
5-[3-[4-[(3-propyl-5-butyl-1H-1,2,4-triazol-1-yl)methyl]phenyl]-4-pyridinyl]-1H-tetrazole;
5-[3-[4-[(3-isopropyl-5-butyl-1H-1,2,4-triazol-1-yl)methyl]phenyl]-4-pyridinyl]-1H-tetrazole;
5-[3-[4-[(3,5-dibutyl-1H-1,2,4-triazol-1-yl)methyl]phenyl]-4-pyridinyl]-1H-tetrazole;
5-[3-[4-[(3-secbutyl-5-butyl-1H-1,2,4-triazol-1-yl)methyl]phenyl]-4-pyridinyl]-1H-tetrazole;
5-[3-[4-[(3-isobutyl-5-butyl-1H-1,2,4-triazol-1-yl)methyl]phenyl]-4-pyridinyl]-1H-tetrazole;
5-[3-[4-[(3-tertbutyl-5-butyl-1H-1,2,4-triazol-1-yl)methyl]phenyl]-4-pyridinyl]-1H-tetrazole;
5-[3-[4-[(3-pentyl-5-butyl-1H-1,2,4-triazol-1-yl)methyl]phenyl]-4-pyridinyl]-1H-tetrazole;
5-[3-[4-[(3-isopentyl-5-butyl-1H-1,2,4-triazol-1-yl)methyl]phenyl]-4-pyridinyl]-1H-tetrazole;

5-[3-[4-[(3-cyclohexyl-5-butyl-1H-1,2,4-triazol-1-yl)methyl]phenyl]-4-pyridinyl]-1H-tetrazole;
5-[3-[4-[(3-cyclohexylmethyl-5-butyl-1H-1,2,4-triazol-1-yl)methyl]phenyl]-4-pyridinyl]-1H-tetrazole;
5-[3-[4-[(3-phenyl-5-butyl-1H-1,2,4-triazol-1-yl)methyl]phenyl]-4-pyridinyl]-1H-tetrazole;
5-[3-[4-[(3-phenylmethyl-5-butyl-1H-1,2,4-triazol-1-yl)methyl]phenyl]-4-pyridinyl]-1H-tetrazole;
5-[3-[4-[[3-(2-cyclohexylethyl)-5-butyl-1H-1,2,4-triazol-1-yl]methyl]phenyl]-4-pyridinyl]-1H-tetrazole;
5-[3-[4-[[3-(2-phenylethyl)-5-butyl-1H-1,2,4-triazol-1-yl]methyl]phenyl]-4-pyridinyl]-1H-tetrazole;
5-[3-[4-[[3-(1-oxo-2-phenylethyl)-5-butyl-1H-1,2,4-triazol-1-yl]methyl]phenyl]-4-pyridinyl]-1H-tetrazole;
5-[3-[4-[[3-(1-oxobutyl)-5-butyl-1H-1,2,4-triazol-1-yl]methyl]phenyl]-4-pyridinyl]-1H-tetrazole;
5-[3-[4-[[3-(1,1-difluorobutyl)-5-butyl-1H-1,2,4-triazol-1-yl]methyl]phenyl]-4-pyridinyl]-1H-tetrazole; and
5-[3-[4-[[3-(1,1-dimethoxybutyl)-5-butyl-1H-1,2,4-triazol-1-yl]methyl]phenyl]-4-pyridinyl]-1H-tetrazole.

A fifth subclass of compounds of Formula I which is of even more particular interest consists of those compounds of Formula VI

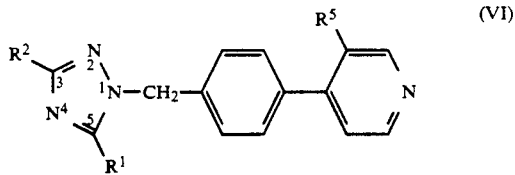

wherein m is one; wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, 2-butenyl, 3-butenyl, 2-butynyl, 3-butynyl and 2-hydroxybutyl; wherein $R^2$ is selected from ethyl, n-propyl, isopropyl, n-butyl, sec-butyl, isobutyl, 4-methylbutyl, n-pentyl, 1-oxo-2-phenylethyl, 1-oxo-2-cyclohexylethyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, 1-butenyl, 2-butenyl, 3-butenyl, 1-butynyl, 2-butynyl, 3-butynyl, propylthio and butylthio; wherein $R^5$ is an acidic group selected from $CO_2H$ and

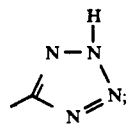

or a tautomer thereof or a pharmaceutically-acceptable salt thereof.

A family of specific compounds of particular interest within Formula VI consists of compounds and pharmaceutically-acceptable salts thereof as follows:
4-[4-[(3-methyl-5-propyl-1H-1,2,4-triazol-1-yl)methyl]phenyl]-3-pyridininecarboxylic acid;
4-[4-[(3-ethyl-5-propyl-1H-1,2,4-triazol-1-yl)methyl]phenyl]-3-pyridininecarboxylic acid;
4-[4-[(3,5-dipropyl-1H-1,2,4-triazol-1-yl)methyl]phenyl]-3-pyridininecarboxylic acid;
4-[4-[(3-isopropyl-5-propyl-1H-1,2,4-triazol-1-yl)methyl]phenyl]-3-pyridininecarboxylic acid;
4-[4-[(3-butyl-5-propyl-1H-1,2,4-triazol-1-yl)methyl]phenyl]-3-pyridininecarboxylic acid;
4-[4-[(3-secbutyl-5-propyl-1H-1,2,4-triazol-1-yl)methyl]phenyl]-3-pyridininecarboxylic acid;
4-[4-[(3-isobutyl-5-propyl-1H-1,2,4-triazol-1-yl)methyl]phenyl]-3-pyridininecarboxylic acid;
4-[4-[(3-tertbutyl-5-propyl-1H-1,2,4-triazol-1-yl)methyl]phenyl]-3-pyridininecarboxylic acid;
4-[4-[(3-pentyl-5-propyl-1H-1,2,4-triazol-1-yl)methyl]phenyl]-3-pyridininecarboxylic acid;
4-[4-[(3-isopentyl-5-propyl-1H-1,2,4-triazol-1-yl)methyl]phenyl]-3-pyridininecarboxylic acid;
4-[4-[(3-cyclohexyl-5-propyl-1H-1,2,4-triazol-1-yl)methyl]phenyl]-3-pyridininecarboxylic acid;
4-[4-[(3-cyclohexylmethyl-5-propyl-1H-1,2,4-triazol-1-yl)methyl]phenyl]-3-pyridininecarboxylic acid;
4-[4-[(3-benzoyl-5-propyl-1H-1,2,4-triazol-1-yl)methyl]phenyl]-3-pyridininecarboxylic acid;
4-[4-[(3-phenyl-5-propyl-1H-1,2,4-triazol-1-yl)methyl]phenyl]-3-pyridininecarboxylic acid;
4-[4-[(3-phenylmethyl-5-propyl-1H-1,2,4-triazol-1-yl)methyl]phenyl]-3-pyridininecarboxylic acid;
4-[4-[(3-cyclohenanoyl-5-propyl-1H-1,2,4-triazol-1-yl)methyl]phenyl]-3-pyridininecarboxylic acid;
4-[4-[[3-(2-phenylethyl)-5-propyl-1H-1,2,4-triazol-1-yl]methyl]phenyl]-3-pyridininecarboxylic acid;
4-[4-[[3-(1-oxo-2-cyclohexylethyl)-5-propyl-1H-1,2,4-triazol-1-yl]methyl]phenyl]-3-pyridininecarboxylic acid;
4-[4-[[3-(2-cyclohexylethyl)-5-propyl-1H-1,2,4-triazol-1-yl]methyl]phenyl]-3-pyridininecarboxylic acid;
4-[4-[[3-(1-oxo-2-phenylethyl)-5-propyl-1H-1,2,4-triazol-1-yl]methyl]phenyl]-3-pyridininecarboxylic acid;
4-[4-[[3-(1,1-dimethoxypropyl)-5-propyl-1H-1,2,4-triazol-1-yl]methyl]phenyl]-3-pyridininecarboxylic acid;
4-[4-[[3-(1,1-dimethoxybutyl)-5-propyl-1H-1,2,4-triazol-1-yl]methyl]phenyl]-3-pyridininecarboxylic acid;
4-[4-[[3-(1,1-dimethoxypentyl)-5-propyl-1H-1,2,4-triazol-1-yl]methyl]phenyl]-3-pyridininecarboxylic acid;
4-[4-[[3-(1-oxopropyl)-5-propyl-1H-1,2,4-triazol-1-yl]methyl]phenyl]-3-pyridininecarboxylic acid;
4-[4-[[3-(1-oxobutyl)-5-propyl-1H-1,2,4-triazol-1-yl]methyl]phenyl]-3-pyridininecarboxylic acid;
4-[4-[[3-(1-oxopentyl)-5-propyl-1H-1,2,4-triazol-1-yl]methyl]phenyl]-3-pyridininecarboxylic acid;
4-[4-[[3-(1,1-difluorobutyl)-5-propyl-1H-1,2,4-triazol-1-yl]methyl]phenyl]-3-pyridininecarboxylic acid;
4-[4-[(3-methyl-5-butyl-1H-1,2,4-triazol-1-yl)methyl]phenyl]-3-pyridininecarboxylic acid;
4-[4-[(3-ethyl-5-butyl-1H-1,2,4-triazol-1-yl)methyl]phenyl]-3-pyridininecarboxylic acid;
4-[4-[(3-propyl-5-butyl-1H-1,2,4-triazol-1-yl)methyl]phenyl]-3-pyridininecarboxylic acid;
4-[4-[(3-isopropyl-5-butyl-1H-1,2,4-triazol-1-yl)methyl]phenyl]-3-pyridininecarboxylic acid;
4-[4-[(3,5-dibutyl-1H-1,2,4-triazol-1-yl)methyl]phenyl]-3-pyridininecarboxylic acid;
4-[4-[(3-secbutyl-5-butyl-1H-1,2,4-triazol-1-yl)methyl]phenyl]-3-pyridininecarboxylic acid;
4-[4-[(3-isobutyl-5-butyl-1H-1,2,4-triazol-1-yl)methyl]phenyl]-3-pyridininecarboxylic acid;

4-[4-[(3-tertbutyl-5-butyl-1H-1,2,4-triazol-1-yl)methyl]-phenyl]-3-pyridininecarboxylic acid;
4-[4-[(3-pentyl-5-butyl-1H-1,2,4-triazol-1-yl)methyl]-phenyl]-3-pyridininecarboxylic acid;
4-[4-[(3-isopentyl-5-butyl-1H-1,2,4-triazol-1-yl)methyl]-phenyl]-3-pyridininecarboxylic acid;
4-[4-[(3-cyclohexyl-5-butyl-1H-1,2,4-triazol-1-yl)methyl]phenyl]-3-pyridininecarboxylic acid;
4-[4-[(3-cyclohexylmethyl-5-butyl-1H-1,2,4-triazol-1-yl)methyl]phenyl]-3-pyridininecarboxylic acid;
4-[4-[(3-benzoyl-5-butyl-1H-1,2,4-triazol-1-yl)methyl]-phenyl]-3-pyridininecarboxylic acid;
4-[4-[(3-phenyl-5-butyl-1H-1,2,4-triazol-1-yl)methyl]-phenyl]-3-pyridininecarboxylic acid;
4-[4-[(3-phenylmethyl-5-butyl-1H-1,2,4-triazol-1-yl)methyl]phenyl]-3-pyridininecarboxylic acid;
4-[4-[(3-cyclohenanoyl-5-butyl-1H-1,2,4-triazol-1-yl)methyl]phenyl]-3-pyridininecarboxylic acid;
4-[4-[[3-(2-phenylethyl)-5-butyl-1H-1,2,4-triazol-1-yl]methyl]phenyl]-3-pyridininecarboxylic acid;
4-[4-[[3-(1-oxo-2-cyclohexylethyl)-5-butyl-1H-1,2,4-triazol-1-yl]methyl]phenyl]-3-pyridininecarboxylic acid;
4-[4-[[3-(2-cyclohexylethyl)-5-butyl-1H-1,2,4-triazol-1-yl]methyl]phenyl]-3-pyridininecarboxylic acid;
4-[4-[[3-(1-oxo-2-phenylethyl)-5-butyl-1H-1,2,4-triazol-1-yl]methyl]phenyl]-3-pyridininecarboxylic acid;
4-[4-[[3-(1,1-dimethoxypropyl)-5-butyl-1H-1,2,4-triazol-1-yl]methyl]phenyl]-3-pyridininecarboxylic acid;
4-[4-[[3-(1,1-dimethoxybutyl)-5-butyl-1H-1,2,4-triazol-1-yl]methyl]phenyl]-3-pyridininecarboxylic acid;
4-[4-[[3-(1,1-dimethoxypentyl)-5-butyl-1H-1,2,4-triazol-1-yl]methyl]phenyl]-3-pyridininecarboxylic acid;
4-[4-[[3-(1-oxopropyl)-5-butyl-1H-1,2,4-triazol-1-yl]methyl]phenyl]-3-pyridininecarboxylic acid;
4-[4-[[3-(1-oxobutyl)-5-butyl-1H-1,2,4-triazol-1-yl]methyl]phenyl]-3-pyridininecarboxylic acid;
4-[4-[[3-(1-oxopentyl)-5-butyl-1H-1,2,4-triazol-1-yl]methyl]phenyl]-3-pyridininecarboxylic acid;
4-[4-[[3-(1,1-difluorobutyl)-5-butyl-1H-1,2,4-triazol-1-yl]methyl]phenyl]-3-pyridininecarboxylic acid;
4-[4-[(3-methyl-5-pentyl-1H-1,2,4-triazol-1-yl)methyl]-phenyl]-3-pyridininecarboxylic acid;
4-[4-[(3-ethyl-5-pentyl-1H-1,2,4-triazol-1-yl)methyl]-phenyl]-3-pyridininecarboxylic acid;
4-[4-[(3-propyl-5-pentyl-1H-1,2,4-triazol-1-yl)methyl]-phenyl]-3-pyridininecarboxylic acid;
4-[4-[(3-isopropyl-5-pentyl-1H-1,2,4-triazol-1-yl)methyl]phenyl]-3-pyridininecarboxylic acid;
4-[4-[(3-butyl-5-pentyl-1H-1,2,4-triazol-1-yl)methyl]-phenyl]-3-pyridininecarboxylic acid;
4-[4-[(3-secbutyl-5-pentyl-1H-1,2,4-triazol-1-yl)methyl]-phenyl]-3-pyridininecarboxylic acid;
4-[4-[(3-isobutyl-5-pentyl-1H-1,2,4-triazol-1-yl)methyl]-phenyl]-3-pyridininecarboxylic acid;
4-[4-[(3-tertbutyl-5-pentyl-1H-1,2,4-triazol-1-yl)methyl]-phenyl]-3-pyridininecarboxylic acid;
4-[4-[(3,5-dipentyl-1H-1,2,4-triazol-1-yl)methyl]-phenyl]-3-pyridininecarboxylic acid;
4-[4-[(3-isopentyl-5-pentyl-1H-1,2,4-triazol-1-yl)methyl]phenyl]-3-pyridininecarboxylic acid;
4-[4-[(3-cyclohexyl-5-pentyl-1H-1,2,4-triazol-1-yl)methyl]phenyl]-3-pyridininecarboxylic acid;
4-[4-[(3-cyclohexylmethyl-5-pentyl-1H-1,2,4-triazol-1-yl)methyl]phenyl]-3-pyridininecarboxylic acid;
4-[4-[(3-benzoyl-5-pentyl-1H-1,2,4-triazol-1-yl)methyl]-phenyl]-3-pyridininecarboxylic acid;
4-[4-[(3-phenyl-5-pentyl-1H-1,2,4-triazol-1-yl)methyl]-phenyl]-3-pyridininecarboxylic acid;
4-[4-[(3-phenylmethyl-5-pentyl-1H-1,2,4-triazol-1-yl)methyl]phenyl]-3-pyridininecarboxylic acid;
4-[4-[(3-cyclohenanoyl-5-pentyl-1H-1,2,4-triazol-1-yl)methyl]phenyl]-3-pyridininecarboxylic acid;
4-[4-[[3-(2-phenylethyl)-5-pentyl-1H-1,2,4-triazol-1-yl]methyl]phenyl]-3-pyridininecarboxylic acid;
4-[4-[[3-(1-oxo-2-cyclohexylethyl)-5-pentyl-1H-1,2,4-triazol-1-yl]methyl]phenyl]-3-pyridininecarboxylic acid;
4-[4-[[3-(2-cyclohexylethyl)-5-pentyl-1H-1,2,4-triazol-1-yl]methyl]phenyl]-3-pyridininecarboxylic acid;
4-[4-[[3-(1-oxo-2-phenylethyl)-5-pentyl-1H-1,2,4-triazol-1-yl]methyl]phenyl]-3-pyridininecarboxylic acid;
4-[4-[[3-(1,1-dimethoxypropyl)-5-pentyl-1H-1,2,4-triazol-1-yl]methyl]phenyl]-3-pyridininecarboxylic acid;
4-[4-[[3-(1,1-dimethoxybutyl)-5-pentyl-1H-1,2,4-triazol-1-yl]methyl]phenyl]-3-pyridininecarboxylic acid;
4-[4-[[3-(1,1-dimethoxypentyl)-5-pentyl-1H-1,2,4-triazol-1-yl]methyl]phenyl]-3-pyridininecarboxylic acid;
4-[4-[[3-(1-oxopropyl)-5-pentyl-1H-1,2,4-triazol-1-yl]methyl]phenyl]-3-pyridininecarboxylic acid;
4-[4-[[3-(1-oxobutyl)-5-pentyl-1H-1,2,4-triazol-1-yl]methyl]phenyl]-3-pyridininecarboxylic acid;
4-[4-[[3-(1-oxopentyl)-5-pentyl-1H-1,2,4-triazol-1-yl]methyl]phenyl]-3-pyridininecarboxylic acid;
4-[4-[[3-(1,1-difluorobutyl)-5-pentyl-1H-1,2,4-triazol-1-yl]methyl]phenyl]-3-pyridininecarboxylic acid;
5-[4-[4-[(3-methyl-5-propyl-1H-1,2,4-triazol-1-yl)methyl]phenyl]-3-pyridinyl]-1H-tetrazole;
5-[4-[4-[(3-ethyl-5-propyl-1H-1,2,4-triazol-1-yl)methyl]-phenyl]-3-pyridinyl]-1H-tetrazole;
5-[4-[4-[(3,5-dipropyl-1H-1,2,4-triazol-1-yl)methyl]-phenyl]-3-pyridinyl]-1H-tetrazole;
5-[4-[4-[(3-isopropyl-5-propyl-1H-1,2,4-triazol-1-yl)methyl]phenyl]-3-pyridinyl]-1H-tetrazole;
5-[4-[4-[(3-butyl-5-propyl-1H-1,2,4-triazol-1-yl)methyl]-phenyl]-3-pyridinyl]-1H-tetrazole;
5-[4-[4-[(3-secbutyl-5-propyl-1H-1,2,4-triazol-1-yl)methyl]phenyl]-3-pyridinyl]-1H-tetrazole;
5-[4-[4-[(3-isobutyl-5-propyl-1H-1,2,4-triazol-1-yl)methyl]phenyl]-3-pyridinyl]-1H-tetrazole;
5-[4-[4-[(3-tertbutyl-5-propyl-1H-1,2,4-triazol-1-yl)methyl]phenyl]-3-pyridinyl]-1H-tetrazole;
5-[4-[4-[(3-pentyl-5-propyl-1H-1,2,4-triazol-1-yl)methyl]phenyl]-3-pyridinyl]-1H-tetrazole;
5-[4-[4-[(3-isopentyl-5-propyl-1H-1,2,4-triazol-1-yl)methyl]phenyl]-3-pyridinyl]-1H-tetrazole;
5-[4-[4-[(3-cyclohexyl-5-propyl-1H-1,2,4-triazol-1-yl)methyl]phenyl]-3-pyridinyl]-1H-tetrazole;
5-[4-[4-[(3-cyclohexylmethyl-5-propyl-1H-1,2,4-triazol-1-yl)methyl]phenyl]-3-pyridinyl]-1H-tetrazole;
5-[4-[4-[(3-benzoyl-5-propyl-1H-1,2,4-triazol-1-yl)methyl]phenyl]-3-pyridinyl]-1H-tetrazole;
5-[4-[4-[(3-phenyl-5-propyl-1H-1,2,4-triazol-1-yl)methyl]phenyl]-3-pyridinyl]-1H-tetrazole;
5-[4-[4-[(3-phenylmethyl-5-propyl-1H-1,2,4-triazol-1-yl)methyl]phenyl]-3-pyridinyl]-1H-tetrazole;
5-[4-[4-[(3-cyclohenanoyl-5-propyl-1H-1,2,4-triazol-1-yl)methyl]phenyl]-3-pyridinyl]-1H-tetrazole;
5-[4-[4-[[3-(2-phenylethyl)-5-propyl-1H-1,2,4-triazol-1-yl]methyl]phenyl]-3-pyridinyl]-1H-tetrazole;

5-[4-[4-[[3-(1-oxo-2-cyclohexylethyl)-5-propyl-1H-1,2,4-triazol-1-yl]methyl]phenyl]-3-pyridinyl]-1H-tetrazole;

5-[4-[4-[[3-(2-cyclohexylethyl)-5-propyl-1H-1,2,4-triazol-1-yl]methyl]phenyl]-3-pyridinyl]-1H-tetrazole;

5-[4-[4-[[3-(1-oxo-2-phenylethyl)-5-propyl-1H-1,2,4-triazol-1-yl]methyl]phenyl]-3-pyridinyl]-1H-tetrazole;

5-[4-[4-[[3-(1,1-dimethoxypropyl)-5-propyl-1H-1,2,4-triazol-1-yl]methyl]phenyl]-3-pyridinyl]-1H-tetrazole;

5-[4-[4-[[3-(1,1-dimethoxybutyl)-5-propyl-1H-1,2,4-triazol-1-yl]methyl]phenyl]-3-pyridinyl]-1H-tetrazole;

5-[4-[4-[[3-(1,1-dimethoxypentyl)-5-propyl-1H-1,2,4-triazol-1-yl]methyl]phenyl]-3-pyridinyl]-1H-tetrazole;

5-[4-[4-[[3-(1-oxopropyl)-5-propyl-1H-1,2,4-triazol-1-yl]methyl]phenyl]-3-pyridinyl]-1H-tetrazole;

5-[4-[4-[[3-(1-oxobutyl)-5-propyl-1H-1,2,4-triazol-1-yl]methyl]phenyl]-3-pyridinyl]-1H-tetrazole;

5-[4-[4-[[3-(1-oxopentyl)-5-propyl-1H-1,2,4-triazol-1-yl]methyl]phenyl]-3-pyridinyl]-1H-tetrazole;

5-[4-[4-[[3-(1,1-difluorobutyl)-5-propyl-1H-1,2,4-triazol-1-yl]methyl]phenyl]-3-pyridinyl]-1H-tetrazole;

5-[4-[4-[(3-methyl-5-butyl-1H-1,2,4-triazol-1-yl)methyl]phenyl]-3-pyridinyl]-1H-tetrazole;

5-[4-[4-[(3-ethyl-5-butyl-1H-1,2,4-triazol-1-yl)methyl]phenyl]-3-pyridinyl]-1H-tetrazole;

5-[4-[4-[(3-propyl-5-butyl-1H-1,2,4-triazol-1-yl)methyl]phenyl]-3-pyridinyl]-1H-tetrazole;

5-[4-[4-[(3-isopropyl-5-butyl-1H-1,2,4-triazol-1-yl)methyl]phenyl]-3-pyridinyl]-1H-tetrazole;

5-[4-[4-[(3,5-dibutyl-1H-1,2,4-triazol-1-yl)methyl]phenyl]-3-pyridinyl]-1H-tetrazole;

5-[4-[4-[(3-secbutyl-5-butyl-1H-1,2,4-triazol-1-yl)methyl]phenyl]-3-pyridinyl]-1H-tetrazole;

5-[4-[4-[(3-isobutyl-5-butyl-1H-1,2,4-triazol-1-yl)methyl]phenyl]-3-pyridinyl]-1H-tetrazole;

5-[4-[4-[(3-tertbutyl-5-butyl-1H-1,2,4-triazol-1-yl)methyl]phenyl]-3-pyridinyl]-1H-tetrazole;

5-[4-[4-[(3-pentyl-5-butyl-1H-1,2,4-triazol-1-yl)methyl]phenyl]-3-pyridinyl]-1H-tetrazole;

5-[4-[4-[(3-isopentyl-5-butyl-1H-1,2,4-triazol-1-yl)methyl]phenyl]-3-pyridinyl]-1H-tetrazole;

5-[4-[4-[(3-cyclohexyl-5-butyl-1H-1,2,4-triazol-1-yl)methyl]phenyl]-3-pyridinyl]-1H-tetrazole;

5-[4-[4-[(3-cyclohexylmethyl-5-butyl-1H-1,2,4-triazol-1-yl)methyl]phenyl]-3-pyridinyl]-1H-tetrazole;

5-[4-[4-[(3-benzoyl-5-butyl-1H-1,2,4-triazol-1-yl)methyl]phenyl]-3-pyridinyl]-1H-tetrazole;

5-[4-[4-[(3-phenyl-5-butyl-1H-1,2,4-triazol-1-yl)methyl]phenyl]-3-pyridinyl]-1H-tetrazole;

5-[4-[4-[(3-phenylmethyl-5-butyl-1H-1,2,4-triazol-1-yl)methyl]phenyl]-3-pyridinyl]-1H-tetrazole;

5-[4-[4-[(3-cyclohenanoyl-5-butyl-1H-1,2,4-triazol-1-yl)methyl]phenyl]-3-pyridinyl]-1H-tetrazole;

5-[4-[4-[[3-(2-phenylethyl)-5-butyl-1H-1,2,4-triazol-1-yl]methyl]phenyl]-3-pyridinyl]-1H-tetrazole;

5-[4-[4-[[3-(1-oxo-2-cyclohexylethyl)-5-butyl-1H-1,2,4-triazol-1-yl]methyl]phenyl]-3-pyridinyl]-1H-tetrazole;

5-[4-[4-[[3-(2-cyclohexylethyl)-5-butyl-1H-1,2,4-triazol-1-yl]methyl]phenyl]-3-pyridinyl]-1H-tetrazole;

5-[4-[4-[[3-(1-oxo-2-phenylethyl)-5-butyl-1H-1,2,4-triazol-1-yl]methyl]phenyl]-3-pyridinyl]-1H-tetrazole;

5-[4-[4-[[3-(1,1-dimethoxypropyl)-5-butyl-1H-1,2,4-triazol-1-yl]methyl]phenyl]-3-pyridinyl]-1H-tetrazole;

5-[4-[4-[[3-(1,1-dimethoxybutyl)-5-butyl-1H-1,2,4-triazol-1-yl]methyl]phenyl]-3-pyridinyl]-1H-tetrazole;

5-[4-[4-[[3-(1,1-dimethoxypentyl)-5-butyl-1H-1,2,4-triazol-1-yl]methyl]phenyl]-3-pyridinyl]-1H-tetrazole;

5-[4-[4-[[3-(1-oxopropyl)-5-butyl-1H-1,2,4-triazol-1-yl]methyl]phenyl]-3-pyridinyl]-1H-tetrazole;

5-[4-[4-[[3-(1-oxobutyl)-5-butyl-1H-1,2,4-triazol-1-yl]methyl]phenyl]-3-pyridinyl]-1H-tetrazole;

5-[4-[4-[[3-(1-oxopentyl)-5-butyl-1H-1,2,4-triazol-1-yl]methyl]phenyl]-3-pyridinyl]-1H-tetrazole;

5-[4-[4-[[3-(1,1-difluorobutyl)-5-butyl-1H-1,2,4-triazol-1-yl]methyl]phenyl]-3-pyridinyl]-1H-tetrazole;

5-[4-[4-[(3-methyl-5-pentyl-1H-1,2,4-triazol-1-yl)methyl]phenyl]-3-pyridinyl]-1H-tetrazole;

5-[4-[4-[(3-ethyl-5-pentyl-1H-1,2,4-triazol-1-yl)methyl]phenyl]-3-pyridinyl]-1H-tetrazole;

5-[4-[4-[(3-propyl-5-pentyl-1H-1,2,4-triazol-1-yl)methyl]phenyl]-3-pyridinyl]-1H-tetrazole;

5-[4-[4-[(3-isopropyl-5-pentyl-1H-1,2,4-triazol-1-yl)methyl]phenyl]-3-pyridinyl]-1H-tetrazole;

5-[4-[4-[(3-butyl-5-pentyl-1H-1,2,4-triazol-1-yl)methyl]phenyl]-3-pyridinyl]-1H-tetrazole;

5-[4-[4-[(3-secbutyl-5-pentyl-1H-1,2,4-triazol-1-yl)methyl]phenyl]-3-pyridinyl]-1H-tetrazole;

5-[4-[4-[(3-isobutyl-5-pentyl-1H-1,2,4-triazol-1-yl)methyl]phenyl]-3-pyridinyl]-1H-tetrazole;

5-[4-[4-[(3-tertbutyl-5-pentyl-1H-1,2,4-triazol-1-yl)methyl]phenyl]-3-pyridinyl]-1H-tetrazole;

5-[4-[4-[(3,5-dipentyl-1H-1,2,4-triazol-1-yl)methyl]phenyl]-3-pyridinyl]-1H-tetrazole;

5-[4-[4-[(3-isopentyl-5-pentyl-1H-1,2,4-triazol-1-yl)methyl]phenyl]-3-pyridinyl]-1H-tetrazole;

5-[4-[4-[(3-cyclohexyl-5-pentyl-1H-1,2,4-triazol-1-yl)methyl]phenyl]-3-pyridinyl]-1H-tetrazole;

5-[4-[4-[(3-cyclohexylmethyl-5-pentyl-1H-1,2,4-triazol-1-yl)methyl]phenyl]-3-pyridinyl]-1H-tetrazole;

5-[4-[4-[(3-benzoyl-5-pentyl-1H-1,2,4-triazol-1-yl)methyl]phenyl]-3-pyridinyl]-1H-tetrazole;

5-[4-[4-[(3-phenyl-5-pentyl-1H-1,2,4-triazol-1-yl)methyl]phenyl]-3-pyridinyl]-1H-tetrazole;

5-[4-[4-[(3-phenylmethyl-5-pentyl-1H-1,2,4-triazol-1-yl)methyl]phenyl]-3-pyridinyl]-1H-tetrazole;

5-[4-[4-[(3-cyclohenanoyl-5-pentyl-1H-1,2,4-triazol-1-yl)methyl]phenyl]-3-pyridinyl]-1H-tetrazole;

5-[4-[4-[[3-(2-phenylethyl)-5-pentyl-1H-1,2,4-triazol-1-yl]methyl]phenyl]-3-pyridinyl]-1H-tetrazole;

5-[4-[4-[[3-(1-oxo-2-cyclohexylethyl)-5-pentyl-1H-1,2,4-triazol-1-yl]methyl]phenyl]-3-pyridinyl]-1H-tetrazole;

5-[4-[4-[[3-(2-cyclohexylethyl)-5-pentyl-1H-1,2,4-triazol-1-yl]methyl]phenyl]-3-pyridinyl]-1H-tetrazole;

5-[4-[4-[[3-(1-oxo-2-phenylethyl)-5-pentyl-1H-1,2,4-triazol-1-yl]methyl]phenyl]-3-pyridinyl]-1H-tetrazole;

5-[4-[4-[[3-(1,1-dimethoxypropyl)-5-pentyl-1H-1,2,4-triazol-1-yl]methyl]phenyl]-3-pyridinyl]-1H-tetrazole;

5-[4-[4-[[3-(1,1-dimethoxybutyl)-5-pentyl-1H-1,2,4-triazol-1-yl]methyl]phenyl]-3-pyridinyl]-1H-tetrazole;

5-[4-[4-[[3-(1,1-dimethoxypentyl)-5-pentyl-1H-1,2,4-triazol-1-yl]methyl]phenyl]-3-pyridinyl]-1H-tetrazole;
5-[4-[4-[[3-(1-oxopropyl)-5-pentyl-1H-1,2,4-triazol-1-yl]methyl]phenyl]-3-pyridinyl]-1H-tetrazole;
5-[4-[4-[[3-(1-oxobutyl)-5-pentyl-1H-1,2,4-triazol-1-yl]methyl]phenyl]-3-pyridinyl]-1H-tetrazole;
5-[4-[4-[[3-(1-oxopentyl)-5-pentyl-1H-1,2,4-triazol-1-yl]methyl]phenyl]-3-pyridinyl]-1H-tetrazole; and
5-[4-[4-[[3-(1,1-difluorobutyl)-5-pentyl-1H-1,2,4-triazol-1-yl]methyl]phenyl]-3-pyridinyl]-1H-tetrazole.

A family of specific compounds of more particular interest within Formula VI consists of the following compounds and pharmaceutically-acceptable salts thereof as follows:

4-[4-[(3-methyl-5-butyl-1H-1,2,4-triazol-1-yl)methyl]phenyl]-3-pyridinecarboxylic acid;
4-[4-[(3-ethyl-5-butyl-1H-1,2,4-triazol-1-yl)methyl]phenyl]-3-pyridinecarboxylic acid;
4-[4-[(3-propyl-5-butyl-1H-1,2,4-triazol-1-yl)methyl]phenyl]-3-pyridinecarboxylic acid;
4-[4-[(3-isopropyl-5-butyl-1H-1,2,4-triazol-1-yl)methyl]phenyl]-3-pyridinecarboxylic acid;
4-[4-[(3,5-dibutyl-1H-1,2,4-triazol-1-yl)methyl]phenyl]-3-pyridinecarboxylic acid;
4-[4-[(3-secbutyl-5-butyl-1H-1,2,4-triazol-1-yl)methyl]phenyl]-3-pyridinecarboxylic acid;
4-[4-[(3-isobutyl-5-butyl-1H-1,2,4-triazol-1-yl)methyl]phenyl]-3-pyridinecarboxylic acid;
4-[4-[(3-tertbutyl-5-butyl-1H-1,2,4-triazol-1-yl)methyl]phenyl]-3-pyridinecarboxylic acid;
4-[4-[(3-pentyl-5-butyl-1H-1,2,4-triazol-1-yl)methyl]phenyl]-3-pyridinecarboxylic acid;
4-[4-[(3-isopentyl-5-butyl-1H-1,2,4-triazol-1-yl)methyl]phenyl]-3-pyridinecarboxylic acid;
4-[4-[(3-cyclohexyl-5-butyl-1H-1,2,4-triazol-1-yl)methyl]phenyl]-3-pyridinecarboxylic acid;
4-[4-[(3-cyclohexylmethyl-5-butyl-1H-1,2,4-triazol-1-yl)methyl]phenyl]-3-pyridinecarboxylic acid;
4-[4-[(3-phenyl-5-butyl-1H-1,2,4-triazol-1-yl)methyl]phenyl]-3-pyridinecarboxylic acid;
4-[4-[(3-phenylmethyl-5-butyl-1H-1,2,4-triazol-1-yl)methyl]phenyl]-3-pyridinecarboxylic acid;
4-[4-[[3-(2-cyclohexylethyl)-5-butyl-1H-1,2,4-triazol-1-yl]methyl]phenyl]-3-pyridinecarboxylic acid;
4-[4-[[3-(2-phenylethyl)-5-butyl-1H-1,2,4-triazol-1-yl]methyl]phenyl]-3-pyridinecarboxylic acid;
4-[4-[[3-(1-oxo-2-phenylethyl)-5-butyl-1H-1,2,4-triazol-1-yl]methyl]phenyl]-3-pyridinecarboxylic acid;
4-[4-[[3-(1-oxobutyl)-5-butyl-1H-1,2,4-triazol-1-yl]methyl]phenyl]-3-pyridinecarboxylic acid;
4-[4-[[3-(1,1-difluorobutyl)-5-butyl-1H-1,2,4-triazol-1-yl]methyl]phenyl]-3-pyridinecarboxylic acid;
4-[4-[[3-(1,1-dimethoxybutyl)-5-butyl-1H-1,2,4-triazol-1-yl]methyl]phenyl]-3-pyridinecarboxylic acid;
5-[4-[4-[(3-methyl-5-butyl-1H-1,2,4-triazol-1-yl)methyl]phenyl]-3-pyridinyl]-1H-tetrazole;
5-[4-[4-[(3-ethyl-5-butyl-1H-1,2,4-triazol-1-yl)methyl]phenyl]-3-pyridinyl]-1H-tetrazole;
5-[4-[4-[(3-propyl-5-butyl-1H-1,2,4-triazol-1-yl)methyl]phenyl]-3-pyridinyl]-1H-tetrazole;
5-[4-[4-[(3-isopropyl-5-butyl-1H-1,2,4-triazol-1-yl)methyl]phenyl]-3-pyridinyl]-1H-tetrazole;
5-[4-[4-[(3,5-dibutyl-1H-1,2,4-triazol-1-yl)methyl]phenyl]-3-pyridinyl]-1H-tetrazole;
5-[4-[4-[(3-secbutyl-5-butyl-1H-1,2,4-triazol-1-yl)methyl]phenyl]-3-pyridinyl]-1H-tetrazole;
5-[4-[4-[(3-isobutyl-5-butyl-1H-1,2,4-triazol-1-yl)methyl]phenyl]-3-pyridinyl]-1H-tetrazole;
5-[4-[4-[(3-tertbutyl-5-butyl-1H-1,2,4-triazol-1-yl)methyl]phenyl]-3-pyridinyl]-1H-tetrazole;
5-[4-[4-[(3-pentyl-5-butyl-1H-1,2,4-triazol-1-yl)methyl]phenyl]-3-pyridinyl]-1H-tetrazole;
5-[4-[4-[(3-isopentyl-5-butyl-1H-1,2,4-triazol-1-yl)methyl]phenyl]-3-pyridinyl]-1H-tetrazole;
5-[4-[4-[(3-cyclohexyl-5-butyl-1H-1,2,4-triazol-1-yl)methyl]phenyl]-3-pyridinyl]-1H-tetrazole;
5-[4-[4-[(3-cyclohexylmethyl-5-butyl-1H-1,2,4-triazol-1-yl)methyl]phenyl]-3-pyridinyl]-1H-tetrazole;
5-[4-[4-[(3-phenyl-5-butyl-1H-1,2,4-triazol-1-yl)methyl]phenyl]-3-pyridinyl]-1H-tetrazole;
5-[4-[4-[(3-phenylmethyl-5-butyl-1H-1,2,4-triazol-1-yl)methyl]phenyl]-3-pyridinyl]-1H-tetrazole;
5-[4-[4-[[3-(2-cyclohexylethyl)-5-butyl-1H-1,2,4-triazol-1-yl]methyl]phenyl]-3-pyridinyl]-1H-tetrazole;
5-[4-[4-[[3-(2-phenylethyl)-5-butyl-1H-1,2,4-triazol-1-yl]methyl]phenyl]-3-pyridinyl]-1H-tetrazole;
5-[4-[4-[[3-(1-oxo-2-phenylethyl)-5-butyl-1H-1,2,4-triazol-1-yl]methyl]phenyl]-3-pyridinyl]-1H-tetrazole;
5-[4-[4-[[3-(1-oxobutyl)-5-butyl-1H-1,2,4-triazol-1-yl]methyl]phenyl]-3-pyridinyl]-1H-tetrazole;
5-[4-[4-[[3-(1,1-difluorobutyl)-5-butyl-1H-1,2,4-triazol-1-yl]methyl]phenyl]-3-pyridinyl]-1H-tetrazole; and
5-[4-[4-[[3-(1,1-dimethoxybutyl)-5-butyl-1H-1,2,4-triazol-1-yl]methyl]phenyl]-3-pyridinyl]-1H-tetrazole.

A sixth subclass of compounds of Formula I which is of even more particular interest consists of those compounds of Formula VII

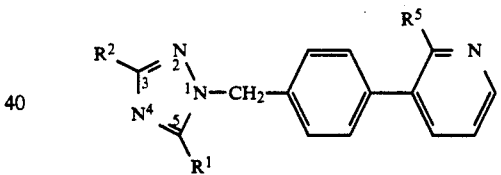

wherein m is one; wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, 2-butenyl, 3-butenyl, 2-butynyl, 3-butynyl and 2-hydroxybutyl; wherein $R^2$ is selected from ethyl, n-propyl, isopropyl, n-butyl, sec-butyl, isobutyl, 4-methylbutyl, n-pentyl, 1-oxo-2-phenylethyl, 1-oxo-2-cyclohexylethyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, 1-butenyl, 2-butenyl, 3-butenyl, 1-butynyl, 2-butynyl, 3-butynyl, propylthio and butylthio; wherein $R^5$ is an acidic group selected from $CO_2H$ and

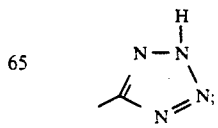

or a tautomer thereof or a pharmaceutically-acceptable salt thereof.

A family of specific compounds of particular interest within Formula VII consists of compounds and pharmaceutically-acceptable salts thereof as follows:

3-[4-[(3-methyl-5-propyl-1H-1,2,4-triazol-1-yl)methyl]phenyl]-2-pyridininecarboxylic acid;
3-[4-[(3-ethyl-5-propyl-1H-1,2,4-triazol-1-yl)methyl]phenyl]-2-pyridininecarboxylic acid;
3-[4-[(3,5-dipropyl-1H-1,2,4-triazol-1-yl)methyl]phenyl]-2-pyridininecarboxylic acid;
3-[4-[(3-isopropyl-5-propyl-1H-1,2,4-triazol-1-yl)methyl]phenyl]-2-pyridininecarboxylic acid;
3-[4-[(3-butyl-5-propyl-1H-1,2,4-triazol-1-yl)methyl]phenyl]-2-pyridininecarboxylic acid;
3-[4-[(3-secbutyl-5-propyl-1H-1,2,4-triazol-1-yl)methyl]phenyl]-2-pyridininecarboxylic acid;
3-[4-[(3-isobutyl-5-propyl-1H-1,2,4-triazol-1-yl)methyl]phenyl]-2-pyridininecarboxylic acid;
3-[4-[(3-tertbutyl-5-propyl-1H-1,2,4-triazol-1-yl)methyl]phenyl]-2-pyridininecarboxylic acid;
3-[4-[(3-pentyl-5-propyl-1H-1,2,4-triazol-1-yl)methyl]phenyl]-2-pyridininecarboxylic acid;
3-[4-[(3-isopentyl-5-propyl-1H-1,2,4-triazol-1-yl)methyl]phenyl]-2-pyridininecarboxylic acid;
3-[4-[(3-cyclohexyl-5-propyl-1H-1,2,4-triazol-1-yl)methyl]phenyl]-2-pyridininecarboxylic acid;
3-[4-[(3-cyclohexylmethyl-5-propyl-1H-1,2,4-triazol-1-yl)methyl]phenyl]-2-pyridininecarboxylic acid;
3-[4-[(3-benzoyl-5-propyl-1H-1,2,4-triazol-1-yl)methyl]phenyl]-2-pyridininecarboxylic acid;
3-[4-[(3-phenyl-5-propyl-1H-1,2,4-triazol-1-yl)methyl]phenyl]-2-pyridininecarboxylic acid;
3-[4-[(3-phenylmethyl-5-propyl-1H-1,2,4-triazol-1-yl)methyl]phenyl]-2-pyridininecarboxylic acid;
3-[4-[(3-cyclohenanoyl-5-propyl-1H-1,2,4-triazol-1-yl)methyl]phenyl]-2-pyridininecarboxylic acid;
3-[4-[[3-(2-phenylethyl)-5-propyl-1H-1,2,4-triazol-1-yl]methyl]phenyl]-2-pyridininecarboxylic acid;
3-[4-[(3-(1-oxo-2-cyclohexylethyl)-5-propyl-1H-1,2,4-triazol-1-yl]methyl]phenyl]-2-pyridininecarboxylic acid;
3-[4-[[3-(2-cyclohexylethyl)-5-propyl-1H-1,2,4-triazol-1-yl]methyl]phenyl]-2-pyridininecarboxylic acid;
3-[4-[[3-(1-oxo-2-phenylethyl)-5-propyl-1H-1,2,4-triazol-1-yl]methyl]phenyl]-2-pyridininecarboxylic acid;
3-[4-[[3-(1,1-dimethoxypropyl)-5-propyl-1H-1,2,4-triazol-1-yl]methyl]phenyl]-2-pyridininecarboxylic acid;
3-[4-[[3-(1,1-dimethoxybutyl)-5-propyl-1H-1,2,4-triazol-1-yl]methyl]phenyl]-2-pyridininecarboxylic acid;
3-[4-[[3-(1,1-dimethoxypentyl)-5-propyl-1H-1,2,4-triazol-1-yl]methyl]phenyl]-2-pyridininecarboxylic acid;
3-[4-[[3-(1-oxopropyl)-5-propyl-1H-1,2,4-triazol-1-yl]methyl]phenyl]-2-pyridininecarboxylic acid;
3-[4-[[3-(1-oxobutyl)-5-propyl-1H-1,2,4-triazol-1-yl]methyl]phenyl]-2-pyridininecarboxylic acid;
3-[4-[[3-(1-oxopentyl)-5-propyl-1H-1,2,4-triazol-1-yl]methyl]phenyl]-2-pyridininecarboxylic acid;
3-[4-[[3-(1,1-difluorobutyl)-5-propyl-1H-1,2,4-triazol-1-yl]methyl]phenyl]-2-pyridininecarboxylic acid;
3-[4-[(3-methyl-5-butyl-1H-1,2,4-triazol-1-yl)methyl]phenyl]-2-pyridininecarboxylic acid;
3-[4-[(3-ethyl-5-butyl-1H-1,2,4-triazol-1-yl)methyl]phenyl]-2-pyridininecarboxylic acid;
3-[4-[(3-propyl-5-butyl-1H-1,2,4-triazol-1-yl)methyl]phenyl]-2-pyridininecarboxylic acid;
3-[4-[(3-isopropyl-5-butyl-1H-1,2,4-triazol-1-yl)methyl]phenyl]-2-pyridininecarboxylic acid;
3-[4-[(3,5-dibutyl-1H-1,2,4-triazol-1-yl)methyl]phenyl]-2-pyridininecarboxylic acid;
3-[4-[(3-secbutyl-5-butyl-1H-1,2,4-triazol-1-yl)methyl]phenyl]-2-pyridininecarboxylic acid;
3-[4-[(3-isobutyl-5-butyl-1H-1,2,4-triazol-1-yl)methyl]phenyl]-2-pyridininecarboxylic acid;
3-[4-[(3-tertbutyl-5-butyl-1H-1,2,4-triazol-1-yl)methyl]phenyl]-2-pyridininecarboxylic acid;
3-[4-[(3-pentyl-5-butyl-1H-1,2,4-triazol-1-yl)methyl]phenyl]-2-pyridininecarboxylic acid;
3-[4-[(3-isopentyl-5-butyl-1H-1,2,4-triazol-1-yl)methyl]phenyl]-2-pyridininecarboxylic acid;
3-[4-[(3-cyclohexyl-5-butyl-1H-1,2,4-triazol-1-yl)methyl]phenyl]-2-pyridininecarboxylic acid;
3-[4-[(3-cyclohexylmethyl-5-butyl-1H-1,2,4-triazol-1-yl)methyl]phenyl]-2-pyridininecarboxylic acid;
3-[4-[(3-benzoyl-5-butyl-1H-1,2,4-triazol-1-yl)methyl]phenyl]-2-pyridininecarboxylic acid;
3-[4-[(3-phenyl-5-butyl-1H-1,2,4-triazol-1-yl)methyl]phenyl]-2-pyridininecarboxylic acid;
3-[4-[(3-phenylmethyl-5-butyl-1H-1,2,4-triazol-1-yl)methyl]phenyl]-2-pyridininecarboxylic acid;
3-[4-[(3-cyclohenanoyl-5-butyl-1H-1,2,4-triazol-1-yl)methyl]phenyl]-2-pyridininecarboxylic acid;
3-[4-[[3-(2-phenylethyl)-5-butyl-1H-1,2,4-triazol-1-yl]methyl]phenyl]-2-pyridininecarboxylic acid;
3-[4-[[3-(1-oxo-2-cyclohexylethyl)-5-butyl-1H-1,2,4-triazol-1-yl]methyl]phenyl]-2-pyridininecarboxylic acid;
3-[4-[[3-(2-cyclohexylethyl)-5-butyl-1H-1,2,4-triazol-1-yl]methyl]phenyl]-2-pyridininecarboxylic acid;
3-[4-[[3-(1-oxo-2-phenylethyl)-5-butyl-1H-1,2,4-triazol-1-yl]methyl]phenyl]-2-pyridininecarboxylic acid;
3-[4-[[3-(1,1-dimethoxypropyl)-5-butyl-1H-1,2,4-triazol-1-yl]methyl]phenyl]-2-pyridininecarboxylic acid;
3-[4-[[3-(1,1-dimethoxybutyl)-5-butyl-1H-1,2,4-triazol-1-yl]methyl]phenyl]-2-pyridininecarboxylic acid;
3-[4-[[3-(1,1-dimethoxylpentyl)-5-butyl-1H-1,2,4-triazol-1-yl]methyl]phenyl]-2-pyridininecarboxylic acid;
3-[4-[[3-(1-oxopropyl)-5-butyl-1H-1,2,4-triazol-1-yl]methyl]phenyl]-2-pyridininecarboxylic acid;
3-[4-[[3-(1-oxobutyl)-5-butyl-1H-1,2,4-triazol-1-yl]methyl]phenyl]-2-pyridininecarboxylic acid;
3-[4-[[3-(1-oxopentyl)-5-butyl-1H-1,2,4-triazol-1-yl]methyl]phenyl]-2-pyridininecarboxylic acid;
3-[4-[[3-(1,1-difluorobutyl)-5-1H-1,2,4-triazol-1-yl]methyl]phenyl]-2-pyridininecarboxylic acid;
3-[4-[(3-methyl-5-pentyl-1H-1,2,4-triazol-1-yl)methyl]phenyl]-2-pyridininecarboxylic acid;
3-[4-[(3-ethyl-5-pentyl-1H-1,2,4-triazol-1-yl)methyl]phenyl]-2-pyridininecarboxylic acid;
3-[4-[(3-propyl-5-pentyl-1H-1,2,4-triazol-1-yl)methyl]phenyl]-2-pyridininecarboxylic acid;
3-[4-[(3-isopropyl-5-pentyl-1H-1,2,4-triazol-1-yl)methyl]phenyl]-2-pyridininecarboxylic acid;
3-[4-[(3-butyl-5-pentyl-1H-1,2,4-triazol-1-yl)methyl]phenyl]-2-pyridininecarboxylic acid;
3-[4-[(3-secbutyl-5-pentyl-1H-1,2,4-triazol-1-yl)methyl]phenyl]-2-pyridininecarboxylic acid;
3-[4-[(3-isobutyl-5-pentyl-1H-1,2,4-triazol-1-yl)methyl]phenyl]-2-pyridininecarboxylic acid;
3-[4-[(3-tertbutyl-5-pentyl-1H-1,2,4-triazol-1-yl)methyl]phenyl]-2-pyridininecarboxylic acid;

3-[4-[(3,5-dipentyl-1H-1,2,4-triazol-1-yl)methyl]-
phenyl]-2-pyridininecarboxylic acid;
3-[4-[(3-isopentyl-5-pentyl-1H-1,2,4-triazol-1-yl)methyl]phenyl]-2-pyridininecarboxylic acid;
3-[4-[(3-cyclohexyl-5-pentyl-1H-1,2,4-triazol-1-yl)methyl]phenyl]-2-pyridininecarboxylic acid;
3-[4-[(3-cyclohexylmethyl-5-pentyl-1H-1,2,4-triazol-1-yl)methyl]phenyl]-2-pyridininecarboxylic acid;
3-[4-[(3-benzoyl-5-pentyl-1H-1,2,4-triazol-1-yl)methyl]phenyl]-2-pyridininecarboxylic acid;
3-[4-[(3-phenyl-5-pentyl-1H-1,2,4-triazol-1-yl)methyl]phenyl]-2-pyridininecarboxylic acid;
3-[4-[(3-phenylmethyl-5-pentyl-1H-1,2,4-triazol-1-yl)methyl]phenyl]-2-pyridininecarboxylic acid;
3-[4-[(3-cyclohenanoyl-5-pentyl-1H-1,2,4-triazol-1-yl)methyl]phenyl]-2-pyridininecarboxylic acid;
3-[4-[[3-(2-phenylethyl)-5-pentyl-1H-1,2,4-triazol-1-yl]methyl]phenyl]-2-pyridininecarboxylic acid;
3-[4-[[3-(1-oxo-2-cyclohexylethyl)-5-pentyl-1H-1,2,4-triazol-1-yl]methyl]phenyl]-2-pyridininecarboxylic acid;
3-[4-[[3-(2-cyclohexylethyl)-5-pentyl-1H-1,2,4-triazol-1-yl]methyl]phenyl]-2-pyridininecarboxylic acid;
3-[4-[[3-(1-oxo-2-phenylethyl)-5-pentyl-1H-1,2,4-triazol-1-yl]methyl]phenyl]-2-pyridininecarboxylic acid;
3-[4-[[3-(1,1-dimethoxypropyl)-5-pentyl-1H-1,2,4-triazol-1-yl]methyl]phenyl]-2-pyridininecarboxylic acid;
3-[4-[[3-(1,1-dimethoxybutyl)-5-pentyl-1H-1,2,4-triazol-1-yl]methyl]phenyl]-2-pyridininecarboxylic acid;
3-[4-[[3-(1,1-dimethoxypentyl)-5-pentyl-1H-1,2,4-triazol-1-yl]methyl]phenyl]-2-pyridininecarboxylic acid;
3-[4-[[3-(1-oxopropyl)-5-pentyl-1H-1,2,4-triazol-1-yl]methyl]phenyl]-2-pyridininecarboxylic acid;
3-[4-[[3-(1-oxobutyl)-5-pentyl-1H-1,2,4-triazol-1-yl]methyl]phenyl]-2-pyridininecarboxylic acid;
3-[4-[[3-(1-oxopentyl)-5-pentyl-1H-1,2,4-triazol-1-yl]methyl]phenyl]-2-pyridininecarboxylic acid;
3-[4-[[3-(1,1-difluorobutyl)-5-pentyl-1H-1,2,4-triazol-1-yl]methyl]phenyl]-2-pyridininecarboxylic acid;
5-[3-[4-[(3-methyl-5-propyl-1H-1,2,4-triazol-1-yl)methyl]phenyl]-2-pyridinyl]-1H-tetrazole;
5-[3-[4-[(3-ethyl-5-propyl-1H-1,2,4-triazol-1-yl)methyl]phenyl]-2-pyridinyl]-1H-tetrazole;
5-[3-[4-[(3,5-dipropyl-1H-1,2,4-triazol-1-yl)methyl]phenyl]-2-pyridinyl]-1H-tetrazole;
5-[3-[4-[(3-isopropyl-5-propyl-1H-1,2,4-triazol-1-yl)methyl]phenyl]-2-pyridinyl]-1H-tetrazole;
5-[3-[4-[(3-butyl-5-propyl-1H-1,2,4-triazol-1-yl)methyl]phenyl]-2-pyridinyl]-1H-tetrazole;
5-[3-[4-[(3-secbutyl-5-propyl-1H-1,2,4-triazol-1-yl)methyl]phenyl]-2-pyridinyl]-1H-tetrazole;
5-[3-[4-[(3-isobutyl-5-propyl-1H-1,2,4-triazol-1-yl)methyl]phenyl]-2-pyridinyl]-1H-tetrazole;
5-[3-[4-[(3-tertbutyl-5-propyl-1H-1,2,4-triazol-1-yl)methyl]phenyl]-2-pyridinyl]-1H-tetrazole;
5-[3-[4-[(3-pentyl-5-propyl-1H-1,2,4-triazol-1-yl)methyl]phenyl]-2-pyridinyl]-1H-tetrazole;
5-[3-[4-[(3-isopentyl-5-propyl-1H-1,2,4-triazol-1-yl)methyl]phenyl]-2-pyridinyl]-1H-tetrazole;
5-[3-[4-[(3-cyclohexyl-5-propyl-1H-1,2,4-triazol-1-yl)methyl]phenyl]-2-pyridinyl]-1H-tetrazole;
5-[3-[4-[(3-cyclohexylmethyl-5-propyl-1H-1,2,4-triazol-1-yl)methyl]phenyl]-2-pyridinyl]-1H-tetrazole;
5-[3-[4-[(3-benzoyl-5-propyl-1H-1,2,4-triazol-1-yl)methyl]phenyl]-2-pyridinyl]-1H-tetrazole;
5-[3-[4-[(3-phenyl-5-propyl-1H-1,2,4-triazol-1-yl)methyl]phenyl]-2-pyridinyl]-1H-tetrazole;
5-[3-[4-[(3-phenylmethyl-5-propyl-1H-1,2,4-triazol-1-yl)methyl]phenyl]-2-pyridinyl]-1H-tetrazole;
5-[3-[4-[(3-cyclohenanoyl-5-propyl-1H-1,2,4-triazol-1-yl)methyl]phenyl]-2-pyridinyl]-1H-tetrazole;
5-[3-[4-[[3-(2-phenylethyl)-5-propyl-1H-1,2,4-triazol-1-yl]methyl]phenyl]-2-pyridinyl]-1H-tetrazole;
5-[3-[4-[[3-(1-oxo-2-cyclohexylethyl)-5-propyl-1H-1,2,4-triazol-1-yl]methyl]phenyl]-2-pyridinyl]-1H-tetrazole;
5-[3-[4-[[3-(2-cyclohexylethyl)-5-propyl-1H-1,2,4-triazol-1-yl]methyl]phenyl]-2-pyridinyl]-1H-tetrazole;
5-[3-[4-[[3-(1-oxo-2-phenylethyl)-5-propyl-1H-1,2,4-triazol-1-yl]methyl]phenyl]-2-pyridinyl]-1H-tetrazole;
5-[3-[4-[[3-(1,1-dimethoxypropyl)-5-propyl-1H-1,2,4-triazol-1-yl]methyl]phenyl]-2-pyridinyl]-1H-tetrazole;
5-[3-[4-[[3-(1,1-dimethoxybutyl)-5-propyl-1H-1,2,4-triazol-1-yl]methyl]phenyl]-2-pyridinyl]-1H-tetrazole;
5-[3-[4-[[3-(1,1-dimethoxypentyl)-5-propyl-1H-1,2,4-triazol-1-yl]methyl]phenyl]-2-pyridinyl]-1H-tetrazole;
5-[3-[4-[[3-(1-oxopropyl)-5-propyl-1H-1,2,4-triazol-1-yl]methyl]phenyl]-2-pyridinyl]-1H-tetrazole;
5-[3-[4-[[3-(1-oxobutyl)-5-propyl-1H-1,2,4-triazol-1-yl]methyl]phenyl]-2-pyridinyl]-1H-tetrazole;
5-[3-[4-[[3-(1-oxopentyl)-5-propyl-1H-1,2,4-triazol-1-yl]methyl]phenyl]-2-pyridinyl]-1H-tetrazole;
5-[3-[4-[[3-(1,1-difluorobutyl)-5-propyl-1H-1,2,4-triazol-1-yl]methyl]phenyl]-2-pyridinyl]-1H-tetrazole;
5-[3-[4-[(3-methyl-5-butyl-1H-1,2,4-triazol-1-yl)methyl]phenyl]-2-pyridinyl]-1H-tetrazole;
5-[3-[4-[(3-ethyl-5-butyl-1H-1,2,4-triazol-1-yl)methyl]phenyl]-2-pyridinyl]-1H-tetrazole;
5-[3-[4-[(3-propyl-5-butyl-1H-1,2,4-triazol-1-yl)methyl]phenyl]-2-pyridinyl]-1H-tetrazole;
5-[3-[4-[(3-isopropyl-5-butyl-1H-1,2,4-triazol-1-yl)methyl]phenyl]-2-pyridinyl]-1H-tetrazole;
5-[3-[4-[(3,5-dibutyl-1H-1,2,4-triazol-1-yl)methyl]phenyl]-2-pyridinyl]-1H-tetrazole;
5-[3-[4-[(3-secbutyl-5-butyl-1H-1,2,4-triazol-1-yl)methyl]phenyl]-2-pyridinyl]-1H-tetrazole;
5-[3-[4-[(3-isobutyl-5-butyl-1H-1,2,4-triazol-1-yl)methyl]phenyl]-2-pyridinyl]-1H-tetrazole;
5-[3-[4-[(3-tertbutyl-5-butyl-1H-1,2,4-triazol-1-yl)methyl]phenyl]-2-pyridinyl]-1H-tetrazole;
5-[3-[4-[(3-pentyl-5-butyl-1H-1,2,4-triazol-1-yl)methyl]phenyl]-2-pyridinyl]-1H-tetrazole;
5-[3-[4-[(3-isopentyl-5-butyl-1H-1,2,4-triazol-1-yl)methyl]phenyl]-2-pyridinyl]-1H-tetrazole;
5-[3-[4-[(3-cyclohexyl-5-butyl-1H-1,2,4-triazol-1-yl)methyl]phenyl]-2-pyridinyl]-1H-tetrazole;
5-[3-[4-[(3-cyclohexylmethyl-5-butyl-1H-1,2,4-triazol-1-yl)methyl]phenyl]-2-pyridinyl]-1H-tetrazole;
5-[3-[4-[(3-benzoyl-5-butyl-1H-1,2,4-triazol-1-yl)methyl]phenyl]-2-pyridinyl]-1H-tetrazole;
5-[3-[4-[(3-phenyl-5-butyl-1H-1,2,4-triazol-1-yl)methyl]phenyl]-2-pyridinyl]-1H-tetrazole;
5-[3-[4-[(3-phenylmethyl-5-butyl-1H-1,2,4-triazol-1-yl)methyl]phenyl]-2-pyridinyl]-1H-tetrazole;
5-[3-[4-[(3-cyclohenanoyl-5-butyl-1H-1,2,4-triazol-1-yl)methyl]phenyl]-2-pyridinyl]-1H-tetrazole;
5-[3-[4-[[3-(2-phenylethyl)-5-butyl-1H-1,2,4-triazol-1-yl]methyl]phenyl]-2-pyridinyl]-1H-tetrazole;

5-[3-[4-[[3-(1-oxo-2-cyclohexylethyl)-5-butyl-1H-1,2,4-triazol-1-yl]methyl]phenyl]-2-pyridinyl]-1H-tetrazole;

5-[3-[4-[[3-(2-cyclohexylethyl)-5-butyl-1H-1,2,4-triazol-1-yl]methyl]phenyl]-2-pyridinyl]-1H-tetrazole;

5-[3-[4-[[3-(1-oxo-2-phenylethyl)-5-butyl-1H-1,2,4-triazol-1-yl]methyl]phenyl]-2-pyridinyl]-1H-tetrazole;

5-[3-[4-[[3-(1,1-dimethoxypropyl)-5-butyl-1H-1,2,4-triazol-1-yl]methyl]phenyl]-2-pyridinyl]-1H-tetrazole;

5-[3-[4-[[3-(1,1-dimethoxybutyl)-5-butyl-1H-1,2,4-triazol-1-yl]methyl]phenyl]-2-pyridinyl]-1H-tetrazole;

5-[3-[4-[[3-(1,1-dimethoxypentyl)-5-butyl-1H-1,2,4-triazol-1-yl]methyl]phenyl]-2-pyridinyl]-1H-tetrazole;

5-[3-[4-[[3-(1-oxopropyl)-5-butyl-1H-1,2,4-triazol-1-yl]methyl]phenyl]-2-pyridinyl]-1H-tetrazole;

5-[3-[4-[[3-(1-oxobutyl)-5-butyl-1H-1,2,4-triazol-1-yl]methyl]phenyl]-2-pyridinyl]-1H-tetrazole;

5-[3-[4-[[3-(1-oxopentyl)-5-butyl-1H-1,2,4-triazol-1-yl]methyl]phenyl]-2-pyridinyl]-1H-tetrazole;

5-[3-[4-[[3-(1,1-difluorobutyl)-5-butyl-1H-1,2,4-triazol-1-yl]methyl]phenyl]-2-pyridinyl]-1H-tetrazole;

5-[3-[4-[(3-methyl-5-pentyl-1H-1,2,4-triazol-1-yl)methyl]phenyl]-2-pyridinyl]-1H-tetrazole;

5-[3-[4-[(3-ethyl-5-pentyl-1H-1,2,4-triazol-1-yl)methyl]phenyl]-2-pyridinyl]-1H-tetrazole;

5-[3-[4-[(3-propyl-5-pentyl-1H-1,2,4-triazol-1-yl)methyl]phenyl]-2-pyridinyl]-1H-tetrazole;

5-[3-[4-[(3-isopropyl-5-pentyl-1H-1,2,4-triazol-1-yl)methyl]phenyl]-2-pyridinyl]-1H-tetrazole;

5-[3-[4-[(3-butyl-5-pentyl-1H-1,2,4-triazol-1-yl)methyl]phenyl]-2-pyridinyl]-1H-tetrazole;

5-[3-[4-[(3-secbutyl-5-pentyl-1H-1,2,4-triazol-1-yl)methyl]phenyl]-2-pyridinyl]-1H-tetrazole;

5-[3-[4-[(3-isobutyl-5-pentyl-1H-1,2,4-triazol-1-yl)methyl]phenyl]-2-pyridinyl]-1H-tetrazole;

5-[3-[4-[(3-tertbutyl-5-pentyl-1H-1,2,4-triazol-1-yl)methyl]phenyl]-2-pyridinyl]-1H-tetrazole;

5-[3-[4-[(3,5-dipentyl-1H-1,2,4-triazol-1-yl)methyl]phenyl]-2-pyridinyl]-1H-tetrazole;

5-[3-[4-[(3-isopentyl-5-pentyl-1H-1,2,4-triazol-1-yl)methyl]phenyl]-2-pyridinyl]-1H-tetrazole;

5-[3-[4-[(3-cyclohexyl-5-pentyl-1H-1,2,4-triazol-1-yl)methyl]phenyl]-2-pyridinyl]-1H-tetrazole;

5-[3-[4-[(3-cyclohexylmethyl-5-pentyl-1H-1,2,4-triazol-1-yl)methyl]phenyl]-2-pyridinyl]-1H-tetrazole;

5-[3-[4-[(3-benzoyl-5-pentyl-1H-1,2,4-triazol-1-yl)methyl]phenyl]-2-pyridinyl]-1H-tetrazole;

5-[3-[4-[(3-phenyl-5-pentyl-1H-1,2,4-triazol-1-yl)methyl]phenyl]-2-pyridinyl]-1H-tetrazole;

5-[3-[4-[(3-phenylmethyl-5-pentyl-1H-1,2,4-triazol-1-yl)methyl]phenyl]-2-pyridinyl]-1H-tetrazole;

5-[3-[4-[(3-cyclohenanoyl-5-pentyl-1H-1,2,4-triazol-1-yl)methyl]phenyl]-2-pyridinyl]-1H-tetrazole;

5-[3-[4-[[3-(2-phenylethyl)-5-pentyl-1H-1,2,4-triazol-1-yl]methyl]phenyl]-2-pyridinyl]-1H-tetrazole;

5-[3-[4-[[3-(1-oxo-2-cyclohexylethyl)-5-pentyl-1H-1,2,4-triazol-1-yl]methyl]phenyl]-2-pyridinyl]-1H-tetrazole;

5-[3-[4-[[3-(2-cyclohexylethyl)-5-pentyl-1H-1,2,4-triazol-1-yl]methyl]phenyl]-2-pyridinyl]-1H-tetrazole;

5-[3-[4-[[3-(1-oxo-2-phenylethyl)-5-pentyl-1H-1,2,4-triazol-1-yl]methyl]phenyl]-2-pyridinyl]-1H-tetrazole;

5-[3-[4-[[3-(1,1-dimethoxypropyl)-5-pentyl-1H-1,2,4-triazol-1-yl]methyl]phenyl]-2-pyridinyl]-1H-tetrazole;

5-[3-[4-[[3-(1,1-dimethoxybutyl)-5-pentyl-1H-1,2,4-triazol-1-yl]methyl]phenyl]-2-pyridinyl]-1H-tetrazole;

5-[3-[4-[[3-(1,1-dimethoxypentyl)-5-pentyl-1H-1,2,4-triazol-1-yl]methyl]phenyl]-2-pyridinyl]-1H-tetrazole;

5-[3-[4-[[3-(1-oxopropyl)-5-pentyl-1H-1,2,4-triazol-1-yl]methyl]phenyl]-2-pyridinyl]-1H-tetrazole;

5-[3-[4-[[3-(1-oxobutyl)-5-pentyl-1H-1,2,4-triazol-1-yl]methyl]phenyl]-2-pyridinyl]-1H-tetrazole;

5-[3-[4-[[3-(1-oxopentyl)-5-pentyl-1H-1,2,4-triazol-1-yl]methyl]phenyl]-2-pyridinyl]-1H-tetrazole; and 5-[3-[4-[[3-(1,1-difluorobutyl)-5-pentyl-1H-1,2,4-triazol-1-yl]methyl]phenyl]-2-pyridinyl]-1H-tetrazole.

A family of specific compounds of more particular interest within Formula VII consists of compounds and pharmaceutically-acceptable salts thereof as follows:

3-[4-[(3-methyl-5-butyl-1H-1,2,4-triazol-1-yl)methyl]phenyl]-2-pyridinecarboxylic acid;

3-[4-[(3-ethyl-5-butyl-1H-1,2,4-triazol-1-yl)methyl]phenyl]-2-pyridinecarboxylic acid;

3-[4-[(3-propyl-5-butyl-1H-1,2,4-triazol-1-yl)methyl]phenyl]-2-pyridinecarboxylic acid;

3-[4-[(3-isopropyl-5-butyl-1H-1,2,4-triazol-1-yl)methyl]phenyl]-2-pyridinecarboxylic acid;

3-[4-[(3,5-dibutyl-1H-1,2,4-triazol-1-yl)methyl]phenyl]-2-pyridinecarboxylic acid;

3-[4-[(3-secbutyl-5-butyl-1H-1,2,4-triazol-1-yl)methyl]phenyl]-2-pyridinecarboxylic acid;

3-[4-[(3-isobutyl-5-butyl-1H-1,2,4-triazol-1-yl)methyl]phenyl]-2-pyridinecarboxylic acid;

3-[4-[(3-tertbutyl-5-butyl-1H-1,2,4-triazol-1-yl)methyl]phenyl]-2-pyridinecarboxylic acid;

3-[4-[(3-pentyl-5-butyl-1H-1,2,4-triazol-1-yl)methyl]phenyl]-2-pyridinecarboxylic acid;

3-[4-[(3-isopentyl-5-butyl-1H-1,2,4-triazol-1-yl)methyl]phenyl]-2-pyridinecarboxylic acid;

3-[4-[(3-cyclohexyl-5-butyl-1H-1,2,4-triazol-1-yl)methyl]phenyl]-2-pyridinecarboxylic acid;

3-[4-[(3-cyclohexylmethyl-5-butyl-1H-1,2,4-triazol-1-yl)methyl]phenyl]-2-pyridinecarboxylic acid;

3-[4-[(3-phenyl-5-butyl-1H-1,2,4-triazol-1-yl)methyl]phenyl]-2-pyridinecarboxylic acid;

3-[4-[(3-phenylmethyl-5-butyl-1H-1,2,4-triazol-1-yl)methyl]phenyl]-2-pyridinecarboxylic acid;

3-[4-[[3-(2-cyclohexylethyl)-5-butyl-1H-1,2,4-triazol-1-yl]methyl]phenyl]-2-pyridinecarboxylic acid;

3-[4-[[3-(2-phenylethyl)-5-butyl-1H-1,2,4-triazol-1-yl]methyl]phenyl]-2-pyridinecarboxylic acid;

3-[4-[[3-(1-oxo-2-phenylethyl)-5-butyl-1H-1,2,4-triazol-1-yl]methyl]phenyl]-2-pyridinecarboxylic acid;

3-[4-[[3-(1-oxobutyl)-5-butyl-1H-1,2,4-triazol-1-yl]methyl]phenyl]-2-pyridinecarboxylic acid;

3-[4-[[3-(1,1-difluorobutyl)-5-butyl-1H-1,2,4-triazol-1-yl]methyl]phenyl]-2-pyridinecarboxylic acid;

3-[4-[[3-(1,1-dimethoxybutyl)-5-butyl-1H-1,2,4-triazol-1-yl]methyl]phenyl]-2-pyridinecarboxylic acid;

5-[3-[4-[(3-methyl-5-butyl-1H-1,2,4-triazol-1-yl)methyl]phenyl]-2-pyridinyl]-1H-tetrazole;

5-[3-[4-[(3-ethyl-5-butyl-1H-1,2,4-triazol-1-yl)methyl]phenyl]-2-pyridinyl]-1H-tetrazole;

5-[3-[4-[(3-propyl-5-butyl-1H-1,2,4-triazol-1-yl)methyl]phenyl]-2-pyridinyl]-1H-tetrazole;

5-[3-[4-[(3-isopropyl-5-butyl-1H-1,2,4-triazol-1-yl)methyl]phenyl]-2-pyridinyl]-1H-tetrazole;

5-[3-[4-[(3,5-dibutyl-1H-1,2,4-triazol-1-yl)methyl]-phenyl]-2-pyridinyl]-1H-tetrazole;
5-[3-[4-[(3-secbutyl-5-butyl-1H-1,2,4-triazol-1-yl)methyl]phenyl]-2-pyridinyl]-1H-tetrazole;
5-[3-[4-[(3-isobutyl-5-butyl-1H-1,2,4-triazol-1-yl)methyl]phenyl]-2-pyridinyl]-1H-tetrazole;
5-[3-[4-[(3-tertbutyl-5-butyl-1H-1,2,4-triazol-1-yl)methyl]phenyl]-2-pyridinyl]-1H-tetrazole;
5-[3-[4-[(3-pentyl-5-butyl-1H-1,2,4-triazol-1-yl)methyl]phenyl]-2-pyridinyl]-1H-tetrazole;
5-[3-[4-[(3-isopentyl-5-butyl-1H-1,2,4-triazol-1-yl)methyl]phenyl]-2-pyridinyl]-1H-tetrazole;
5-[3-[4-[(3-cyclohexyl-5-butyl-1H-1,2,4-triazol-1-yl)methyl]phenyl]-2-pyridinyl]-1H-tetrazole;
5-[3-[4-[(3-cyclohexylmethyl-5-butyl-1H-1,2,4-triazol-1-yl)methyl]phenyl]-2-pyridinyl]-1H-tetrazole;
5-[3-[4-[(3-phenyl-5-butyl-1H-1,2,4-triazol-1-yl)methyl]phenyl]-2-pyridinyl]-1H-tetrazole;
5-[3-[4-[(3-phenylmethyl-5-butyl-1H-1,2,4-triazol-1-yl)methyl]phenyl]-2-pyridinyl]-1H-tetrazole;
5-[3-[4-[[3-(2-cyclohexylethyl)-5-butyl-1H-1,2,4-triazol-1-yl]methyl]phenyl]-2-pyridinyl]-1H-tetrazole;
5-[3-[4-[[3-(2-phenylethyl)-5-butyl-1H-1,2,4-triazol-1-yl]methyl]phenyl]-2-pyridinyl]-1H-tetrazole;
5-[3-[4-[[3-(1-oxo-2-phenylethyl)-5-butyl-1H-1,2,4-triazol-1-yl]methyl]phenyl]-2-pyridinyl]-1H-tetrazole;
5-[3-[4-[[3-(1-oxobutyl)-5-butyl-1H-1,2,4-triazol-1-yl]methyl]phenyl]-2-pyridinyl]-1H-tetrazole;
5-[3-[4-[[3-(1,1-difluorobutyl)-5-butyl-1H-1,2,4-triazol-1-yl]methyl]phenyl]-2-pyridinyl]-1H-tetrazole; and
5-[3-[4-[[3-(1,1-dimethoxybutyl)-5-butyl-1H-1,2,4-triazol-1-yl]methyl]phenyl]-2-pyridinyl]-1H-tetrazole.

The term "hydrido" denotes a single hydrogen atom (H). This hydrido group may be attached, for example, to an oxygen atom to form a hydroxyl group; or, as another example, one hydrido group may be attached to a carbon atom to form a

group; or, as another example, two hydrido groups may be attached to a carbon atom to form a —CH$_2$— group. Where the term "alkyl" is used, either alone or within other terms such as "haloalkyl" and ""hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about five carbon atoms. The term "cycloalkyl" embraces cyclic radicals having three to about ten ring carbon atoms, preferably three to about six carbon atoms, such as cyclopropyl, cyclobutyl, cyclopentyl and cyclohexyl. The term "haloalkyl" embraces radicals wherein any one or more of the alkyl carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two fluoro atoms, such as difluoromethyl and difluorobutyl groups, or two chloro atoms, such as a dichloromethyl group, or one fluoro atom and one chloro atom, such as a fluoro-chloromethyl group. Examples of a polyhaloalkyl are trifluoromethyl, 1,1-difluoroethyl, 2,2,2-trifluoroethyl, perfluoroethyl and 2,2,3,3-tetrafluoropropyl groups. The term "difluoroalkyl" embraces alkyl groups having two fluoro atoms substituted on any one or two of the alkyl group carbon atoms. The terms "alkylol" and "hydroxyalkyl" embrace linear or branched alkyl groups having one to about ten carbon atoms any one of which may be substituted with one or more hydroxyl groups. The term "alkenyl" embraces linear or branched radicals having two to about twenty carbon atoms, preferably three to about ten carbon atoms, and containing at least one carbon-carbon double bond, which carbon-carbon double bond may have either cis or trans geometry within the alkenyl moiety. The term "alkynyl" embraces linear or branched radicals having two to about twenty carbon atoms, preferably two to about ten carbon atoms, and containing at least one carbon-carbon triple bond. The term "cycloalkenyl" embraces cyclic radicals having three to about ten ring carbon atoms including one or more double bonds involving adjacent ring carbons. The terms "alkoxy" and "alkoxyalkyl" embrace linear or branched oxy-containing radicals each having alkyl portions of one to about ten carbon atoms, such as methoxy group. The term "alkoxyalkyl" also embraces alkyl radicals having two or more alkoxy groups attached to the alkyl radical, that is, to form monoalkoxyalkyl and dialkoxyalkyl groups. The "alkoxy" or "alkoxyalkyl" radicals may be further substituted with one or more halo atoms, such as fluoro, chloro or bromo, to provide haloalkoxy or haloalkoxyalkyl groups. The term "alkylthio" embraces radicals containing a linear or branched alkyl group, of one to about ten carbon atoms attached to a divalent sulfur atom, such as a methythio group. Preferred aryl groups are those consisting of one, two, or three benzene rings. The term "aryl" embraces aromatic radicals such as phenyl, naphthyl and biphenyl. The term "aralkyl" embraces aryl-substituted alkyl radicals such as benzyl, diphenylmethyl, triphenylmethyl, phenylethyl, phenylbutyl and diphenylethyl. The terms "benzyl" and "phenylmethyl" are interchangeable. The terms "aryloxy" and "arylthio" denote radical respectively, aryl groups having an oxygen or sulfur atom through which the radical is attached to a nucleus, examples of which are phenoxy and phenylthio. The terms "sulfinyl" and "sulfonyl", whether used alone or linked to other terms, denotes respectively divalent radicals SO and SO$_2$. The term "aralkoxy", alone or within another term, embraces an aryl group attached to an alkoxy group to form, for example, benzyloxy. The term "acyl" whether used alone, or within a term such as acyloxy, denotes a radical provided by the residue after removal of hydroxyl from an organic acid, examples of such radical being acetyl and benzoyl. "Lower alkanoyl" is an example of a more prefered sub-class of acyl. The term "amido" denotes a radical consisting of nitrogen atom attached to a carbonyl group, which radical may be further substituted in the manner described herein. The amido radical can be attached to the nucleus of a compound of the invention through the carbonyl moiety or through the nitrogen atom of the amido radical. The term "alkenylalkyl" denotes a radical having a double-bond unsaturation site between two carbons, and which radical may consist of only two carbons or may be further substituted with alkyl groups which may optionally contain additional double-bond unsaturation. The term "heteroaryl" embraces aromatic ring systems containing one or two hetero atoms selected from oxygen, nitrogen and sulfur in a ring system having five or six ring members, examples of which are thienyl, furanyl, pyridinyl, thiazolyl, pyrimidyl and isoxazolyl. Such heteroaryl may be attached as a substituent through a carbon atom of the heteroaryl ring system, or may be attached through a carbon atom of a moiety substituted on a heteroaryl ring-member carbon atom, for example, through the methylene substituent of imidazolemethyl moiety. Also, such heteroaryl may be attached through a ring nitrogen atom as long as aromaticity of the heteroaryl moiety is preserved after attachment. For any of the foregoing defined radicals, preferred radicals are those containing from one to about ten carbon atoms.

Specific examples of alkyl groups are methyl, ethyl, n-propyl, isopropyl, n-butyl, sec-butyl, isobutyl, tert-butyl, n-pentyl, isopentyl, methylbutyl, dimethylbutyl and neopentyl. Typical alkenyl and alkynyl groups may have one unsaturated bond, such as an allyl group, or may have a plurality of unsaturated bonds, with such plurality of bonds either adjacent, such as allene-type structures, or in conjugation, or separated by several saturated carbons.

Compounds of Formula I have been found to inhibit the action of angiotensin II in mammals. Angiotensin II is a potent vasoconstrictor and participates in the formation of aldosterone which regulates sodium and water balance in mammals. Thus, compounds of Formula I are therapeutically useful in methods for treating hypertension by administering to a hypertensive patient a therapeutically-effective amount of a compound of Formula I. The phrase "hypertensive patient" means, in this context, a mammalian subject suffering from or afflicted by the effects of hypertension or susceptible to a hypertensive condition if not treated to prevent or control such hypertension.

Also included in the family of compounds of Formula I are isomeric forms including diastereoisomers, regioisomers and the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methansulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactaric and galacturonic acid. Suitable pharmaceutically-acceptable base addition salts of compounds of Formula I include metallic salts made from aluminium, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

GENERAL SYNTHETIC PROCEDURES

The compounds of the invention can be synthesized according to the following procedures of Schemes I-XX, wherein the R substituents are as defined for Formula I, above, except where further noted.

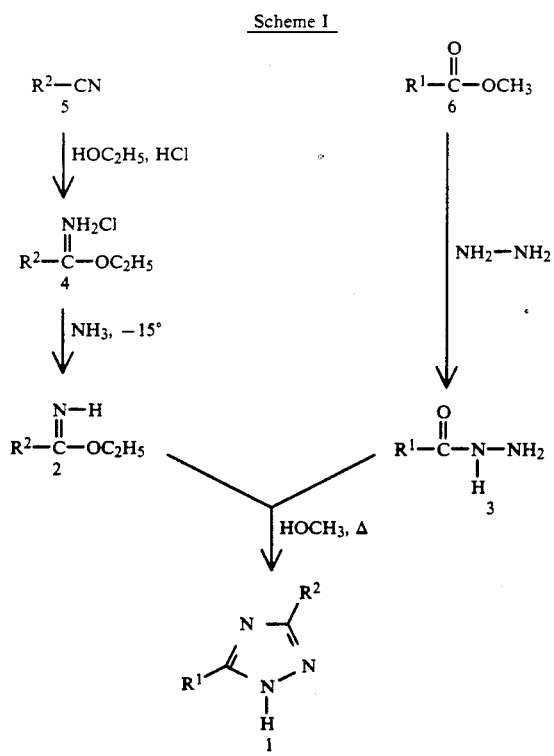

Scheme I

Synthetic Scheme I shows the preparation of 1H-1,2,4-triazoles 1 from ethyl iminoesters 2 and the corresponding hydrizide 3 via the general procedure outlined by H. Paul, G. Hilgetog, and G. Jahnchen, *Chem. Ber.*, 101, 2033 (1968). The free iminoesters 2 can be prepared from the corresponding iminoester hydrochlorides 4, which in turn can be prepared from the corresponding nitrile 5; the procedures for the preparation of 2 and 4 from 5 are outlined by P. Reynaud and R. D. Moreau, *Bull. Soc. Chim. France*, 2997 (1964). The hydrazides 3 can be either purchased or prepared from the corresponding methyl esters 6 and hydrazine.

Scheme II

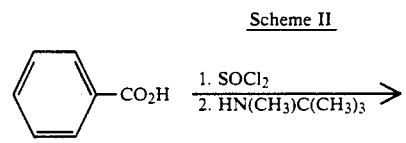

-continued
Scheme II

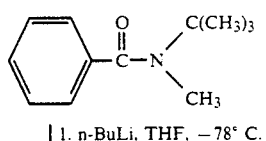

1. n-BuLi, THF, −78° C.
2. B(OCH₃)₃
3. H₃O⁺

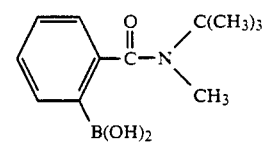

7
[R⁵ = CON(CH₃)C(CH₃)₃]

Synthetic Scheme II shows the preparation of the boronic acid 7 where R⁵ equals N-methyl-N-tertbutyl-carboxamide. In step 1, benzoic acid is treated with thionyl chloride to give the corresponding acid chloride which is subsequently reacted with N-tertbutyl-N-methylamine to give N-tertbutyl-N-methylbenzamide. In step 2, the amide is ortho-metalated and subsequently reacted with trimethyl borate. The free boronic acid 7 is produced on hydroylsis.

Scheme IV

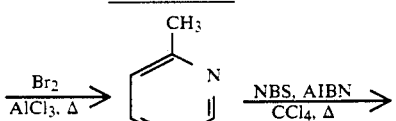

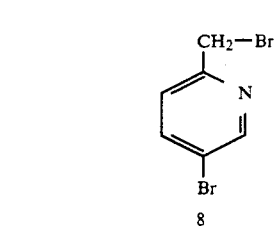

8

Synthetic Scheme IV shows the preparation of 2-bromomethyl-5-bromopyridine (8) from 2-picoline (Aldrich). In step 1, 2-picoline is reacted with bromine in the presence of a large excess of aluminum chloride at elevated temperatures to give 5-bromo-2-picoline (9). In step 2, 9 is reacted with NBS to give the 2-pyridinyl-methyl bromide 8.

Scheme III

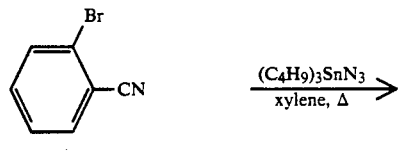 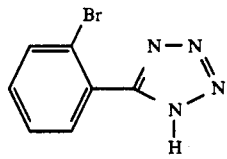

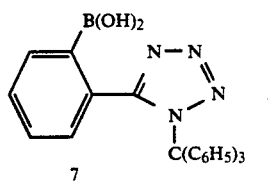 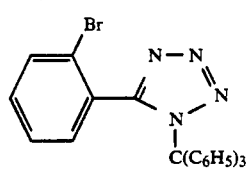

7
[R⁵ = CN₄C(C₆H₅)₃]

Synthetic Scheme III shows the preparation of the boronic acid 7 where R⁵ equals N-triphenylmethyl-1H-tetrazole. In step 1, 2-bromobenzonitrile (Aldrich) is reacted with tributyltin azide to give the corresponding tetrazole. In step 2, the tetrazole is reacted with triphenylmethyl chloride in the presence of triethylamine to give the protected bromophenyltetrazole. In step 3, halogen-metal interchange with n-butyllithium generates the corresponding ortho-lithiated species which is reacted with trimethyl borate. The free boronic acid 7 is produced on hydrolysis.

Scheme V

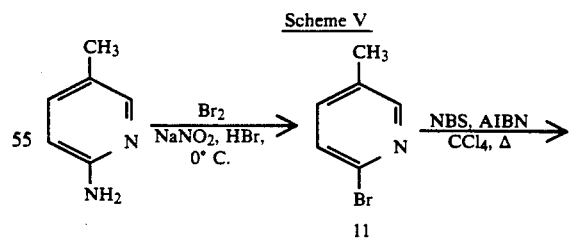

11

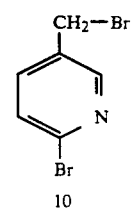

10

Synthetic Scheme V shows the preparation of 2-bromo-5-bromomethylpyridine (10) from 2-amino-5-picoline (Aldrich). In step 1, 2-amino-5-picoline is reacted with bromine in the presence of hydrobromic acid and sodium nitrite at 0° C. to give 2-bromo-5-picoline (11). In step 2, 11 is reacted with NBS to give the 3-pyridinylmethyl bromide 10.

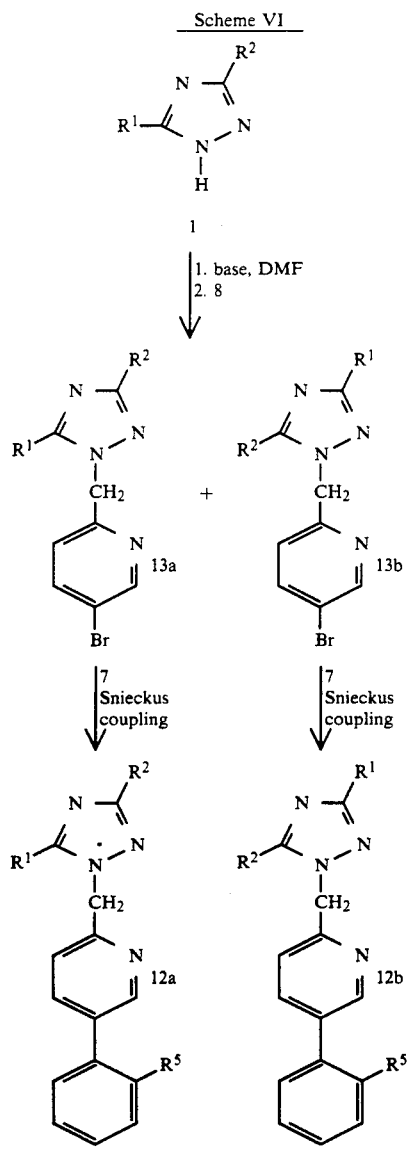

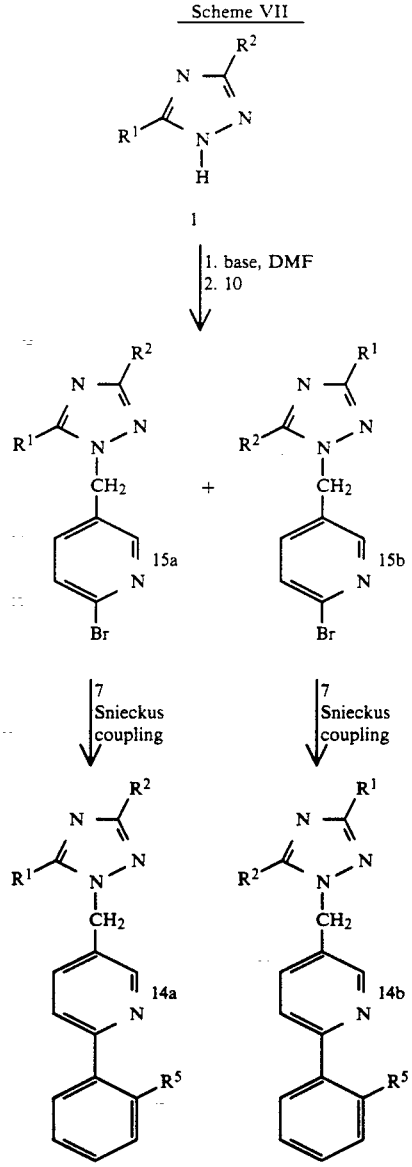

Synthetic Scheme VI shows the preparation of both 2-pyridinyl regioisomers 12a and 12b from the appropriate 1H-1,2,4-triazole 1 and the 2-pyridinyl alkylating reagent 8 (Scheme IV). In the first step, 1 is treated with a base, such as sodium hydride, to generate the corresponding anion which is reacted with 8 to give a mixture of regioisomers 13a and 13b. This isomer mixture may be converted to a mixture of the corresponding analogs 12a and 12b by treatment with the appropriate boronic acid 7 (Scheme II or Scheme III) via a Snieckus coupling [see M. J. Sharp and V. Snieckus, Tetrahedron Lett., 5997(1985)] with subsequent separation of regioisomers 12a and 12b by chromatographic methods. Or, the isomers 13a and 13b may be separated by chromatographic methods, and each isomer may be reacted with the appropriate boronic acid 7 to provide the angiotensin II antagonists 12a and 12b of this invention.

Synthetic Scheme VII shows the preparation of both 3-pyridinyl regioisomers 14a and 14b from the appropriate 1H-1,2,4-triazole 1 (Scheme I) and the 3-pyridinyl alkylating reagent 10 (Scheme V). In the first step, 1 is treated with a base, such as sodium hydride, to generate the corresponding anion which is reacted with 10 to give a mixture of regioisomers 15a and 15b. This isomer mixture may be converted to a mixture of the corresponding analogs 14a and 14b by treatment with the appropriate boronic acid 7 (Scheme II or Scheme III) via a Snieckus coupling [see M. J. Sharp and V. Snieckus, Tetrahedron Lett., 5997(1985)] with subsequent separation of the regioisomers 14a and 14b by chromatographic methods. Or, the isomers 15a and 15b may be separated by chromatographic methods, and each isomer may be reacted with the appropriate boronic acid 7 to provide the angiotensin II antagonists 14a and 14b of this invention.

Scheme VIII

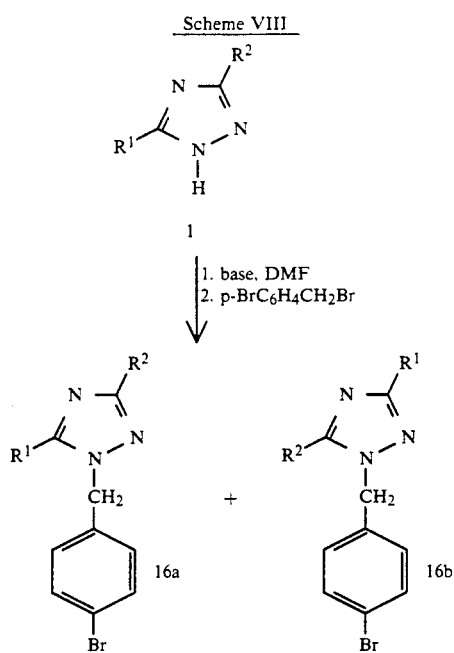

Synthetic Scheme VIII shows the preparation of both benzyl regioisomers 16a and 16b from the appropriate 1H-1,2,4-triazole 1 (Scheme I) and 4-bromobenzyl bromide. The 1H-1,2,4-triazole 1 is treated with a base, such as sodium hydride, to generate the corresponding anion which is reacted with 4-bromobenzyl bromide to give a mixture of regioisomers 16a and 16b; the regioisomers 12a and 12b may be separated by chromatographic methods.

Scheme IX

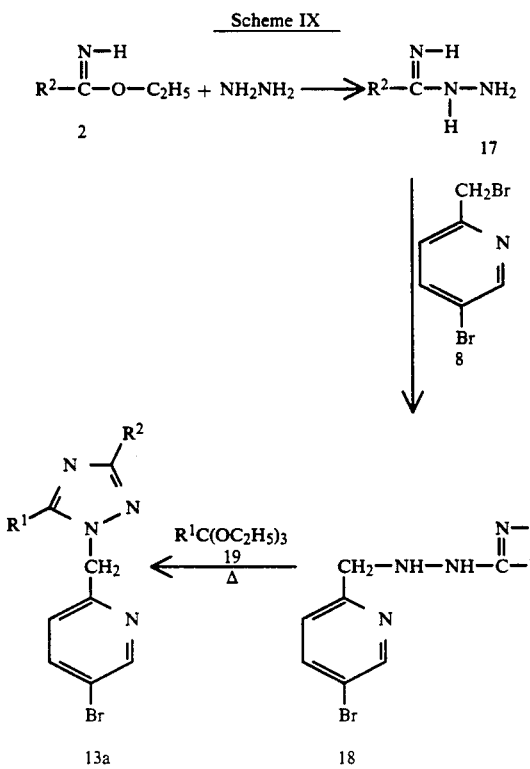

Synthetic Scheme IX shows the regioselective synthesis of isomer 13a. In step 1, the imidate 2 (Scheme I) is reacted with hydrazine to give amidazone 17. In Step 3 this intermediate is reacted with the 2-pyridinyl alkylating agent 8 (Scheme IV) to give the intermediate 18 which is then cyclized in step 3 in the presence of heat and an appropriate orthoester 19 to yield the corresponding product regioisomer 13a.

Scheme X

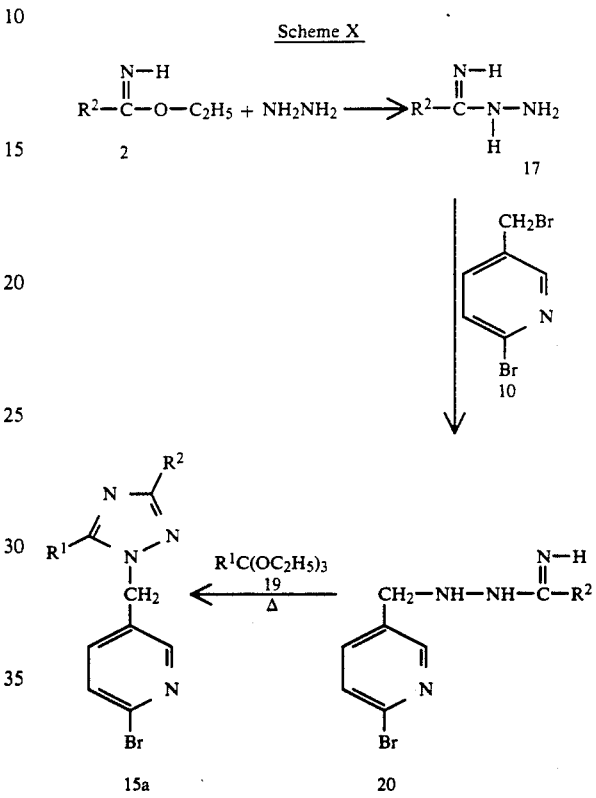

Synthetic Scheme X shows the regioselective synthesis of isomer 15a. In step 1, the imidate 2 (Scheme I) is reacted with hydrazine to give amidazone 17. In step 2, this intermediate is reacted with the 3-pyridinyl alkylating agent 10 (Scheme V) to give intermediate 20 which is then cyclized in step 3 in the presence of heat and an appropriate orthoester 19 to yield the corresponding product regioisomer 15a.

Scheme XI

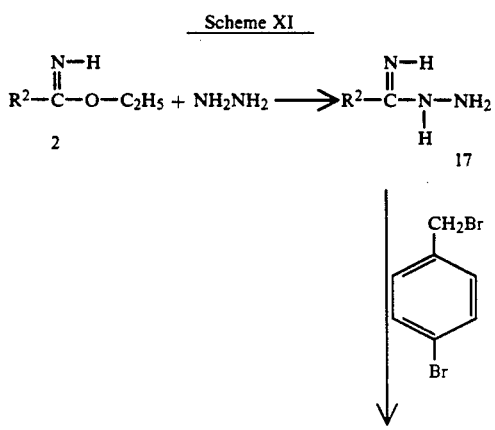

Scheme XI

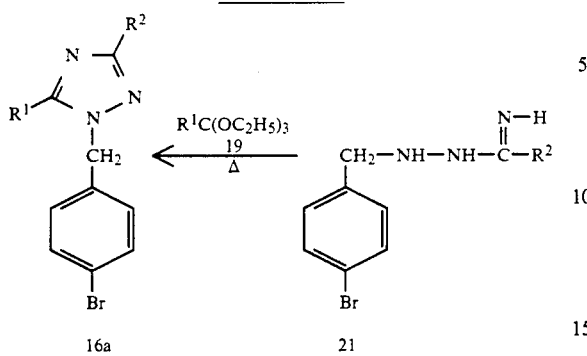

Synthetic Scheme XI shows the regioselective synthesis of isomer 16a. In step 1, the imidate 2 (Scheme I) is reacted with hydrazine to give amidazone 17. In step 2, this intermediate is reacted with the 4-bromobenzyl bromide to give intermediate 21 which is then cyclized in step 3 in the presence of heat and an appropriate orthoester 19 to yield the corresponding product regioisomer 16a.

Scheme XII

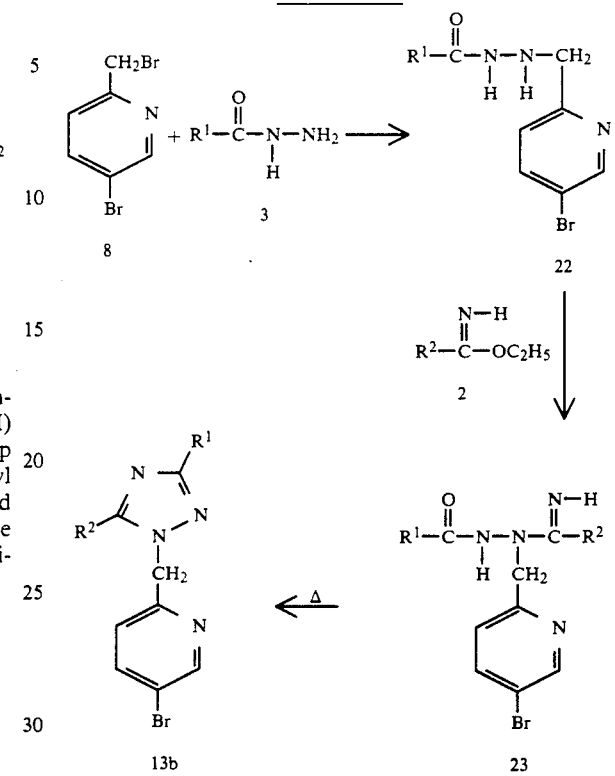

Synthetic Scheme XII shows the regioselective synthesis of isomer 13b. In step 1, the 2-pyridinyl alkylating agent 8 (Scheme IV) is reacted with an appropriate hydrazide 3 to provide substituted hydrazide 22. In step 2, an imidate 2 (Scheme I) is reacted with hydrazide 22 to provide intermediate 23 which cyclizes in step 3 upon heating to provide the corresponding product regioisomer 13b.

Scheme XIII

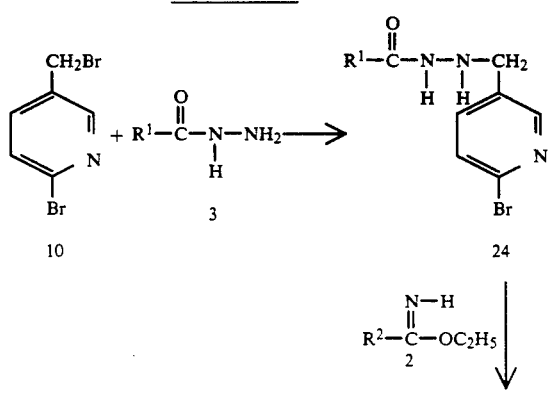

Scheme XIII

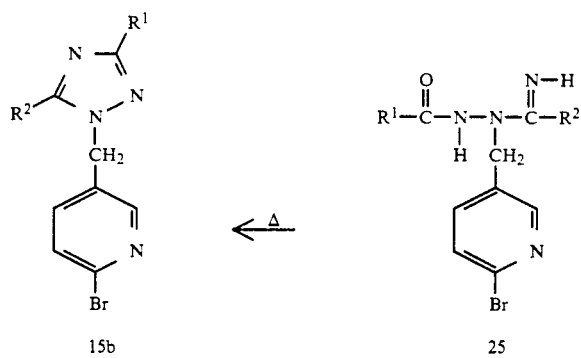

Synthetic Scheme XIII shows the regioselective synthesis of isomer 15b. In step 1, the 3-pyridinyl alkylating agent 10 (Scheme V) is reacted with an appropriate hydrazide 3 to provide substituted hydrazide 24. In step 2, an imidate 2 (Scheme I) is reacted with hydrazide 24 to provide intermediate 25 which cyclizes in step 3 upon heating to provide the corresponding product regioisomer 15b.

Scheme XIV

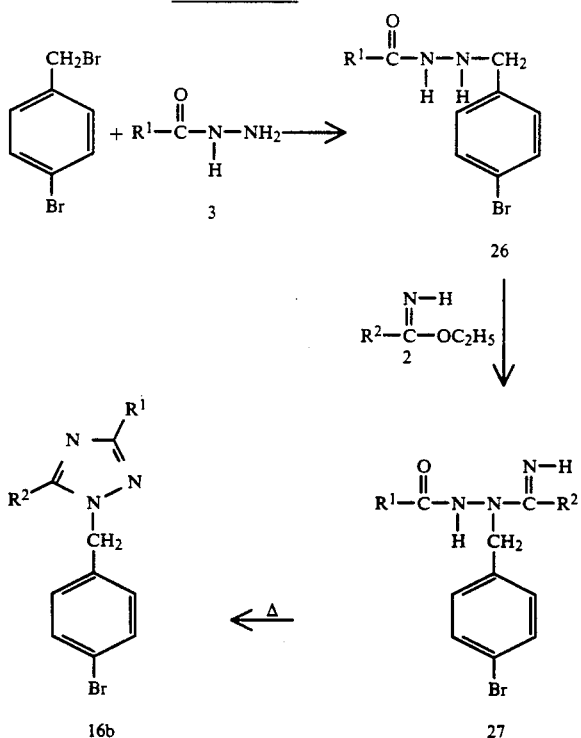

Synthetic Scheme XIV shows the regioselective synthesis of isomer 16b. In step 1, the 4-bromobenzyl bromide is reacted with an appropriate hydrazide 3 to provide substituted hydrazide 26. In step 2, an imidate 2 (Scheme I) is reacted with hydrazide 26 to provide intermediate 27 which cyclizes in step 3 upon heating to provide the corresponding product regioisomer 16b.

Scheme XV

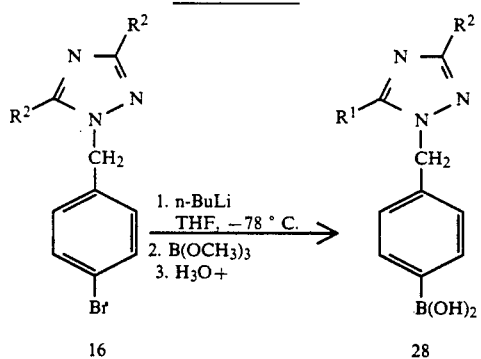

Synthetic Scheme XV shows the preparation of 1-benzyl-1H-1,2,4-triazole boronic acid coupling reagents 28 from the corresponding 4-bromophenylmethyl analogs 16a and 16b (Scheme VIII, Scheme XI, and Scheme XIV). Halogenmetal interchange generates the corresponding lithiated species from 16 which is reacted with trimethyl borate. The free triazole boronic acid coupling reagents 28 are produced on acid hydroysis.

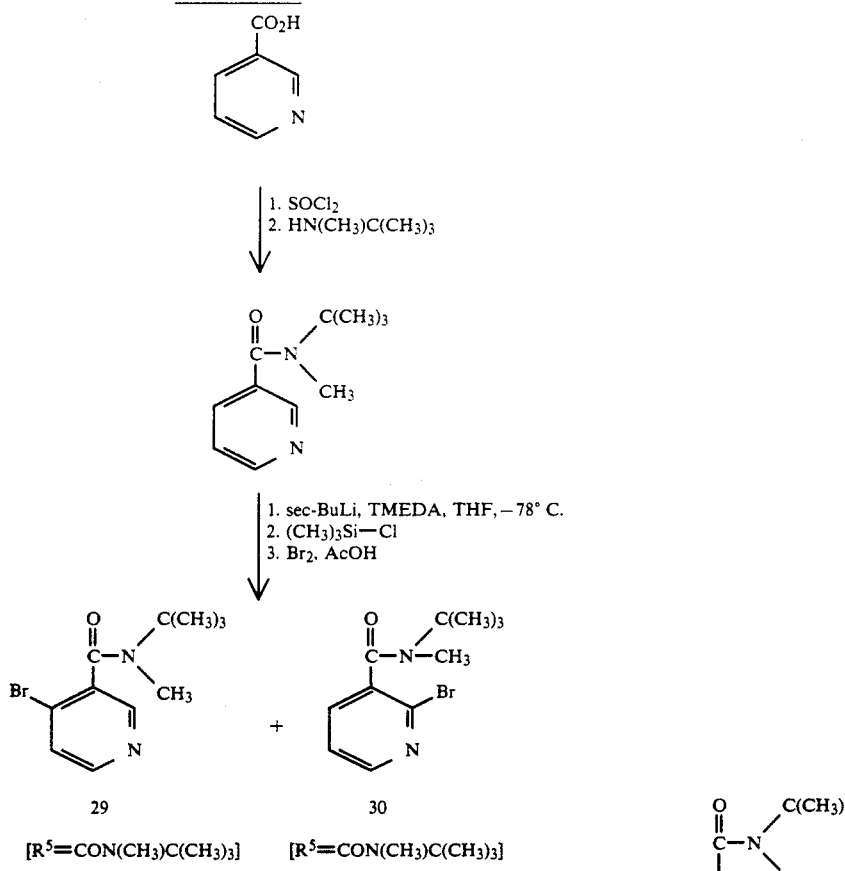

Scheme XVI

Synthetic Scheme XVI shows the preparation of the 4-bromopyridine coupling reagent 29 [R⁵=CON(CH₃)C(CH₃)₃] and the 2-bromopyridine coupling reagent 30 [R⁵=CON(CH₃)C(CH₃)₃] from nicotinic acid. In step 1, N-methyl-N-tertbutylnicotinamide is prepared from nicotinoyl chloride and N-methyl-N-tertbutylamine. In step 2, ortho-metalalion with sec-butyllithium gives a mixture of regioanions which are reacted with trimethylsilyl chloride; subsequent conversion to the corresponding bromides on treatment with bromine in acetic acid and separation of the regioisomers by chromatography provides 29 and 30.

Scheme XVII

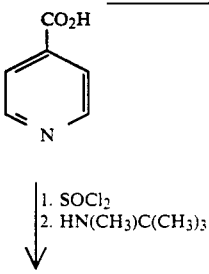

-continued
Scheme XVII

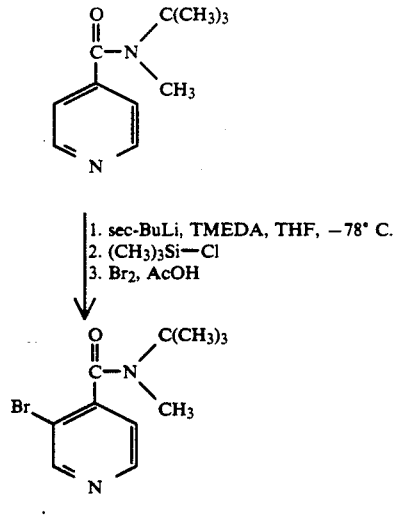

Synthetic Scheme XVII shows the preparation of the 3-bromopyridine coupling reagent 31 [R⁵=CON(CH₃)C(CH₃)₃] from isonicotinic acid. In step 1, N-methyl-N-tertbutylisonicotinamide is prepared from isonicotinoyl chloride and N-methyl-N-tertbutylamine. In step 2, reaction with sec-butyllithium gives the ortholithiated species which is reacted with trimethylsilyl chloride and subsequently converted to the corresponding bromide 31 on treatment with bromine in acetic acid.

Scheme XVIII

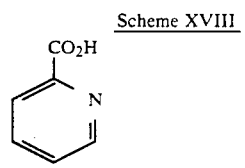

1. SOCl₂
2. HN(CH₃)C(CH₃)₃

↓

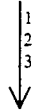

1. sec-BuLi, TMEDA, THF, −78° C.
2. (CH₃)₃Si—Cl
3. Br₂, AcOH

↓

-continued
Scheme XVIII

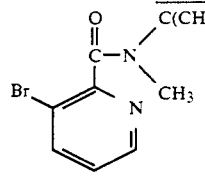

32 [R⁵ = CON(CH₃)C(CH₃)₃]

Synthetic Scheme XVIII shows the preparation of 3-bromopyridine coupling reagent 32 [R⁵=CON(CH₃)C(CH₃)₃] from picolinic acid. In step 1, N-methyl-N-tertbutylpicolinamide is prepared from picolinoyl chloride and N-methyl-N-tertbutylamine. In step 2, reaction with sec-butyllithium gives the ortho-lithiated species which is reacted with trimethylsilyl chloride and subsequently converted to the corresponding bromide 32 on treatment with bromine in acetic acid.

Scheme XIX

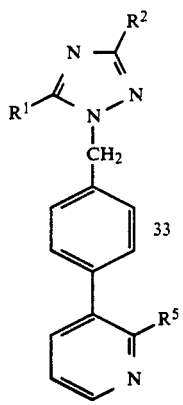

↑ Snieckus coupling 32

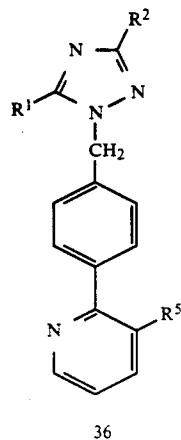  ←Snieckus coupling 30— 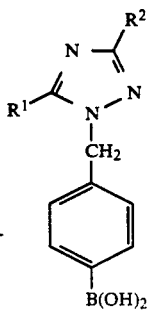 —Snieckus coupling 29→ 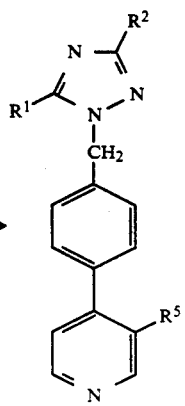

36

↓ Snieckus coupling 31

34

Scheme XIX

-continued

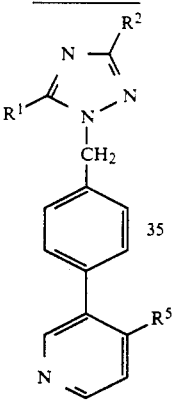

Synthetic Scheme XIX shows the preparation of 1-(pyridinylbenzyl)-1H-1,2,4-triazoles 33, 34, 35, and 36 from the triazole boronic acids 28 (Scheme XV) and the corresponding bromo coupling reagents 32 (Scheme XVIII), 29 (Scheme XVI), 31 (Scheme XVII), and 30 (Scheme XVI), respectively. The boronic acids 28 are reacted with the bromo coupling reagents, 32, 29, 31, and 34 in the presence of a palladium zero catalyst via a Snieckus coupling [see M. J. Sharp and V. Snieckus, Tetrahedron Lett., 5997 (1985)] to give the angiotensin II antagonists 33, 34, 35, and 36, respectively, of this invention.

In step 4, the acid analog 37 is reacted with oxalyl chloride and subsequently with anhydrous ammonia to give the primary amide 42. In step 5, the amide 42 is reacted with triphenylphosphine in carbon tetrachloride at 50° C. to give the corresponding nitrile 43. In step 6, the nitrile 43 is reacted with trialkyltin azide in xylene at reflux to provide the 1H-tetrazole angiotensin II antagonists of this invention.

The following Examples 1–4 are detailed descriptions of the methods of preparation of compounds of Formulas I through VII. These detailed preparations fall within the scope of, and serve to exemplify, the above

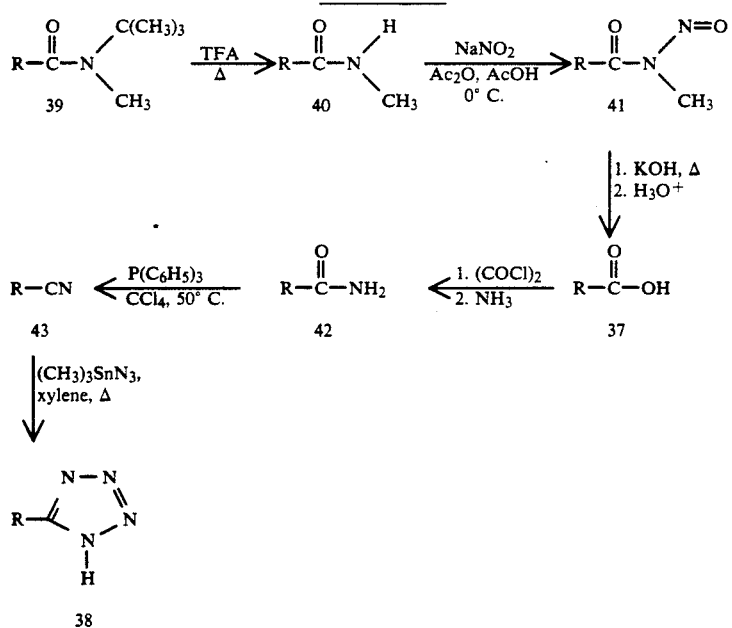

Synthetic Scheme XX shows the preparation of carboxylic acid analogs 37 and 1H-tetrazole analogs 38 from analogs which have $R^5 = CON(CH_3)C(CH_3)_3$ In step 1, the N-methyl-N-tertbutylamide analog 39 is reacted with trifluoroacetic acid at reflux to give the N-methylamide 40. In step 2, the N-methylamide 40 is reacted with sodium nitrite in acetic anhydride/acetic acid at 0° C. to give the corresponding N-methyl-N-nitrosoamide 41. In step 3, the N-methyl-N-nitrosamide 41 is hydrolyzed in base to give the corresponding carboxylic acid angiotensin II antagonists of this invention.

described General Synthetic Procedures which form part of the invention. These Examples are presented for illustrative purposes only and are not intended as a restriction on the scope of the invention. All parts are by weight unless otherwise indicated.

EXAMPLE 1

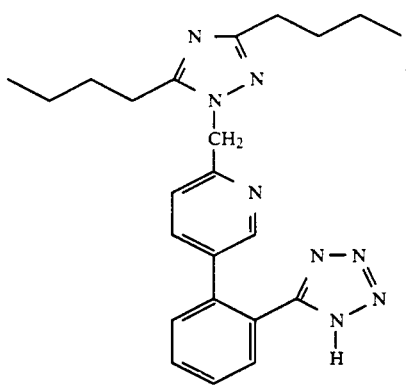

5-[2-[6-[(3,5-dibutyl-1H-1,2,4-triazol-1-yl)methyl]-3-pyridinyl]phenyl]-1H-tetrazole

Step 1: Preparation of 5-bromo-2-picoline

Under nitrogen with stirring, 69.8 mL (0.71 mol) of 2-picoline (Aldrich) was treated with 227 g (1.7 mol) of anhydrous aluminum chloride. The suspension was heated to 100° C., treated with 36.1 mL (0.7 mol) of bromine, and stirred overnight. The reaction was cautiously poured onto crushed ice, treated with a solution of 20 g of sodium sulfite in 200 mL of water, treated with sufficient aqueous sodium hydroxide (50%) to dissolve all aluminum as aluminate, extracted three times with ether, dried (MgSO$_4$), and concentrated in vacuo. Purification by silica gel chromatography (Waters Prep-500A) using ethyl acetate/hexane (15:85) gave 30.4 g (25%) of 5-bromo-2-picoline as a light brown solid: NMR (CDCl$_3$) δ2.50 (s, 3H), 7.05 (d, J=8 Hz, 1H), 7.67 (dd, J=8 and 2 Hz), 8.54 (d, J=2 Hz, 1H).

Step 2: Preparation of 5-bromo-2-bromomethylpyridine

A 4.69 g (27 mmol) sample of 5-bromo-2-picoline from step 1 was dissolved in 250 mL of carbon tetrachloride, treated with 4.85 g (27 mmol) of N-bromosuccinimide (NBS) and 400 mg (2.4 mmol) of azobisisobutyronitrile (AIBN), and stirred at reflux for 3 h. Filtration and concentration in vacuo provided crude 5-bromo-2-bromomethylpyridine which was 64% monobrominated by NMR; no purification was attempted: NMR (CDCl$_3$) δ4.50 (s, 2H), 7.34 (d, J=8 Hz, 1H), 7.82 (dd, J=8 and 2 Hz, 1H), 8.63 (d, J=2 Hz, 1H).

Step 3: Preparation of 3,5-dibutyl-1H-1,2,4-triazole

A solution of 64.5 g (0.50 mol) of ethyl iminovalerate [P. Reynaud and R. C. Moreau, *Bull. Soc. Chim. France*, 2997 (1964)] in 100 mL of methanol was added slowly to 58.0 g (0.50 mol) of valeric acid hydrazide (Lancaster Synthesis) in 400 mL of methanol at 0° C. under a nitrogen atmosphere. After the addition was complete, the reaction was allowed to warm to ambient temperature and then stir at reflux for 2 days. The solvent was removed in vacuo; purification by silica gel chromatography (Waters Prep-500A) using ethyl acetate/hexane (80:20) gave 78.9 g (93%) of a colorless solid: mp 50.5°–51.5° C.; NMR (CDCl$_3$) δ0.88 (t, J=7 Hz, 6H), 1.28–1.33 (m, 4H), 1.63–1.77 (m, 4H), 2.72 (t, J=7 Hz, 4H); MS (FAB) m/e rel intensity) 183 (12%), 182 (100), 181 (3), 180 (6), 152 (8), 139 (4); HRMS. Calc'd for M+H: 182.1657. Found: 182.1661.

Step 4: Preparation of 5-bromo-2-[(3,5-dibutyl-1H-1,2,4-triazol-1-yl)methyl]-pyridine Under nitrogen 3.19 g (18 mmol) of solid 3,5-dibutyl-1H-1,2,4-triazole from step 3 was added in small portions of 25 mmol of sodium hydride in 45 ml of dimethylformamide (DMF); stirring was continued until hydrogen evolution had ceased. The anion solution was cooled to 3° C. and treated with a solution of the crude 5-bromo-2-bromomethylpyridine from step 2 (17 mmol) in 20 ml of dry DMF. The reaction was allowed to warm to ambient temperature and stir overnight. Methanol (10 ml) was added to destroy any unreacted sodium hydride and the DMF was removed in vacuo. The residue was dissolved in ethyl acetate, washed with water, and dried (MgSO$_4$). Silica gel chromatography (Waters Prep-500A) using ethyl acetate/hexane (40:60) gave 4.16 g (69% from triazole) of 5-bromo-2-[(3,5-dibutyl-1H-1,2,4-triazol-1-yl)methyl]pyridine as a brown oil: NMR (CDCl$_3$) δ0.88 (t, J=7 Hz, 3H), 0.93 (t, J=7 Hz, 3H), 1.23–1.46 (m, 4H), 1.59–1.78 (m, 4H), 2.63–2.74 (m, 4H), 5.30 (s, 2H), 6.92 (d, J=8 Hz, 1H), 7.72 (dd, J=8 and 2 Hz, 1H), 8.61 (d, J=2 Hz, 1H).

Step 5: Preparation of 2-(N-triphenylmethyltetrazol-5-yl)phenylboronic acid

A 64 g (350 mmol) sample of 2-bromobenzonitrile (Aldrich) was dissolved in 650 mL of xylene and treated with 22.75 g (350 mmol) of sodium azide and 95 mL (350 mmol) of tributyltin chloride at reflux for 48 h. The reaction was filtered; the filtrate was treated with 50 mL of anhydrous tetrahydrofuran (THF) and 20 g (550 mmol) of hydrogen chloride. The reaction was stirred for 2 h; filtration gave 59.6 g (76%) of 5-(2-bromophenyl)-1H-tetrazole: mp 178°–180° C.; NMR (DMSO-d$_6$) δ7.50–7.64 (m, 2H), 7.67–7.74 (m, 1H), 7.83–7.91 (m, 1H). A 41.8 g (187 mmol) sample of this material was dissolved in 650 mL of methylene chloride and treated with 55.5 g (193 mmol) of triphenylmethyl chloride and 30 mL (220 mmol) of anhydrous triethylamine. The reaction was stirred overnight at reflux, cooled to ambient temperature, washed with water, dried (MgSO$_4$), and concentrated in vacuo. Recrystallization from toluene/hexane gave 80.7 g (92%) of N-triphenylmethyl-5-(2-bromophenyl)-1H-tetrazole: mp 160°–162° C.; NMR (CDCl$_3$) δ7.14–7.21 (m, 6H), 7.26–7.45 (m, 11H), 7.70 (dd, J=8 and 1.5 Hz, 1H), 7.89 (dd, J=7.5 and 2 Hz, 1H). A 34.05 g (73.0 mmol) sample of this material was dissolved in 1700 mL of THF under a nitrogen atmosphere and treated with 73 mmol of n-butyllithium in hexane. The reaction was allowed to stir for 17 min and then was treated with 24.9 mL (220 mmol) of trimethyl borate. The reaction was allowed to come to ambient temperature overnight while stirring, quenched with 10 mL of methanol, and concentrated in vacuo. The residue was dissolved in 1M NaOH and extracted with toluene to remove any unreacted starting material. The pH was adjusted to 6 with 6M HCl and the product extracted with toluene and dried (MgSO$_4$). Hexane was added and the solution was placed in the freezer overnight. Filtration provided 31.3 g (99%) of 2-(N-triphenylmethyltetrazol-5-yl)phenylboronic acid: NMR (CDCl$_3$) δ7.13–7.21 (m, 7H), 7.33–7.42 (m, 8H), 7.49–7.55 (m, 2H), 8.15–8.19 (m, 1H), 8.21–8.26 (m, 1H).

Step 6: Preparation of 5-[2-[6-[(3,5-dibutyl-1H-1,2,4-triazol-1-yl)methyl]-3-pyridinyl]phenyl]-1H-tetrazole Under nitrogen, 2.04 g (5.8 mmol) of 5-bromo-2-[(3,5-dibutyl-1H-1,2,4-triazol-1-yl)methyl]pyridine from step 4 and 2.83 g (6.6 mmol) of 2-(N-triphenylmethyltetrazol-5-yl)phenylboronic acid from step 5 were treated with 1.0 g (0.86 mmol) of tetrakis(triphenylphosphine)palladium zero, 18 mL of toluene, 14 mL of ethanol, and 7.5 mL of 2M aqueous sodium carbonate. The reaction mixture was heated to reflux and vigorously stirred overnight. The product was purified by reverse phase chromatography (Waters Deltaprep-3000) using acetonitrile/water (20–40:80–60) (0.05% TFA). The pure fractions (by analytical HPLC) were combined, the acetonitrile removed in vacuo, the pH adjusted to four with dilute sodium hydroxide, and the resulting suspension extracted 4 times with ether. The extracts were combined, dried (MgSO$_4$), and concentrated in vacuo to give 710 mg (30%) of 5-[2-[6-[(3,5-dibutyl-1H-1,2,4-triazol-1-yl)methyl]-3-pyridinyl]phenyl]-1H-tetrazole as a colorless solid: mp 136°–138° C.; NMR (CD$_3$OD) δ0.88–0.98 (m, 6H), 1.27–1.45 (m, 4H), 1.60–1.75 (m, 4H), 2.66 (t, J=7 Hz, 2H), 2.84 (t, J=7 Hz, 2H), 5.45 (s, 2H), 7.21 (d, J=8 Hz, 1H), 7.56–7.68 (m, 3H), 7.70–7.78 (m, 2H), 8.29 (d, J=2 Hz, 1H); MS (FAB) m/e (rel intensity) 417 (100), 389 (10), 374 (10), 360 (10), 208 (35), 182 (25); HRMS. Calc'd for M+H: 417.2515. Found: 417.2486.

EXAMPLE 2

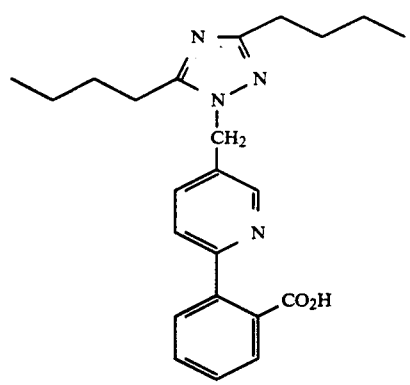

2-[5-[(3,5-dibutyl-1H-1,2,4-triazol-1-yl)methyl]-2-pyridinyl]benzoic acid

Step 1: Preparation of 2-bromo-5-picoline

A solution of 1500 mL (14 mol) of 48% hydrobromic acid was cooled to 10° C. and 300 g (2.8 mol) of 2-amino-5-picoline (Aldrich) was added slowly. The solution was maintained at or below 0° C. while 450 mL (8.8 mol) of bromine was added dropwise. After the bromine addition was complete, a solution of 500 g (7.3 mol) of sodium nitrite in 1000 mL of water was added slowly over 6 h. The reaction pH was adjusted by the careful addition of 1500 mL (56 mol) of 50% sodium hydroxide at such a rate that the temperature was maintained below 30° C. The product precipitated from the nearly colorless reaction mixture; filtration gave 450 g (94%) of 2-bromo-5-picoline as a yellow powder: mp 38°–40° C.; NMR 7.27 (s, 1H), 7.28 (s, 1H), 7.12 (br s, 1H).

Step 2: Preparation of N-methyl-N-tertbutylbenzamide

Under nitrogen, 96.7 g (1.1 mol) of N-methyl-N-tertbutylamine and 111 g (1.1 mol) of triethylamine was dissolved in 1050 mL of anhydrous tetrahydrofuran (THF). The solution was cooled to 0° C. and treated with 140.6 g (1.0 mol) of benzoyl chloride. The reaction was allowed to slowly warm to ambient temperature and stir overnight. Filtration and subsequent concentration in vacuo of the filtrate gave the crude product which was purified by sublimation (65°, 0.2 torr) to give 184 g (96%) of colorless N-methyl-N-tertbutybenzamide: mp 80.5°–82.0° C.; NMR (CDCl$_3$) δ1.52 (s, 9H), 2.87 (s, 3H), 7.34–7.40 (m, 3H), 7.40–7.46 (m, 2H).

Step 3: Preparation of 2-(N-methyl-N-tertbutylcarboxamido)phenylboronic acid Under nitrogen, a solution of 50.0 g (262 mmol) of N-methyl-N-tertbutylbenzamide from step 2 and 44 mL (292 mmol) of tetramethylethylenediamine (TMEDA) in 3350 mL of anhydrous THF was cooled to −78° C. and slowly treated with 262 mmol of sec-butyllithium in cyclohexane. After 1 h at −78° C., the reaction was treated with 45 mL (393 mmol) of trimethyl borate and allowed to slowly warm to ambient temperature overnight with stirring. The reaction was concentrated in vacuo; the residue was dissolved in 1M sodium hydroxide and extracted with methylene chloride. The pH of the aqueous phase was adjusted to six with dilute hydrochloric acid and extracted with methylene chloride; the organic layer was dried (MgSO$_4$) and concentrated in vacuo to give 55.7 g (90%) of a 80:20 mixture of syn-/anti isomers of 2-(N-methyl-N-tertbutylcarboxamido)phenylboronic acid as a pale yellow glass: NMR (CDCl$_3$) δ1.30 (s, syn C(CH$_3$)$_3$, 7.3H), 1.54 (s, anti C(CH$_3$)$_3$, 1.7H), 2.81 (s, anti CH$_3$, 0.6H), 2.94 (s, syn CH$_3$, 2.4H), 7.29–7.46 (m, 3H), 7.95–8.01 (m, 1H).

Step 4: Preparation of N-methyl-N-tertbutyl-2-(5-methyl-2-pyridinyl)benzamide Under nitrogen, 4.44 g (25.8 mmol) of 2-bromo-5-picoline from step 1 in 60 mL of toluene was treated with 6.75 g (29 mmol) of 2-(N-methyl-N-tertbutylcarboxamido)phenylboronic acid from step 3, 1.0 g of tetrakis(triphenylphosphine)palladium zero, 26 mL of ethanol, and 29 mL of 2M sodium carbonate; this mixture was heated to reflux and vigorously stirred for 24 h. The reaction was partitioned between water and ether; the organic layer was separated, dried (MgSO$_4$), and concentrated in vacuo. Purification by silica gel chromatography (Waters Prep-500A) using ethyl acetate/hexane (1:2) gave 6.51 g (90%) of N-methyl-N-tertbutyl-2-(5-methyl-2-pyridinyl)benzamide as an oil: NMR (CDCl$_3$) δ1.40 (s, 9H), 2.33 (s, 3H), 2.61 (s, 3H), 7.27–7.33 (m, 1H), 7.35–7.41 (m, 2H), 7.47–7.51 (m, 2H), 7.60–7.66 (m, 1H), 8.43 (br s, 1H).

Step 5: Preparation of sodium 2-(5-methyl-2-pyridinyl)benzoate

Under nitrogen, 6.5 g (23 mmol) of N-methyl-N-tertbutyl-2-(6-methyl-3-pyridinyl)benzamide from step 4 was treated with 65 mL of anhydrous trifluoroacetic acid (TFA) at reflux for 6 h. The reaction was concentrated in vacuo and the residue dissolved in water. The pH was adjusted to 10 with aqueous sodium hydroxide and lyophilized to give the sodium salt of 2-(5-methyl-2-pyridinyl)benzoic acid as a colorless solid: NMR [CDCl$_3$/CF$_3$CO$_2$H (97:3)] δ2.62 (s, 3H), 7.42-7.48 (m, 1H), 7.67-7.80 (m, 3H), 8.18-8.24 (m, 1H), 8.28 (dd, J=8 and 2 Hz, 1H), 7.67-7.80 (m, 3H), 8.18-8.24 (m, 1H), 8.28 (dd, J=8 and 2 Hz, 1H), 8.61 (s, 1H); MS (FAB) m/e (rel intensity) 214 (20), 196 (100); HRMS. Calc'd for M+H: 214.0868. Found: 214.0846.

Step 6: Preparation of ethyl 2-(5-methyl-2-pyridinyl)benzoate

Under nitrogen, the crude sodium salt from step 5 was suspended in 50 mL of chloroform and treated with 9 mL (103 mmol) of oxalyl chloride. The reaction was stirred for 72 h, filtered under nitrogen, and concentrated in vacuo; the residue was dissolved in absolute ethanol. Concentration in vacuo gave 2.0 g (8 mmol) of ethyl 2-(5-methyl-2-pyridinyl)benzoate as a brown oil: NMR (CDCl$_3$)δ1.09 (t, J=7 Hz, 3H), 2.36 (s, 3H), 4.15 (q, J=7 Hz, 2H), 7.34 (d, J=8 Hz, 1H), 7.38-7.48 (m, 1H), 7.48-7.58 (m, 3H), 7.80 (d, J=8 Hz, 1H), 8.46 (s, 1H).

Step 7: Preparation of ethyl 2-(5-bromomethyl-2-pyridinyl)benzoate

Under nitrogen, the crude ethyl 2-(5-methyl-2-pyridinyl)benzoate from step 6 was treated with 1.7 g (9.5 mmol) of NBS and 160 mg (0.66 mmol) of benzoyl peroxide in 145 mL of anhydrous carbon tetrachloride at reflux for 2.5 h. The reaction was filtered under nitrogen and concentrated in vacuo to give crude ethyl 2-(5-bromomethyl-2-pyridinyl)benzoate; no purification was attempted.

Step 8: Preparation of ethyl 2-[5-[(3,5-dibutyl-1H-1,2,4-triazol-1-yl)methyl]-2-pyridinyl]benzoate Under nitrogen, 630 mg (3.5 mmol) of 3,5-dibutyl-1H-1,2,4-triazole from step 3 of Example 1 was added in small portions to 5.4 mmol of sodium hydride in 8 mL of DMF; stirring was continued until hydrogen evolution had ceased. The anion solution was cooled to 0° C. and treated with a solution of the crude ethyl 2-(5-bromomethyl-2-pyridinyl)benzoate from step 7 in 10 mL of DMF. The reaction was stirred at ambient temperature overnight, quench with 1 mL of absolute ethanol, and concentrated in vacuo; the resulting residue was redissolved in methylene chloride, filtered, and reconcentrated in vacuo to give crude ethyl 2-[5-[(3,5-dibutyl-1H-1,2,4-triazol-1-yl)methyl]-2-pyridinyl]benzoate.

Step 9: Preparation of 2-[5-[(3,5-dibutyl-1H-1,2,4-triazol-1-yl)methyl]-2-pyridinyl]benzoic acid A 1.0 g sample of the crude ethyl 2-[5-[(3,5-dibutyl-1H-1,2,4-triazol-1-yl)methyl]-2-pyridinyl]benzoate from step 8 in 10 mL of water was treated with 3 mL of 10% aqueous sodium hydroxide and stirred at ambient temperature overnight. The reaction mixture was washed with 30 mL of ether and the pH adjusted to six with dilute hydrochloric acid. Purification by reverse phase chromatography (Waters Deltaprep-3000) using isocratic acetonitrile/water (28:72) (0.05% TFA) gave 5 mg of 2-[5-[(3,5-dibutyl-1H-1,2,4-triazol-1-yl)methyl]-2-pyridinyl]benzoic acid: NMR (D$_2$O+NaO$_3$S(CH$_2$)$_3$Si(CH$_3$)$_3$]δ0.80 (t, J=7 Hz, 3H), 0.86 (t, J=7 Hz, 3H), 1.19-1.33 (m, 4H), 1.54-1.68 (m, 4H), 2.65 (t, J=7 Hz, 2H), 2.82 (t, J=7 Hz, 2H), 5.43 (s, 2H), 7.45-7.59 (m, 5H), 7.64 (dd, J=8 and 2 Hz, 1H), 8.37-8.45 (m, 1H); MS (FAB) m/e (rel intensity) 393 (80), 375 (30), 212 (40), 182 (100); HRMS. Calc'd for M+Li: 399.2373. Found: 399.2374.

EXAMPLE 3

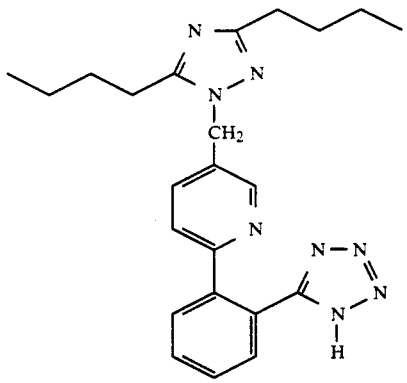

5-[2-[5-[(3,5-dibutyl-1H-1,2,4-triazol-1-yl)methyl]-2-pyridinyl]phenyl]-1H-tetrazole

Step 1: Preparation of 2-bromo-5-bromomethylpyridine

A solution of 296.3 g (1.72 mol) of 2-bromo-5-picoline from step 1 of Example 2 in 6000 mL of carbon tetrachloride was treated with 306.5 g (1.72 mol) of N-bromosuccinimide (NBS) and 28.3 g (173 mmol) of azobisisobutyronitrile (AIBN). The reaction was stirred at reflux under nitrogen for 3 h, filtered, and concentrated in vacuo providing 476 g of crude 2-bromo-5-bromomethylpyridine as a brownish yellow solid (NMR indicates that this material is only 60% monobromomethyl product): NMR (CDCl$_3$)δ4.42 (s, 2H), 7.48 (d, J=9 Hz, 1H), 7.60 (dd, J=9 and 3 Hz, 1H), 8.37 (d, J=3 Hz, 1H).

Step 2: Preparation of 2-bromo-5-[(3,5-dibutyl-1H-1,2,4-triazol-1-yl)methyl]-pyridine Under nitrogen, 3.15 g (17 mmol) of solid 3,5-dibutyl-1H-1,2,4-triazole from step 3 of Example 1 was added in small portions to 33 mmol of sodium hydride in 31 ml of dimethylformamide (DMF); stirring was continued until hydrogen evolution had ceased. The anion solution was cooled to 0° C. and treated with a solution of 7.9 g (19 mmol) of crude 2-bromo-5-bromomethylpyridine from step 1 in 10 ml of dry DMF. The reaction was allowed to warm to ambient temperature and stir overnight. Methanol (10 ml) was added to destroy any unreacted sodium hydride and the DMF was removed in vacuo. The residue was dissolved in ethyl acetate, washed with water, and dried (MgSO$_4$). Silica gel chromatography (Waters Prep-500A) using ethyl acetate/hexane (60:40) gave 4.8 g (47%) of 2-bromo-5-[(3,5-dibutyl-1H-1,2,4-triazol-1-yl)methyl]pyridine as an oil: NMR (CDCl$_3$)δ0.88 (t, J=7 Hz, 1H), 0.92 (t, J=7 Hz, 1H), 1.27-1.44 (m, 4H), 1.59-1.76 (m, 4H), 2.60-2.71 (m, 4H), 5.18 (s, 2H), 7.35 (dd, J=8 and 3 Hz, 1H), 7.46 (d, J=8 Hz, 1H), 8.23 (d, J=3 Hz, 1H).

Step 3: Preparation of 5-[2-[5-[(3,5-dibutyl-1H-1,2,4-triazol-1-yl)methyl]-2-pyridinyl]phenyl]-1H-tetrazole.

Under nitrogen, 1.03 g (2.9 mmol) of 2-bromo-5-[(3,5-dibutyl-1H-1,2,4-triazol-1-yl)methyl]pyridine from step 2 and 2.46 g (5.7 mmol) of 2-(N-triphenylmethyltetrazol-5-yl)phenylboronic acid from step 5 of Example 1 were treated with 1.0 g (0.86 mmol) of tetrakis(triphenyl-phosphine)palladium zero, 15 mL of toluene, 10 mL of ethanol, and 6.3 mL of 2M aqueous sodium carbonate. The reaction mixture was heated to reflux and vigorously stirred overnight. The product was purified by reverse phase chromatography (Waters Deltaprep-3000) using acetonitrile/water (20–40:80–60) (0.05% TFA). The pure fractions (by analytical HPLC) were combined, the acetonitrile removed in vacuo, the pH adjusted to four with dilute sodium hydroxide, and the resulting suspension extracted 4 times with ether. The extracts were combined, dried (MgSO$_4$), and concentrated in vacuo to give 340 mg (28%) of 5-[2-[5-[(3,5-dibutyl-1H-1,2,4-triazol-1-yl)methyl]-2-pyridinyl]phenyl-1H-tetrazole as a colorless solid: mp 139°–141° C.; NMR (CD$_3$OD)δ0.90 (t, J=7 Hz, 3H), 0.93 (t, J=7 Hz, 3H), 1.29–1.44 (m, 4H), 1.58–1.75 (m, 4H), 2.65 (t, J=7 Hz, 2H), 2.81 (t, J=7 Hz, 2H), 5.40 (s, 2H), 7.47 (d, J=8 Hz, 1H), 7.61–7.77 (m, 5H), 8.33 (d, J=2 Hz, 1H); MS (FAB) m/e (rel intensity) 417 (100), 208 (30); HRMS. Calc'd for M+H: 417.2515. Found: 417.2527.

EXAMPLE 4

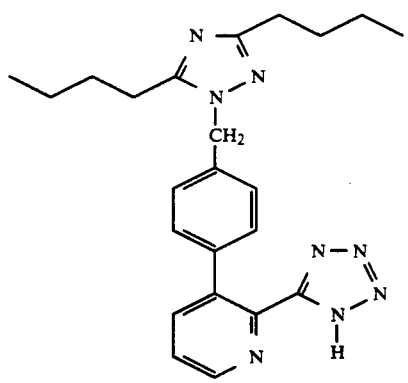

5-[3-[4-[(3,5-dibutyl-1H-1,2,4-triazol-1-yl)methyl]-phenyl]-2-pyridinyl]-1H-tetrazole A solution of 199 g (1.26 mol) of 3-bromopyridine (Aldrich) in 1000 mL of glacial acetic acid was treated with 200 mL of 30% hydrogen peroxide. The reaction was heated to 100° C., stirred for 4 h, and retreated with an additional 100 mL of 30% hydrogen peroxide. This mixture was stirred at 100° C. for 4 days, concentrated in vacuo, and the residue dissolved in 400 mL of water. The pH of the resulting solution was adjusted to ten with potassium carbonate and continuously extracted with methylene chloride for 48 h. The methylene chloride extracts were dried (MgSO$_4$), concentrated in vacuo, and distilled to give 156.8 g (71%) of 3-bromopyridine N-oxide as a colorless oil: bp 116°–117° C. (0.2 torr); NMR (CDCl$_3$)δ7.20 (t, J=7 Hz, 1H), 7.43 (d, J=8 Hz, 1H), 8.17 (d, J=7 Hz, 1H), 8.37 (d, J=2 Hz, 1H).

Step 2: Preparation of 2-cyano-3-bromopyridine

Under nitrogen, a solution of 156 g (0.90 mol) of 3-bromopyridine N-oxide from step 1 was dissolved in 1000 mL of acetonitrile and treated with 256 mL (1.84 mol) of triethylamine and 275 g (2.8 mol) of trimethylsilyl cyanide. The reaction was stirred at reflux overnight and concentrated in vacuo; the residue was dissolved in 2.5M aqueous sodium hydroxide and extracted with methylene chloride. The organic phase was dried (MgSO$_4$) and concentrated in vacuo; this residue was decolorized with carbon and recrystallized from methanol to give 42.2 g (26%) of 2-cyano-3-bromopyridine as a cream colored solid: mp 97°–98° C.; NMR (CDCl$_3$)δ7.42 (dd, J=8 and 5 Hz, 1H), 8.05 (dd, J=8 and 2 Hz, 1H), 8.67 (dd, J=5 and 2 Hz, 1H).

Step 3: Preparation of 4-tolylboronic acid

Under nitrogen, a solution of 94.1 g (0.55 mol) of 4-bromotoluene in 400 mL of anhydrous THF was treated with 14.5 g (0.60 mol) of magnesium turnings. The reaction was stirred at reflux for 2 h, cooled to −78° C., treated with a solution of 156 mL (1.38 mol) of trimethyl borate in 475 mL of THF, stirred for 1 h, and allowed to warm to ambient temperature. The reaction mixture was concentrated in vacuo and partitioned between aqueous base and methylene chloride. The pH of the aqueous phase was adjusted to one with hydrochloric acid and extracted with methylene chloride. The organic phase was dried (MgSO$_4$) and concentrated in vacuo to give 4-tolylboronic acid: NMR (CDCl$_3$)δ2.45 (s, 3H), 7.31 (d, J=8 Hz, 2H), 8.13 (d, J=8 Hz, 2H).

Step 4: Preparation of 2-cyano-3-(4-tolyl)pyridine

Under nitrogen, 13.91 g (76 mmol) of 2-cyano-3-bromopyridine from step 2 and 11.41 g (84 mmol) of 4-tolylboronic acid from step 3 were treated with 2.65 g (2.3 mmol) of tetrakis(triphenylphosphine)palladium zero, 155 mL of toluene, 60 mL of ethanol, and 77 mL of 2M aqueous sodium carbonate. The reaction mixture was heated to reflux and vigorously stirred overnight. The product crystallized from the reaction mixture after several days at ambient temperature. Filtration provided 5.02 g (34%) of 2-cyano-3-(4-tolyl)pyridine as a colorless solid: mp 136°–138° C.; NMR (CDCl$_3$) δ2.44 (s, 3H), 7.34 (d, J=8 Hz, 2H), 7.47 (d, J=8 Hz, 2H), 7.56 (dd, J=8 and 5 Hz, 1H), 7.85 (dd, J=8 and 2Hz, 1H), 8.68 (dd, J=5 and 2 Hz, 1H); MS (70 eV) m/e (rel intensity) 194 (100).

Step 5: Preparation of 2-cyano-3-(4-α-bromotolyl)pyridine

Under nitrogen, a solution of 5.0 g (26 mmol) of 2-cyano-3-(4-tolyl)pyridine from step 4 in 450 mL of carbon tetrachloride was treated with 4.6 g (26 mmol) of NBS and 500 mg (2.1 mmol) of benzoyl peroxide. The reaction was stirred at reflux for 2 h, filtered, and concentrated in vacuo to give 6.98 g of crude 2-cyano-3-(4-α-bromotolyl)pyridine which was 75% monobrominated by NMR as an oil; no purification was attempted: NMR (CDCl$_3$) δ4.56 (s, 2H), 7.54–7.62 (m, 5H), 7.86 (dd, J=8 and 2 Hz, 1H), 8.72 (dd, J=5 and 2 Hz, 1H).

Step 6: Preparation of 2-cyano-3-[4-[(3,5-dibutyl-1H-1,2,4-triazol-1-yl)methyl]phenyl]pyridine Under nitrogen, 3.13 g (17 mmol) of solid 3,5-dibutyl-1H-1,2,4-triazole from step 3 of Example 1 was added in small portions to 20 mmol of sodium hydride in 47 ml of dimethylformamide (DMF); stirring was continued until hydrogen evolution had ceased. The anion solution was cooled to −22° C. and treated with a solution of 6.90 g (19 mmol) of crude 2-cyano-3-(4-α-bromotolyl)pyridine from step 5 in 20 ml of dry DMF. The reaction was allowed to warm to ambient temperature and stir overnight. Methanol (10 ml) was added to destroy any unreacted sodium hydride and the DMF was removed in vacuo. The residue was dissolved in ethyl acetate, washed with water, and dried (MgSO₄). Silica gel chromatography (Waters Prep-500A) using ethyl acetate/hexane (1:1) gave 5.48 g (86%) of 2-cyano-3-[4-[(3,5-dibutyl-1H-1,2,4-triazol-1-yl)methyl]phenyl]pyridine as an oil: NMR (CDCl$_3$) δ0.88 (t, J=7 Hz, 3H), 0.93 (t, J=7 Hz, 3H), 1.28–1.46 (m, 4H), 1.61–1.78 (m, 4H), 2.66 (t, J=7 Hz, 2H), 2.69 (t, J=7 Hz, 2H), 5.31 (s, 2H), 7.27 (d, J=8 Hz, 2H), 7.50–7.60 (m, 3H), 7.82 (dd, J=8 and 2 Hz, 1H), 8.69 (dd, J=5 and 2 Hz, 1H); MS (FAB) m/e (rel intensity) 374 (80), 193 (100), 182 (30) 166 (13).

Step 7: Preparation of 5-[3-[4-[(3,5-dibutyl-1H-1,2,4-triazol-1-yl)methyl]phenyl]-2-pyridinyl]-1H-tetrazole Under nitrogen, a solution of 5.40 g (15 mmol) of 2-cyano-3-[4-[(3,5-dibutyl-1H-1,2,4-triazol-1-yl)methyl]phenyl]pyridine from step 6 in 55 mL of toluene was treated with 4.90 g (24 mmol) of trimethyltin azide. The reaction was stirred at reflux for 3 days and concentrated in vacuo. The residue was dissolved in 94 mL of acetic acid/water (9:1) and stirred at ambient temperature for 3 days. The reaction was concentrated in vacuo, redissolved in acetonitrile, filtered, and reconcentrated in vacuo to give the crude product as an orange oil. A small sample of this material was purified by reverse phase chromatograph (Waters Deltaprep-3000) using isocratic acetonitrile/water (25:75) (0.05% TFA) providing 5-[3-[4-[(3,5-dibutyl-1H-1,2,4-triazol-1-yl)methyl]phenyl]-2-pyridinyl]-1H-tetrazole as a colorless solid: NMR (CDCl$_3$) δ0.88 (t, J=7 Hz, 3H), 0.92 (t, J=7 Hz, 3H), 1.30–1.45 (m, 4H), 1.61–1.80 (m, 4H), 2.80 (t, J=7 Hz, 2H), 2.90 (t, J=7 Hz, 2H), 5.33 (s, 2H), 7.21 (d, J=9 Hz, 2H), 7.28 (d, J=9 Hz, 2H), 7.49–7.56 (m, 1H), 7.78 (dd, J=8 and 2 Hz, 1H), 8.72 (dd, J=5 and 2 Hz, 1H); MS (FAB) m/e (rel intensity), 417 (100), 208 (90), 182 (60); HRMS. Calc'd for M+H: 417.2517. Found: 417.2520.

BIOLOGICAL EVALUATION

Assay A: Angiotensin II Binding Activity

Compounds of the invention were tested for ability to bind to the smooth muscle angiotensin II receptor using a rat uterine membrane preparation. Angiotensin II (AII) was purchased from Peninsula Labs. $^{125}$I-angiotensin II (specific activity of 2200 Ci/mmol) was purchased from Du Pont-New England Nuclear. Other chemicals were obtained from Sigma Chemical Co. This assay was carried out according to the method of Douglas et al [*Endocrinology*, 106, 120–124 (1980)]. Rat uterine membranes were prepared from fresh tissue. All procedures were carried out at 4° C. Uteri were stripped of fat and homogenized in phosphate-buffered saline at pH 7.4 containing 5 mM EDTA. The homogenate was centrifuged at 1500×g for 20 min., and the supernatant was recentrifuged at 100,000×g for 60 min. The pellet was resuspended in buffer consisting of 2 mM EDTA and 50 mM Tris-HCl (pH 7.5) to a final protein concentration of 4 mg/ml. Assay tubes were charged with 0.25 ml of a solution containing 5 mM MgCl$_2$, 2 mM EDTA, 0.5% bovine serum albumin, 50 mM Tris-HCl, pH 7.5 and $^{125}$I-AII (approximately 10$^5$ cpm) in the absence or in the presence of unlabelled ligand. The reaction was initiated by the addition of membrane protein and the mixture was incubated at 25° C. for 60 min. The incubation was terminated with ice-cold 50 mM Tris-HCl (pH 7.5) and the mixture was filtered to separate membrane-bound labelled peptide from the free ligand. The incubation tube and filter were washed with ice-cold buffer. Filters were assayed for radioactivity in a Micromedic gamma counter. Nonspecific binding was defined as binding in the presence of 10 μM of unlabelled AII. Specific binding was calculated as total binding minus nonspecific binding. The receptor binding affinity of an AII antagonist compound was indicated by the concentration (IC$_{50}$) of the tested AII antagonist which gives 50% displacement of the total specifically bound $^{125}$I-AII from the high affinity AII receptor. Binding data were analyzed by a nonlinear least-squares curve fitting program. Results are reported in Table I.

Assay B: In Vitro Vascular Smooth Muscle-Response for AII

The compounds of the invention were tested for antagonist activity in rabbit aortic rings. Male New Zealand white rabbits (2–2.5 kg) were sacrificed using an overdose of pentobarbital and exsanguinated via the carotid arteries. The thoracic aorta was removed, cleaned of adherent fat and connective tissue and then cut into 3-mm ring segments. The endothelium was removed from the rings by gently sliding a rolled-up piece of filter paper into the vessel lumen. The rings were then mounted in a water-jacketed tissue bath, maintained at 37° C., between moveable and fixed ends of a stainless steel wire with the moveable end attached to an FT03 Grass transducer coupled to a Model 7D Grass Polygraph for recording isometric force responses. The bath was filled with 20 ml of oxygenated (95% oxygen-5% carbon dioxide) Krebs solution of the following composition (mM): 130 NaCl, 15 NaHCO$_3$, 15 KCl, 1.2 NaH$_2$PO$_4$, 1.2 MgSO$_4$, 2.5 CaCl$_2$, and 11.4 glucose. The preparations were equilibrated for one hour before approximately one gram of passive tension was placed on the rings. Angiotensin II concentration-response curves were then recorded (3×10$^{-10}$ to 1×10$^{-5}$M). Each concentration of AII was allowed to elicit its maximal contraction, and then AII was washed out repeatedly for 30 minutes before rechallenging with a higher concentration of AII. Aorta rings were exposed to the test antagonist at 10$^{-5}$M for 5 minutes before challenging with AII. Adjacent segments of the same aorta ring were used for all concentration-response curves in the presence or absence of the test antagonist. The effectiveness of the test compound was expressed in terms of pA$_2$ values and were calculated according to H. O. Schild [*Br. J. Pharmacol. Chemother*,, 2, 189–206 (1947)]. The pA$_2$ value is the concentration of the antagonist which increases the $EC_{50}$ value for AII by a factor of two. Each test antagonist was evaluated in aorta rings from two rabbits. Results are reported in Table I.

TABLE I

In Vitro Angiotensin II
Activity of Compounds of the Invention

| Test Compound Example # | [1]Assay A $IC_{50}$ (nM) | [2]Assay B $pA_2$ |
|---|---|---|
| 1 | 6.9 | 7.88/8.01 |
| 2 | 120 | — |
| 3 | 6.9 | 8.57/8.24 |
| 4 | 110 | 7.11/6.60 |

[1]Assay A: Angiotensin II Binding Activity
[2]Assay B: In Vitro Vascular Smooth Muscle Response

Assay C: In Vivo Intragastric Pressor Assay Response for AII Antagonists

Male Sprague-Dawley rats weighing 225–300 grams were anesthetized with methohexital (30 mg/kg, i.p.) and catheters were implanted into the femoral artery and vein. The catheters were tunneled subcutaneously to exit dorsally, posterior to the head and between the scapulae. The catheters were filled with heparin (1000 units/ml of saline). The rats were returned to their cage and allowed regular rat chow and water ad libitum. After full recovery from surgery (3–4 days), rats were placed in Lucite holders and the arterial line was connected to a pressure transducer. Arterial pressure was recorded on a Gould polygraph (mmHg). Angiotensin II was administered as a 30 ng/kg bolus via the venous catheter delivered in a 50 μl volume with a 0.2 ml saline flush. The pressor response in mm Hg was measured by the difference from pre-injection arterial pressure to the maximum pressure achieved. The AII injection was repeated every 10 minutes until three consecutive injections yielded responses within 4 mmHg of each other. These three responses were then averaged and represented the control response to AII. The test compound was suspended in 0.5% methylcellulose in water and was administered by gavage. The volume administered was 2 ml/kg body weight. The standard dose was 3 mg/kg. Angiotensin II bolus injections were given at 30, 45, 60, 75, 120, 150, and 180 minutes after gavage. The pressor response to AII was measured at each time point. The rats were then returned to their cage for future testing. A minimum of 3 days was allowed between tests. Percent inhibition was calculated for each time point following gavage by the following formula: [(Control Response-Response at time point)/Control Response] × 100. Results are shown in Table II.

TABLE II

Blood Pressure Response of Angiotesin II Treated Rats Following Administration of Angiotesin II Antagonist of the Invention A. % Inhibition of Blood Pressure Elevation by Administration of Ex. #1 Compound

| *Time (min) | Rat A | Rat B | Rat C | Rats A-C Mean ± SE |
|---|---|---|---|---|
| 0 | 0 | 0 | 0 | 0 |
| 30 | 14 | 11 | 16 | 14 ± 2 |
| 45 | 20 | 15 | 6 | 14 ± 4 |
| 60 | 40 | 26 | 29 | 31 ± 4 |
| 75 | 33 | 23 | 2 | 20 ± 9 |
| 90 | 37 | 21 | 10 | 23 ± 8 |
| 120 | 37 | 23 | 16 | 26 ± 6 |
| 150 | 40 | 23 | −4 | 20 ± 13 |
| 180 | 33 | 13 | 10 | 19 ± 7 |

B. % Inhibition of Blood Pressure Elevation by Administration of Ex. #3 Compound

| *Time (min) | Rat A | Rat B | Rat C | Rat D | Rat E | Rats A-E Mean ± SE |
|---|---|---|---|---|---|---|
| 0 | 0 | 0 | 0 | 0 | 0 | 0 |
| 30 | 64 | 55 | 15 | 21 | 52 | 42 ± 10 |
| 45 | 67 | 71 | 12 | 14 | 43 | 41 ± 13 |
| 60 | 52 | 55 | 46 | 36 | 38 | 46 ± 4 |
| 75 | 45 | 53 | 27 | 36 | 43 | 41 ± 4 |
| 90 | 60 | 50 | 46 | 26 | 29 | 42 ± 6 |
| 120 | 41 | 50 | 53 | 34 | 29 | 41 ± 5 |
| 150 | 38 | 53 | 50 | 29 | 16 | 37 ± 7 |
| 180 | 24 | 40 | 62 | 3 | 16 | 29 ± 10 |

*Time of AII bolus injection

Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A compound of the formula

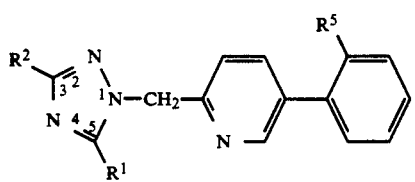

wherein R¹ is selected from methyl, ethyl, n-propyl, isopropyl, n-butyl, sec-butyl, isobutyl, tert-butyl, isopentyl, n-pentyl, neopentyl, phenyl, benzyl, phenethyl, cyclohexyl, cyclohexylmethyl, 2-butenyl, 3-butenyl, 2-butynyl, 3-butynyl and 2-hydroxybutyl; wherein R² is selected from methyl, ethyl, n-propyl, isopropyl, n-butyl, sec-butyl, isobutyl, isopentyl, tert-butyl, n-pentyl, neopentyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, acetyl, 1butenyl, 2-butenyl, 3-butenyl, 1-butynyl, 2-butynyl, 3-butynyl, propylthio, butylthio,

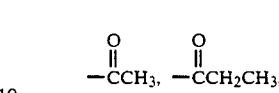

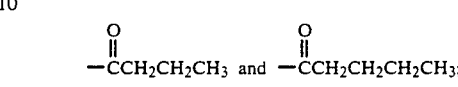

wherein R₅ is COOH or

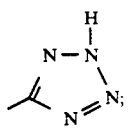

or a tautomer thereof or a pharmaceutically-acceptable salt thereof.

2. Compound of claim 1 selected from compounds, and their pharmaceutically-acceptable salts, of the group of compounds consisting of 2-[6-[(3-methyl-5-butyl-1H-1,2,4-triazol-1-yl)methyl]-3-pyridinyl]benzoic acid;

2-[6-[(3-ethyl-5-butyl-1H-1,2,4-triazol-1-yl)methyl]-3-pyridinyl]benzoic acid;

2-[6-[(3-propyl-5-butyl-1H-1,2,4-triazol-1-yl)methyl]-3-pyridinyl]benzoic acid;

2-[6-[(3-isopropyl-5-butyl-1H-1,2,4-triazol-1-yl)methyl]-3-pyridinyl]benzoic acid;

2-[6-[(3,5-dibutyl-1H-1,2,4-triazol-1-yl)methyl]-3-pyridinyl]benzoic acid;

2-[6-[(3-secbutyl-5-butyl-1H-1,2,4-triazol-1-yl)methyl]-3-pyridinyl]benzoic acid;

2-[6-[(3-isobutyl-5-butyl-1H-1,2,4-triazol-1-yl)methyl]-3-pyridinyl]benzoic acid;

2-[6-[(3-tertbutyl-5-butyl-1H-1,2,4-triazol-1-yl)methyl]-3-pyridinyl]benzoic acid;

2-[6-[(3-pentyl-5-butyl-1H-1,2,4-triazol-1-yl)methyl]-3-pyridinyl]benzoic acid;

2-[6-[(3-isopentyl-5-butyl-1H-1,2,4-triazol-1-yl)methyl]-3-pyridinyl]benzoic acid;

2-[6-[(3-cyclohexyl-5-butyl-1H-1,2,4-triazol-1-yl)methyl]-3-pyridinyl]benzoic acid;

2-[6-[(3-cyclohexylmethyl-5-butyl-1H-1,2,4-triazol-1-yl)methyl]-3-pyridinyl]benzoic acid;

2-[6-[(3-phenyl-5-butyl-1H-1,2,4-triazol-1-yl)methyl]-3-pyridinyl]benzoic acid;

2-[6-[(3-phenylmethyl-5-butyl-1H-1,2,4-triazol-1-yl)methyl]-3-pyridinyl]benzoic acid;

2-[6-[[3-(2-cyclohexylethyl)-5-butyl-1H-1,2,4-triazol-1-yl]methyl]-3-pyridinyl]benzoic acid;

2-[6-[[3-(2-phenylethyl)-5-butyl-1H-1,2,4-triazol-1-yl]methyl]-3-pyridinyl]benzoic acid;

2-[6-[[3-(1-oxo-2-phenylethyl)-5-butyl-1H-1,2,4-triazol-1-yl]methyl]-3-pyridinyl]benzoic acid;

2-[6-[[3-(1-oxobutyl)-5-butyl-1H-1,2,4-triazol-1-yl]methyl]-3-pyridinyl]benzoic acid;

2-[6-[[3-(1,1-difluorobutyl)-5-butyl-1H-1,2,4-triazol-1-yl]methyl]-3-pyridinyl]benzoic acid;

2-[6-[[3-(1,1-dimethoxybutyl)-5-butyl-1H-1,2,4-triazol-1-yl]methyl]-3-pyridinyl]benzoic acid;

5-[2-[6-[(3-methyl-5-butyl-1H-1,2,4-triazol-1-yl)methyl]-3-pyridinyl]phenyl]-1H-tetrazole;

5-[2-[6-[(3-ethyl-5-butyl-1H-1,2,4-triazol-1-yl)methyl]-3-pyridinyl]phenyl]-1H-tetrazole;
5-[2-[6-[(3-propyl-5-butyl-1H-1,2,4-triazol-1-yl)methyl]-3-pyridinyl]phenyl]-1H-tetrazole;
5-[2-[6-[3-isopropyl-5-butyl-1H-1,2,4-triazol-1-yl)methyl]-3-pyridinyl]phenyl]-1H-tetrazole;
5-[2-[6-[(3,5-dibutyl-1H-1,2,4-triazol-1-yl)methyl]-3-pyridinyl]phenyl]-1H-tetrazole;
5-[2-[6-[(3-secbutyl-5-butyl-1H-1,2,4-triazol-1-yl)methyl]-3-pyridinyl]phenyl]-1H-tetrazole;
5-[2-[6-[(3-isobutyl-5-butyl-1H-1,2,4-triazol-1-yl)methyl]-3-pyridinyl]phenyl]-1H-tetrazole;
5-[2-[6-[(3-tertbutyl-5-butyl-1H-1,2,4-triazol-1-yl)methyl]-3-pyridinyl]phenyl]-1H-tetrazole;
5-[2-[6-[(3-pentyl-5-butyl-1H-1,2,4-triazol-1-yl)methyl]-3-pyridinyl]phenyl]-1H-tetrazole;
5-[2-[6-[(3-isopentyl-5-butyl-1H-1,2,4-triazol-1-yl)methyl]-3-pyridinyl]phenyl]-1H-tetrazole;
5-[2-[6-[(3-cyclohexyl-5-butyl-1H-1,2,4-triazol-1-yl)methyl]-3-pyridinyl]phenyl]-1H-tetrazole;
5-[2-[6-[(3-cyclohexylmethyl-5-butyl-1H-1,2,4-triazol-1-yl)methyl]-3-pyridinyl]phenyl]-1H-tetrazole;
5-[2-[6-[(3-phenyl-5-butyl-1H-1,2,4-triazol-1-yl)methyl]-3-pyridinyl]phenyl]-1H-tetrazole;
5-[2-[6-[(3-phenylmethyl-5-butyl-1H-1,2,4-triazol-1-yl)methyl]-3-pyridinyl]phenyl]-1H-tetrazole;
5-[2-[6-[[3-(2-cyclohexylethyl)-5-butyl-1H-1,2,4-triazol-1-yl]methyl]-3-pyridinyl]phenyl]-1H-tetrazole;
5-[2-[6-[[3-(2-phenylethyl)-5-butyl-1H-1,2,4-triazol-1-yl]methyl]-3-pyridinyl]phenyl]-1H-tetrazole;
5-[2-[6-[[3-(1-oxo-2-phenylethyl)-5-butyl-1H-1,2,4-triazol-1-yl]methyl]-3-pyridinyl]phenyl]-1H-tetrazole;
5-[2-[6-[[3-(1-oxobutyl)-5-butyl-1H-1,2,4-triazol-1-yl]methyl]-3-pyridinyl]phenyl]-1H-tetrazole;
5-[2-[6-[[3-(1,1-difluorobutyl)-5-butyl-1H-1,2,4-triazol-1-yl]methyl]-3-pyridinyl]phenyl]-1H-tetrazole; and
5-[2-[6-[[3-(1,1-dimethoxybutyl)-5-butyl-1H-1,2,4-triazol-1-yl]methyl]-3-pyridinyl]phenyl]-1H-tetrazole.

3. Compound of claim 2 which is 5-[2-[6-[(3,5-dibutyl-1H-1,2,4-triazol-1-yl)methyl]-3-pyridinyl]phenyl-1H-tetrazole or a pharmaceutically-acceptable salt thereof.

4. A compound of the formula

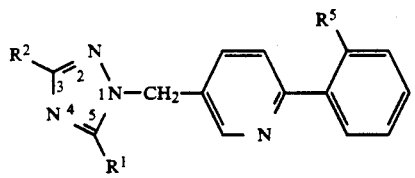

wherein $R^1$ is selected from methyl, ethyl, n-propyl, isopropyl, n-butyl, sec-butyl, isobutyl, tert-butyl, isopentyl, n-pentyl, neopentyl, phenyl, benzyl, phenethyl, cyclohexyl, cyclohexylmethyl, 2-butenyl, 3-butenyl, 2-butynyl, 3-butynyl and 2-hydroxybutyl; wherein $R^2$ is selected from methyl, ethyl, n-propyl, isopropyl, n-butyl, sec-butyl, isobutyl, isopentyl, tert-butyl, n-pentyl, neopentyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, acetyl, 1-butenyl, 2-butenyl, 3-butenyl, 1-butynyl, 2-butynyl, 3-butynyl, propylthio, butylthio,

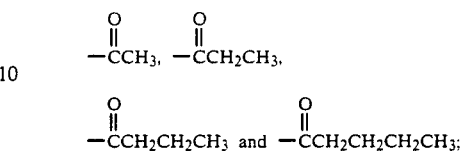

wherein $R^5$ is COOH or

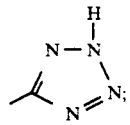

or a tautomer thereof or a pharmaceutically-acceptable salt thereof.

5. Compound of claim 4 selected from compounds, and their pharmaceutically-acceptable salts, of the group of compounds consisting of
2-[5-[(3-methyl-5-butyl-1H-1,2,4-triazol-1-yl)methyl]-2-pyridinyl]benzoic acid;
2-[5-[(3-ethyl-5-butyl-1H-1,2,4-triazol-1-yl)methyl]-2-pyridinyl]benzoic acid;
2-[5-[(3-propyl-5-butyl-1H-1,2,4-triazol-1-yl)methyl]-2-pyridinyl]benzoic acid;
2-[5-[(3-isopropyl-5-butyl-1H-1,2,4-triazol-1-yl)methyl]-2-pyridinyl]benzoic acid;
2-[5-[(3,5-dibutyl-1H-1,2,4-triazol-1-yl)methyl]-2-pyridinyl]benzoic acid;
2-[5-[(3-secbutyl-5-butyl-1H-1,2,4-triazol-1-yl)methyl]-2-pyridinyl]benzoic acid;
2-[5-[(3-isobutyl-5-butyl-1H-1,2,4-triazol-1-yl)methyl]-2-pyridinyl]benzoic acid;
2-[5-[(3-tertbutyl-5-butyl-1H-1,2,4-triazol-1-yl)methyl]-2-pyridinyl]benzoic acid;
2-[5-[(3-pentyl-5-butyl-1H-1,2,4-triazol-1-yl)methyl]-2-pyridinyl]benzoic acid;
2-[5-[(3-isopentyl-5-butyl-1H-1,2,4-triazol-1-yl)methyl]-2-pyridinyl]benzoic acid;
2-[5-[(3-cyclohexyl-5-butyl-1H-1,2,4-triazol-1-yl)methyl]-2-pyridinyl]benzoic acid;
2-[5-[(3-cyclohexylmethyl-5-butyl-1H-1,2,4-triazol-1-yl)methyl]-2-pyridinyl]benzoic acid;
2-[5-[(3-phenyl-5-butyl-1H-1,2,4-triazol-1-yl)methyl]-2-pyridinyl]benzoic acid;
2-[5-[(3-phenylmethyl-5-butyl-1H-1,2,4-triazol-1-yl)methyl]-2-pyridinyl]benzoic acid;
2-[5-[[3-(2-cyclohexylethyl)-5-butyl-1H-1,2,4-triazol-1-yl]methyl]-2-pyridinyl]benzoic acid;
2-[5-[[3-(2-phenylethyl)-5-butyl-1H-1,2,4-triazol-1-yl]methyl]-2-pyridinyl]benzoic acid;
2-[5-[[3-(1-oxo-2-phenylethyl)-5-butyl-1H-1,2,4-triazol-1-yl]methyl]-2-pyridinyl]benzoic acid;
2-[5-[[3-(1-oxobutyl)-5-butyl-1H-1,2,4-triazol-1-yl]methyl]-2-pyridinyl]benzoic acid;
2-[5-[[3-(1,1-difluorobutyl)-5-butyl-1H-1,2,4-triazol-1-yl]methyl]-2-pyridinyl]benzoic acid;
2-[5-[[3-(1,1-dimethoxybutyl)-5-butyl-1H-1,2,4-triazol-1-yl]methyl]-2-pyridinyl]benzoic acid;

5-[2-[5-[(3-methyl-5-butyl-1H-1,2,4-triazol-1-yl)methyl]-2-pyridinyl]phenyl]-1H-tetrazole;
5-[2-[5-[(3-ethyl-5-butyl-1H-1,2,4-triazol-1-yl)methyl]-2-pyridinyl]phenyl]-1H-tetrazole;
5-[2-[5-[(3-propyl-5-butyl-1H-1,2,4-triazol-1-yl)methyl]-2-pyridinyl]phenyl]-1H-tetrazole;
5-[2-[5-[(3-isopropyl-5-butyl-1H-1,2,4-triazol-1-yl)methyl]-2-pyridinyl]phenyl]-1H-tetrazole;
5-[2-[5-[(3,5-dibutyl-1H-1,2,4-triazol-1-yl)methyl]-2-pyridinyl]phenyl]-1H-tetrazole;
5-[2-[5-[(3-secbutyl-5-butyl-1H-1,2,4-triazol-1-yl)methyl]-2-pyridinyl]phenyl]-1H-tetrazole;
5-[2-[5-[(3-isobutyl-5-butyl-1H-1,2,4-triazol-1-yl)methyl]-2-pyridinyl]phenyl]-1H-tetrazole;
5-[2-[5-[(3-tertbutyl-5-butyl-1H-1,2,4-triazol-1-yl)methyl]-2-pyridinyl]phenyl]-1H-tetrazole;
5-[2-[5-[(3-pentyl-5-butyl-1H-1,2,4-triazol-1-yl)methyl]-2-pyridinyl]phenyl]-1H-tetrazole;
5-[2-[5-[(3-isopentyl-5-butyl-1H-1,2,4-triazol-1-yl)methyl]-2-pyridinyl]phenyl]-1H-tetrazole;
5-[2-[5-[(3-cyclohexyl-5-butyl-1H-1,2,4-triazol-1-yl)methyl]-2-pyridinyl]phenyl]-1H-tetrazole;
5-[2-[5-[(3-cyclohexylmethyl-5-butyl-1H-1,2,4-triazol-1-yl)methyl]-2-pyridinyl]-phenyl]-1H-tetrazole;
5-[2-[5-[(3-phenyl-5-butyl-1H-1,2,4-triazol-1-yl)methyl]-2-pyridinyl]phenyl]-1H-tetrazole;
5-[2-[5-[(3-phenylmethyl-5-butyl-1H-1,2,4-triazol-1-yl)methyl]-2-pyridinyl]phenyl]-1H-tetrazole;
5-[2-[5-[[3-(2-cyclohexylethyl)-5-butyl-1H-1,2,4-triazol-1-yl]methyl]-2-pyridinyl]phenyl]-1H-tetrazole;
5-[2-[5-[[3-(2-phenylethyl)-5-butyl-1H-1,2,4-triazol-1-yl]methyl]-2-pyridinyl]phenyl]-1H-tetrazole;
5-[2-[5-[[3-(1-oxo-2-phenylethyl)-5-butyl-1H-1,2,4-triazol-1-yl]methyl]-2-pyridinyl]phenyl]-1H-tetrazole;
5-[2-[5-[[3-(1-oxobutyl)-5-butyl-1H-1,2,4-triazol-1-yl]methyl]-2-pyridinyl]phenyl]-1H-tetrazole;
5-[2-[5-[[3-(1,1-difluorobutyl)-5-butyl-1H-1,2,4-triazol-1-yl]methyl]-2-pyridinyl]phenyl]-1H-tetrazole; and
5-[2-[5-[[3-(1,1-dimethoxybutyl)-5-butyl-1H-1,2,4-triazol-1-yl]methyl]-2-pyridinyl]phenyl]-1H-tetrazole.

6. Compound of claim 5 which is 2-[5-[(3,5-dibutyl-1H-1,2,4-triazol-1-yl)methyl]-2-pyridinyl]benzoic acid or a pharmaceutically-acceptable salt thereof.

7. Compound of claim 5 which is 5-[2-[5-[(3,5-dibutyl-1H-1,2,4-triazol-1-yl)methyl]-2-pyridinyl]phenyl-1H-tetrazole or a pharmaceutically-acceptable salt thereof.

8. A compound of the formula

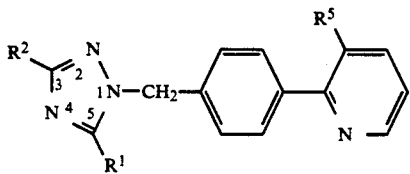

wherein R¹ is selected from methyl, ethyl, n-propyl, isopropyl, n-butyl, sec-butyl, isobutyl, tert-butyl, isopentyl, n-pentyl, neopentyl, phenyl, benzyl, phenethyl, cyclohexyl, cyclohexylmethyl, 2-butenyl, 3-butenyl, 2-butynyl, 3-butynyl and 2-hydroxybutyl; wherein R² is selected from methyl, ethyl, n-propyl, isopropyl, n-butyl, sec-butyl, isobutyl, isopentyl, tert-butyl, n-pentyl, neopentyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, acetyl, 1-butenyl, 2-butenyl, 3-butenyl, 1-butynyl, 2-butynyl, 3-butynyl, propylthio, butylthio,

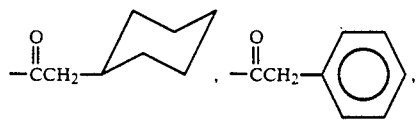

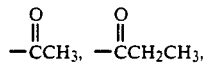

wherein R⁵ is COOH or

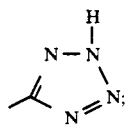

or a tautomer thereof or a pharmaceutically-acceptable salt thereof.

9. Compound of claim 8 selected from compounds, and their pharmaceutically-acceptable salts, of the group of compounds consisting of
2-[4-[(3-methyl-5-butyl-1H-1,2,4-triazol-1-yl)methyl]-phenyl]-3-pyridinecarboxylic acid;
2-[4-[(3-ethyl-5-butyl-1H-1,2,4-triazol-1-yl)methyl]-phenyl]-3-pyridinecarboxylic acid;
2-[4-[(3-propyl-5-butyl-1H-1,2,4-triazol-1-yl)methyl]-phenyl]-3-pyridinecarboxylic acid;
2-[4-[(3-isopropyl-5-butyl-1H-1,2,4-triazol-1-yl)methyl]-phenyl]-3-pyridinecarboxylic acid;
2-[4-[(3,5-dibutyl-1H-1,2,4-triazol-1-yl)methyl]phenyl]-3-pyridinecarboxylic acid;
2-[4-[(3-secbutyl-5-butyl-1H-1,2,4-triazol-1-yl)methyl]-phenyl]-3-pyridinecarboxylic acid;
2-[4-[(3-isobutyl-5-butyl-1H-1,2,4-triazol-1-yl)methyl]-phenyl]-3-pyridinecarboxylic acid;
2-[4-[(3-tertbutyl-5-butyl-1H-1,2,4-triazol-1-yl)methyl]-phenyl]-3-pyridinecarboxylic acid;
2-[4-[(3-pentyl-5-butyl-1H-1,2,4-triazol-1-yl)methyl]-phenyl]-3-pyridinecarboxylic acid;
2-[4-[(3-isopentyl-5-butyl-1H-1,2,4-triazol-1-yl)methyl]-phenyl]-3-pyridinecarboxylic acid;
2-[4-[(3-cyclohexyl-5-butyl-1H-1,2,4-triazol-1-yl)methyl]phenyl]-3-pyridinecarboxylic acid;
2-[4-[(3-cyclohexylmethyl-5-butyl-1H-1,2,4-triazol-1-yl)methyl]phenyl]-3-pyridinecarboxylic acid;
2-[4-[(3-phenyl-5-butyl-1H-1,2,4-triazol-1-yl)methyl]-phenyl]-3-pyridinecarboxylic acid;
2-[4-[(3-phenylmethyl-5-butyl-1H-1,2,4-triazol-1-yl)methyl]phenyl]-3-pyridinecarboxylic acid;
2-[4-[[3-(2-cyclohexylethyl)-5-butyl-1H-1,2,4-triazol-1-yl]methyl]phenyl]-3-pyridinecarboxylic acid;
2-[4-[[3-(2-phenylethyl)-5-butyl-1H-1,2,4-triazol-1-yl]methyl]phenyl]-3-pyridinecarboxylic acid;
2-[4-[[3-(1-oxo-2-phenylethyl)-5-butyl-1H-1,2,4-triazol-1-yl]methyl]phenyl]-3-pyridinecarboxylic acid;
2-[4-[[3-(1-oxobutyl)-5-butyl-1H-1,2,4-triazol-1-yl]methyl]phenyl]-3-pyridinecarboxylic acid;

2-[4-[[3-(1,1-difluorobutyl)-5-butyl-1H-1,2,4-triazol-1-yl]methyl]phenyl]-3-pyridinecarboxylic acid;

2-[4-[[3-(1,1-dimethoxybutyl)-5-butyl-1H-1,2,4-triazol-1-yl]methyl]phenyl]-3-pyridinecarboxylic acid;

5-[2-[4-[(3-methyl-5-butyl-1H-1,2,4-triazol-1-yl)methyl]phenyl]-3-pyridinyl]-1H-tetrazole;

5-[2-[4-[(3-ethyl-5-butyl-1H-1,2,4-triazol-1-yl)methyl]phenyl]-3-pyridinyl]-1H-tetrazole;

5-[2-[4-[(3-propyl-5-butyl-1H-1,2,4-triazol-1-yl)methyl]phenyl]-3-pyridinyl]-1H-tetrazole;

5-[2-[4-[(3-isopropyl-5-butyl-1H-1,2,4-triazol-1-yl)methyl]phenyl]-3-pyridinyl]-1H-tetrazole;

5-[2-[4-[(3,5-dibutyl-1H-1,2,4-triazol-1-yl)methyl]phenyl]-3-pyridinyl]-1H-tetrazole;

5-[2-[4-[(3-secbutyl-5-butyl-1H-1,2,4-triazol-1-yl)methyl]phenyl]-3-pyridinyl]-1H-tetrazole;

5-[2-[4-[(3-isobutyl-5-butyl-1H-1,2,4-triazol-1-yl)methyl]phenyl]-3-pyridinyl]-1H-tetrazole;

5-[2-[4-[(3-tertbutyl-5-butyl-1H-1,2,4-triazol-1-yl)methyl]phenyl]-3-pyridinyl]-1H-tetrazole;

5-[2-[4-[(3-pentyl-5-butyl-1H-1,2,4-triazol-1-yl)methyl]phenyl]-3-pyridinyl]-1H-tetrazole;

5-[2-[4-[(3-isopentyl-5-butyl-1H-1,2,4-triazol-1-yl)methyl]phenyl]-3-pyridinyl]-1H-tetrazole;

5-[2-[4-[(3-cyclohexyl-5-butyl-1H-1,2,4-triazol-1-yl)methyl]phenyl]-3-pyridinyl]-1H-tetrazole;

5-[2-[4-[(3-cyclohexylmethyl-5-butyl-1H-1,2,4-triazol-1-yl)methyl]phenyl]-3-pyridinyl]-1H-tetrazole;

5-[2-[4-[(3-phenyl-5-butyl-1H-1,2,4-triazol-1-yl)methyl]phenyl]-3-pyridinyl]-1H-tetrazole;

5-[2-[4-[(3-phenylmethyl-5-butyl-1H-1,2,4-triazol-1-yl)methyl]phenyl]-3-pyridinyl]-1H-tetrazole;

5-[2-[4-[[3-(2-cyclohexylethyl)-5-butyl-1H-1,2,4-triazol-1-yl]methyl]phenyl]-3-pyridinyl]-1H-tetrazole;

5-[2-[4-[[3-(2-phenylethyl)-5-butyl-1H-1,2,4-triazol-1-yl]methyl]phenyl]-3-pyridinyl]-1H-tetrazole;

5-[2-[4-[[3-(1-oxo-2-phenylethyl)-5-butyl-1H-1,2,4-triazol-1-yl]methyl]phenyl]-3-pyridinyl]-1H-tetrazole;

5-[2-[4-[[3-(1-oxobutyl)-5-butyl-1H-1,2,4-triazol-1-yl]methyl]phenyl]-3-pyridinyl]-1H-tetrazole;

5-[2-[4-[[3-(1,1-difluorobutyl)-5-butyl-1H-1,2,4-triazol-1-yl]methyl]phenyl]-3-pyridinyl]-1H-tetrazole; and 5-[2-[4-[[3-(1,1-dimethoxybutyl)-5-butyl-1H-1,2,4-triazol-1-yl]methyl]phenyl]-3-pyridinyl]-1H-tetrazole.

10. A compound of the formula wherein $R^1$ is selected from methyl, ethyl, n-propyl, isopropyl, n-butyl, sec-butyl, isobutyl, tert-butyl, isopentyl, n-pentyl, neopentyl, phenyl, benzyl, phenethyl, cyclohexyl, cyclohexylmethyl, 2-butenyl, 3-butenyl, 2-butynyl, 3-butynyl and 2-hydroxybutyl; wherein $R^2$ is selected from methyl, ethyl, n-propyl, isopropyl, n-butyl, sec-butyl, isobutyl, isopentyl, tert-butyl, n-pentyl, neopentyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, acetyl, 1-butenyl, 2-butenyl, 3-butenyl, 1-butynyl, 2-butynyl, 3-butynyl, propylthio, butylthio, wherein $R^5$ is COOH or or a tautomer thereof or a pharmaceutically-acceptable salt thereof.

11. Compound of claim 10 selected from compounds, and their pharmaceutically-acceptable salts, of the group of compounds consisting of 3-[4-[(3-methyl-5-butyl-1H-1,2,4-triazol-1-yl)methyl]phenyl]-4-pyridinecarboxylic acid;

3-[4-[(3-ethyl-5-butyl-1H-1,2,4-triazol-1-yl)methyl]phenyl]-4-pyridinecarboxylic acid;

3-[4-[(3-propyl-5-butyl-1H-1,2,4-triazol-1-yl)methyl]phenyl]-4-pyridinecarboxylic acid;

3-[4-[(3-isopropyl-5-butyl-1H-1,2,4-triazol-1-yl)methyl]phenyl]-4-pyridinecarboxylic acid;

3-[4-[(3,5-dibutyl-1H-1,2,4-triazol-1-yl)methyl]phenyl]-4-pyridinecarboxylic acid;

3-[4-[(3-secbutyl-5-butyl-1H-1,2,4-triazol-1-yl)methyl]phenyl]-4-pyridinecarboxylic acid;

3-[4-[(3-isobutyl-5-butyl-1H-1,2,4-triazol-1-yl)methyl]phenyl]-4-pyridinecarboxylic acid;

3-[4-[(3-tertbutyl-5-butyl-1H-1,2,4-triazol-1-yl)methyl]phenyl]-4-pyridinecarboxylic acid;

3-[4-[(3-pentyl-5-butyl-1H-1,2,4-triazol-1-yl)methyl]phenyl]-4-pyridinecarboxylic acid;

3-[4-[(3-isopentyl-5-butyl-1H-1,2,4-triazol-1-yl)methyl]phenyl]-4-pyridinecarboxylic acid;

3-[4-[(3-cyclohexyl-5-butyl-1H-1,2,4-triazol-1-yl)methyl]phenyl]-4-pyridinecarboxylic acid;

3-[4-[(3-cyclohexylmethyl-5-butyl-1H-1,2,4-triazol-1-yl)methyl]phenyl]-4-pyridinecarboxylic acid;

3-[4-[(3-phenyl-5-butyl-1H-1,2,4-triazol-1-yl)methyl]phenyl]-4-pyridinecarboxylic acid;

3-[4-[(3-phenylmethyl-5-butyl-1H-1,2,4-triazol-1-yl)methyl]phenyl]-4-pyridinecarboxylic acid;

3-[4-[[3-(2-cyclohexylethyl)-5-butyl-1H-1,2,4-triazol-1-yl]methyl]phenyl]-4-pyridinecarboxylic acid;

3-[4-[[3-(2-phenylethyl)-5-butyl-1H-1,2,4-triazol-1-yl]methyl]phenyl]-4-pyridinecarboxylic acid;

3-[4-[[3-(1-oxo-2-phenylethyl)-5-butyl-1H-1,2,4-triazol-1-yl]methyl]phenyl]-4-pyridinecarboxylic acid;

3-[4-[[3-(1-oxobutyl)-5-butyl-1H-1,2,4-triazol-1-yl]methyl]phenyl]-4-pyridinecarboxylic acid;

3-[4-[[3-(1,1-difluorobutyl)-5-butyl-1H-1,2,4-triazol-1-yl]methyl]phenyl]-4-pyridinecarboxylic acid;

3-[4-[[3-(1,1-dimethoxybutyl)-5-butyl-1H-1,2,4-triazol-1-yl]methyl]phenyl]-4-pyridinecarboxylic acid;

5-[3-[4-[(3-methyl-5-butyl-1H-1,2,4-triazol-1-yl)methyl]phenyl]-4-pyridinyl]-1H-tetrazole;

5-[3-[4-[(3-ethyl-5-butyl-1H-1,2,4-triazol-1-yl)methyl]phenyl]-4-pyridinyl]-1H-tetrazole;

5-[3-[4-[(3-propyl-5-butyl-1H-1,2,4-triazol-1-yl)methyl]phenyl]-4-pyridinyl]-1H-tetrazole;

5-[3-[4-[(3-isopropyl-5-butyl-1H-1,2,4-triazol-1-yl)methyl]phenyl]-4-pyridinyl]-1H-tetrazole;

5-[3-[4[(3,5-dibutyl-1H-1,2,4-triazol-1-yl)methyl]phenyl]-4-pyridinyl]-1H-tetrazole;

5-[3-[4-[(3-secbutyl-5-butyl-1H-1,2,4-triazol-1-yl)methyl]phenyl]-4-pyridinyl]-1H-tetrazole;

5-[3-[4-[(3-isobutyl-5-butyl-1H-1,2,4-triazol-1-yl)methyl]phenyl]-4-pyridinyl]-1H-tetrazole;

5-[3-[4-[(3-tertbutyl-5-butyl-1H-1,2,4-triazol-1-yl)methyl]phenyl]-4-pyridinyl]-1H-tetrazole;

5-[3-[4-[(3-pentyl-5-butyl-1H-1,2,4-triazol-1-yl)methyl]phenyl]-4-pyridinyl]-1H-tetrazole;

5-[3-[4-[(3-isopentyl-5-butyl-1H-1,2,4-triazol-1-yl)methyl]phenyl]-4-pyridinyl]-1H-tetrazole;

5-[3-[4-[(3-cyclohexyl-5-butyl-1H-1,2,4-triazol-1-yl)methyl]phenyl]-4-pyridinyl]-1H-tetrazole;

5-[3-[4-[(3-cyclohexylmethyl-5-butyl-1H-1,2,4-triazol-1-yl)methyl]phenyl]-4-pyridinyl]-1H-tetrazole;

5-[3-[4-[(3-phenyl-5-butyl-1H-1,2,4-triazol-1-yl)methyl]phenyl]-4-pyridinyl]-1H-tetrazole;

5-[3-[4-[(3-phenylmethyl-5-butyl-1H-1,2,4-triazol-1-yl)methyl]phenyl]-4-pyridinyl]-1H-tetrazole;

5-[3-[4-[[3-(2-cyclohexylethyl)-5-butyl-1H-1,2,4-triazol-1-yl]methyl]phenyl]-4-pyridinyl]-1H-tetrazole;

5-[3-[4-[[3-(2-phenylethyl)-5-butyl-1H-1,2,4-triazol-1-yl]methyl]phenyl]-4-pyridinyl]-1H-tetrazole;

5-[3-[4-[[3-(1-oxo-2-phenylethyl)-5-butyl-1H-1,2,4-triazol-1-yl]methyl]phenyl]-4-pyridinyl]-1H-tetrazole;

5-[3-[4-[[3-(1-oxobutyl)-5-butyl-1H-1,2,4-triazol-1-yl]methyl]phenyl]-4-pyridinyl]-1H-tetrazole;

5-[3-[4-[[3-(1,1-difluorobutyl)-5-butyl-1H-1,2,4-triazol-1-yl]methyl]phenyl]-4-pyridinyl]-1H-tetrazole; and 5-[3-[4-[[3-(1,1-dimethoxybutyl)-5-butyl-1H-1,2,4-triazol-1-yl]methyl]phenyl]-4-pyridinyl]-1H-tetrazole.

12. A compound of the formula

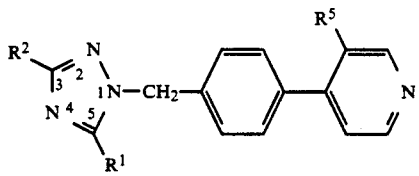

wherein $R^1$ is selected from methyl, ethyl, n-propyl, isopropyl, n-butyl, sec-butyl, isobutyl, tert-butyl, isopentyl, n-pentyl, neopentyl, phenyl, benzyl, phenethyl, cyclohexyl, cyclohexylmethyl, 2-butenyl, 3-butenyl, 2-butynyl, 3-butynyl and 2-hydroxybutyl; wherein $R^2$ is selected from methyl, ethyl, n-propyl, isopropyl, n-butyl, sec-butyl, isobutyl, isopentyl, tert-butyl, n-pentyl, neopentyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, acetyl, 1-butenyl, 2-butenyl, 3-butenyl, 1-butynyl, 2-butynyl, 3-butynyl, propylthio, butylthio,

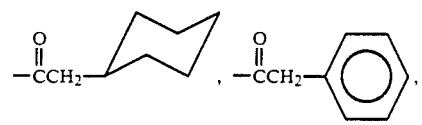

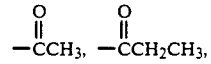

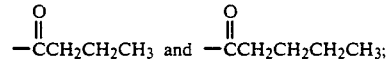

wherein $R^5$ is COOH or

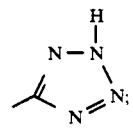

or a tautomer thereof or a pharmaceutically-acceptable salt thereof.

13. Compound of claim 12 selected from compounds, and their pharmaceutically-acceptable salts, of the group of compounds consisting of 4-[4-[(3-methyl-5-butyl-1H-1,2,4-triazol-1-yl)methyl]phenyl]-3-pyridinecarboxylic acid;

4-[4-[(3-ethyl-5-butyl-1H-1,2,4-triazol-1-yl)methyl]phenyl]-3-pyridinecarboxylic acid;

4-[4-[(3-propyl-5-butyl-1H-1,2,4-triazol-1-yl)methyl]phenyl]-3-pyridinecarboxylic acid;

4-[4-[(3-isopropyl-5-butyl-1H-1,2,4-triazol-1-yl)methyl]phenyl]-3-pyridinecarboxylic acid;

4-[4-[(3,5-dibutyl-1H-1,2,4-triazol-1-yl)methyl]phenyl]-3-pyridinecarboxylic acid;

4-[4-[(3-secbutyl-5-butyl-1H-1,2,4-triazol-1-yl)methyl]phenyl]-3-pyridinecarboxylic acid;

4-[4-[(3-isobutyl-5-butyl-1H-1,2,4-triazol-1-yl)methyl]phenyl]-3-pyridinecarboxylic acid;

4-[4-[(3-tertbutyl-5-butyl-1H-1,2,4-triazol-1-yl)methyl]phenyl]-3-pyridinecarboxylic acid;

4-[4-[(3-pentyl-5-butyl-1H-1,2,4-triazol-1-yl)methyl]phenyl]-3-pyridinecarboxylic acid;

4-[4-[(3-isopentyl-5-butyl-1H-1,2,4-triazol-1-yl)methyl]phenyl]-3-pyridinecarboxylic acid;

4-[4-[(3-cyclohexyl-5-butyl-1H-1,2,4-triazol-1-yl)methyl]phenyl]-3-pyridinecarboxylic acid;

4-[4-[(3-cyclohexylmethyl-5-butyl-1H-1,2,4-triazol-1-yl)methyl]phenyl]-3-pyridinecarboxylic acid;

4-[4-[(3-phenyl-5-butyl-1H-1,2,4-triazol-1-yl)methyl]phenyl]-3-pyridinecarboxylic acid;

4-[4-[(3-phenylmethyl-5-butyl-1H-1,2,4-triazol-1-yl)methyl]phenyl]-3-pyridinecarboxylic acid;

4-[4-[[3-(2-cyclohexylethyl)-5-butyl-1H-1,2,4-triazol-1-yl]methyl]phenyl]-3-pyridinecarboxylic acid;

4-[4-[[3-(2-phenylethyl)-5-butyl-1H-1,2,4-triazol-1-yl]methyl]phenyl]-3-pyridinecarboxylic acid;

4-[4-[[3-(1-oxo-2-phenylethyl)-5-butyl-1H-1,2,4-triazol-1-yl]methyl]phenyl]-3-pyridinecarboxylic acid;

4-[4-[[3-(1-oxobutyl)-5-butyl-1H-1,2,4-triazol-1-yl]methyl]phenyl]-3-pyridinecarboxylic acid;

4-[4-[[3-(1,1-difluorobutyl)-5-butyl-1H-1,2,4-triazol-1-yl]methyl]phenyl]-3-pyridinecarboxylic acid;

4-[4-[[3-(1,1-dimethoxybutyl)-5-butyl-1H-1,2,4-triazol-1-yl]methyl]phenyl]-3-pyridinecarboxylic acid;
5-[4-[4-[(3-methyl-5-butyl-1H-1,2,4-triazol-1-yl)methyl]phenyl]-3-pyridinyl]-1H-tetrazole;
5-[4-[4-[(3-ethyl-5-butyl-1H-1,2,4-triazol-1-yl)methyl]phenyl]-3-pyridinyl]-1H-tetrazole;
5-[4-[4-[(3-propyl-5-butyl-1H-1,2,4-triazol-1-yl)methyl]phenyl]-3-pyridinyl]-1H-tetrazole;
5-[4-[4-[(3-isopropyl-5-butyl-1H-1,2,4-triazol-1-yl)methyl]phenyl]-3-pyridinyl]-1H-tetrazole;
5-[4-[4-[(3,5-dibutyl-1H-1,2,4-triazol-1-yl)methyl]phenyl]-3-pyridinyl]-1H-tetrazole;
5-[4-[4-[(3-secbutyl-5-butyl-1H-1,2,4-triazol-1-yl)methyl]phenyl]-3-pyridinyl]-1H-tetrazole;
5-[4-[4-[(3-isobutyl-5-butyl-1H-1,2,4-triazol-1-yl)methyl]phenyl]-3-pyridinyl]-1H-tetrazole;
5-[4-[4-[(3-tertbutyl-5-butyl-1H-1,2,4-triazol-1-yl)methyl]phenyl]-3-pyridinyl]-1H-tetrazole;
5-[4-[4-[(3-pentyl-5-butyl-1H-1,2,4-triazol-1-yl)methyl]phenyl]-3-pyridinyl]-1H-tetrazole;
5-[4-[4-[(3-isopentyl-5-butyl-1H-1,2,4-triazol-1-yl)methyl]phenyl]-3-pyridinyl]-1H-tetrazole;
5-[4-[4-[(3-cyclohexyl-5-butyl-1H-1,2,4-triazol-1-yl)methyl]phenyl]-3-pyridinyl]-1H-tetrazole;
5-[4-[4-[(3-cyclohexylmethyl-5-butyl-1H-1,2,4-triazol-1-yl)methyl]phenyl]-3-pyridinyl]-1H-tetrazole;
5-[4-[4-[(3-phenyl-5-butyl-1H-1,2,4-triazol-1-yl)methyl]phenyl]-3-pyridinyl]-1H-tetrazole;
5-[4-[4-[(3-phenylmethyl-5-butyl-1H-1,2,4-triazol-1-yl)methyl]phenyl]-3-pyridinyl]-1H-tetrazole;
5-[4-[4-[[3-(2-cyclohexylethyl)-5-butyl-1H-1,2,4-triazol-1-yl]methyl]phenyl]-3-pyridinyl]-1H-tetrazole;
5-[4-[4-[[3-(2-phenylethyl)-5-butyl-1H-1,2,4-triazol-1-yl]methyl]phenyl]-3-pyridinyl]-1H-tetrazole;
5-[4-[4-[[3-(1-oxo-2-phenylethyl)-5-butyl-1H-1,2,4-triazol-1-yl]methyl]phenyl]-3-pyridinyl]-1H-tetrazole;
5-[4-[4-[[3-(1-oxobutyl)-5-butyl-1H-1,2,4-triazol-1-yl]methyl]phenyl]-3-pyridinyl]-1H-tetrazole;
5-[4-[4-[[3-(1,1-difluorobutyl)-5-butyl-1H-1,2,4-triazol-1-yl]methyl]phenyl]-3-pyridinyl]-1H-tetrazole; and
5-[4-[4-[[3-(1,1-dimethoxybutyl)-5-butyl-1H-1,2,4-triazol-1-yl]methyl]phenyl]-3-pyridinyl]-1H-tetrazole.

14. A compound of the formula

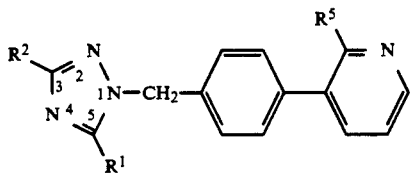

wherein $R^1$ is selected from methyl, ethyl, n-propyl, isopropyl, n-butyl, sec-butyl, isobutyl, tert-butyl, isopentyl, n-pentyl, neopentyl, phenyl, benzyl, phenethyl, cyclohexyl, cyclohexylmethyl, 2-butenyl, 3-butenyl, 2-butynyl, 3-butynyl and 2-hydroxybutyl; wherein $R^2$ is selected from methyl, ethyl, n-propyl, isopropyl, n-butyl, sec-butyl, isobutyl, isopentyl, tert-butyl, n-pentyl, neopentyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, acetyl, 1-butenyl, 2-butenyl, 3-butenyl, 1-butynyl, 2-butynyl, 3-butynyl, propylthio, butylthio,

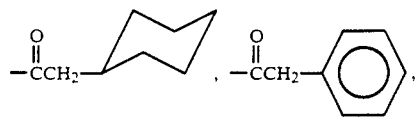

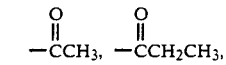

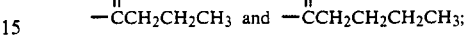

wherein $R^5$ is COOH or

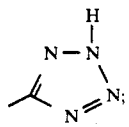

or a tautomer thereof or a pharmaceutically-acceptable salt thereof.

15. Compound of claim 14 selected from compounds, and their pharmaceutically-acceptable salts, of the group of compounds consisting of
3-[4-[(3-methyl-5-butyl-1H-1,2,4-triazol-1-yl)methyl]phenyl]-2-pyridinecarboxylic acid;
3-[4-[(3-ethyl-5-butyl-1H-1,2,4-triazol-1-yl)methyl]phenyl]-2-pyridinecarboxylic acid;
3-[4-[(3-propyl-5-butyl-1H-1,2,4-triazol-1-yl)methyl]phenyl]-2-pyridinecarboxylic acid;
3-[4-[(3-isopropyl-5-butyl-1H-1,2,4-triazol-1-yl)methyl]phenyl]-2-pyridinecarboxylic acid;
3-[4-[(3,5-dibutyl-1H-1,2,4-triazol-1-yl)methyl]phenyl]-2-pyridinecarboxylic acid;
3-[4-[(3-secbutyl-5-butyl-1H-1,2,4-triazol-1-yl)methyl]phenyl]-2-pyridinecarboxylic acid;
3-[4-[(3-isobutyl-5-butyl-1H-1,2,4-triazol-1-yl)methyl]phenyl]-2-pyridinecarboxylic acid;
3-[4-[(3-tertbutyl-5-butyl-1H-1,2,4-triazol-1-yl)methyl]phenyl]-2-pyridinecarboxylic acid;
3-[4-[(3-pentyl-5-butyl-1H-1,2,4-triazol-1-yl)methyl]phenyl]-2-pyridinecarboxylic acid;
3-[4-[(3-isopentyl-5-butyl-1H-1,2,4-triazol-1-yl)methyl]phenyl]-2-pyridinecarboxylic acid;
3-[4-[(3-cyclohexyl-5-butyl-1H-1,2,4-triazol-1-yl)methyl]phenyl]-2-pyridinecarboxylic acid;
3-[4-[(3-cyclohexylmethyl-5-butyl-1H-1,2,4-triazol-1-yl)methyl]phenyl]-2-pyridinecarboxylic acid;
3-[4-[(3-phenyl-5-butyl-1H-1,2,4-triazol-1-yl)methyl]phenyl]-2-pyridinecarboxylic acid;
3-[4-[(3-phenylmethyl-5-butyl-1H-1,2,4-triazol-1-yl)methyl]phenyl]-2-pyridinecarboxylic acid;
3-[4-[[3-(2-cyclohexylethyl)-5-butyl-1H-1,2,4-triazol-1-yl]methyl]phenyl]-2-pyridinecarboxylic acid;
3-[4-[[3-(2-phenylethyl)-5-butyl-1H-1,2,4-triazol-1-yl]methyl]phenyl]-2-pyridinecarboxylic acid;
3-[4-[[3-(1-oxo-2-phenylethyl)-5-butyl-1H-1,2,4-triazol-1-yl]methyl]phenyl]-2-pyridinecarboxylic acid;
3-[4-[[3-(1-oxobutyl)-5-butyl-1H-1,2,4-triazol-1-yl]methyl]phenyl]-2-pyridinecarboxylic acid;
3-[4-[[3-(1,1-difluorobutyl)-5-butyl-1H-1,2,4-triazol-1-yl]methyl]phenyl]-2-pyridinecarboxylic acid;

3-[4-[[3-(1,1-dimethoxybutyl)-5-butyl-1H-1,2,4-triazol-1-yl]methyl]phenyl]-2-pyridinecarboxylic acid;
5-[3-[4-[(3-methyl-5-butyl-1H-1,2,4-triazol-1-yl)methyl]phenyl]-2-pyridinyl]-1H-tetrazole;
5-[3-[4-[(3-ethyl-5-butyl-1H-1,2,4-triazol-1-yl)methyl]phenyl]-2-pyridinyl]-1H-tetrazole;
5-[3-[4-[(3-propyl-5-butyl-1H-1,2,4-triazol-1-yl)methyl]phenyl]-2-pyridinyl]-1H-tetrazole;
5-[3-[4-[(3-isopropyl-5-butyl -1H-1,2,4-triazol-1-yl)methyl]phenyl]-2-pyridinyl]-1H-tetrazole;
5-[3-[4-[(3,5-dibutyl-1H-1,2,4-triazol-1-yl)methyl]phenyl]-2-pyridinyl]-1H-tetrazole;
5-[3-[4-[(3-secbutyl-5-butyl-1H-1,2,4-triazol-1-yl)methyl]phenyl]-2-pyridinyl]-1H-tetrazole;
5-[3-[4-[(3-isobutyl-5-butyl-1H-1,2,4-triazol-1-yl)methyl]phenyl]-2-pyridinyl]-1H-tetrazole;
5-[3-[4-[(3-tertbutyl-5-butyl-1H-1,2,4-triazol-1-yl)methyl]phenyl]-2-pyridinyl]-1H-tetrazole;
5-[3-[4-[(3-pentyl-5-butyl-1H-1,2,4-triazol-1-yl)methyl]phenyl]-2-pyridinyl]-1H-tetrazole;
5-[3-[4-[(3-isopentyl-5-butyl-1H-1,2,4-triazol-1-yl)methyl]phenyl]-2-pyridinyl]-1H-tetrazole;
5-[3-[4-[(3-cyclohexyl-5-butyl-1H-1,2,4-triazol-1-yl)methyl]phenyl]-2-pyridinyl]-1H-tetrazole;
5-[3-[4-[(3-cyclohexylmethyl-5-butyl-1H-1,2,4-triazol-1-yl)methyl]phenyl]-2-pyridinyl]-1H-tetrazole;
5-[3-[4-[(3-phenyl-5-butyl-1H-1,2,4-triazol-1-yl)methyl]phenyl]-2-pyridinyl]-1H-tetrazole;
5-[3-[4-[(3-phenylmethyl-5-butyl-1H-1,2,4-triazol-1-yl)methyl]phenyl]-2-pyridinyl]-1H-tetrazole;
5-[3-[4-[[3-(2-cyclohexylethyl)-5-butyl-1H-1,2,4-triazol-1-yl]methyl]phenyl]-2-pyridinyl]-1H-tetrazole;
5-[3-[4-[[3-(2-phenylethyl)-5-butyl-1H-1,2,4-triazol-1-yl]methyl]phenyl]-2-pyridinyl]-1H-tetrazole;
5-[3-[4-[[3-(1-oxo-2-phenylethyl)-5-butyl-1H-1,2,4-triazol-1-yl]methyl]phenyl]-2-pyridinyl]-1H-tetrazole;
5-[3-[4-[[3-(1-oxobutyl)-5-butyl-1H-1,2,4-triazol-1-yl]methyl]phenyl]-2-pyridinyl]-1H-tetrazole;
5-[3-[4-[[3-(1,1-difluorobutyl)-5-butyl-1H-1,2,4-triazol-1-yl]methyl]phenyl]-2-pyridinyl]-1H-tetrazole; and
5-[3-[4-[[3-(1,1-dimethoxybutyl)-5-butyl-1H-1,2,4-triazol-1-yl]methyl]phenyl]-2-pyridinyl]-1H-tetrazole.

16. Compound of claim 15 which is 5-[3-[4-[(3,5-dibutyl-1H-1,2,4-triazol-1-yl)methyl]phenyl-2-pyridinyl]-1H-tetrazole or a pharmaceutically-acceptable salt thereof.

17. A pharmaceutical composition comprising a therapeutically-effective amount of an angiotensin II antagonist compound and a pharmaceutically-acceptable carrier or diluent, said antagonist compound selected from a family of compounds of the formula

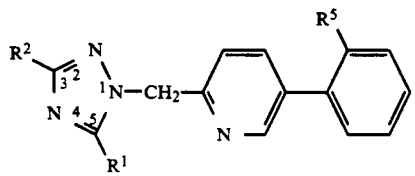

wherein $R^1$ is selected from methyl, ethyl, n-propyl, isopropyl, n-butyl, sec-butyl, isobutyl, tert-butyl, isopentyl, n-pentyl, neopentyl, phenyl, benzyl, phenethyl, cyclohexyl, cyclohexylmethyl, 2-butenyl, 3-butenyl, 2-butynyl, 3-butynyl and 2-hydroxybutyl; wherein $R^2$ is selected from methyl, ethyl, n-propyl, isopropyl, n-butyl, sec-butyl, isobutyl, isopentyl, tert-butyl, n-pentyl, neopentyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, acetyl, 1-butenyl, 2-butenyl, 3-butenyl, 1-butynyl, 2-butynyl, 3-butynyl, propylthio, butylthio,

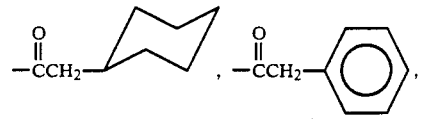

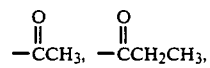

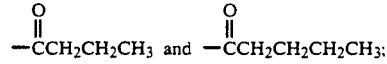

wherein $R_5$ is COOH or

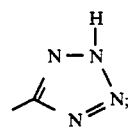

or a tautomer thereof or a pharmaceutically-acceptable salt thereof.

18. The composition of claim 17 wherein said angiotensin II antagonist compound is selected from compounds, and their pharmaceutically-acceptable salts, of the group of compounds consisting of 2-[6-[(3-methyl-5-butyl-1H-1,2,4-triazol-1-yl)methyl]-3-pyridinyl]benzoic acid;
2-[6-[(3-ethyl-5-butyl-1H-1,2,4-triazol-1-yl)methyl]-3-pyridinyl]benzoic acid;
2-[6-[(3-propyl-5-butyl-1H-1,2,4-triazol-1-yl)methyl]-3-pyridinyl]benzoic acid;
2-[6-[(3-isopropyl-5-butyl-1H-1,2,4-triazol-1-yl)methyl]-3-pyridinyl]benzoic acid;
2-[6-[(3,5-dibutyl-1H-1,2,4-triazol-1-yl)methyl]-3-pyridinyl]benzoic acid;
2-[6-[(3-secbutyl-5-butyl-1H-1,2,4-triazol-1-yl)methyl]-3-pyridinyl]benzoic acid;
2-[6-[(3-isobutyl-5-butyl-1H-1,2,4-triazol-1-yl)methyl]-3-pyridinyl]benzoic acid;
2-[6-[(3-tertbutyl-5-butyl-1H-1,2,4-triazol-1-yl)methyl]-3-pyridinyl]benzoic acid;
2-[6-[(3-pentyl-5-butyl-1H-1,2,4-triazol-1-yl)methyl]-3-pyridinyl]benzoic acid;
2-[6-[(3-isopentyl-5-butyl-1H-1,2,4-triazol-1-yl)methyl]-3-pyridinyl]benzoic acid;
2-[6-[(3-cyclohexyl-5-butyl-1H-1,2,4-triazol-1-yl)methyl]-3-pyridinyl]benzoic acid;
2-[6-[(3-cyclohexylmethyl-5-butyl-1H-1,2,4-triazol-1-yl)methyl]-3-pyridinyl]benzoic acid;
2-[6-[(3-phenyl-5-butyl-1H-1,2,4-triazol-1-yl)methyl]-3-pyridinyl]benzoic acid;
2-[6-[(3-phenylmethyl-5-butyl-1H-1,2,4-triazol-1-yl)methyl]-3-pyridinyl]benzoic acid;
2-[6-[[3-(2-cyclohexylethyl)-5-butyl-1H-1,2,4-triazol-1-yl]methyl]-3-pyridinyl]benzoic acid;

2-[6-[[3-(2-phenylethyl)-5-butyl-1H-1,2,4-triazol-1-yl]methyl]-3-pyridinyl]benzoic acid;

2-[6-[[3-(1-oxo-2-phenylethyl)-5-butyl-1H-1,2,4-triazol-1-yl]methyl]-3-pyridinyl]benzoic acid;

2-[6-[[3-(1-oxobutyl)-5-butyl-1H-1,2,4-triazol-1-yl]methyl]-3-pyridinyl]benzoic acid;

2-[6-[[3-(1,1-difluorobutyl)-5-butyl-1H-1,2,4-triazol-1-yl]methyl]-3-pyridinyl]benzoic acid;

2-[6-[[3-(1,1-dimethoxybutyl)-5-butyl-1H-1,2,4-triazol-1-yl]methyl]-3-pyridinyl]benzoic acid;

5-[2-[6-[(3-methyl-5-butyl-1H-1,2,4-triazol-1-yl)methyl]-3-pyridinyl]phenyl]-1H-tetrazole;

5-[2-[6-[(3-ethyl-5-butyl-1H-1,2,4-triazol-1-yl)methyl]-3-pyridinyl]phenyl]-1H-tetrazole;

5-[2-[6-[(3-propyl-5-butyl-1H-1,2,4-triazol-1-yl)methyl]-3-pyridinyl]phenyl]-1H-tetrazole;

5-[2-[6-[(3-isopropyl-5-butyl-1H-1,2,4-triazol-1-yl)methyl]-3-pyridinyl]phenyl]-1H-tetrazole;

5-[2-[6-[(3,5-dibutyl-1H-1,2,4-triazol-1-yl)methyl]-3-pyridinyl]phenyl]-1H-tetrazole;

5-[2-[6-[(3-secbutyl-5-butyl-1H-1,2,4-triazol-1-yl)methyl]-3-pyridinyl]phenyl]-1H-tetrazole;

5-[2-[6-[(3-isobutyl-5-butyl-1H-1,2,4-triazol-1-yl)methyl]-3-pyridinyl]phenyl]-1H-tetrazole;

5-[2-[6-[(3-tertbutyl-5-butyl-1H-1,2,4-triazol-1-yl)methyl]-3-pyridinyl]phenyl]-1H-tetrazole;

5-[2-[6-[(3-pentyl-5-butyl-1H-1,2,4-triazol-1-yl)methyl]-3-pyridinyl]phenyl]-1H-tetrazole;

5-[2-[6-[(3-isopentyl-5-butyl-1H-1,2,4-triazol-1-yl)methyl]-3-pyridinyl]phenyl]-1H-tetrazole;

5-[2-[6-[(3-cyclohexyl-5-butyl-1H-1,2,4-triazol-1-yl)methyl]-3-pyridinyl]phenyl]-1H-tetrazole;

5-[2-[6-[(3-cyclohexylmethyl-5-butyl-1H-1,2,4-triazol-1-yl)methyl]-3-pyridinyl]phenyl]-1H-tetrazole;

5-[2-[6-[(3-phenyl-5-butyl-1H-1,2,4-triazol-1-yl)methyl]-3-pyridinyl]phenyl]-1H-tetrazole;

5-[2-[6-[(3-phenylmethyl-5-butyl-1H-1,2,4-triazol-1-yl)methyl]-3-pyridinyl]phenyl]-1H-tetrazole;

5-[2-[6-[[3-(2-cyclohexylethyl)-5-butyl-1H-1,2,4-triazol-1-yl]methyl]-3-pyridinyl]phenyl]-1H-tetrazole;

5-[2-[6-[[3-(2-phenylethyl)-5-butyl-1H-1,2,4-triazol-1-yl]methyl]-3-pyridinyl]phenyl]-1H-tetrazole;

5-[2-[6-[[3-(1-oxo-2-phenylethyl)-5-butyl-1H-1,2,4-triazol-1-yl]methyl]-3-pyridinyl]phenyl]-1H-tetrazole;

5-[2-[6-[[3-(1-oxobutyl)-5-butyl-1H-1,2,4-triazol-1-yl]methyl]-3-pyridinyl]phenyl]-1H-tetrazole;

5-[2-[6-[[3-(1,1-difluorobutyl)-5-butyl-1H-1,2,4-triazol-1-yl]methyl]-3-pyridinyl]phenyl]-1H-tetrazole; and 5-[2-[6-[[3-(1,1-dimethoxybutyl)-5-butyl-1H-1,2,4-triazol-1-yl]methyl]-3-pyridinyl]phenyl]-1H-tetrazole.

19. The composition of claim 18 wherein said angiotensin II antagonist compound is 5-[2-[6-[(3,5-dibutyl-1H-1,2,4-triazol-1-yl)methyl]-3-pyridinyl]phenyl-1H-tetrazole or a pharmaceutically-acceptable salt thereof.

20. A pharmaceutical composition comprising a therapeutically-effective amount of an angiotensin II antagonist compound and a pharmaceutically-acceptable carrier or diluent, said antagonist compound selected from a family of compounds of the formula

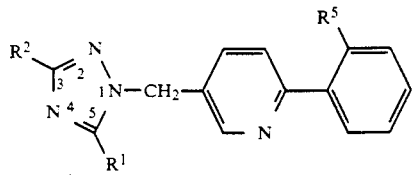

wherein $R^1$ is selected from methyl, ethyl, n-propyl, isopropyl, n-butyl, sec-butyl, isobutyl, tert-butyl, isopentyl, n-pentyl, neopentyl, phenyl, benzyl, phenethyl, cyclohexyl, cyclohexylmethyl, 2-butenyl, 3-butenyl, 2-butynyl, 3-butynyl and 2-hydroxybutyl; wherein $R^2$ is selected from methyl, ethyl, n-propyl, isopropyl, n-butyl, sec-butyl, isobutyl, isopentyl, tert-butyl, n-pentyl, neopentyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, acetyl, 1-butenyl, 2-butenyl, 3-butenyl, 1-butynyl, 2-butynyl, 3-butynyl, propylthio, butylthio,

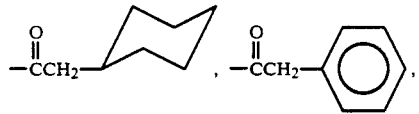

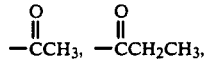

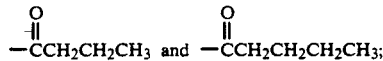

wherein $R^5$ is COOH or

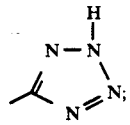

or a tautomer thereof or a pharmaceutically-acceptable salt thereof.

21. The composition of claim 20 wherein said angiotensin II antagonist compound is selected from compounds, and their pharmaceutically-acceptable salts, of the group of compounds consisting of 2-[5-[(3-methyl-5-butyl-1H-1,2,4-triazol-1-yl)methyl]-2-pyridinyl]benzoic acid;

2-[5-[(3-ethyl-5-butyl-1H-1,2,4-triazol-1-yl)methyl]-2-pyridinyl]benzoic acid;

2-[5-[(3-propyl-5-butyl-1H-1,2,4-triazol-1-yl)methyl]-2-pyridinyl]benzoic acid;

2-[5-[(3-isopropyl-5-butyl-1H-1,2,4-triazol-1-yl)methyl]-2-pyridinyl]benzoic acid;

2-[5-[(3,5-dibutyl-1H-1,2,4-triazol-1-yl)methyl]-2-pyridinyl]benzoic acid;

2-[5-[(3-secbutyl-5-butyl-1H-1,2,4-triazol-1-yl)methyl]-2-pyridinyl]benzoic acid;

2-[5-[(3-isobutyl-5-butyl-1H-1,2,4-triazol-1-yl)methyl]-2-pyridinyl]benzoic acid;

2-[5-[(3-tertbutyl-5-butyl-1H-1,2,4-triazol-1-yl)methyl]-2-pyridinyl]benzoic acid;

2-[5-[(3-pentyl-5-butyl-1H-1,2,4-triazol-1-yl)methyl]-2-pyridinyl]benzoic acid;
2-[5-[(3-isopentyl-5-butyl-1H-1,2,4-triazol-1-yl)methyl]-2-pyridinyl]benzoic acid;
2-[5-[(3-cyclohexyl-5-butyl-1H-1,2,4-triazol-1-yl)methyl]-2-pyridinyl]benzoic acid;
2-[5-[(3-cyclohexylmethyl-5-butyl-1H-1,2,4-triazol-1-yl)methyl]-2-pyridinyl]benzoic acid;
2-[5-[(3-phenyl-5-butyl-1H-1,2,4-triazol-1-yl)methyl]-2-pyridinyl]benzoic acid;
2-[5-[(3-phenylmethyl-5-butyl-1H-1,2,4-triazol-1-yl)methyl]-2-pyridinyl]benzoic acid;
2-[5-[[3-(2-cyclohexylethyl)-5-butyl-1H-1,2,4-triazol-1-yl]methyl]-2-pyridinyl]benzoic acid;
2-[5-[[3-(2-phenylethyl)-5-butyl-1H-1,2,4-triazol-1-yl]methyl]-2-pyridinyl]benzoic acid;
2-[5-[[3-(1-oxo-2-phenylethyl)-5-butyl-1H-1,2,4-triazol-1-yl]methyl]-2-pyridinyl]benzoic acid;
2-[5-[[3-(1-oxobutyl)-5-butyl-1H-1,2,4-triazol-1-yl]methyl]-2-pyridinyl]benzoic acid;
2-[5-[[3-(1,1-difluorobutyl)-5-butyl-1H-1,2,4-triazol-1-yl]methyl]-2-pyridinyl]benzoic acid;
2-[5-[[3-(1,1-dimethoxybutyl)-5-butyl-1H-1,2,4-triazol-1-yl]methyl]-2-pyridinyl]benzoic acid;
5-[2-[5-[(3-methyl-5-butyl-1H-1,2,4-triazol-1-yl)methyl]-2-pyridinyl]phenyl]-1H-tetrazole;
5-[2-[5-[(3-ethyl-5-butyl-1H-1,2,4-triazol-1-yl)methyl]-2-pyridinyl]phenyl]-1H-tetrazole;
5-[2-[5-[(3-propyl-5-butyl-1H-1,2,4-triazol-1-yl)methyl]-2-pyridinyl]phenyl]-1H-tetrazole;
5-[2-[5-[(3-isopropyl-5-butyl-1H-1,2,4-triazol-1-yl)methyl]-2-pyridinyl]phenyl]-1H-tetrazole;
5-[2-[5-[(3,5-dibutyl-1H-1,2,4-triazol-1-yl)methyl]-2-pyridinyl]phenyl]-1H-tetrazole;
5-[2-[5-[(3-secbutyl-5-butyl-1H-1,2,4-triazol-1-yl)methyl]-2-pyridinyl]phenyl]-1H-tetrazole;
5-[2-[5-[(3-isobutyl-5-butyl-1H-1,2,4-triazol-1-yl)methyl]-2-pyridinyl]phenyl]-1H-tetrazole;
5-[2-[5-[(3-tertbutyl-5-butyl-1H-1,2,4-triazol-1-yl)methyl]-2-pyridinyl]phenyl]-1H-tetrazole;
5-[2-[5-[(3-pentyl-5-butyl-1H-1,2,4-triazol-1-yl)methyl]-2-pyridinyl]phenyl]-1H-tetrazole;
5-[2-[5-[(3-isopentyl-5-butyl-1H-1,2,4-triazol-1-yl)methyl]-2-pyridinyl]phenyl]-1H-tetrazole;
5-[2-[5-[(3-cyclohexyl-5-butyl-1H-1,2,4-triazol-1-yl)methyl]-2-pyridinyl]phenyl]-1H-tetrazole;
5-[2-[5-[(3-cyclohexylmethyl-5-butyl-1H-1,2,4-triazol-1-yl)methyl]-2-pyridinyl]phenyl]-1H-tetrazole;
5-[2-[5-[(3-phenyl-5-butyl-1H-1,2,4-triazol-1-yl)methyl]-2-pyridinyl]phenyl]-1H-tetrazole;
5-[2-[5-[(3-phenylmethyl-5-butyl-1H-1,2,4-triazol-1-yl)methyl]-2-pyridinyl]phenyl]-1H-tetrazole;
5-[2-[5-[[3-(2-cyclohexylethyl)-5-butyl-1H-1,2,4-triazol-1-yl]methyl]-2-pyridinyl]phenyl]-1H-tetrazole;
5-[2-[5-[[3-(2-phenylethyl)-5-butyl-1H-1,2,4-triazol-1-yl]methyl]-2-pyridinyl]phenyl]-1H-tetrazole;
5-[2-[5-[[3-(1-oxo-2-phenylethyl)-5-butyl-1H-1,2,4-triazol-1-yl]methyl]-2-pyridinyl]phenyl]-1H-tetrazole;
5-[2-[5-[[3-(1-oxobutyl)-5-butyl-1H-1,2,4-triazol-1-yl]methyl]-2-pyridinyl]phenyl]-1H-tetrazole;
5-[2-[5-[[3-(1,1-difluorobutyl)-5-butyl-1H-1,2,4-triazol-1-yl]methyl]-2-pyridinyl]phenyl]-1H-tetrazole; and
5-[2-[5-[[3-(1,1-dimethoxybutyl)-5-butyl-1H-1,2,4-triazol-1-yl]methyl]-2-pyridinyl]phenyl]-1H-tetrazole.

22. The composition of claim 21 wherein said angiotensin II antagonist compound is 2-[5-[(3,5-dibutyl-1H-1,2,4-triazol-1-yl)methyl]-2-pyridinyl]benzoic acid or a pharmaceutically-acceptable salt thereof.

23. The composition of claim 21 wherein said antiotensin II antagonist compound is 5-[2-[5-[(3,5-dibutyl-1H-1,2,4-triazol-1-yl)methyl]-2-pyridinyl]phenyl]-1H-tetrazole or a pharmaceutically-acceptable salt thereof.

24. A pharmaceutical composition comprising a therapeutically-effective amount of an angiotensin II antagonist compound and a pharmaceutically-acceptable carrier or diluent, said antagonist compound selected from a family of compounds of the formula

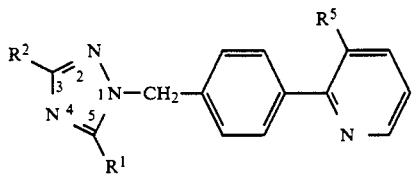

wherein $R^1$ is selected from methyl, ethyl, n-propyl, isopropyl, n-butyl, sec-butyl, isobutyl, tert-butyl, isopentyl, n-pentyl, neopentyl, phenyl, benzyl, phenethyl, cyclohexyl, cyclohexylmethyl, 2-butenyl, 3-butenyl, 2-butynyl, 3-butynyl and 2-hydroxybutyl; wherein $R^2$ is selected from methyl, ethyl, n-propyl, isopropyl, n-butyl, sec-butyl, isobutyl, isopentyl, tert-butyl, n-pentyl, neopentyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, acetyl, 1-butenyl, 2-butenyl, 3-butenyl, 1-butynyl, 2-butynyl, 3-butynyl, propylthio, butylthio,

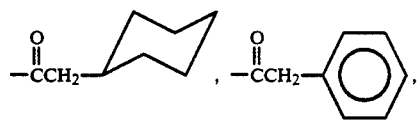

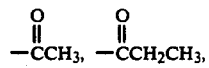

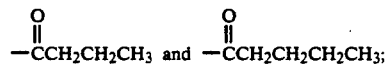

wherein $R^5$ is COOH or

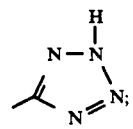

or a tautomer thereof or a pharmaceutically-acceptable salt thereof.

25. The composition of claim 24 wherein said angiotensin II antagonist compound is selected from compounds, and their pharmaceutically-acceptable salts, of the group of compounds consisting of
2-[4-[(3-methyl-5-butyl-1H-1,2,4-triazol-1-yl)methyl]phenyl]-3-pyridinecarboxylic acid;
2-[4-[(3-ethyl-5-butyl-1H-1,2,4-triazol-1-yl)methyl]phenyl]-3-pyridinecarboxylic acid;

2-[4-[(3-propyl-5-butyl-1H-1,2,4-triazol-1-yl)methyl]-phenyl]-3-pyridinecarboxylic acid;
2-[4-[(3-isopropyl-5-butyl-1H-1,2,4-triazol-1-yl)methyl]-phenyl]-3-pyridinecarboxylic acid;
2-[4-[(3,5-dibutyl-1H-1,2,4-triazol-1-yl)methyl]phenyl]-3-pyridinecarboxylic acid;
2-[4-[(3-secbutyl-5-butyl-1H-1,2,4-triazol-1-yl)methyl]-phenyl]-3-pyridinecarboxylic acid;
2-[4-[(3-isobutyl-5-butyl-1H-1,2,4-triazol-1-yl)methyl]-phenyl]-3-pyridinecarboxylic acid;
2-[4-[(3-tertbutyl-5-butyl-1H-1,2,4-triazol-1-yl)methyl]-phenyl]-3-pyridinecarboxylic acid;
2-[4-[(3-pentyl-5-butyl-1H-1,2,4-triazol-1-yl)methyl]-phenyl]-3-pyridinecarboxylic acid;
2-[4-[(3-isopentyl-5-butyl-1H-1,2,4-triazol-1-yl)methyl]-phenyl]-3-pyridinecarboxylic acid;
2-[4-[(3-cyclohexyl-5-butyl-1H-1,2,4-triazol-1-yl)methyl]phenyl]-3-pyridinecarboxylic acid;
2-[4-[(3-cyclohexylmethyl-5-butyl-1H-1,2,4-triazol-1-yl)methyl]phenyl]-3-pyridinecarboxylic acid;
2-[4-[(3-phenyl-5-butyl-1H-1,2,4-triazol-1-yl)methyl]-phenyl]-3-pyridinecarboxylic acid;
2-[4-[(3-phenylmethyl-5-butyl-1H-1,2,4-triazol-1-yl)methyl]phenyl]-3-pyridinecarboxylic acid;
2-[4-[[3-(2-cyclohexylethyl)-5-butyl-1H-1,2,4-triazol-1-yl]methyl]phenyl]-3-pyridinecarboxylic acid;
2-[4-[[3-(2-phenylethyl)-5-butyl-1H-1,2,4-triazol-1-yl]methyl]phenyl]-3-pyridinecarboxylic acid;
2-[4-[[3-(1-oxo-2-phenylethyl)-5-butyl-1H-1,2,4-triazol-1-yl]methyl]phenyl]-3-pyridinecarboxylic acid;
2-[4-[[3-(1-oxobutyl)-5-butyl-1H-1,2,4-triazol-1-yl]methyl]phenyl]-3-pyridinecarboxylic acid;
2-[4-[[3-(1,1-difluorobutyl)-5-butyl-1H-1,2,4-triazol-1-yl]methyl]phenyl]-3-pyridinecarboxylic acid;
2-[4-[[3-(1,1-dimethoxybutyl)-5-butyl-1H-1,2,4-triazol-1-yl]methyl]phenyl]-3-pyridinecarboxylic acid;
5-[2-[4-[(3-methyl-5-butyl-1H-1,2,4-triazol-1-yl)methyl]phenyl]-3-pyridinyl]-1H-tetrazole;
5-[2-[4-[(3-ethyl-5-butyl-1H-1,2,4-triazol-1-yl)methyl]-phenyl]-3-pyridinyl]-1H-tetrazole;
5-[2-[4-[(3-propyl-5-butyl-1H-1,2,4-triazol-1-yl)methyl]-phenyl]-3-pyridinyl]-1H-tetrazole;
5-[2-[4-[(3-isopropyl-5-butyl-1H-1,2,4-triazol-1-yl)methyl]phenyl]-3-pyridinyl]-1H-tetrazole;
5-[2-[4-[(3,5-dibutyl-1H-1,2,4-triazol-1-yl)methyl]-phenyl]-3-pyridinyl]-1H-tetrazole;
5-[2-[4-[(3-secbutyl-5-butyl-1H-1,2,4-triazol-1-yl)methyl]phenyl]-3-pyridinyl]-1H-tetrazole;
5-[2-[4-[(3-isobutyl-5-butyl-1H-1,2,4-triazol-1-yl)methyl]phenyl]-3-pyridinyl]-1H-tetrazole;
5-[2-[4-[(3-tertbutyl-5-butyl-1H-1,2,4-triazol-1-yl)methyl]phenyl]-3-pyridinyl]-1H-tetrazole;
5-[2-[4-[(3-pentyl-5-butyl-1H-1,2,4-triazol-1-yl)methyl]phenyl]-3-pyridinyl]-1H-tetrazole;
5-[2-[4-[(3-isopentyl-5-butyl-1H-1,2,4-triazol-1-yl)methyl]phenyl]-3-pyridinyl]-1H-tetrazole;
5-[2-[4-[(3-cyclohexyl-5-butyl-1H-1,2,4-triazol-1-yl)methyl]phenyl]-3-pyridinyl]-1H-tetrazole;
5-[2-[4-[(3-cyclohexylmethyl-5-butyl-1H-1,2,4-triazol-1-yl)methyl]phenyl]-3-pyridinyl]-1H-tetrazole;
5-[2-[4-[(3-phenyl-5-butyl-1H-1,2,4-triazol-1-yl)methyl]-phenyl]-3-pyridinyl]-1H-tetrazole;
5-[2-[4-[(3-phenylmethyl-5-butyl-1H-1,2,4-triazol-1-yl)methyl]phenyl]-3-pyridinyl]-1H-tetrazole;
5-[2-[4-[[3-(2-cyclohexylethyl)-5-butyl-1H-1,2,4-triazol-1-yl]methyl]phenyl]-3-pyridinyl]-1H-tetrazole;
5-[2-[4-[[3-(2-phenylethyl)-5-butyl-1H-1,2,4-triazol-1-yl]methyl]phenyl]-3-pyridinyl]-1H-tetrazole;
5-[2-4-[[3-(1-oxo-2-phenylethyl)-5-butyl-1H-1,2,4-triazol-1-yl]methyl]phenyl]-3-pyridinyl]-1H-tetrazole;
5-[2-[4-[[3-(1-oxobutyl)-5-butyl-1H-1,2,4-triazol-1-yl]methyl]phenyl]-3-pyridinyl]-1H-tetrazole;
5-[2-[4-[[3-(1,1-difluorobutyl)-5-butyl-1H-1,2,4-triazol-1-yl]methyl]phenyl]-3-pyridinyl]-1H-tetrazole; and
5-[2-[4-[[3-(1,1-dimethoxybutyl)-5-butyl-1H-1,2,4-triazol-1-yl]methyl]phenyl]-3-pyridinyl]-1H-tetrazole.

26. A pharmaceutical composition comprising a therapeutically-effective amount of an angiotensin II antagonist compound and a pharmaceutically-acceptable carrier or diluent, said antagonist compound selected from a family of compounds of the formula

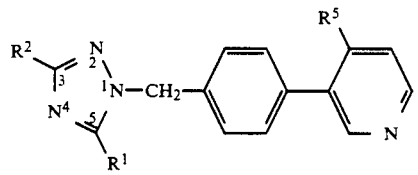

wherein $R^1$ is selected from methyl, ethyl, n-propyl, isopropyl, n-butyl, sec-butyl, isobutyl, tert-butyl, isopentyl, n-pentyl, neopentyl, phenyl, benzyl, phenethyl, cyclohexyl, cyclohexylmethyl, 2-butenyl, 3-butenyl, 2-butynyl, 3-butynyl and 2-hydroxybutyl; wherein $R^2$ is selected from methyl, ethyl, n-propyl, isopropyl, n-butyl, sec-butyl, isobutyl, isopentyl, tert-butyl, n-pentyl, neopentyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, acetyl, 1-butenyl, 2-butenyl, 3-butenyl, 1-butynyl, 2-butynyl, 3-butynyl, propylthio, butylthio,

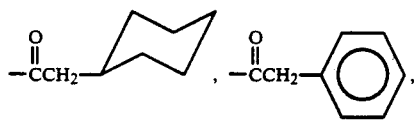

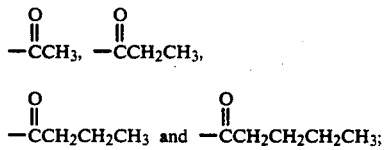

wherein $R^5$ is COOH or

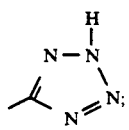

or a tautomer thereof or a pharmaceutically-acceptable salt thereof.

27. The composition of claim 26 wherein said angiotensin II antagonist compound is selected from compounds, and their pharmaceutically-acceptable salts, of the group of compounds consisting of 3-[4-[(3-methyl-5-butyl-1H-1,2,4-triazol-1-yl)methyl]-phenyl]-4-pyridinecarboxylic acid;
3-[4-[(3-ethyl-5-butyl-1H-1,2,4-triazol-1-yl)methyl]-phenyl]-4-pyridinecarboxylic acid;
3-[4-[(3-propyl-5-butyl-1H-1,2,4-triazol-1-yl)methyl]-phenyl]-4-pyridinecarboxylic acid;
3-[4-[(3-isopropyl-5-butyl-1H-1,2,4-triazol-1-yl)methyl]-phenyl]-4-pyridinecarboxylic acid;
3-[4-[(3,5-dibutyl-1H-1,2,4-triazol-1-yl)methyl]phenyl]-4-pyridinecarboxylic acid;
3-[4-[(3-secbutyl-5-butyl-1H-1,2,4-triazol-1-yl)methyl]-phenyl]-4-pyridinecarboxylic acid;
3-[4-[(3-isobutyl-5-butyl-1H-1,2,4-triazol-1-yl)methyl]-phenyl]-4-pyridinecarboxylic acid;
3-[4-[(3-tertbutyl-5-butyl-1H-1,2,4-triazol-1-yl)methyl]-phenyl]-4-pyridinecarboxylic acid;
3-[4-[(3-pentyl-5-butyl-1H-1,2,4-triazol-1-yl)methyl]-phenyl]-4-pyridinecarboxylic acid;
3-[4-[(3-isopentyl-5-butyl-1H-1,2,4-triazol-1-yl)methyl]-phenyl]-4-pyridinecarboxylic acid;
3-[4-[(3-cyclohexyl-5-butyl-1H-1,2,4-triazol-1-yl)methyl]phenyl]-4-pyridinecarboxylic acid;
3-[4-[(3-cyclohexylmethyl-5-butyl-1H-1,2,4-triazol-1-yl)methyl]phenyl]-4-pyridinecarboxylic acid;
3-[4-[(3-phenyl-5-butyl-1H-1,2,4-triazol-1-yl)methyl]-phenyl]-4-pyridinecarboxylic acid;
3-[4-[(3-phenylmethyl-5-butyl-1H-1,2,4-triazol-1-yl)methyl]phenyl]-4-pyridinecarboxylic acid;
3-[4-[[3-(2-cyclohexylethyl)-5-butyl-1H-1,2,4-triazol-1-yl]methyl]phenyl]-4-pyridinecarboxylic acid;
3-[4-[[3-(2-phenylethyl)-5-butyl-1H-1,2,4-triazol-1-yl]methyl]phenyl]-4-pyridinecarboxylic acid;
3-[4-[[3-(1-oxo-2-phenylethyl)-5-butyl-1H-1,2,4-triazol-1-yl]methyl]phenyl]-4-pyridinecarboxylic acid;
3-[4-[[3-(1-oxobutyl)-5-butyl-1H-1,2,4-triazol-1-yl]methyl]phenyl]-4-pyridinecarboxylic acid;
3-[4-[[3-(1,1-difluorobutyl)-5-butyl-1H-1,2,4-triazol-1-yl]methyl]phenyl]-4-pyridinecarboxylic acid;
3-[4-[[3-(1,1-dimethoxybutyl)-5-butyl-1H-1,2,4-triazol-1-yl]methyl]phenyl]-4-pyridinecarboxylic acid;
5-[3-[4-[(3-methyl-5-butyl-1H-1,2,4-triazol-1-yl)methyl]phenyl]-4-pyridinyl]-1H-tetrazole;
5-[3-[4-[(3-ethyl-5-butyl-1H-1,2,4-triazol-1-yl)methyl]phenyl]-4-pyridinyl]-1H-tetrazole;
5-[3-[4-[(3-propyl-5-butyl-1H-1,2,4-triazol-1-yl)methyl]phenyl]-4-pyridinyl]-1H-tetrazole;
5-[3-[4-[(3-isopropyl-5-butyl-1H-1,2,4-triazol-1-yl)methyl]phenyl]-4-pyridinyl]-1H-tetrazole;
5-[3-[4-[(3,5-dibutyl-1H-1,2,4-triazol-1-yl)methyl]phenyl]-4-pyridinyl]-1H-tetrazole;
5-[3-[4-[(3-secbutyl-5-butyl-1H-1,2,4-triazol-1-yl)methyl]phenyl]-4-pyridinyl]-1H-tetrazole;
5-[3-[4-[(3-isobutyl-5-butyl-1H-1,2,4-triazol-1-yl)methyl]phenyl]-4-pyridinyl]-1H-tetrazole;
5-[3-[4-[(3-tertbutyl-5-butyl-1H-1,2,4-triazol-1-yl)methyl]phenyl]-4-pyridinyl]-1H-tetrazole;
5-[3-[4-[(3-pentyl-5-butyl-1H-1,2,4-triazol-1-yl)methyl]phenyl]-4-pyridinyl]-1H-tetrazole;
5-[3-[4-[(3-isopentyl-5-butyl-1H-1,2,4-triazol-1-yl)methyl]phenyl]-4-pyridinyl]-1H-tetrazole;
5-[3-[4-[(3-cyclohexyl-5-butyl-1H-1,2,4-triazol-1-yl)methyl]phenyl]-4-pyridinyl]-1H-tetrazole;
5-[3-[4-[(3-cyclohexylmethyl-5-butyl-1H-1,2,4-triazol-1-yl)methyl]phenyl]-4-pyridinyl]-1H-tetrazole;
5-[3-[4-[(3-phenyl-5-butyl-1H-1,2,4-triazol-1-yl)methyl]phenyl]-4-pyridinyl]-1H-tetrazole;
5-[3-[4-[(3-phenylmethyl-5-butyl-1H-1,2,4-triazol-1-yl)methyl]phenyl]-4-pyridinyl]-1H-tetrazole;
5-[3-[4-[[3-(2-cyclohexylethyl)-5-butyl-1H-1,2,4-triazol-1-yl]methyl]phenyl]-4-pyridinyl]-1H-tetrazole;
5-[3-[4-[[3-(2-phenylethyl)-5-butyl-1H-1,2,4-triazol-1-yl]methyl]phenyl]-4-pyridinyl]-1H-tetrazole;
5-[3-[4-[[3-(1-oxo-2-phenylethyl)-5-butyl-1H-1,2,4-triazol-1-yl]methyl]phenyl]-4-pyridinyl]-1H-tetrazole;
5-[3-[4-[[3-(1-oxobutyl)-5-butyl-1H-1,2,4-triazol-1-yl]methyl]phenyl]-4-pyridinyl]-1H-tetrazole;
5-[3-[4-[[3-(1,1-difluorobutyl)-5-butyl-1H-1,2,4-triazol-1-yl]methyl]phenyl]-4-pyridinyl]-1H-tetrazole; and
5-[3-[4-[[3(1,1-dimethoxybutyl)-5-butyl-1H-1,2,4-triazol-1-yl]methyl]phenyl]-4-pyridinyl]-1H-tetrazole.

28. A pharmaceutical composition comprising a therapeuticall-effective amount of an angiotensin II antagonist compound and a pharmaceutically-acceptable carrier or diluent, said antagonist compound selected from a family of compounds of the formula

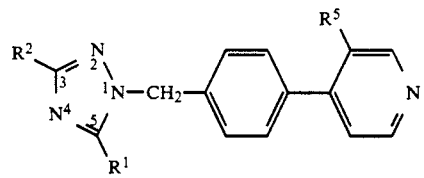

wherein $R^1$ is selected from methyl, ethyl, n-propyl, isopropyl, n-butyl, sec-butyl, isobutyl, tert-butyl, isopentyl, n-pentyl, neopentyl, phenyl, benzyl, phenethyl, cyclohexyl, cyclohexylmethyl, 2-butenyl, 3-butenyl, 2-butynyl, 3-butynyl and 2-hydroxybutyl; wherein $R^2$ is selected from methyl, ethyl, n-propyl, isopropyl, n-butyl, sec-butyl, isobutyl, isopentyl, tert-butyl, n-pentyl, neopentyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, acetyl, 1-butenyl, 2-butenyl, 3-butenyl, 1-butynyl, 2-butynyl, 3-butynyl, propylthio, butylthio,

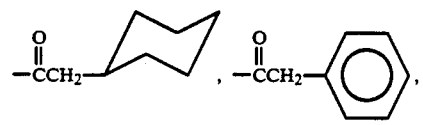

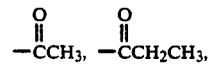

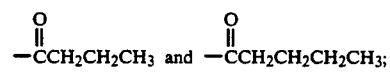

wherein $R^5$ is COOH or

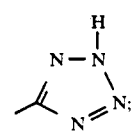

or a tautomer thereof or a pharmaceutically-acceptable salt thereof.

29. The composition of claim 28 wherein said angiotensin II antagonist compound is selected from compounds, and their pharmaceutically-acceptable salts, of the group of compounds consisting of 4-[4-[(3-methyl-5-butyl-1H-1,2,4-triazol-1-yl)methyl]-phenyl]-3-pyridinecarboxylic acid;

4-[4-[(3-ethyl-5-butyl-1H-1,2,4-triazol-1-yl)methyl]-phenyl]-3-pyridinecarboxylic acid;

4-[4-[(3-propyl-5-butyl-1H-1,2,4-triazol-1-yl)methyl]-phenyl]-3-pyridinecarboxylic acid;

4-[4-[(3-isopropyl-5-butyl-1H-1,2,4-triazol-1-yl)methyl]-phenyl]-3-pyridinecarboxylic acid;

4-[4-[(3,5-dibutyl-1H-1,2,4-triazol-1-yl)methyl]phenyl]-3-pyridinecarboxylic acid;

4-[4-[(3-secbutyl-5-butyl-1H-1,2,4-triazol-1-yl)methyl]-phenyl]-3-pyridinecarboxylic acid;

4-[4-[(3-isobutyl-5-butyl-1H-1,2,4-triazol-1-yl)methyl]-phenyl]-3-pyridinecarboxylic acid;

4-[4-[(3-tertbutyl-5-butyl-1H-1,2,4-triazol-1-yl)methyl]-phenyl]-3-pyridinecarboxylic acid;

4-[4-[(3-pentyl-5-butyl-1H-1,2,4-triazol-1-yl)methyl]-phenyl]-3-pyridinecarboxylic acid;

4-[4-[(3-isopentyl-5-butyl-1H-1,2,4-triazol-1-yl)methyl]-phenyl]-3-pyridinecarboxylic acid;

4-[4-[(3-cyclohexyl-5-butyl-1H-1,2,4-triazol-1-yl)methyl]phenyl]-3-pyridinecarboxylic acid;

4-[4-[(3-cyclohexylmethyl-5-butyl-1H-1,2,4-triazol-1-yl)methyl]phenyl]-3-pyridinecarboxylic acid;

4-[4-[(3-phenyl-5-butyl-1H-1,2,4-triazol-1-yl)methyl]-phenyl]-3-pyridinecarboxylic acid;

4-[4-[(3-phenylmethyl-5-butyl-1H-1,2,4-triazol-1-yl)methyl]phenyl]-3-pyridinecarboxylic acid;

4-[4-[[3-(2-cyclohexylethyl)-5-butyl-1H-1,2,4-triazol-1-yl]methyl]phenyl]-3-pyridinecarboxylic acid;

4-[4-[[3-(2-phenylethyl)-5-butyl-1H-1,2,4-triazol-1-yl]methyl]phenyl]-3-pyridinecarboxylic acid;

4-[4-[[3-(1-oxo-2-phenylethyl)-5-butyl-1H-1,2,4-triazol-1-yl]methyl]phenyl]-3-pyridinecarboxylic acid;

4-[4-[[3-(1-oxobutyl)-5-butyl-1H-1,2,4-triazol-1-yl]methyl]phenyl]-3-pyridinecarboxylic acid;

4-[4-[[3-(1,1-difluorobutyl)-5-butyl-1H-1,2,4-triazol-1-yl]methyl]phenyl]-3-pyridinecarboxylic acid;

4-[4-[[3-(1,1-dimethoxybutyl)-5-butyl-1H-1,2,4-triazol-1-yl]methyl]phenyl]-3-pyridinecarboxylic acid;

5-[4-[4-[(3-methyl-5-butyl-1H-1,2,4-triazol-1-yl)methyl]phenyl]-3-pyridinyl]-1H-tetrazole;

5-[4-[4-[(3-ethyl-5-butyl-1H-1,2,4-triazol-1-yl)methyl]-phenyl]-3-pyridinyl]-1H-tetrazole;

5-[4-[4-[(3-propyl-5-butyl-1H-1,2,4-triazol-1-yl)methyl]-phenyl]-3-pyridinyl]-1H-tetrazole;

5-[4-[4-[(3-isopropyl-5-butyl-1H-1,2,4-triazol-1-yl)methyl]phenyl]-3-pyridinyl]-1H-tetrazole;

5-[4-[4-[(3,5-dibutyl-1H-1,2,4-triazol-1-yl)methyl]-phenyl]-3-pyridinyl]-1H-tetrazole;

5-[4-[4-[(3-secbutyl-5-butyl-1H-1,2,4-triazol-1-yl)methyl]phenyl]-3-pyridinyl]-1H-tetrazole;

5-[4-[4-[(3-isobutyl-5-butyl-1H-1,2,4-triazol-1-yl)methyl]phenyl]-3-pyridinyl]-1H-tetrazole;

5-[4-[4-[(3-tertbutyl-5-butyl-1H-1,2,4-triazol-1-yl)methyl]phenyl]-3-pyridinyl]-1H-tetrazole;

5-[4-[4-[(3-pentyl-5-butyl-1H-1,2,4-triazol-1-yl)methyl]-phenyl]-3-pyridinyl]-1H-tetrazole;

5-[4-[4-[(3-isopentyl-5-butyl-1H-1,2,4-triazol-1-yl)methyl]phenyl]-3-pyridinyl]-1H-tetrazole;

5-[4-[4-[(3-cyclohexyl-5-butyl-1H-1,2,4-triazol-1-yl)methyl]phenyl]-3-pyridinyl]-1H-tetrazole;

5-[4-[4-[(3-cyclohexylmethyl-5-butyl-1H-1,2,4-triazol-1-yl)methyl]phenyl]-3-pyridinyl]-1H-tetrazole;

5-[4-[4-[(3phenyl-5-butyl-1H-1,2,4-triazol-1-yl)methyl]-phenyl]-3-pyridinyl]-1H-tetrazole;

5-[4-[4-[(3-phenylmethyl-5-butyl-1H-1,2,4-triazol-1-yl)methyl]phenyl]-3-pyridinyl]-1H-tetrazole;

5-[4-[4-[[3-(2-cyclohexylethyl)-5-butyl-1H-1,2,4-triazol-1-yl]methyl]phenyl]-3-pyridinyl]-1H-tetrazole;

5-[4-[4-[[3-(2-phenylethyl)-5-butyl-1H-1,2,4-triazol-1-yl]methyl]phenyl]-3-pyridinyl]-1H-tetrazole;

5-[4-[4-[[3-(1-oxo-2-phenylethyl)-5-butyl-1H-1,2,4-triazol-1-yl]methyl]phenyl]-3-pyridinyl]-1H-tetrazole;

5-[4-[4-[[3-(1-oxobutyl)-5-butyl-1H-1,2,4-triazol-1-yl]methyl]phenyl]-3-pyridinyl]-1H-tetrazole;

5-[4-[4-[[3-(1,1-difluorobutyl)-5-butyl-1H-1,2,4-triazol-1-yl]methyl]phenyl]-3-pyridinyl]-1H-tetrazole; and 5-[4-[4-[[3-(1,1-dimethoxybutyl)-5-butyl-1H-1,2,4-triazol-1-yl]methyl]phenyl]-3-pyridinyl]-1H-tetrazole.

30. A pharmaceutical composition comprising a therapeutically-effective amount of an angiotensin II antagonist compound and a pharmaceutically-acceptable carrier or diluent, said antagonist compound selected from a family of compounds of the formula

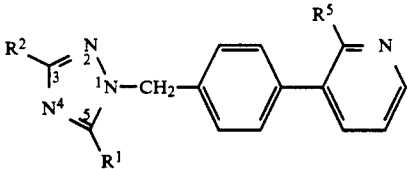

wherein $R^1$ is selected from methyl, ethyl, n-propyl, isopropyl, n-butyl, sec-butyl, isobutyl, tert-butyl, isopentyl, n-pentyl, neopentyl, phenyl, benzyl, phenethyl, cyclohexyl, cyclohexylmethyl, 2-butenyl, 3-butenyl, 2-butynyl, 3-butynyl and 2-hydroxybutyl; wherein $R^2$ is selected from methyl, ethyl, n-propyl, isopropyl, n-butyl, sec-butyl, isobutyl, isopentyl, tert-butyl, n-pentyl, neopentyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, acetyl, 1-butenyl, 2-butenyl, 3-butenyl, 1-butynyl, 2-butynyl, 3-butynyl, propylthio, butylthio,

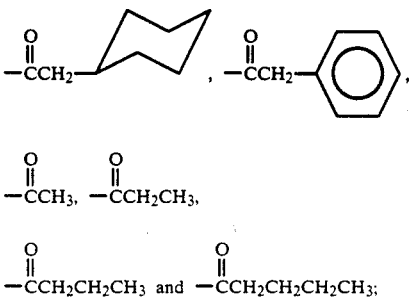

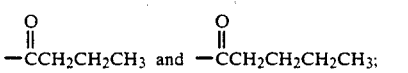

wherein $R^5$ is COOH or

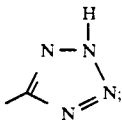

or a tautomer thereof or a pharmaceutically-acceptable salt thereof.

31. The composition of claim 30 wherein said angiotensin II antagonist compound is selected from compounds, and their pharmaceutically-acceptable salts, of the group of compounds consisting of 3-[4-[(3-methyl-5-butyl-1H-1,2,4-triazol-1-yl)methyl]phenyl]-2-pyridinecarboxylic acid;
3-[4-[(3-ethyl-5-butyl-1H-1,2,4-triazol-1-yl)methyl]phenyl]-2-pyridinecarboxylic acid;
3-[4-[(3-propyl-5-butyl-1H-1,2,4-triazol-1-yl)methyl]phenyl]-2-pyridinecarboxylic acid;
3-[4-[(3-isopropyl-5-butyl-1H-1,2,4-triazol-1-yl)methyl]phenyl]-2-pyridinecarboxylic acid;
3-[4-[(3,5-dibutyl-1H-1,2,4-triazol-1-yl)methyl]phenyl]-2-pyridinecarboxylic acid;
3-[4-[(3-secbutyl-5-butyl-1H-1,2,4-triazol-1-yl)methyl]phenyl]-2-pyridinecarboxylic acid;
3-[4-[(3-isobutyl-5-butyl-1H-1,2,4-triazol-1-yl)methyl]phenyl]-2-pyridinecarboxylic acid;
3-[4-[(3-tertbutyl-5-butyl-1H-1,2,4-triazol-1-yl)methyl]phenyl]-2-pyridinecarboxylic acid;
3-[4-[(3-pentyl-5-butyl-1H-1,2,4-triazol-1-yl)methyl]phenyl]-2-pyridinecarboxylic acid;
3-[4-[(3-isopentyl-5-butyl-1H-1,2,4-triazol-1-yl)methyl]phenyl]-2-pyridinecarboxylic acid;
3-[4-[(3-cyclohexyl-5-butyl-1H-1,2,4-triazol-1-yl)methyl]phenyl]-2-pyridinecarboxylic acid;
3-[4-[(3-cyclohexylmethyl-5-butyl-1H-1,2,4-triazol-1-yl)methyl]phenyl]-2-pyridinecarboxylic acid;
3-[4-[(3-phenyl-5-butyl-1H-1,2,4-triazol-1-yl)methyl]phenyl]-2-pyridinecarboxylic acid;
3-[4-[(3-phenylmethyl-5-butyl-1H-1,2,4-triazol-1-yl)methyl]phenyl]-2-pyridinecarboxylic acid;
3-[4-[[3-(2-cyclohexylethyl)-5-butyl-1H-1,2,4-triazol-1-yl]methyl]phenyl]-2-pyridinecarboxylic acid;
3-[4-[[3-(2-phenylethyl)-5-butyl-1H-1,2,4-triazol-1-yl]methyl]phenyl]-2-pyridinecarboxylic acid;
3-[4-[[3-(1-oxo-2-phenylethyl)-5-butyl-1H-1,2,4-triazol-1-yl]methyl]phenyl]-2-pyridinecarboxylic acid;
3-[4-[[3-(1-oxobutyl)-5-butyl-1H-1,2,4-triazol-1-yl]methyl]phenyl]-2-pyridinecarboxylic acid;
3-[4-[[3-(1,1-difluorobutyl)-5-butyl-1H-1,2,4-triazol-1-yl]methyl]phenyl]-2-pyridinecarboxylic acid;
3-[4-[[3-(1,1-dimethoxybutyl)-5-butyl-1H-1,2,4-triazol-1-yl]methyl]phenyl]-2-pyridinecarboxylic acid;
5-[3-[4-[(3-methyl-5-butyl-1H-1,2,4-triazol-1-yl)methyl]phenyl]-2-pyridinyl]-1H-tetrazole;
5-[3-[4-[(3-ethyl-5-butyl-1H-1,2,4-triazol-1-yl)methyl]phenyl]-2-pyridinyl]-1H-tetrazole;
5-[3-[4-[(3-propyl-5-butyl-1H-1,2,4-triazol-1-yl)methyl]phenyl]-2-pyridinyl]-1H-tetrazole;
5-[3-[4-[(3-isopropyl-5-butyl-1H-1,2,4-triazol-1-yl)methyl]phenyl]-2-pyridinyl]-1H-tetrazole;
5-[3-[4-[(3,5-dibutyl-1H-1,2,4-triazol-1-yl)methyl]phenyl]-2-pyridinyl]-1H-tetrazole;
5-[3-[4-[(3-secbutyl-5-butyl-1H-1,2,4-triazol-1-yl)methyl]phenyl]-2-pyridinyl]-1H-tetrazole;
5-[3-[4-[(3-isobutyl-5-butyl-1H-1,2,4-triazol-1-yl)methyl]phenyl]-2-pyridinyl]-1H-tetrazole;
5-[3-[4-[(3-tertbutyl-5-butyl-1H-1,2,4-triazol-1-yl)methyl]phenyl]-2-pyridinyl]-1H-tetrazole;
5-[3-[4-[(3-pentyl-5-butyl-1H-1,2,4-triazol-1-yl)methyl]phenyl]-2-pyridinyl]-1H-tetrazole;
5-[3-[4-[(3-isopentyl-5-butyl-1H-1,2,4-triazol-1-yl)methyl]phenyl]-2-pyridinyl]-1H-tetrazole;
5-[3-[4-[(3-cyclohexyl-5-butyl-1H-1,2,4-triazol-1-yl)methyl]phenyl]-2-pyridinyl]-1H-tetrazole;
5-[3-[4-[(3-cyclohexylmethyl-5-butyl-1H-1,2,4-triazol-1-yl)methyl]phenyl]-2-pyridinyl]-1H-tetrazole;
5-[3-[4-[(3-phenyl-5-butyl-1H-1,2,4-triazol-1-yl)methyl]phenyl]-2-pyridinyl]-1H-tetrazole;
5-[3-[4-[(3-phenylmethyl-5-butyl-1H-1,2,4-triazol-1-yl)methyl]phenyl]-2-pyridinyl]-1H-tetrazole;
5-[3-[4-[[3-(2-cyclohexylethyl)-5-butyl-1H-1,2,4-triazol-1-yl]methyl]phenyl]-2-pyridinyl]-1H-tetrazole;
5-[3-[4-[[3-(2-phenylethyl)-5-butyl-1H-1,2,4-triazol-1-yl]methyl]phenyl]-2-pyridinyl]-1H-tetrazole;
5-[3-[4-[[3-(1-oxo-2-phenylethyl)-5-butyl-1H-1,2,4-triazol-1-yl]methyl]phenyl]-2-pyridinyl]-1H-tetrazole;
5-[3-[4-[[3-(1-oxobutyl)-5-butyl-1H-1,2,4-triazol-1-yl]methyl]phenyl]-2-pyridinyl]-1H-tetrazole;
5-[3-[4-[[3-(1,1-difluorobutyl)-5-butyl-1H-1,2,4-triazol-1-yl]methyl]phenyl]-2-pyridinyl]-1H-tetrazole; and
5-[3-[4-[[3-(1,1-dimethoxybutyl)-5-butyl-1H-1,2,4-triazol-1-yl]methyl]phenyl]-2-pyridinyl]-1H-tetrazole.

32. The composition of claim 31 wherein said angiotensin II antagonist compound is 5-[3-[4-[(3,5-dibutyl-1H-1,2,4-triazol-1-yl)methyl]phenyl-2-pyridinyl]-1H-tetrazole or a pharmaceutically-acceptable salt thereof.

* * * * *